United States Patent
Brode, III et al.

(10) Patent No.: US 6,451,574 B1
(45) Date of Patent: Sep. 17, 2002

(54) PROTEINASE K VARIANTS HAVING DECREASED ADSORPTION AND INCREASED HYDROLYSIS

(75) Inventors: Philip Frederick Brode, III, Cincinnati, OH (US); Bobby Lee Barnett, Cincinnati, OH (US); Donn Nelton Rubingh, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/935,887

(22) Filed: Sep. 23, 1997

Related U.S. Application Data

(63) Continuation of application No. 08/401,574, filed on Mar. 9, 1995.

(51) Int. Cl.[7] .......................... C12N 9/58; C12N 15/57; C12N 15/74; C11D 3/386
(52) U.S. Cl. .................. 435/219; 435/69.1; 435/252.3; 435/320.1; 435/471; 510/392; 536/23.2
(58) Field of Search ................................. 435/221, 222, 435/69.1, 252.31, 320.1, 471; 536/23.2; 510/305, 320, 375

(56) References Cited

U.S. PATENT DOCUMENTS

| | | | |
|---|---|---|---|
| 4,760,025 A | | 7/1988 | Estell et al. ................. 435/222 |
| 4,908,773 A | | 3/1990 | Pantoliano et al. .......... 364/496 |
| 4,914,031 A | | 4/1990 | Zukowsky et al. .......... 435/222 |
| 4,980,288 A | | 12/1990 | Bryan et al. ................. 435/222 |
| 4,990,452 A | | 2/1991 | Bryan et al. ................. 435/222 |
| 5,013,657 A | | 5/1991 | Bryan et al. ............. 435/172.3 |
| 5,116,741 A | | 5/1992 | Bryan et al. ................... 435/87 |
| 5,118,623 A | * | 6/1992 | Boguslawski et al. ....... 510/374 |
| 5,155,033 A | * | 10/1992 | Estell et al. ................. 435/221 |
| 5,182,204 A | * | 1/1993 | Estell et al. ................. 435/222 |
| 5,185,258 A | * | 2/1993 | Caldwell et al. ............ 435/220 |
| 5,208,158 A | * | 5/1993 | Bech et al. .................. 435/219 |
| 5,217,878 A | * | 6/1993 | van Eekelen et al. ...... 435/69.1 |
| 5,240,632 A | * | 8/1993 | Brumbaugh .................. 252/95 |
| 5,244,791 A | * | 9/1993 | Estell ......................... 435/68.1 |
| 5,246,849 A | | 9/1993 | Bryan et al. ................. 435/220 |
| 5,260,207 A | * | 11/1993 | Pantoliano et al. .......... 435/221 |
| 5,275,945 A | * | 1/1994 | Hsiao et al. ................. 435/221 |
| RE34,606 E | * | 5/1994 | Estell et al. ................. 510/392 |
| 5,310,675 A | * | 5/1994 | Estell et al. ............. 435/320.1 |
| 5,316,941 A | * | 5/1994 | Estell et al. .............. 435/252.3 |
| 5,324,653 A | * | 6/1994 | van Eckelen et al. ........ 435/221 |
| 5,336,611 A | * | 8/1994 | van Eekelen et al. ........ 435/221 |
| 5,340,735 A | * | 8/1994 | Christianson et al. ....... 435/221 |
| 5,346,823 A | * | 9/1994 | Estell et al. ................. 435/221 |
| 5,352,603 A | * | 10/1994 | Vetter et al. ................. 435/221 |
| 5,371,008 A | * | 12/1994 | Carter et al. ................. 435/222 |
| 5,371,190 A | * | 12/1994 | Carter et al. ................. 530/350 |
| 5,389,307 A | * | 2/1995 | Lindegaard et al. ......... 510/320 |
| 5,397,705 A | * | 3/1995 | Zukowski et al. ........... 435/222 |
| 5,403,737 A | * | 4/1995 | Abrahmsen et al. ....... 435/252.3 |

(List continued on next page.)

FOREIGN PATENT DOCUMENTS

| | | | |
|---|---|---|---|
| AU | 8772281 | | 11/1987 |
| EP | 0 251 446 A2 | * | 4/1987 |
| EP | 0 260 105 | | 3/1988 |
| EP | 0 328 229 A1 | * | 8/1989 |
| EP | 0 357 157 A1 | * | 3/1990 |
| EP | 0 380 362 | | 8/1990 |
| EP | 0 398 539 | | 11/1990 |
| EP | 0 405 901 A1 | | 1/1991 |
| EP | 0 405 902 A1 | | 1/1991 |
| WO | 87/04461 | | 7/1987 |
| WO | 87/05050 | | 8/1987 |
| WO | WO 88/08033 A1 | * | 10/1988 |
| WO | 89/06279 | | 1/1989 |
| WO | WO 89/07642 A1 | * | 8/1989 |
| WO | WO 89/09830 A1 | * | 10/1989 |
| WO | 91 /00345 | | 1/1991 |
| WO | WO 91/14420 A1 | * | 11/1991 |
| WO | WO 92/02615 A1 | * | 2/1992 |
| WO | WO 92/08778 A1 | * | 5/1992 |
| WO | 92/11357 | | 7/1992 | ............ C12N/9/56 |
| WO | WO 92/11357 | * | 7/1992 |
| WO | WO 94/02618 | * | 2/1994 |
| WO | 95/07991 | | 3/1995 | ........... C12N/15/57 |
| WO | WO 95/30010 A1 | * | 4/1995 |
| WO | WO 95/30011 A1 | * | 4/1995 |
| WO | WO 88/08028 A1 | * | 10/1998 |

OTHER PUBLICATIONS

Thomas, P. G., et al., 1985, "Tailoring the pH dependence of enzyme catalysis using protein engineering to change a single amino acid at BPN' position 99: D99S reduces pKa", Nature, vol. 318, pp. 375–376.*

Russell, A. J. & Fersht, A. R., 1987, "Rational modification of enzyme catalysis by engineering surface charge", Nature, vol. 328, pp. 496–500.*

(List continued on next page.)

*Primary Examiner*—Charles L. Patterson, Jr.
*Assistant Examiner*—William W. Moore
(74) *Attorney, Agent, or Firm*—Bart S. Hersko; Brahm J. Corstanje; Karen F. Clark

(57) ABSTRACT

The present invention relates to Proteinase K variants having a modified amino acid sequence of wild-type Proteinase K amino acid sequence, the wild-type amino acid sequence comprising a first loop region, a second loop region, a third loop region, a fourth loop region, a fifth loop region and a sixth loop region; wherein the modified amino acid sequence comprises different amino acids than that occurring in wild-type Proteinase K (i.e., substitution) at specifically identified positions in one or more of the loop regions whereby the Proteinase K variant has decreased adsorption to, and increased hydrolysis of, an insoluble substrate as compared to the wild-type Proteinase K. The present invention also relates to DNA sequences encoding such Proteinase K variants. The present invention also relates to compositions comprising such Proteinase K variants for cleaning a variety of surfaces.

70 Claims, No Drawings

U.S. PATENT DOCUMENTS

| | | | | | |
|---|---|---|---|---|---|
| 5,441,882 | A | * | 8/1995 | Estell et al. | 435/222 |
| 5,453,372 | A | * | 9/1995 | Vetter et al. | 435/222 |
| 5,470,733 | A | * | 11/1995 | Bryan et al. | 435/222 |
| 5,472,855 | A | * | 12/1995 | Carter et al. | 435/68.1 |
| 5,482,849 | A | * | 1/1996 | Branner et al. | 435/222 |
| 5,500,364 | A | * | 3/1996 | Christianson et al. | 435/221 |
| 5,567,601 | A | * | 10/1996 | Bryan et al. | 435/222 |
| 5,629,173 | A | * | 5/1997 | Abrahmsen et al. | 435/68.1 |
| 5,631,217 | A | * | 5/1997 | Branner et al. | 510/320 |
| 5,652,136 | A | * | 7/1997 | Carter et al. | 435/252.3 |
| 5,665,587 | A | * | 9/1997 | Aaslyng et al. | 435/221 |
| 5,677,272 | A | * | 10/1997 | Ghosh et al. | 510/306 |
| 5,679,630 | A | * | 10/1997 | Baeck et al. | 510/305 |
| 5,700,676 | A | * | 12/1997 | Bott et al. | 435/221 |
| 5,707,848 | A | * | 1/1998 | Bryan et al. | 435/6 |
| 5,736,512 | A | * | 4/1998 | Abrahmsen et al. | 514/12 |
| 5,741,664 | A | * | 4/1998 | Ballinger et al. | 435/68.1 |
| 5,741,694 | A | * | 4/1998 | Hastrup et al. | 435/222 |
| 5,763,257 | A | * | 6/1998 | Bott et al. | 435/221 |
| 5,801,038 | A | * | 9/1998 | Bott et al. | 435/221 |
| 5,801,039 | A | * | 9/1998 | Maurer et al. | 435/221 |
| 5,955,340 | A | * | 9/1999 | Bott et al. | 435/221 |
| 5,972,682 | A | * | 10/1999 | Bott et al. | 435/221 |
| 5,985,639 | A | * | 11/1999 | Christianson et al. | 435/221 |
| 6,197,567 | B1 | * | 3/2001 | Aaslyng et al. | 435/221 |
| 6,197,589 | B1 | * | 3/2001 | Maurer et al. | 435/471 |
| 6,271,012 | B1 | * | 8/2001 | van Eekelen et al. | 435/221 |
| 6,287,841 | B1 | * | 9/2001 | Mulleners et al. | 435/221 |

OTHER PUBLICATIONS

Abrahmsén, L., J. Tom, J. Burnier, K. A. Butcher, A. Kossiakoff and J. A. Wells, "Engineering Subtilisin and Its Substrates for Efficient Ligation of Peptide Bonds in Aqueous Solution", Biochemistry, vol. 30, No. 17, pp. 4151–4159 (no month identified 1991).

Arnold, F.H., "Engineering Enzymes for Non–aqueous Solvents", TibTech, vol. 8, pp. 244–249 (Sep. 1990).

Braxton, S. and J. A. Wells, "The Importance of a Distal Hydrogen Bonding Group in Stabilizing the Transition State in Subtilisin BPN'", The Journal of Biological Chemistry, vol. 266, No. 18, pp. 11797–11800 (Jun. 1991).

Brode, P. F., III and D. S. Rauch, "Subtilisin BPN': Activity on an Immobilized Substrate", Langmuir, vol. 8, No. 5, pp. 1325–1329 (no month identified 1992).

Brode, P.F. III, C.R. Erwin, D.S. Rauch, E.S. Wang, J.M. Armpriester, B.L. Barnett, M.D. Bauer, P.R. Green, D.A. Thaman, and D.N. Rubingh, "Surface Active Variants of Subtilisin BPN': Interfacial Hydrolysis", Abstract, Keystone Symposium (Mar. 6–11, 1994).

Carter, P., L. Abrahmsén and J. A. Wells, "Probing the Mechanism and Improving the Rate of Substrate–Assisted Catalysis in Subtilisin BPN'", Biochemistry, vol. 30, No. 25, pp. 6142–6148 (no month identified 1991).

Carter, P. and J. A. Wells, "Functional Interaction Among Catalytic Residues in Subtilisin BPN'", Proteins: Structure, Function, and Genetics, vol. 7, pp. 335–342, (no month identified 1990).

Cunningham, B. C. and J. A. Wells, "Improvement in the Alkaline Stability of Subtilisin Using An Efficient Random Mutagenesis and Screening Procedure", Protein Engineering, vol. 1, No. 4, pp. 319–325 (no month identified 1987).

Egmond, M. R., W. P. Antheunisse, P. Ravestein, A. T. A. Mooren and J. de Vlieg, "Engineering Surface Charges In A Subtilisin", First International Symposium on *Subtilisin Enzymes*, Hamburg, Germany, (Sep. 1992).

Estell, D.A., "Engineering Enzymes for Improved Performance in Industrial Applications", Journal of Biotechnology, vol. 28, No. 1, pp. 25–30 (Jan. 1993).

Hopp, T. P. and K. R. Woods, "Prediction of Protein Antigenic Determinants From Amino Acid Sequences", Proc. Natl. Acad. Sci. USA, vol. 78, No. 6, pp. 3824–3828 (Jun. 1981).

Mitchinson, C. and J.A. Wells, "Protein Engineering of Disulfide Bonds in Subtilisin BPN'", Biochemistry, vol. 28, No. 11, pp. 4807–4815 (no month identified 1989).

Mizushima, N., D. Spellmeyer, S. Hirono, D. Pearlman and P. Kollman, "Free Energy Perturbation Calculations on Binding and Catalysis ater Mutating Threonine 220 in Subtilisin", Journal of Biological Chemistry, vol. 266, No. 18, pp. 11801–11809 (Jun. 1991).

Pantoliano, M.W., M. Whitlow, J.F. Wood, S.W. Dodd, K.D. Hardman, M.L. Rollence and P.N. Bryan, "Large Increases in General Stability for Subtilisin BPN' through Incremental Changes in the Free Energy of Unfolding", Biochemistry, vol. 28, No. 18, pp. 7205–7213 (no month identified 1989).

Russell, A. J. and A. R. Fersht, "Rational Modification of Enzyme Catalysis by Engineering Surface Charge", Nature, vol. 328, pp. 496–500 (Aug. 1987).

Siezen, R.J., W.M. de Vos, J.A.M. Leunissen and B.W. Dijkstra, "Homology Modelling and Protein Engineering Strategy of Subtilases, the Family of Subtilisin–like Serine Proteinases", Prot. Eng., vol. 4, No. 7, pp. 719–737 (no month identified 1991).

Sternberg, M. J. E., F. R. F. Hayes, A. J. Russell, P. G. Thomas and A. R. Fersht, "Prediction of Electrostatic Effects of Engineering of Protein Charges", Nature, vol. 330, pp. 86–88 (Nov. 1987).

Wells, J.A., B.C. Cunningham, T.P. Graycar and D.A. Estell, "Recruitment of Substrate–specificity Properties from One Enzyme into a Related One by Protein Engineering", Proc. Natl. Acad. Sci., USA, vol. 84, pp. 5167–5171 (Aug. 1987).

Wells, J.A. and D.A. Estell, "Subtilisin—An Enzyme Designed to be Engineered", TIBS 13, pp. 291–297 (Aug. 1988).

Wong, C.–H. S.–T. Chen, W. J. Hennen, J. A. Bibbs, Y.–F. Wang, J. L.–C. Liu, M. W. Pantoliano, M. Whitlow and P. N. Bryan, "Enzymes in Organic Synthesis: Use of Subtilisin and a Highly Stable Mutant Derived from Multiple Site–Specific Mutations", J. Am. Chem. Soc., vol. 112, No. 3, pp. 945–953 (no month identified 1990).

* cited by examiner

US 6,451,574 B1

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 384 amino acids
        (B) TYPE: amino acid
        (C) STRANDEDNESS: single
        (D) TOPOLOGY: linear (xi) SEQUENCE DESCRIPTION: SEQ ID NO:1:

```
Met Arg Leu Ser Val Leu Leu Ser Leu Leu Pro Leu Ala Leu Gly Ala
1               5                   10                  15

Pro Ala Val Glu Gln Arg Ser Glu Ala Ala Pro Leu Ile Glu Ala Arg
            20                  25                  30

Gly Glu Met Val Ala Asn Lys Tyr Ile Val Lys Phe Lys Glu Gly Ser
        35                  40                  45

Ala Leu Ser Ala Leu Asp Ala Ala Met Glu Lys Ile Ser Gly Lys Pro
    50                  55                  60

Asp His Val Tyr Lys Asn Val Phe Ser Gly Phe Ala Ala Thr Leu Asp
65                  70                  75                  80

Glu Asn Met Val Arg Val Leu Arg Ala His Pro Asp Val Glu Tyr Ile
                85                  90                  95

Glu Gln Asp Ala Val Val Thr Ile Asn Ala Ala Gln Thr Asn Ala Pro
            100                 105                 110

Trp Gly Leu Ala Arg Ile Ser Ser Thr Ser Pro Gly Thr Ser Thr Tyr
        115                 120                 125

Tyr Tyr Asp Glu Ser Ala Gly Gln Gly Ser Cys Val Tyr Val Ile Asp
    130                 135                 140

Thr Gly Ile Glu Ala Ser His Pro Glu Phe Glu Gly Arg Ala Gln Met
145                 150                 155                 160
```

-continued

```
Val Lys Thr Tyr Tyr Tyr Ser Ser Arg Asp Gly Asn Gly His Gly Thr
            165             170             175

His Cys Ala Gly Thr Val Gly Ser Arg Thr Tyr Gly Val Ala Lys Lys
            180             185             190

Thr Gln Leu Phe Gly Val Lys Val Leu Asp Asp Asn Gly Ser Gly Gln
        195             200             205

Tyr Ser Thr Ile Ile Ala Gly Met Asp Phe Val Ala Ser Asp Lys Asn
    210              215             220

Asn Arg Asn Cys Pro Lys Gly Val Val Ala Ser Leu Ser Leu Gly Gly
225             230             235             240

Gly Tyr Ser Ser Ser Val Asn Ser Ala Ala Arg Leu Gln Ser Ser
            245             250             255

Gly Val Met Val Ala Val Ala Ala Gly Asn Asn Asn Ala Asp Ala Arg
            260             265             270

Asn Tyr Ser Pro Ala Ser Glu Pro Ser Val Cys Thr Val Gly Ala Ser
        275             280             285

Asp Arg Tyr Asp Arg Arg Ser Ser Phe Ser Asn Tyr Gly Ser Val Leu
    290             295             300

Asp Ile Phe Gly Pro Gly Thr Ser Ile Leu Ser Thr Trp Ile Gly Gly
305             310             315             320

Ser Thr Arg Ser Ile Ser Gly Thr Ser Met Ala Thr Pro His Val Ala
            325             330             335

Gly Leu Ala Ala Tyr Leu Met Thr Leu Gly Lys Thr Thr Ala Ala Ser
            340             345             350

Ala Cys Arg Tyr Ile Ala Asp Thr Ala Asn Lys Gly Asp Leu Ser Asn
            355             360             365

Ile Pro Phe Gly Thr Val Asn Leu Leu Ala Tyr Asn Asn Tyr Gln Ala
    370             375             380
```

PROTEINASE K VARIANTS HAVING DECREASED ADSORPTION AND INCREASED HYDROLYSIS

This is a continuation of application Ser. No. 08/401,574, filed on Mar. 9, 1995.

TECHNICAL FIELD

The present invention relates to novel enzyme variants useful in a variety of cleaning compositions, and DNA sequences encoding such enzyme variants.

BACKGROUND

Enzymes make up the largest class of naturally occurring proteins Each class of enzyme generally catalyzes (accelerates a reaction without being consumed) a different kind of chemical reaction. One class of enzymes is known as proteases, are known for their ability to hydrolyze (break down a compound into two or more simpler compounds with the uptake of the H and OH parts of a water molecule on either side of the chemical bond cleaved) other proteins. This ability to hydrolyze proteins has been taken advantage of by incorporating naturally occurring and protein engineered proteases as an additive to laundry detergent preparations. Many stains on clothes are proteinaceous and widespecificity proteases can substantially improve removal of such stains.

Unfortunately, the efficacy level of these proteins in their natural, bacterial environment, frequently does not translate into the relatively unnatural wash environment. Specifically, protease characteristics such as thermal stability, pH stability, oxidative stability and substrate specificity are not necessarily optimized for utilization outside the natural environment of the enzyme.

The amino acid sequence of the protease determines the characteristics of the protease. A change of the amino acid sequence of the protease may alter the properties of the enzyme to varying degrees, or may even inactivate the enzyme, depending upon the location, nature and/or magnitude of the change in the amino acid sequence. Several approaches have been taken to alter the wild-type amino acid sequence of proteases in an attempt to improve their properties, with the goal of increasing the efficacy of the protease in the wash environment. These approaches include altering the amino acid sequence to enhance thermal stability and to improve oxidation stability under quite diverse conditions.

Despite the variety of approaches described in the art, there is a continuing need for new effective variants of proteases useful for cleaning a variety of surfaces.

OBJECTS OF THE PRESENT INVENTION

It is an object of the present invention to provide Proteinase K enzyme variants having improved hydrolysis versus the wild-type of the enzyme.

It is also an object of the present invention to provide cleaning compositions comprising these subtilisin enzyme variants.

SUMMARY

The present invention relates to Proteinase K variants having a modified amino acid sequence of wild-type Proteinase K amino acid sequence, the wild-type amino acid sequence comprising a first loop region, a second loop region, a third loop region, a fourth loop region and a fifth loop region; wherein the modified amino acid sequence comprises different amino acids than that occurring in wild-type Proteinase K (i.e., substitution) at specifically identified positions in one or more of the loop regions whereby the Proteinase K variant has decreased adsorption to, and increased hydrolysis of, an insoluble substrate as compared to the wild-type Proteinase K. The present invention also relates to DNA sequences encoding such Proteinase K variants. The present invention also relates to compositions comprising such Proteinase K variants for cleaning a variety of surfaces.

DESCRIPTION

I. Proteinase K Variants

This invention pertains to subtilisin enzymes, in particular Proteinase K, that have been modified by mutating the various nucleotide sequences that code for the enzyme, thereby modifying the amino acid sequence of the enzyme. The modified subtilisin enzymes (hereinafter, "Proteinase K variants") of the present invention have decreased adsorption to and increased hydrolysis of an insoluble substrate as compared to the wild-type subtilisin. The present invention also pertains to DNA sequences encoding for such Proteinase K variants.

The subtilisin enzymes of this invention belong to a class of enzymes known as proteases. A protease is a catalyst for the cleavage of peptide bonds. One type of protease is a serine protease. A serine protease is distinguished by the fact that there is an essential serine residue at the active site.

The observation that an enzyme's rate of hydrolysis of soluble substrates increases with enzyme concentration is well documented. It would therefore seem plausible that for surface bound substrates, such as is encountered in many cleaning applications, the rate of hydrolysis would increase with increasing surface concentration. This has been shown to be the case. (Brode, P. F. III and D. S. Rauch, LANGMUIR, "Subtilisin BPN': Activity on an Immobilized Substrate", Vol. 8, pp. 1325–1329 (1992)). In fact, a linear dependence of rate upon surface concentration was found for insoluble substrates when the surface concentration of the enzyme was varied. (Rubingh, D. N. and M. D. Bauer, "Catalysis of Hydrolysis by Proteases at the Protein-Solution Interface," in POLYMER SOLUTIONS, BLENDS AND INTERFACES, Ed. by I. Noda and D. N. Rubingh, Elsevier, p. 464 (1992)). Surprisingly, when seeking to apply this principle in the search for variant proteases which give better cleaning performance, we did not find that enzymes which adsorb more give better performance. In fact, we surprisingly determined the opposite to be the case: decreased adsorption by an enzyme to a substrate resulted in increased hydrolysis of the substrate (i.e., better cleaning performance).

While not wishing to be bound by theory, it is believed that improved performance, when comparing one variant to another, is a result of the fact that enzymes which adsorb less are also less tightly bound and therefore more highly mobile on the surface from which the insoluble protein substrate is to be removed. At comparable enzyme solution concentrations, this increased mobility is sufficient to outweigh any advantage that is conferred by delivering a higher concentration of enzyme to the surface.

The mutations described herein are designed to change (i.e., decrease) the adsorption of the enzyme to surface-bound soils. In Proteinase K, certain amino acids form exterior loops on the enzyme molecule. For purposes of discussion, these loops shall be referred to as first, second, third, fourth and fifth loop regions. Specifically, positions 64–71 form the first loop region; positions 95–107 form the second loop region; positions 133–140 form the third loop region; positions 160–170 form the fourth loop region; positions 190–194 form the fifth loop region; and positions 203–223 form the sixth loop region (position numbering analogous to positions in the amino acid sequence for wild-type subtilisin Proteinase K (SEQ ID NO:1)).

It is believed that these loop regions play a significant role in the adsorption of the enzyme molecule to a surface-bound peptide, and specific mutations in one or more of these loop regions will have a significant effect on this adsorption. While not wishing to be bound by theory, it is believed that the loop regions are important to the adsorption of the Proteinase K molecule for at least two reasons. First, the amino acids which comprise the loop regions can make close contacts with any surfaces to which the molecule is exposed. Second, the proximity of the loop regions to the active-site and binding pocket of the Proteinase K molecule gives them a role in the catalytically productive adsorption of the enzyme to surface-bound substrates (peptides/protein soils).

As used herein, "variant" means an enzyme having an amino acid sequence which differs from that of wild-type.

As used herein, "mutant Proteinase K DNA" means a DNA sequence coding for a Proteinase K variant.

As used herein, "wild-type Proteinase K" refers to an enzyme represented by SEQ ID NO:1. The amino acid sequence for Proteinase K is further described by Gunkel, F. A. and Gassen H. G., "Proteinase K from Tritirachium album Limber: Characterization of the Chromosomal Gene and Expression of the cDNA in *Escherichia coli*", EUR. J. BIOCHEM., Vol. 179, pp. 185–194 (1989), incorporated herein by reference.

As used herein, the term "Proteinase K wild-type amino acid sequence" encompasses SEQ ID NO:1 as well as SEQ ID NO:1 having modifications to the amino acid sequence other than at any of positions 64–71, 95–107, 133–140, 160–170, 190–194 and 203–223.

As used herein, "more hydrophilic amino acid" refers to any other amino acid having greater hydrophilicity than a subject amino acid with reference to the hydrophilicity table below. The following hydrophilicity table (Table 1) lists amino acids in descending order of increasing hydrophilicity (see Hopp, T. P., and Woods, K. R., "Prediction of Protein Antigenic Determinants from Amino Acid Sequences", *PROCEEDINGS OF THE NATIONAL ACADEMY OF SCIENCE USA*, Vol. 78, pp. 3824–3828,1981, incorporated herein by reference).

TABLE 1

| Amino Acid | Hydrophilicity Value |
| --- | --- |
| Trp | −3.4 |
| Phe | −2.5 |
| Tyr | −2.3 |
| Leu, Ile | −1.8 |
| Val | −1.5 |
| Met | −1.3 |
| Cys | −1.0 |
| Ala, His | −0.5 |
| Thr | −0.4 |
| Pro, Gly | −0.0 |
| Gln, Asn | 0.2 |

TABLE 1-continued

| Amino Acid | Hydrophilicity Value |
| --- | --- |
| Ser | 0.3 |
| $Arg^+$, $Lys^+$, $Glu^-$, $Asp^-$ | 3.0 |

Table 1 also indicates which amino acids carry a charge (this characteristic being based on a pH of from about 8–9). The positively charged amino acids are Arg and Lys, the negatively charged amino acids are Glu and Asp, and the remaining amino acids are neutral. In a preferred embodiment of the present invention, the substituting amino acid is either neutral or negatively charged, more preferably negatively charged (i.e., Glu or Asp).

Therefore, for example, the statement "substitute Gln with an equally or more hydrophilic amino acid which is neutral or has a negative charge" means Gln would be substituted with Asn (which is equally hydrophilic to Gln), or Ser, Glu or Asp (which are more hydrophilic than Gln); each of which are neutral or have a negative charge, and have a greater hydrophilicity value as compared to Gln. Likewise, the statement "substitute Pro with a more hydrophilic amino acid which is neutral or has a negative charge" means Pro would be substituted with Gln, Asn, Ser, Glu or Asp.

In one embodiment of the present invention, the Proteinase K variant has a modified amino acid sequence of Proteinase K wild-type amino acid sequence, wherein the wild-type amino acid sequence comprises a substitution at one or more positions in one or more of the first loop region, the second loop region, the third loop region, the fourth loop region, the fifth loop region or the sixth loop region; whereby the Proteinase K variant has decreased adsorption to, and increased hydrolysis of, an insoluble substrate as compared to the wild-type Proteinase K.

In a preferred embodiment of the present invention, the substituting amino acid for one or more of the positions in one or more of the loop regions is, with reference to Table 1, neutral or negatively charged and equally or more hydrophylic, preferably more hydrophylic, than the amino acid at the subject position in the wild-type amino acid sequence.

A. Substitutions in the First Loop Region

When a substitution occurs in the first loop region, the substitution occurs at one or more of positions 64, 65, 66, 67, 68, 70 or 71.

When a substitution occurs at position 64, the substituting amino acid is Asp or Glu.

When a substitution occurs at position 65, the substituting amino acid is Glu.

When a substitution occurs at position 66, the substituting amino acid is Asn, Asp, Gln, Glu, Pro or Ser.

When a substitution occurs at position 67, the substituting amino acid is Asp, Gln, Glu or Ser.

When a substitution occurs at position 68, the substituting amino acid is Asn, Asp, Gln, Glu, Pro or Ser.

When a substitution occurs at position 70, the substituting amino acid is Asn, Asp, Gln, Glu, Pro or Ser.

When a substitution occurs at position 71, the substituting amino acid is Asn, Asp, Gln, Glu, Gly, Pro or Ser.

B. Substitutions in the Second Loop Region

When a substitution occurs in the second loop region, the substitution occurs at one or more of positions 95, 96, 97, 98, 99, 100, 101, 102, 103, 104, 105, 106 or 107.

When a substitution occurs at position 95, the substituting amino acid is Ala, Asn, Asp, Cys, Gln, Glu, Gly, His, Met, Pro, Ser or Thr.

When a substitution occurs at position 96, the substituting amino acid is Ala, Asn, Asp, Cys, Gln, Glu, Gly, His, Ile, Met, Pro, Ser, Thr or Val.

When a substitution occurs at position 97, the substituting amino acid is Glu.

When a substitution occurs at position 98, the substituting amino acid is Glu.

When a substitution occurs at position 99, the substituting amino acid is Asp, Gln, Glu or Ser.

When a substitution occurs at position 100, the substituting amino acid is Asn, Asp, Gln, Glu, Pro or Ser.

When a substitution occurs at position 101, the substituting amino acid is Asp or Glu.

When a substitution occurs at position 102, the substituting amino acid is Asn, Asp, Gln, Glu, Pro or Ser.

When a substitution occurs at position 103, the substituting amino acid is Asn, Asp, Glu or Ser.

When a substitution occurs at position 104, the substituting amino acid is Ala, Asn, Asp, Cys, Gln, Glu, Gly, His, Ile, Leu, Met, Pro, Ser, Thr or Val.

When a substitution occurs at position 105, the substituting amino acid is Asp or Glu.

When a substitution occurs at position 106, the substituting amino acid is Asn, Asp, Gln, Glu, Gly, Pro or Ser.

When a substitution occurs at position 107, the substituting amino acid is Ala, Asn, Asp, Cys, Gln, Glu, Gly, His, Leu, Met, Pro, Ser, Thr or Val.

C. Substitutions in the Third Loop Region

When a substitution occurs in the third loop region, the substitution occurs at one or more of positions 133, 134, 135, 136, 137, 138, 139 or 140 wherein When a substitution occurs at position 133, the substituting amino acid is Ala, Asn, Asp, Cys, Gln, Glu, Gly, His, Ile, Met, Pro, Ser, Thr or Val.

When a substitution occurs at position 134, the substituting amino acid is Asn, Asp, Gln, Glu, Pro or Ser.

When a substitution occurs at position 135, the substituting amino acid is Asn, Asp, Gln, Glu, Pro or Ser.

When a substitution occurs at position 136, the substituting amino acid is Asn, Asp, Gln, Glu, Pro or Ser.

When a substitution occurs at position 137, the substituting amino acid is Ala, Asn, Asp, Cys, Gln, Glu, Gly, His, Ile, Leu, Met, Pro, Ser, Thr or Val.

When a substitution occurs at position 138, the substituting amino acid is Asp or Glu.

When a substitution occurs at position 139, the substituting amino acid is Asp or Glu. and When a substitution occurs at position 140, the substituting amino acid is Asp or Glu.

D. Substitutions in the Fourth Loop Region

When a substitution occurs in the fourth loop region, the substitution occurs at one or more of positions 160, 161, 162, 163, 164, 165, 166, 167, 168, 169 or 170. wherein When a substitution occurs at position 160, the substituting amino acid is Asn, Asp, Gln, Glu, Pro or Ser.

When a substitution occurs at position 161, the substituting amino acid is Asp, Gln, Glu or Ser.

When a substitution occurs at position 162, the substituting amino acid is Asp, Gln, Glu or Ser.

When a substitution occurs at position 163, the substituting amino acid is Asp, Gln, Glu or Ser.

When a substitution occurs at position 164, the substituting amino acid is Asn, Asp, Gln, Glu, Gly, His, Pro, Ser or Thr.

When a substitution occurs at position 165, the substituting amino acid is Glu.

When a substitution occurs at position 166, the substituting amino acid is Asn, Asp, Gln, Glu, Gly, His, Pro, Ser or Thr.

When a substitution occurs at position 167, the substituting amino acid is Asp or Glu.

When a substitution occurs at position 168, the substituting amino acid is Asp, Gln, Glu or Ser.

When a substitution occurs at position 169, the substituting amino acid is Ala, Asn, Asp, Cys, Gln, Glu, Gly, His, Ile, Leu, Met, Pro, Ser, Thr or Val. and When a substitution occurs at position 170, the substituting amino acid is Asp or Glu.

E. Substitutions in the Fifth Loop Region

When a substitution occurs in the fifth loop region, the substitution occurs at one or more of positions 190, 191, 192, 193 or 194. wherein When a substitution occurs at position 190, the substituting amino acid is Asp or Glu.

When a substitution occurs at position 191, the substituting amino acid is Asp or Glu.

When a substitution occurs at position 192, the substituting amino acid is Ala, Asn, Asp, Cys, Gln, Glu, Gly, His, Ile, Leu, Met, Pro, Ser, Thr, Tyr or Val.

When a substitution occurs at position 193, the substituting amino acid is Asp or Glu. and When a substitution occurs at position 194, the substituting amino acid is Asp, Gln, Glu or Ser. and F. Substitutions in the Sixth Loop Region When a substitution occurs in the sixth loop region, the substitution occurs at one or more of positions 203, 204, 205, 206, 207, 208, 209, 210, 211, 212, 213, 214, 215, 216, 217, 218, 219, 220, 221, 222 or 223. wherein When a substitution occurs at position 203, the substituting amino acid is Asn, Asp, Gln, Glu, Pro or Ser.

When a substitution occurs at position 204, the substituting amino acid is Asn, Asp, Gln, Glu, Gly or Ser.

When a substitution occurs at position 205, the substituting amino acid is Asn, Asp, Gln, Glu, Pro or Ser.

When a substitution occurs at position 206, the substituting amino acid is Asn, Asp, Gln, Glu, Gly, Pro or Ser.

When a substitution occurs at position 207, the substituting amino acid is Asp or Glu.

When a substitution occurs at position 208, the substituting amino acid is Ala, Asn, Asp, Cys, Gln, Glu, Gly, His, Leu, Met, Pro, Ser, Thr or Val.

When a substitution occurs at position 209, the substituting amino acid is Ala, Asn, Asp, Cys, Gln, Glu, Gly, His, Ile, Met, Pro, Ser, Thr or Val.

When a substitution occurs at position 210, the substituting amino acid is Asp or Glu.

When a substitution occurs at position 211, the substituting amino acid is Asn, Asp, Gln, Glu, Gly, Pro or Ser.

When a substitution occurs at position 212, the substituting amino acid is Ala, Asn, Asp, Cys, Gln, Glu, Gly, His, Ile, Leu, Met, Phe, Pro, Ser, Thr, Tyr or Val.

When a substitution occurs at position 213, the substituting amino acid is Ala, Asn, Asp, Cys, Gln, Glu, Gly, His, Leu, Met, Pro, Ser, Thr or Val.

When a substitution occurs at position 214, the substituting amino acid is Asn, Asp, Gln, Glu, Pro or Ser.

When a substitution occurs at position 215, the substituting amino acid is Asn, Asp, Gln, Glu, Pro or Ser.

When a substitution occurs at position 216, the substituting amino acid is Asp or Glu.

When a substitution occurs at position 217, the substituting amino acid is Asn, Asp, Gln, Glu, Gly, Pro or Ser.

When a substitution occurs at position 218, the substituting amino acid is Asp or Glu.

When a substitution occurs at position 219, the substituting amino acid is Asp or Glu.

When a substitution occurs at position 220, the substituting amino acid is Ala, Asn, Asp, Cys, Gln, Glu, Gly, His, Leu, Met, Pro, Ser, Thr or Val.

When a substitution occurs at position 221, the substituting amino acid is Asp or Glu.

When a substitution occurs at position 222, the substituting amino acid is Asn, Asp, Gln, Glu, Pro or Ser. and When a substitution occurs at position 223, the substituting amino acid is Asn, Asp, Gln, Glu, Gly, Pro or Ser.

G. Preparation of Enzyme Variants

EXAMPLE 1

Mutant Proteinase K DNA

A phagemid ("PKP") containing the wild type Proteinase K gene is constructed. The 2.8 Kbp Pvu II restriction enzyme fragment of plasmid pUC119, (Vieira, J. and Messing, J., "Production of Single-Stranded Plasmid DNA", 153 *METHODS IN ENZYMOLOGY* 3–11 (1989)) is cloned into the Pvu II site of plasmid pUB110 (Bacillus Genetic Stock Center, Columbus, Ohio 1E9). The pUC119-pUB110 hybrid plasmid is named pJMA601. Into pJMA601 is cloned the *Bacillus amyloliquefaciens* subtilisin gene. The subtilisin gene is modified to contain two BamHI sites. One of the BamHI sites is between DNA encoding Gly and Lys, the second and third amino acid residues of the pro region. The other BamHI site follows the TAA stop sequence. A Proteinase K cDNA is amplified from RNA using reverse transcriptase and the polymerase chain reaction with oligonucleotides, each containing a BamHI site in addition to sequences identical to the Proteinase K cDNA. The amplified region consists of the DNA extending from the Ala at the beginning of the pro region of Proteinase K to the carboxy terminal Ala of the mature protease. The amplified segment is used to replace the DNA between two BamHI sites within the *Bacillus amyloliquefaciens* subtilisin gene. Phagemid PKP is transformed into *Eschefchia coli* Ung⁻ strain CJ236 and a single stranded uracil-containing DNA template is produced using the VCSM13 helper phage (Kunkel, T. A., J. D. Roberts and R. A. Zakour, "Rapid and efficient site-specific mutagenesis without phenotypic selection", *METHODS IN ENZYMOLOGY*, Vol. 154, pp. 367–382, (1987); as modified by Yuckenberg, P. D., F. Witney, J. Geisselsoder and J. McClary, "Site-directed in vitro mutagenesis using uracil-containing DNA and phagemid vectors", *DIRECTED MUTAGENESIS—A PRACTICAL APPROACH*, ed. M. J. McPherson, pp. 27–48, (1991); both of which are incorporated herein by reference). A single primer site-directed mutagenesis modification of the method of Zoller and Smith (Zoller, M. J., and M. Smith, "Oligonucleotide-directed mutagenesis using M13-derived vectors: an efficient and general procedure for the production of point mutations in any fragment of DNA:", *NUCLEIC ACIDs RESEARCH*, Vol. 10, pp. 6487–6500, (1982), incorporated herein by reference) is used to produce all mutants (basically as presented by Yuckenberg, et al., 1991, above). Oligonucleotides are made using an Applied Biosystem Inc. 380B DNA synthesizer. Mutagenesis reaction products are transformed into *Eschedchia coli* strain MM294 (American Type Culture Collection *E coli*. 33625). All mutants are confirmed by DNA sequencing and the isolated DNA is transformed into the *Bacillus subtilis* expression strain BG2036 (Yang, M. Y., E. Ferrari and D. J. Henner, (1984), "Cloning of the Neutral Protease Gene of *Bacillus subtilis* and the Use of the Cloned Gene to Create an In Vitro-derived Deletion Mutation", *JOURNAL OF BACTERIOLOGY*, Vol. 160, pp. 15–21). For some of the loop mutants a modified PKP with a frame-shift-stop codon mutation in the corresponding loop is used to produce the uracil template. Oligonucleotides are designed to restore the proper reading frame and to encode for random substitutions at positions 64, 65, 66, 67, 68, 70, 71, 95, 96, 97, 98, 99,100, 101, 102, 103, 104, 105, 106, 107, 133, 134, 135, 136, 137, 138, 139, 140, 160, 161, 162, 163, 164, 165, 166, 167, 168, 169, 170, 190, 191, 192, 193, 194, 203, 204, 205, 206, 207 208, 209, 210, 211, 212, 213, 214, 215, 216, 217, 218, 219, 220, 221, 222 or 223 (equimolar and or variable mixtures of all four nucleotides for all three bases at these codons). Mutations that correct for the frameshift-stop and produce a functional enzyme are identified by their ability to digest casein. The random substitutions are determined by DNA sequencing.

EXAMPLE 2

Fermentation

The *Bacillus subtilis* cells (BG2036) containing a subtilisin mutant of interest are grown to mid-log phase in a one liter culture of LB-lucose broth and inoculated into a Biostat ED fermenter (B. Braun Biotech, Inc., Allentown, Pa.) in a total volume of 10 liters. The fermentation media contains Yeast Extract, starch, antifoam, buffers and trace minerals (see *FERMENTATION: A PRACTICAL APPROACH*, Ed. B. McNeil and L. M. Harvey, 1990). The broth is kept at a constant pH of 7.0 during the fermentation run. Chloramphenical is added for antibiotic selection of mutagenized plasmid. The cells are grown overnight at 37° C. to an $A_{600}$ of about 60 and harvested.

EXAMPLE 3

Purification

The fermentation broth is taken through the following steps to obtain pure enzyme. The broth is cleared of *Bacillus subtilis* cells by centrifugation, and clarified by removing fine particulates with a 100K cutoff membrane. This is followed by concentration on a 10K cutoff membrane, and flow dialysis to reduce the ionic strength and adjust the pH to 5.5 using 0.025M MES buffer (2-(N-morpholino) ethanesulfonic acid). The enzyme is further purified by loading it onto either a cation exchange chromatography column or an affinity adsorption chromatography column and eluting it from the column with a NaCl or a propylene glycol gradient (see Scopes, R. K., *PROTEIN PURIFICATION PRINCIPLES AND PRACTICE*, Springer-Verlag, N.Y. (1984), incorporated herein by reference).

The pNA assay (DelMar, E. G., C. Largman, J. W. Brodrick and M. C. Geokas, *ANAL. BIOCHEM.*, Vol. 99, pp. 316–320, (1979), incorporated herein by reference) is used to determine the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sMPF-pNA). The rate of production of yellow color from the hydrolysis reaction is measured at 410 nm on a spectrophotometer and is proportional to the active enzyme concentration. In addition, absorbance measurements at 280 nm are used to determine the total protein concentration. The active enzyme/total-protein ratio gives the enzyme purity, and is used to identify fractions to be pooled for the stock solution.

To avoid autolysis of the enzyme during storage, an equal weight of propylene glycol is added to the pooled fractions obtained from the chromatography column. Upon completion of the purification procedure the purity of the stock enzyme solution is checked with SDS-PAGE (sodium dodecyl sulfate polyacrylamide gel electrophoresis) and the absolute enzyme concentration is determined via an active site titration method using trypsin inhibitor type II-T: turkey egg white purchased from Sigma Chemical Company (St. Louis, Missouri). The measured conversion factors will show which changes made in the enzyme molecule at the various positions result in the enzyme variant having increased activity over the wild-type, against the soluble substrate pNA.

In preparation for use, the enzyme stock solution is eluted through a Sephadex-G25 (Pharmacia, Piscataway, N.J.) size exclusion column to remove the propylene glycol and exchange the buffer. The MES buffer in the enzyme stock solution is exchanged for 0.1 M Tris buffer (Tris (hydroxymethyl-aminomethane) containing 0.01M $CaCl_2$ and pH adjusted to 8.6 with HCl. All experiments are carried out at pH 8.6 in Tris buffer thermostated at 25° C.

H. Characterization of Enzyme Variants

EXAMPLE 4

Model Surface Preparation

Aminopropyl controlled pore glass (CPG) purchased from CPG Inc. (Fairfield, N.J.) is used as a support for covalently attaching the sAAPF-pNA substrate purchased from Bachem, Inc. (Torrence, Calif.). The reaction is carried out in dimethyl sulfoxide and (1-ethyl-3-[3-(dimethylamino) propyl] carbodiimide hydrochloride) (EDC) is used as a coupling agent. Upon completion (monitored by pNA assay), the excess solvent is removed, and the CPG:sAAPF-pNA is rinsed with dimethyl sulfoxide (DMSO) and doubly-distilled water. This is followed by oven drying with a $N_2$ purge at about 70° C. The reaction scheme and preparation of the immobilized substrate are conducted as described by Brode, P. F. III, and D. S. Rauch, "Subtilisin BPN': Activity on an Immobilized Substrate," *LANGMUIR*, Vol. 8, p. 1325–1329, (1992), incorporated herein by reference.

The CPG surface will have 62,000±7,000 pNA molecules/$\mu m^2$. The surface area will remain unchanged from the value of 50.0 $m^2/g$ reported by CPG Inc. for the CPG as received. This suggests that the procedure used to add sAAPF-pNA to CPG does not damage the porous structure (mean diameter is 486 Å).

EXAMPLE 5

Surface Hydrolysis Assay

Using CPG:sAAPF-pNA, adsorption of an enzyme variant and hydrolysis of a CPG-bound peptide can be measured in a single experiment. A small volume of enzyme variant stock solution is added to a flask containing Tris buffer and CPG:sAAPF-pNA which has been degassed. The flask is shaken on a wrist-action shaker for a period of 90 minutes during which the shaker is stopped at various time intervals (for example, every 2 minutes during the early stages of adsorption hydrolysis—e.g., the first 20 minutes—and every 10 minutes towards the end of the experiment). The CPG:sAAPF-pNA is allowed to settle and the solution is sampled. Both the experimental procedure and the calculation of the adsorption and hydrolysis are conducted as described by Brode et al., 1992, above.

All enzymes are monitored for stability against autolysis and should show no appreciable autolytic loss over the time course of this experiment. Therefore, enzyme adsorption can be determined by measuring solution depletion. The difference between the initial enzyme variant concentration and the concentration measured at each individual time point gives the amount of enzyme variant adsorbed. The amount of pNA hydrolyzed from the surface is measured by taking an absorbance reading on an aliquot of the sample at 410 nm. The total amount of pNA hydrolyzed is calculated by adding the amount sampled and the amount remaining in the flask. This value is corrected by subtracting the amount of pNA that is hydrolyzed by Tris buffer at pH 8.6 when no enzyme is present. This base-hydrolysis ranges from 7–29% of the total hydrolysis depending on the efficiency of the enzyme.

EXAMPLE 6

Soluble Substrate Kinetic Analysis

The rates of hydrolysis of the soluble substrate sAAPF-pNA are monitored by measuring the adsorbance increase as a function of time at 410 nm on a DU-70 spectrophotometer. The enzyme concentration is held constant and is prepared to be in the range of 6–10 nanomolar while the substrate concentration is varied from 90–700 $\mu$M sAAPF-pNA for each kinetic determination. An adsorbance data point is taken each second over a period of 900 seconds and the data are transferred to a LOTUS™ spreadsheet (Lotus Development Corporation, Cambridge, Mass.). Analysis for kinetic parameters is conducted by the standard Lineweaver Burk analysis in which the data in the initial part of the run (generally the first minute) are fit to a linear regression curve to give $v_o$. The $v_o$ and $s_o$ data are plotted in the standard inverse fashion to give $K_M$ and $k_{cat}$.

I. Example Proteinase K Variants

Proteinase K variants of the present invention which have decreased adsorption to and increased hydrolysis of surface bound substrates are exemplified in Tables 2–33, below. In describing the specific mutations, the original amino acid occurring in wild-type is given first, the position number second, and the substituted amino acid third.

TABLE 2

| Loop 1-Single Mutation Variants |
|---|
| Arg64Asp |
| Arg64Glu |
| Asp65Glu |
| Gly66Asn |
| Gly66Asp |
| Gly66Gln |
| Gly66Glu |
| Gly66Pro |
| Gly66Ser |
| Asn67Asp |
| Asn67Gln |
| Asn67Glu |
| Asn67Ser |
| Gly68Asn |
| Gly68Asp |
| Gly68Gln |
| Gly68Glu |
| Gly68Pro |
| Gly68Ser |
| Gly70Asn |
| Gly70Asp |
| Gly70Gln |
| Gly70Glu |
| Gly70Pro |
| Gly70Ser |

TABLE 2-continued

| Loop 1-Single Mutation Variants |
|---|
| Thr71Asn |
| Thr71Asp |
| Thr71Gln |
| Thr71Glu |
| Thr71Gly |
| Thr71Pro |
| Thr71Ser |

TABLE 3

| Loop 1-Double Mutation Variants |
|---|
| Asn67Ser + Thr71Asp |
| Gly66Ser + Thr71Ser |
| Arg64Asp + Thr71Asn |
| Arg64Asp + Gly68Ser |
| Gly66Glu + Gly70Ser |
| Arg64Glu + Gly68Ser |
| Arg64Glu + Gly66Gln |
| Asn67Glu + Gly70Asn |
| Asn67Gln + Thr71Asp |
| Gly66Ser + Gly70Asn |
| Asp65Glu + Gly70Ser |
| Arg64Glu + Gly70Asn |
| Gly66Pro + Thr71Asn |
| Gly70Gln + Thr71Gln |
| Gly68Glu + Gly70Asn |
| Asp65Glu + Thr71Ser |
| Gly68Asp + Gly70Gln |
| Asp65Glu + Gly68Gln |
| Gly70Gln + Thr71Asp |
| Gly68Gln + Gly70Pro |
| Asn67Asp + Gly70Gln |
| Gly66Ser + Asn67Gln |
| Asp65Glu + Gly68Asn |
| Gly68Asp + Gly70Pro |
| Gly66Gln + Thr71Pro |
| Asp65Glu + Thr71Pro |
| Arg64Asp + Gly68Asn |
| Gly68Asn + Thr71Glu |
| Gly66Asn + Thr71Glu |
| Gly68Ser + Thr71Asp |
| Gly68Ser + Thr71Gly |
| Gly66Ser + Gly68Gln |
| Gly66Gln + Gly70Ser |
| Gly66Glu + Gly70Pro |
| Arg64Glu + Gly70Pro |
| Asp65Glu + Thr71Gly |
| Arg64Glu + Thr71Gly |
| Asp65Glu + Gly70Pro |
| Arg64Asp + Gly68Gln |
| Arg64Glu + Gly68Pro |
| Gly66Asn + Gly70Ser |

TABLE 4

| Loop 1-Triple Mutation Variants |
|---|
| Asn67Ser + Gly68Asp + Gly70Ser |
| Asn67Asp + Gly70Asn + Thr71Gly |
| Arg64Glu + Gly66Asn + Gly70Pro |
| Gly66Asp + Gly68Ser + Gly70Ser |
| Asp65Glu + Gly70Gln + Thr71Gln |
| Gly66Glu + Gly68Pro + Gly70Asn |
| Arg64Asp + Gly66Ser + Gly70Gln |
| Gly66Gln + Asn67Gln + Gly68Glu |
| Gly66Glu + Asn67Ser + Thr71Pro |
| Gly66Asn + Gly68Pro + Thr71Gln |
| Arg64Glu + Gly66Gln + Gly68Gln |
| Gly66Asn + Gly68Ser + Gly70Pro |
| Arg64Asp + Gly70Gln + Thr71Gly |
| Asp65Glu + Gly68Gln + Gly70Ser |

TABLE 4-continued

| Loop 1-Triple Mutation Variants |
|---|
| Arg64Glu + Gly66Pro + Gly68Ser |
| Gly66Gln + Asn67Gln + Thr71Gly |
| Arg64Glu + Gly68Pro + Thr71Ser |
| Asn67Asp + Gly70Ser + Thr71Gly |
| Arg64Glu + Gly70Pro + Thr71Gln |
| Asp65Glu + Gly68Gln + Gly70Gln |
| Gly66Pro + Gly68Gln + Thr71Pro |
| Gly66Glu + Asn67Gln + Gly70Pro |
| Gly66Gln + Gly70Ser + Thr71Gln |
| Asp65Glu + Gly68Gln + Gly70Asn |
| Arg64Glu + Gly66Ser + Thr71Pro |
| Asp65Glu + Gly68Ser + Gly70Asn |
| Asp65Glu + Asn67Ser + Gly70Ser |
| Arg64Glu + Gly66Ser + Gly70Pro |
| Asp65Glu + Gly70Gln + Thr71Gly |
| Asp65Glu + Gly68Asn + Gly70Asn |
| Gly68Asn + Gly70Pro + Thr71Asp |
| Arg64Asp + Gly68Ser + Gly70Pro |
| Gly66Asn + Gly68Glu + Gly70Gln |
| Asn67Glu + Gly68Gln + Gly70Asn |
| Gly66Glu + Gly68Pro + Gly70Gln |
| Asn67Asp + Gly68Glu + Gly70Ser |
| Asn67Asp + Gly68Asp + Gly70Asn |
| Arg64Asp + Asp65Glu + Asn67Ser |
| Arg64Asp + Asp65Glu + Gly70Pro |
| Arg64Glu + Asp65Glu + Asn67Gln |

TABLE 5

| Loop 1-Quadruple Mutation Variants |
|---|
| Asp65Glu + Gly68Pro + Gly70Asn + Thr71Asn |
| Asp65Glu + Asn67Gln + Gly68Gln + Gly70Ser |
| Gly66Glu + Asn67Gln + Gly68Asn + Gly70Gln |
| Asp65Glu + Gly66Asn + Gly70Ser + Thr71Gln |
| Asn67Glu + Gly68Glu + Gly70Gln + Thr71Gly |
| Arg64Glu + Gly66Gln + Gly70Asn + Thr71Gln |
| Gly66Pro + Gly68Ser + Gly70Asn + Thr71Gln |
| Arg64Glu + Gly68Pro + Gly70Gln + Thr71Pro |
| Gly66Glu + Gly68Pro + Gly70Asn + Thr71Pro |
| Asp65Glu + Gly66Glu + Asn67Ser + Gly70Pro |
| Asp65Glu + Gly66Asp + Gly68Asn + Thr71Ser |
| Asp65Glu + Gly66Glu + Gly68Pro + Gly70Ser |
| Asp65Glu + Gly66Glu + Gly70Asn + Thr71Gln |
| Arg64Asp + Asp65Glu + Asn67Gln + Gly70Asn |
| Arg64Asp + Asp65Glu + Gly70Pro + Thr71Gln |
| Gly66Glu + Asn67Asp + Gly68Ser + Gly70Ser |
| Gly66Glu + Asn67Glu + Gly70Asn + Thr71Ser |
| Asp65Glu + Gly66Asp + Asn67Glu + Gly68Ser |
| Arg64Glu + Asp65Glu + Gly66Asp + Gly68Pro |
| Gly66Glu + Asn67Asp + Gly68Asp + Gly70Asn |
| Asp65Glu + Asn67Glu + Gly68Ser + Gly70Gln |
| Asp65Glu + Asn67Asp + Gly68Gln + Gly70Ser |
| Asp65Glu + Asn67Glu + Gly68Gln + Gly70Asn |
| Asp65Glu + Gly66Asn + Asn67Glu + Gly70Pro |
| Asp65Glu + Gly66Asp + Gly68Asp + Thr71Asn |
| Asp65Glu + Gly66Glu + Asn67Gln + Gly68Asp |

TABLE 6

| Loop 2-Single Mutation Variants |
|---|
| Val 95Ala |
| Val 95Asn |
| Val 95Asp |
| Val 95Cys |
| Val 95Gln |
| Val 95Glu |
| Val 95Gly |
| Val 95His |
| Val 95Met |
| Val 95Pro |

TABLE 6-continued

Loop 2-Single Mutation Variants

Val 95Ser
Val 95Thr
Leu 96Ala
Leu 96Asn
Leu 96Asp
Leu 96Cys
Leu 96Gln
Leu 96Glu
Leu 96Gly
Leu 96His
Leu 96Ile
Leu 96Met
Leu 96Pro
Leu 96Ser
Leu 96Thr
Leu 96Val
Asp 97Glu
Asp 98Glu
Asn 99Asp
Asn 99Gln
Asn 99Glu
Asn 99Ser
Gly100Asn
Gly100Asp
Gly100Gln
Gly100Glu
Gly100Pro
Gly100Ser
Ser101Asp
Ser101Glu
Gly102Asn
Gly102Asp
Gly102Gln
Gly102Glu
Gly102Pro
Gly102Ser
Gln103Asn
Gln103Asp
Gln103Glu
Gln103Ser
Tyr104Ala
Tyr104Asn
Tyr104Asp
Tyr104Cys
Tyr104Gln
Tyr104Glu
Tyr104Gly
Tyr104His
Tyr104Ile
Tyr104Leu
Tyr104Met
Tyr104Pro
Tyr104Ser
Tyr104Thr
Tyr104Val
Ser105Asp
Ser105Glu
Thr106Asn
Thr106Asp
Thr106Gln
Thr106Glu
Thr106Gly
Thr106Pro
Thr106Ser
Ile107Ala
Ile107Asn
Ile107Asp
Ile107Cys
Ile107Gln
Ile107Glu
Ile107Gly
Ile107His
Ile107Leu
Ile107Met
Ile107Pro
Ile107Ser
Ile107Thr
Ile107Val

TABLE 7

Loop 2-Double Mutation Variants

Val 95Gln + Ser101Glu
Tyr104His + Ile107Asp
Val 95Glu + Ile107Asn
Asn 99Gln + Gln103Asp
Leu 96Gly + Ser105Glu
Val 95Met + Gln103Asp
Ser101Asp + Ile107Thr
Val 95His + Asp 97Glu
Asp 98Glu + Tyr104Leu
Leu 96Cys + Asp 97Glu
Gln103Glu + Tyr104Gln
Gly102Ser + Tyr104Gly
Leu 96Ala + Thr106Pro
Thr106Gln + Ile107Asn
Asn 99Gln + Ile107Asp
Asn 99Glu + Thr106Gly
Gly102Pro + Gln103Asp
Asn 99Asp + Tyr104Thr
Leu 96Ile + Ser101Glu
Val 95Gly + Gln103Ser
Tyr104Leu + Ser105Glu
Gly102Asn + Tyr104Pro
Leu 96Asp + Ile107Leu
Asp 98Glu + Gly102Asn
Leu 96Pro + Gly100Glu
Ser101Asp + Thr106Ser
Gly100Ser + Gln103Asn
Gly102Pro + Tyr104Thr
Leu 96Glu + Ile107Leu
Leu 96Ile + Gly100Asp
Gly100Pro + Ile107Ser
Asp 97Glu + Asn 99Gln
Asp 97Glu + Ile107Cys
Gly102Ser + Gln103Glu
Gly100Asn + Tyr104Asp
Gly100Pro + Thr106Asp
Val 95Pro + Asp 97Glu
Val 95Thr + Gly100Glu
Thr106Pro + Ile107Glu
Ser101Asp + Gly102Asn
Ser105Glu + Ile107Thr
Asn 99Gln + Ser105Asp
Gln103Ser + Ile107Met
Leu 96Asp + Thr106Gly
Val 95Thr + Gly102Asp
Val 95Ala + Ser105Asp
Gly100Asn + Gln103Ser
Gly102Asp + Thr106Gln
Leu 96Asn + Ser105Asp
Gly100Glu + Gly102Pro
Gln103Asp + Ile107His
Tyr104Ala + Ile107Pro
Asp 97Glu + Ile107Pro
Asn 99Glu + Tyr104Asn
Val 95Thr + Asp 98Glu
Gly100Gln + Thr106Gly
Asn 99Glu + Gln103Ser
Val 95His + Ser105Asp
Gly102Pro + Ile107Ala
Asp 97Glu + Gly100Gln

TABLE 8

| Loop 2-Triple Mutation Variants |
|---|
| Val 95Gln + Leu 96Thr + Ser101Glu |
| Ser101Asp + Thr106Ser + Ile107Leu |
| Val 95Asn + Leu 96Asn + Asp 98Glu |
| Gln103Glu + Tyr104Ser + Ile107Ser |
| Val 95Cys + Leu 96Glu + Gly102Ser |
| Val 95His + Tyr104Thr + Ser105Glu |
| Leu 96Pro + Asn 99Asp + Gln103Ser |
| Val 95Ser + Leu 96Asp + Gln103Ser |
| Leu 96Cys + Gly102Gln + Ile107Leu |
| Val 95Ser + Leu 96His + Thr106Pro |
| Leu 96Gln + Gly102Pro + Ser105Asp |
| Leu 96Met + Asn 99Ser + Ser105Asp |
| Leu 96His + Ser101Asp + Tyr104Val |
| Asn 99Asp + Gly100Asn + Gly102Ser |
| Val 95Gly + Gly100Asp + Thr106Pro |
| Leu 96Asn + Tyr104Glu + Ile107Gln |
| Asn 99Asp + Gly102Ser + Tyr104His |
| Val 95Met + Leu 96Gly + Gly100Pro |
| Val 95Ala + Asp 98Glu + Asn 99Ser |
| Asp 97Glu + Tyr104Thr + Ile107His |
| Leu 96Thr + Gly102Gln + Gln103Asp |
| Tyr104Met + Thr106Glu + Ile107Leu |
| Gly100Ser + Gln103Asn + Tyr104Ile |
| Gln103Asn + Tyr104Pro + Thr106Glu |
| Val 95Met + Asp 98Glu + Asn 99Gln |
| Leu 96His + Asp 97Glu + Ile107Met |
| Gly100Asn + Gln103Ser + Ser105Asp |
| Gly102Asn + Gln103Glu + Thr106Pro |
| Val 95Met + Gly100Ser + Gly102Asp |
| Val 95Asp + Leu 96Met + Tyr104Asn |
| Gln103Glu + Tyr104Cys + Ile107Asn |
| Val 95Met + Leu 96Ile + Tyr104Met |
| Val 95Ser + Ser101Glu + Thr106Gly |
| Val 95Pro + Asn 99Asp + Gly100Ser |
| Gly100Ser + Gln103Glu + Ile107Val |
| Gln103Asp + Tyr104Val + Ile107His |
| Gly100Gln + Tyr104Met + Thr106Asp |
| Asn 99Asp + Gly100Ser + Tyr104His |
| Ser101Asp + Gly102Asp + Gln103Ser |
| Asp 98Glu + Asn 99Asp + Tyr104Ala |
| Asp 98Glu + Asn 99Glu + Gly100Gln |
| Gly102Asp + Gln103Asp + Thr106Gln |
| Tyr104Glu + Ser105Asp + Thr106Pro |
| Asp 97Glu + Asp 98Glu + Tyr104Thr |
| Asp 97Glu + Asp 98Glu + Asn 99Asp |
| Asn 99Asp + Gly100Asp + Ser101Glu |
| Gln103Glu + Tyr104Asp + Ile107Glu |
| Leu 96Glu + Asp 97Glu + Gly102Asp |
| Leu 96Glu + Ser101Asp + Gln103Asn |
| Asp 97Glu + Gly100Asp + Ile107His |
| Asp 97Glu + Asn 99Ser + Gly100Asp |
| Gln103Asp + Ser105Glu + Thr106Asn |
| Leu 96Ser + Ser105Asp + Ile107Asp |
| Asp 97Glu + Ser101Glu + Gln103Ser |
| Asp 97Glu + Ser101Glu + Tyr104Met |
| Asn 99Asp + Gly100Ser + Ser101Asp |
| Gln103Asp + Tyr104His + Ile107Glu |
| Asp 97Glu + Gly102Glu + Tyr104Pro |
| Val 95Asp + Gly102Glu + Tyr104Gly |
| Val 95Asp + Asp 97Glu + Ile107Asn |

TABLE 9

| Loop 2-Quadruple Mutation Variants |
|---|
| Val 95Gln + Asp 97Glu + Gly100Ser + Ile107Gln |
| Val 95Ser + Leu 96Pro + Asp 97Glu + Gln103Asn |
| Leu 96Gln + Gly100Ser + Ser101Asn + Thr106Asn |
| Val 95Cys + Asp 97Glu + Gly100Gly + Gly102Ser |
| Leu 96Pro + Gly102Asn + Ser105Asp + Ile107Gln |
| Val 95Ser + Gly100Gln + Ser101Glu + Ile107Asn |
| Leu 96Met + Ser101Glu + Gln103Asn + Thr106Pro |
| Asn 99Asp + Gly100Pro + Gly102Ser + Tyr104Ala |
| Gly100Pro + Gly102Pro + Thr106Gly + Ile107Glu |

TABLE 9-continued

| Loop 2-Quadruple Mutation Variants |
|---|
| Val 95Ser + Gly100Gln + Ser101Asp + Gly102Pro |
| Val 95Gly + Leu 96Val + Thr106Pro + Ile107Asp |
| Val 95Gln + Leu 96Val + Asn 99Asp + Ile107Thr |
| Leu 96Ser + Asp 97Glu + Thr106Gln + Ile107Met |
| Leu 96Thr + Asn 99Gln + Tyr104Val + Ile107Cys |
| Asn 99Glu + Gly100Gln + Gly102Asn + Gln103Ser |
| Val 95Gly + Ser101Glu + Gln103Ser + Thr106Gly |
| Val 95Asn + Leu 96Gln + Asp 98Glu + Gly100Asn |
| Val 95Cys + Gly102Pro + Tyr104Val + Ile107Asp |
| Val 95Met + Leu 96Met + Gly102Glu + Tyr104Thr |
| Val 95Asp + Leu 96Cys + Thr106Ser + Ile107Gly |
| Leu 96Met + Gly100Glu + Ser101Glu + Tyr104Cys |
| Asp 98Glu + Asn 99Glu + Gly102Asn + Ile107Ser |
| Val 95Ser + Asp 97Glu + Asp 98Glu + Asn 99Ser |
| Val 95Gly + Asp 97Glu + Asp 98Glu + Tyr104Ile |
| Leu 96Gly + Asp 97Glu + Asp 98Glu + Asn 99Asp |
| Asp 98Glu + Asn 99Glu + Gly100Glu + Thr106Gly |
| Leu 96Glu + Asp 97Glu + Ser101Asp + Tyr104Ile |
| Asp 97Glu + Gly100Asp + Ser101Glu + Tyr104Leu |
| Asp 97Glu + Asp 98Glu + Gly100Glu + Tyr104Met |
| Gly100Glu + Ser101Asp + Gly102Asp + Ile107Gly |
| Val 95Met + Leu 96Glu + Asp 97Glu + Gly102Asp |
| Asp 97Glu + Gly100Glu + Tyr104Ala + Thr106Gln |
| Asp 97Glu + Asn 99Glu + Tyr104His + Thr106Gly |
| Gly102Ser + Gln103Asp + Ser105Asp + Thr106Ser |
| Asp 97Glu + Ser101Asp + Gly102Pro + Tyr104Ile |
| Asn 99Asp + Gly100Gln + Ser101Asp + Thr106Pro |
| Asn 99Asp + Gly100Ser + Ser101Asp + Ile107Cys |
| Gly102Ser + Gln103Glu + Ser105Asp + Ile107Asp |
| Asp 98Glu + Gly100Glu + Ser101Glu + Gly102Gln |
| Val 95Gly + Asp 98Glu + Asn 99Glu + Ser101Asp |
| Asp 97Glu + Gly102Asp + Gln103Ser + Ile107Met |
| Leu 96Ser + Asp 97Glu + Gly100Glu + Gly102Glu |
| Val 95Thr + Leu 96Glu + Asp 98Glu + Ser101Asp |
| Gly102Glu + Tyr104Ala + Ser105Asp + Thr106Asp |
| Leu 96Met + Ser101Asp + Gln103Glu + Ile107Gln |
| Ser101Asp + Gln103Asp + Tyr104Ser + Ile107Thr |
| Asp 98Glu + Gly100Asn + Ser101Glu + Tyr104Val |
| Val 95Glu + Gly102Glu + Gln103Asn + Tyr104Glu |
| Val 95Thr + Ser101Glu + Gln103Asp + Ile107Glu |
| Ser101Glu + Gln103Asp + Tyr104Met + Ile107Glu |
| Val 95Glu + Ser101Asp + Tyr104His + Ile107Glu |
| Val 95Gly + Asp 97Glu + Gly102Glu + Thr106Glu |
| Val 95Ser + Leu 96Asp + Asn 99Gln + Gln103Glu |
| Leu 96Glu + Gly102Asn + Tyr104Gln + Thr106Glu |
| Val 95Asp + Asp 98Glu + Gly100Asp + Thr106Gly |
| Leu 96Glu + Gly102Asp + Gln103Ser + Ser105Glu |
| Gly100Ser + Ser101Glu + Gln103Asp + Ser105Asp |
| Val 95Met + Gly100Glu + Gly102Asp + Ile107Asp |
| Leu 96Ala + Asp 97Glu + Ser101Asp + Ile107Asp |
| Leu 96Gln + Asp 97Glu + Gln103Asp + Ile107Glu |

TABLE 10

| Loop 3-Single Mutation Variants |
|---|
| Leu133Ala |
| Leu133Asn |
| Leu133Asp |
| Leu133Cys |
| Leu133Gln |
| Leu133Glu |
| Leu133Gly |
| Leu133His |
| Leu133Ile |
| Leu133Met |
| Leu133Pro |
| Leu133Ser |
| Leu133Thr |
| Leu133Val |
| Gly134Asn |
| Gly134Asp |
| Gly134Gln |
| Gly134Glu |

TABLE 10-continued

| Loop 3-Single Mutation Variants |
| --- |
| Gly134Pro |
| Gly134Ser |
| Gly135Asn |
| Gly135Asp |
| Gly135Gln |
| Gly135Glu |
| Gly135Pro |
| Gly135Ser |
| Gly136Asn |
| Gly136Asp |
| Gly136Gln |
| Gly136Glu |
| Gly136Pro |
| Gly136Ser |
| Tyr137Ala |
| Tyr137Asn |
| Tyr137Asp |
| Tyr137Cys |
| Tyr137Gln |
| Tyr137Gln |
| Tyr137Gly |
| Tyr137His |
| Tyr137Ile |
| Tyr137Leu |
| Tyr137Met |
| Tyr137Pro |
| Tyr137Ser |
| Tyr137Thr |
| Tyr137Val |
| Ser138Asp |
| Ser138Glu |
| Ser139Asp |
| Ser139Glu |
| Ser140Asp |
| Ser140Glu |

TABLE 11

| Loop 3-Double Mutation Variants |
| --- |
| Gly134Asn + Ser140Asp |
| Leu133Ala + Gly135Glu |
| Leu133Thr + Ser139Asp |
| Leu133Gln + Ser140Asp |
| Gly136Gln + Ser138Glu |
| Gly134Ser + Ser138Asp |
| Gly136Pro + Ser139Asp |
| Gly135Asn + Ser138Asp |
| Gly135Glu + Gly136Pro |
| Leu133Ile + Ser140Asp |
| Leu133Cys + Ser140Asp |
| Gly134Asn + Gly135Pro |
| Leu133Cys + Gly136Asp |
| Tyr137Asn + Ser139Asp |
| Gly136Asn + Ser140Glu |
| Gly134Glu + Gly135Pro |
| Tyr137Met + Ser140Asp |
| Gly135Gln + Ser139Glu |
| Tyr137Thr + Ser138Glu |
| Leu133Asn + Ser139Glu |
| Gly135Ser + Gly136Gln |
| Leu133Gly + Gly136Ser |
| Leu133Ala + Tyr137His |
| Leu133Val + Gly136Glu |
| Tyr137Ile + Ser139Asp |
| Leu133Ile + Tyr137Gln |
| Gly136Ser + Ser140Asp |
| Gly134Asn + Ser138Glu |
| Gly134Ser + Ser138Glu |
| Gly135Ser + Ser138Asp |
| Gly136Ser + Ser140Glu |
| Gly136Ser + Ser138Glu |
| Leu133Glu + Gly134Asn |
| Leu133Glu + Gly135Gln |

TABLE 11-continued

| Loop 3-Double Mutation Variants |
| --- |
| Gly135Asn + Tyr137Glu |
| Tyr137Thr + Ser139Glu |
| Tyr137Ala + Ser139Glu |
| Gly134Gln + Tyr137Gly |
| Gly135Pro + Tyr137His |
| Leu133Pro + Ser138Glu |
| Leu133Thr + Gly135Ser |
| Gly136Pro + Ser138Glu |
| Gly134Ser + Ser140Asn |
| Leu133Met + Tyr137Ala |
| Tyr137Val + Ser138Glu |
| Gly134Pro + Ser140Glu |
| Leu133Thr + Tyr137Ser |
| Gly135Glu + Gly136Asn |
| Leu133Ala + Ser140Glu |
| Gly134Gln + Ser139Glu |
| Leu133Pro + Tyr137Gly |
| Leu133Val + Gly136Ser |
| Gly136Asp + Tyr137Pro |
| Gly136Asn + Tyr137Val |
| Leu133Ala + Ser138Asp |
| Gly135Gln + Gly136Pro |
| Tyr137Met + Ser138Glu |
| Leu133Gln + Tyr137Asp |
| Tyr137Ser + Ser138Glu |
| Gly134Asp + Gly135Pro |

TABLE 12

| Loop 3-Triple Mutation Variants |
| --- |
| Leu133Cys + Gly135Gln + Tyr137Glu |
| Leu133Ile + Gly134Ser + Gly136Glu |
| Leu133Gly + Gly135Glu + Tyr137Val |
| Leu133Gln + Gly135Gln + Ser139Asp |
| Leu133Asn + Gly135Pro + Tyr137Asn |
| Leu133Val + Gly135Gln + Gly136Ser |
| Gly135Asn + Tyr137Ile + Ser139Glu |
| Leu133Met + Gly136Pro + Ser140Asp |
| Gly134Pro + Gly136Pro + Ser138Glu |
| Gly135Asn + Tyr137Met + Ser138Asp |
| Leu133Ser + Gly136Asn + Tyr137Val |
| Gly134Glu + Gly135Ser + Gly136Pro |
| Gly136Asn + Tyr137Met + Ser140Glu |
| Leu133Ile + Gly136Pro + Tyr137Glu |
| Leu133Met + Gly136Gln + Tyr137Gln |
| Leu133Val + Gly135Pro + Ser139Asp |
| Leu133Asn + Gly135Gln + Tyr137Cys |
| Gly135Pro + Tyr137Met + Ser138Glu |
| Gly136Gln + Tyr137Gly + Ser140Asp |
| Leu133Ser + Gly134Pro + Ser140Asp |
| Leu133Thr + Gly134Asp + Gly135Pro |
| Leu133Ile + Gly135Asn + Ser139Glu |
| Gly135Glu + Gly136Pro + Tyr137His |
| Gly135Asn + Gly136Pro + Ser140Glu |
| Leu133Met + Gly134Ser + Gly136Gln |
| Gly134Pro + Gly135Asn + Ser140Glu |
| Gly135Gln + Gly136Gln + Ser138Asp |
| Gly136Ser + Tyr137Met + Ser138Glu |
| Gly134Pro + Gly136Ser + Ser139Asp |
| Gly134Ser + Tyr137Thr + Ser138Asp |
| Leu133Thr + Gly134Pro + Ser140Asp |
| Gly134Gln + Gly135Pro + Ser140Glu |
| Gly134Pro + Tyr137His + Ser138Asp |
| Leu133Met + Gly134Gln + Ser139Asp |
| Leu133Ser + Gly134Asn + Ser138Glu |
| Gly136Gln + Tyr137Ala + Ser139Glu |
| Leu133Ile + Gly136Asn + Ser139Asp |
| Leu133Ala + Gly135Asp + Gly136Pro |
| Leu133Asn + Ser138Asp + Ser139Glu |
| Gly136Asn + Ser138Asp + Ser139Asp |
| Gly135Asn + Ser138Asp + Ser139Glu |
| Leu133Asp + Gly134Asp + Tyr137His |
| Leu133Asp + Gly134Glu + Gly135Pro |

TABLE 12-continued

| Loop 3-Triple Mutation Variants |
|---|
| Leu133Gly + Gly136Glu + Tyr137Asp |
| Tyr137Ser + Ser139Glu + Ser140Asp |
| Gly134Gln + Ser139Asp + Ser140Asp |
| Gly136Asn + Ser139Asp + Ser140Glu |
| Tyr137Pro + Ser139Asp + Ser140Asp |
| Gly135Ser + Tyr137Glu + Ser138Glu |
| Ser138Asp + Ser139Asp + Ser140Asp |
| Tyr137Glu + Ser138Asp + Ser139Glu |
| Tyr137Ala + Ser138Asp + Ser140Asp |
| Tyr137Thr + Ser138Asp + Ser140Glu |
| Tyr137Gln + Ser138Asp + Ser140Asp |
| Leu133Thr + Ser138Asp + Ser140Glu |
| Gly135Ser + Ser138Asp + Ser140Glu |
| Gly136Gln + Ser138Asp + Ser140Asp |
| Gly135Ser + Ser138Glu + Ser140Asp |
| Gly136Gln + Ser138Glu + Ser140Asp |
| Leu133Val + Ser138Glu + Ser140Glu |

TABLE 13

| Loop 3-Quadruple Mutation Variants |
|---|
| Leu133Ala + Gly134Asn + Tyr137Ser + Ser138Asp |
| Gly134Glu + Gly135Asn + Gly136Asn + Tyr137Cys |
| Leu133Cys + Gly135Asn + Gly136Gln + Ser138Asp |
| Leu133Pro + Gly134Asn + Gly135Ser + Ser139Asp |
| Leu133Val + Gly134Gln + Gly136Gln + Ser140Glu |
| Leu133Asp + Gly134Gln + Gly136Gln + Tyr137Thr |
| Leu133His + Gly135Gln + Gly136Pro + Tyr137Ser |
| Leu133Gly + Gly134Ser + Tyr137Ala + Ser138Asp |
| Leu133Gln + Gly134Gln + Gly135Asn + Ser140Glu |
| Leu133Ser + Gly135Ser + Tyr137Pro + Ser139Glu |
| Leu133Asn + Gly134Asn + Gly136Glu + Tyr137Cys |
| Leu133Met + Gly134Asn + Gly135Gln + Ser138Glu |
| Leu133Asn + Gly134Ser + Tyr137Val + Ser138Glu |
| Gly135Asn + Gly136Pro + Tyr137Cys + Ser139Asp |
| Leu133Ile + Gly135Asp + Gly136Asn + Tyr137Ile |
| Gly134Asp + Gly135Glu + Gly136Gln + Tyr137Thr |
| Leu133Gln + Gly134Glu + Gly135Asp + Tyr137Thr |
| Gly134Ser + Tyr137Val + Ser138Glu + Ser139Glu |
| Gly134Ser + Tyr137Val + Ser138Asp + Ser139Glu |
| Leu133His + Gly135Gln + Ser138Asp + Ser139Asp |
| Leu133Gly + Gly135Pro + Ser138Glu + Ser139Asp |
| Leu133Val + Gly135Pro + Ser138Asp + Ser139Glu |
| Leu133Ser + Gly134Gln + Gly135Asp + Gly136Glu |
| Leu133Ile + Gly134Gln + Ser139Asp + Ser140Asp |
| Leu133Cys + Tyr137Asn + Ser139Asp + Ser140Glu |
| Leu133Ser + Tyr137His + Ser139Glu + Ser140Glu |
| Gly134Pro + Gly136Gln + Ser139Asp + Ser140Glu |
| Gly134Gln + Gly135Ser + Ser139Asp + Ser140Asp |
| Leu133Cys + Gly134Pro + Ser139Glu + Ser140Asp |
| Leu133Ala + Gly136Asn + Tyr137Glu + Ser138Asp |
| Gly136Pro + Ser138Asp + Ser139Glu + Ser140Asp |
| Tyr137Leu + Ser138Asp + Ser139Glu + Ser140Glu |
| Gly135Asn + Ser138Asp + Ser139Asp + Ser140Glu |
| Leu133Gly + Ser138Asp + Ser139Glu + Ser140Glu |
| Leu133Ser + Tyr137Asp + Ser138Asp + Ser139Glu |
| Gly136Gln + Tyr137Asp + Ser138Asp + Ser139Asp |
| Gly136Asn + Tyr137Asp + Ser138Asp + Ser139Glu |
| Gly134Glu + Gly135Asp + Gly136Asp + Tyr137Ile |
| Leu133Gln + Tyr137Val + Ser138Glu + Ser140Asp |
| Gly134Pro + Tyr137Gly + Ser138Asp + Ser140Asp |
| Leu133His + Tyr137Leu + Ser138Glu + Ser140Glu |
| Gly134Gln + Gly135Ser + Ser138Glu + Ser140Glu |
| Leu133Cys + Gly136Ser + Ser138Glu + Ser140Glu |
| Gly135Gln + Gly136Gln + Ser138Asp + Ser140Asp |
| Gly134Pro + Tyr137His + Ser138Asp + Ser140Glu |
| Leu133Gln + Gly134Pro + Gly136Glu + Ser138Asp |
| Leu133His + Gly134Pro + Gly136Asp + Ser138Glu |
| Leu133Ile + Gly135Glu + Tyr137Glu + Ser138Glu |
| Gly134Asn + Gly135Asp + Tyr137Asp + Ser138Glu |
| Gly135Gln + Tyr137Glu + Ser138Asp + Ser140Glu |
| Gly136Asn + Tyr137Glu + Ser138Asp + Ser140Glu |
| Leu133Asn + Tyr137Asp + Ser138Glu + Ser140Asp |

TABLE 13-continued

| Loop 3-Quadruple Mutation Variants |
|---|
| Leu133Cys + Gly136Pro + Tyr137Glu + Ser139Asp |
| Gly134Glu + Gly135Pro + Gly136Asp + Tyr137Glu |
| Gly136Pro + Tyr137Glu + Ser139Asp + Ser140Asp |
| Gly135Ser + Tyr137Glu + Ser139Glu + Ser140Glu |
| Leu133Pro + Gly134Glu + Gly136Asp + Tyr137Cys |
| Gly134Gln + Gly136Asp + Ser138Glu + Ser139Asp |
| Gly135Ser + Gly136Glu + Ser138Glu + Ser139Asp |
| Gly134Asp + Gly135Glu + Gly136Ser + Ser138Asp |

TABLE 14

| Loop 4 - Single Mutation Variants |
|---|
| Gly160Asn |
| Gly160Asp |
| Gly160Gln |
| Gly160Glu |
| Gly160Pro |
| Gly160Ser |
| Asn161Asp |
| Asn161Gln |
| Asn161Glu |
| Asn161Ser |
| Asn162Asp |
| Asn162Gln |
| Asn162Glu |
| Asn162Ser |
| Asn163Asp |
| Asn163Gln |
| Asn163Glu |
| Asn163Ser |
| Ala164Asn |
| Ala164Asp |
| Ala164Gln |
| Ala164Glu |
| Ala164Gly |
| Ala164His |
| Ala164Pro |
| Ala164Ser |
| Ala164Thr |
| Asp165Glu |
| Ala166Asn |
| Ala166Asp |
| Ala166Gln |
| Ala166Glu |
| Ala166Gly |
| Ala166His |
| Ala166Pro |
| Ala166Ser |
| Ala166Thr |
| Arg167Asp |
| Arg167Glu |
| Asn168Asp |
| Asn168Gln |
| Asn168Glu |
| Asn168Ser |
| Tyr169Ala |
| Tyr169Asn |
| Tyr169Asp |
| Tyr169Cys |
| Tyr169Gln |
| Tyr169Glu |
| Tyr169Gly |
| Tyr169His |
| Tyr169Ile |
| Tyr169Leu |
| Tyr169Met |
| Tyr169Pro |
| Tyr169Ser |
| Tyr169Thr |
| Tyr169Val |
| Ser170Asp |
| Ser170Glu |

TABLE 15

Loop 4 - Double Mutation Variants

Gly160Gln + Asp165Glu
Asn161Ser + Asn162Ser
Ala164Thr + Asn168Asp
Gly160Asn + Ser170Glu
Asn161Gln + Asn163Glu
Asn162Ser + Ser170Asp
Gly160Gln + Asn168Glu
Ala166Gly + Ser170Asp
Asn161Glu + Asn162Ser
Asn162Gln + Ser170Asp
Ala166Thr + Ser170Glu
Asn162Ser + Ala164Pro
Gly160Asn + Asn161Gln
Gly160Glu + Ala166Ser
Ala166Gly + Ser170Glu
Ala164His + Ala166Gly
Ala164Asn + Asp165Glu
Asn162Asp + Asn168Ser
Ala164Pro + Asn168Asp
Asn162Asp + Ala164Asn
Tyr169Thr + Ser170Asp
Ala164Glu + Tyr169His
Asp165Glu + Tyr169His
Asn162Glu + Asn168Ser
Gly160Asp + Tyr169Met
Asn162Glu + Ala166Asn
Asn161Glu + Ala166Thr
Asp165Glu + Ala166Asn
Asn161Gln + Tyr169Pro
Asn162Asp + Ala164Thr
Asn162Ser + Arg167Glu
Ala166Pro + Arg167Asp
Ala164Thr + Ser170Asp
Asn163Asp + Ala164Asn
Asp165Glu + Asn168Gln
Asn163Asp + Tyr169Thr
Asn168Asp + Tyr169Gly
Arg167Asp + Asn168Ser
Asn161Ser + Arg167Glu
Asn161Ser + Ser170Glu
Gly160Asp + Ala166Gly
Ala164Asn + Ala166Gln
Gly160Asn + Asn161Glu
Asn162Glu + Ala166Ser
Ala166His + Asn168Asp
Gly160Pro + Ala164Gly
Gly160Asn + Ala164Gly
Ala164Gln + Ser170Asp
Asn161Glu + Ala164Thr
Gly160Glu + Ala166Gly
Ala166Pro + Ser170Asp
Ala166Pro + Tyr169Ala
Gly160Ser + Arg167Glu
Gly160Asp + Ala164Ser
Asn161Gln + Ala164Pro
Asn163Glu + Ala166Gln
Ala164Ser + Asn168Gln
Gly160Glu + Ala164Ser
Gly160Asp + Ala166Gln
Ala164Thr + Asp165Glu

TABLE 16

Loop 4 - Triple Mutation Variants

Gly160Gln + Asn161Ser + Asp165Glu
Ala166Gly + Arg167Glu + Tyr169Cys
Asn162Ser + Ala166Asn + Ser170Asp
Gly160Gln + Asn162Asp + Asn168Ser
Ala164Asn + Asn168Gln + Ser170Glu
Ala164Asp + Ala166Thr + Asn168Ser
Asn163Gln + Ala166Gly + Arg167Glu
Asn162Ser + Ala166His + Asn168Gln
Asp165Glu + Ala166Thr + Asn168Gln

TABLE 16-continued

Loop 4 - Triple Mutation Variants

Asn163Ser + Ala164Pro + Asn168Asp
Gly160Glu + Ala164His + Tyr169Gln
Asn161Gln + Asn163Ser + Ser170Glu
Ala166Thr + Tyr169Leu + Ser170Asp
Gly160Ser + Ala164Asn + Asn168Glu
Asn161Gln + Asn162Glu + Asn163Ser
Asn163Ser + Ala166Ser + Arg167Glu
Ala164Thr + Ala166Gly + Arg167Glu
Ala164Ser + Ala166Gly + Ser170Glu
Asn162Gln + Ala164Gln + Ala166Pro
Asn162Glu + Asn163Gln + Ala164Gly
Asn161Asp + Ala164Asn + Tyr169Val
Gly160Asn + Ala164Glu + Ala166Pro
Asn162Gln + Ala164Pro + Arg167Asp
Asn163Ser + Ala164Ser + Tyr169Gly
Ala166Asn + Arg167Glu + Asn168Ser
Asn163Gln + Asp165Glu + Ala166Ser
Asn162Ser + Ala164His + Asn168Asp
Ala164Ser + Arg167Asp + Asn168Asp
Asn162Ser + Arg167Asp + Asn168Asp
Asn161Asp + Asn162Glu + Asn163Gln
Asn161Asp + Asn162Glu + Asn168Gln
Gly160Glu + Asn161Glu + Ala166Asn
Gly160Glu + Asn161Glu + Ala164Ser
Gly160Pro + Asn162Asp + Asn163Asp
Asn162Asp + Asn163Glu + Ala166Asn
Asn161Glu + Asn162Asp + Asn163Glu
Asn162Glu + Asn163Ser + Ala164Asp
Asp165Glu + Arg167Asp + Tyr169Pro
Asp165Glu + Arg167Asp + Asn168Asp
Ala164Gln + Arg167Asp + Tyr169Asp
Asn161Asp + Asn162Asp + Ala164Asp
Asn161Asp + Asn163Asp + Tyr169Thr
Asn161Asp + Asn163Asp + Ala164Asn
Gly160Glu + Asn162Glu + Asn163Gln
Ala164Asp + Asp165Glu + Arg167Glu
Ala164Pro + Asp165Glu + Asn168Asp
Gly160Asp + Asn162Glu + Ala164Glu
Gly160Pro + Asn168Glu + Ser170Glu
Ala164Glu + Arg167Glu + Asn168Glu
Asn161Glu + Asn163Glu + Asp165Glu
Gly160Asp + Asn162Glu + Asp165Glu
Asp165Glu + Ala166Gly + Tyr169Glu
Gly160Glu + Asn161Asp + Asp165Glu
Arg167Asp + Asn168Glu + Ser170Asp
Asn162Gln + Arg167Asp + Ser170Glu
Asn163Gln + Arg167Glu + Ser170Glu
Asn162Asp + Asp165Glu + Asn168Glu
Asn162Asp + Asp165Glu + Arg167Glu
Gly160Asp + Asn168Glu + Ser170Glu
Gly160Asp + Asp165Glu + Tyr169Gly

TABLE 17

Loop 4 - Quadruple Mutation Variants

Gly160Gln + Asn161Ser + Asn162Ser + Asp165Glu
Gly160Glu + Asn161Ser + Asn162Gln + Asn168Ser
Asn161Ser + Asn163Asp + Ala164Asn + Tyr169Thr
Gly160Ser + Asp165Glu + Ala166Asn + Tyr169Leu
Gly160Gln + Ala166Ser + Arg167Asp + Tyr169His
Gly160Ser + Asn163Gly + Ala166Gly + Ser170Asp
Asn161Gln + Asn163Gln + Ala164Glu + Ala166Gly
Asn161Glu + Asn163Gln + Ala166His + Tyr169Asn
Asn163Gln + Ala166His + Arg167Asp + Asn168Gln
Gly160Gln + Asn162Ser + Asn163Asp + Tyr169Gln
Asn162Glu + Ala166Gln + Asn168Ser + Tyr169Gly
Asn163Glu + Ala166His + Asn168Gln + Tyr169Gln
Gly160Asn + Asn161Ser + Ala164Thr + Ala166Ser
Asn161Gln + Asn162Ser + Asn168Glu + Tyr169Ser
Asn161Gln + Ala166His + Arg167Glu + Tyr169Ala
Asn161Gln + Ala164Gly + Ala166Gln + Tyr169His
Ala164Gln + Asp165Glu + Asn168Ser + Tyr169Met
Ala164Gln + Ala166His + Arg167Glu + Asn168Glu

TABLE 17-continued

| Loop 4 - Quadruple Mutation Variants |
|---|
| Gly160Asn + Asn162Ser + Ala164Glu + Asp165Glu |
| Asn161Asp + Asn162Asp + Ala164Asn + Ala166Ser |
| Asn161Asp + Asn162Asp + Ala164Asn + Ala166Thr |
| Ala164Gln + Ala166Asn + Asn168Asp + Tyr169Asp |
| Gly160Pro + Asn163Asp + Ala164Asp + Ala166Thr |
| Asn161Ser + Asn163Asp + Ala164Asp + Asn168Gln |
| Asn162Asp + Asn163Asp + Ala166Pro + Tyr169Met |
| Asn161Ser + Asn163Gln + Tyr169Asp + Ser170Asp |
| Asn161Ser + Ala166His + Tyr169Asp + Ser170Glu |
| Asn161Glu + Asn162Asp + Asn163Glu + Tyr169Cys |
| Asn161Glu + Asn162Glu + Asn163Asp + Tyr169Ala |
| Asp165Glu + Ala166Gly + Arg167Asp + Asn168Gln |
| Asp165Glu + Arg167Asp + Asn168Gln + Tyr169Val |
| Asn161Asp + Asn163Glu + Ala164Asn + Ala166Gly |
| Asn163Gln + Ala164Asp + Asp165Glu + Arg167Asp |
| Asp165Glu + Ala166Asn + Asn168Asp + Tyr169Glu |
| Asn163Gln + Asp165Glu + Arg167Glu + Tyr169Asp |
| Asp165Glu + Arg167Asp + Asn168Ser + Tyr169Asp |
| Asn163Ser + Asp165Glu + Arg167Asp + Tyr169Glu |
| Asn163Gln + Ala166Thr + Asn168Glu + Ser170Glu |
| Asn161Gln + Ala166Gly + Asn168Asp + Ser170Glu |
| Asn163Glu + Asp165Glu + Ala166Gly + Tyr169Leu |
| Gly160Pro + Asn162Gln + Asn163Asp + Asp165Glu |
| Gly160Glu + Asn163Gln + Asn168Asp + Tyr169Glu |
| Gly160Asp + Ala164Glu + Asp165Glu + Tyr169Ser |
| Asn164Glu + Ala164Asp + Asp165Glu + Tyr169Gln |
| Gly160Asp + Asn162Asp + Ala166Gly + Tyr169Asp |
| Asn161Glu + Asn162Glu + Asp165Glu + Ala166Asn |
| Asn161Asp + Asn162Asp + Asp165Glu + Ala166Gln |
| Asn161Asp + Asn163Asp + Asp165Glu + Asn168Gln |
| Gly160Asp + Asn161Ser + Asn163Glu + Tyr169Gly |
| Gly160Asp + Asn162Asp + Asp165Glu + Asn168Gln |
| Asn161Ser + Arg167Glu + Tyr169Thr + Ser170Asp |
| Asn161Gln + Arg167Glu + Asn168Gln + Ser170Asp |
| Gly160Asp + Asn163Asp + Asp165Glu + Tyr169Ala |
| Gly160Ser + Asn162Glu + Ala164Pro + Asp165Glu |
| Gly160Glu + Arg167Glu + Asn168Glu + Tyr169Gln |
| Asn161Ser + Ala164Asp + Arg167Glu + Tyr169Asn |
| Asn162Ser + Asn163Asp + Ala164Asp + Asn168Asp |
| Asn163Glu + Asp165Glu + Ala166Asn + Arg167Glu |
| Asn163Asp + Asp165Glu + Arg167Asp + Asn168Ser |
| Gly160Glu + Ala164Gly + Asn168Asp + Ser170Asp |

TABLE 18

| Loop 5 - Single Mutation Variants |
|---|
| Ser190Asp |
| Ser190Glu |
| Ser191Asp |
| Ser191Glu |
| Phe192Ala |
| Phe192Asn |
| Phe192Asp |
| Phe192Cys |
| Phe192Gln |
| Phe192Glu |
| Phe192Gly |
| Phe192His |
| Phe192Ile |
| Phe192Leu |
| Phe192Met |
| Phe192Pro |
| Phe192Ser |
| Phe192Thr |
| Phe192Tyr |
| Phe192Val |
| Ser193Asp |
| Ser193Glu |
| Asn194Asp |
| Asn194Gln |
| Asn194Glu |
| Asn194Ser |

TABLE 19

| Loop 5 - Double Mutation Variants |
|---|
| Ser190Asp + Phe192Leu |
| Ser190Glu + Phe192Gln |
| Phe192Glu + Asn194Gln |
| Phe192Tyr + Asn194Glu |
| Ser190Asp + Phe192Ile |
| Ser191Glu + Phe192Ser |
| Ser191Asp + Phe192Gly |
| Ser191Asp + Asn194Ser |
| Ser191Glu + Phe192Thr |
| Ser191Glu + Asn194Gln |
| Ser191Glu + Phe192His |
| Ser191Asp + Phe192Asn |
| Ser190Asp + Phe192Gly |
| Ser191Asp + Asn194Gln |
| Ser191Asp + Phe192Ala |
| Ser190Glu + Phe192Cys |
| Ser190Glu + Phe192Ile |
| Ser191Asp + Phe192Ser |
| Ser190Asp + Asn194Gln |
| Ser191Glu + Phe192Cys |
| Phe192Ser + Asn194Glu |
| Ser191Glu + Phe192Gly |
| Phe192Gly + Asn194Gln |
| Phe192Cys + Asn194Gln |
| Phe192Asn + Asn194Asp |
| Ser190Glu + Phe192Tyr |
| Ser191Glu + Phe192Ala |
| Ser190Glu + Asn194Ser |
| Phe192Ile + Asn194Ser |
| Ser191Glu + Phe192Met |
| Ser190Asp + Phe192Met |
| Ser190Asp + Asn194Ser |
| Phe192Gly + Asn194Asp |
| Phe192His + Asn194Ser |
| Ser190Glu + Asn194Gln |
| Phe192Ala + Asn194Glu |
| Phe192Thr + Asn194Glu |
| Ser190Glu + Phe192Ser |
| Ser191Glu + Phe192Ile |
| Phe192Val + Asn194Glu |
| Phe192Thr + Asn194Asp |
| Ser191Glu + Phe192Pro |
| Ser191Asp + Phe192Leu |
| Phe192Ile + Asn194Glu |
| Ser190Asp + Phe192Thr |
| Ser191Asp + Phe192Ile |
| Phe192Thr + Asn194Gln |
| Phe192Ala + Asn194Gln |
| Ser191Asp + Phe192Tyr |
| Ser190Glu + Phe192Thr |
| Phe192Leu + Asn194Glu |
| Phe192His + Asn194Gln |
| Ser190Asp + Phe192Tyr |
| Phe192Val + Asn194Ser |
| Phe192Asp + Asn194Gln |
| Phe192Gly + Asn194Ser |
| Ser191Asp + Phe192Gln |
| Phe192Asp + Asn194Ser |
| Phe192Thr + Asn194Ser |
| Ser190Glu + Phe192Ala |

TABLE 20

| Loop 5 - Triple Mutation Variants |
|---|
| Ser191Asp + Phe192Met + Asn194Gln |
| Ser191Glu + Phe192Ala + Asn194Gln |
| Ser191Asp + Phe192Leu + Asn194Ser |
| Ser191Glu + Phe192Asn + Asn194Gln |
| Ser190Asp + Phe192Gln + Asn194Gln |
| Ser191Asp + Phe192Ile + Asn194Gln |
| Ser190Asp + Phe192Asn + Asn194Ser |
| Ser191Glu + Phe192Ile + Asn194Ser |
| Ser190Asp + Phe192Leu + Asn194Gln |

TABLE 20-continued

Loop 5 - Triple Mutation Variants

Ser190Asp + Phe192Val + Asn194Ser
Ser190Glu + Phe192Gln + Asn194Ser
Ser191Asp + Phe192Val + Asn194Ser
Ser191Glu + Phe192Ala + Asn194Ser
Ser191Glu + Phe192Cys + Asn194Gln
Ser190Glu + Phe192Val + Asn194Ser
Ser190Glu + Phe192Ile + Asn194Gln
Ser190Glu + Phe192Ser + Asn194Ser
Ser190Glu + Phe192Tyr + Asn194Gln
Ser191Asp + Phe192Ile + Asn194Ser
Ser191Asp + Ser191Glu + Asn194Ser
Ser190Asp + Ser191Asp + Phe192Met
Ser190Glu + Ser191Glu + Phe192Val
Ser190Asp + Ser191Glu + Phe192Ser
Ser190Asp + Ser191Asp + Phe192Thr
Ser190Glu + Ser191Asp + Asn194Ser
Ser190Glu + Ser191Asp + Phe192Asn
Ser190Asp + Ser191Asp + Phe192Asn
Ser190Asp + Ser191Asp + Phe192Val
Ser190Glu + Ser191Glu + Phe192Cys
Ser190Asp + Ser191Glu + Phe192Asn
Ser190Glu + Ser191Glu + Phe192Leu
Ser190Glu + Ser191Asp + Phe192Gly
Ser190Glu + Ser191Glu + Phe192Ser
Ser190Glu + Ser191Glu + Asn194Ser
Ser190Asp + Ser191Asp + Asn194Gln
Ser190Asp + Ser191Asp + Phe192Tyr
Ser190Asp + Ser191Glu + Phe192Met
Ser190Asp + Ser191Asp + Phe192Gly
Ser190Glu + Ser191Asp + Asn194Gln
Ser190Asp + Ser191Glu + Asn194Leu
Ser190Asp + Ser191Glu + Phe192Gly
Ser190Glu + Ser191Asp + Phe192Tyr
Ser190Asp + Ser191Glu + Phe192Thr
Ser190Glu + Ser191Asp + Phe192His
Ser190Asp + Ser191Asp + Phe192Gln
Ser190Glu + Ser191Asp + Phe192Ile
Ser190Asp + Ser191Glu + Asn194Gln
Ser190Asp + Ser191Asp + Phe192Pro
Ser190Glu + Ser191Asp + Phe192Cys
Ser190Asp + Ser191Asp + Asn194Ser
Ser190Asp + Ser191Glu + Phe192Gln
Ser190Glu + Ser191Asp + Phe192Pro
Ser191Asp + Phe192Asp + Asn194Gln
Ser191Asp + Phe192Glu + Asn194Ser
Ser191Asp + Phe192Glu + Asn194Gln
Ser190Asp + Ser191Glu + Phe192Asp
Ser190Asp + Ser191Asp + Phe192Glu
Ser190Glu + Ser191Glu + Phe192Asp
Ser190Glu + Ser191Asp + Phe192Asp
Ser190Glu + Ser191Asp + Phe192Glu

TABLE 21

Loop 6 - Quadruple Mutation Variants

Ser190Glu + Ser191Asp + Phe192Ile + Asn194Ser
Ser190Asp + Ser191Asp + Phe192Gly + Asn194Gln
Ser190Glu + Ser191Asp + Phe192His + Asn194Ser
Ser190Glu + Ser191Asp + Phe192Gln + Asn194Gln
Ser190Asp + Ser191Asp + Phe192Met + Asn194Ser
Ser190Asp + Ser191Glu + Phe192Leu + Asn194Gln
Ser190Glu + Ser191Glu + Phe192Ala + Asn194Ser
Ser190Asp + Ser191Asp + Phe192Pro + Asn194Gln
Ser190Glu + Ser191Glu + Phe192Leu + Asn194Ser
Ser190Glu + Ser191Asp + Phe192His + Asn194Gln
Ser190Glu + Ser191Asp + Phe192Cys + Asn194Gln
Ser190Glu + Ser191Asp + Phe192Thr + Asn194Ser
Ser190Glu + Ser191Asp + Phe192Ser + Asn194Gln
Ser190Glu + Ser191Asp + Phe192Thr + Asn194Gln
Ser190Asp + Ser191Glu + Phe192Ile + Asn194Ser
Ser190Glu + Ser191Asp + Phe192Gln + Asn194Ser
Ser190Asp + Ser191Asp + Phe192Cys + Asn194Gln
Ser190Asp + Ser191Asp + Phe192Pro + Asn194Ser

TABLE 21-continued

Loop 6 - Quadruple Mutation Variants

Ser190Glu + Ser191Glu + Phe192Ala + Asn194Gln
Ser190Asp + Ser191Glu + Phe192Thr + Asn194Ser
Ser190Glu + Ser191Asp + Phe192Leu + Asn194Gln
Ser190Glu + Ser191Asp + Phe192Gly + Asn194Gln
Ser190Asp + Ser191Asp + Phe192Cys + Asn194Ser
Ser190Glu + Ser191Glu + Phe192His + Asn194Gln
Ser190Glu + Ser191Asp + Phe192Asn + Asn194Ser
Ser190Asp + Ser191Asp + Phe192His + Asn194Gln
Ser190Glu + Ser191Glu + Phe192Ile + Asn194Gln
Ser190Asp + Ser191Asp + Phe192Tyr + Asn194Ser
Ser190Glu + Ser191Asp + Phe192Tyr + Asn194Gln
Ser190Glu + Ser191Asp + Phe192Ala + Asn194Ser
Ser190Asp + Ser191Glu + Phe192Ala + Asn194Ser
Ser190Asp + Ser191Glu + Phe192Asn + Asn194Ser
Ser190Glu + Ser191Asp + Phe192Val + Asn194Ser
Ser190Asp + Ser191Asp + Phe192Gln + Asn194Ser
Ser190Asp + Ser191Asp + Phe192Gln + Asn194Gln
Ser190Asp + Ser191Asp + Phe192Leu + Asn194Gln
Ser190Asp + Ser191Asp + Phe192Ser + Asn194Gln
Ser190Glu + Ser191Asp + Phe192Glu + Asn194Ser
Ser190Asp + Ser191Asp + Phe192Asp + Asn194Ser
Ser190Glu + Ser191Asp + Phe192Glu + Asn194Gln
Ser190Glu + Ser191Glu + Phe192Glu + Asn194Ser
Ser190Asp + Ser191Glu + Phe192Glu + Asn194Gln
Ser190Asp + Ser191Asp + Phe192Glu + Asn194Ser
Ser190Glu + Ser191Glu + Phe192Asp + Asn194Ser
Ser190Glu + Ser191Glu + Phe192Asp + Asn194Gln
Ser190Asp + Ser191Asp + Phe192Asp + Asn194Gln
Ser190Asp + Ser191Glu + Phe192Glu + Asn194Ser
Ser190Glu + Ser191Glu + Phe192Tyr + Asn194Glu
Ser190Glu + Ser191Glu + Phe192Met + Asn194Glu
Ser190Asp + Ser191Glu + Phe192Gln + Asn194Asp
Ser190Asp + Ser191Asp + Phe192Ala + Asn194Asp
Ser190Glu + Ser191Glu + Phe192Leu + Asn194Asp
Ser190Glu + Ser191Glu + Phe192Ser + Asn194Asp
Ser190Glu + Ser191Glu + Phe192Met + Asn194Asp
Ser190Asp + Ser191Glu + Phe192Tyr + Asn194Glu
Ser190Asp + Ser191Asp + Phe192His + Asn194Asp
Ser190Glu + Ser191Asp + Phe192Gln + Asn194Asp
Ser190Asp + Ser191Asp + Phe192Asn + Asn194Glu
Ser190Asp + Ser191Glu + Phe192Ile + Asn194Asp

TABLE 22

Loop 6 - Single Mutation Variants

Gly203Asn
Gly203Asp
Gly203Gln
Gly203Glu
Gly203Pro
GLy203Ser
Pro204Asn
Pro204Asp
Pro204Gln
Pro204Glu
Pro204Gly
Pro204Ser
Gly205Asn
Gly205Asp
Gly205Gln
Gly205Glu
Gly205Pro
Gly205Ser
Thr206Asn
Thr206Asp
Thr206Gln
Thr206Glu
Thr206Gly
Thr206Pro
Thr206Ser
Ser207Asp
Ser207Glu

TABLE 22-continued

Loop 6 - Single Mutation Variants

Ile208Ala
Ile208Asn
Ile208Asp
Ile208Cys
Ile208Gln
Ile208Glu
Ile208Gly
Ile208His
Ile208Leu
Ile208Met
Ile208Pro
Ile208Ser
Ile208Thr
Ile208Val
Leu209Ala
Leu209Asn
Leu209Asp
Leu209Cys
Leu209Gln
Leu209Glu
Leu209Gly
Leu209His
Leu208Ile
Leu209Met
Leu209Pro
Leu209Ser
Leu209Thr
Leu209Val
Ser210Asp
Ser210Glu
Thr211Asn
Thr211Asp
Thr211Gln
Thr211Glu
Thr211Gly
Thr211Pro
Thr211Ser
Trp212Ala
Trp212Asn
Trp212Asp
Trp212Cys
Trp212Gln
Trp212Glu
Trp212Gly
Trp212His
Trp212Ile
Trp212Leu
Trp212Met
Trp212Phe
Trp212Pro
Trp212Ser
Trp212Thr
Trp212Tyr
Trp212Val
Ile213Ala
Ile213Asn
Ile213Asp
Ile213Cys
Ile213Gln
Ile213Glu
Ile213Gly
Ile213His
Ile213Leu
Ile213Met
Ile213Pro
Ile213Ser
Ile213Thr
Ile213Val
Gly214Asn
Gly214Asp
Gly214Gln
Gly214Glu
Gly214Pro
Gly214Ser
Gly215Asn
Gly215Asp
Gly215Gln
Gly215Glu
Gly215Pro
Gly215Ser
Ser216Asp
Ser216Glu
Thr217Asn
Thr217Asp
Thr217Gln
Thr217Glu
Thr217Gly
Thr217Pro
Thr217Ser
Arg218Asp
Arg218Glu
Ser219Asp
Ser219Glu
Ile220Ala
Ile220Asn
Ile220Asp
Ile220Cys
Ile220Gln
Ile220Glu
Ile220Gly
Ile220His
Ile220Leu
Ile220Met
Ile220Pro
Ile220Ser
Ile220Thr
Ile220Val
Ser221Asp
Ser221Glu
Gly222Asn
Gly222Asp
Gly222Gln
Gly222Glu
Gly222Pro
Gly222Ser
Thr223Asn
Thr223Asp
Thr223Gln
Thr223Glu
Thr223Gly
Thr223Pro
Thr223Ser

TABLE 23

Loop 6 - Double Mutation Variants

Gly203Gln + Ser219Glu
Thr206Gly + Leu209Ser
Trp212Phe + Ser221Glu
Arg218Glu + Gly222Pro
Gly214Asp + Ile220Ser
Gly215Asp + Thr217Gly
Gly203Asn + Ser219Asp
Trp212Ile + Ser221Glu
Trp212Gln + Ser219Asp
Trp212Cys + Ser219Asp
Thr217Glu + Thr223Pro
Gly214Pro + Ile220Val
Ile208Pro + Thr223Ser
Leu209Gln + Ile220Glu
Thr206Asn + Ile220His
Ile208Ala + Thr217Ser
Pro204Gln + Ser221Asp
Trp212Thr + Thr223Asn
Gly203Asn + Ser219Glu
Gly203Gln + Gly214Pro
Gly214Asp + Gly215Gln
Gly203Ser + Arg218Glu
Thr206Gln + Trp212Asn
Pro204Ser + Ile213Glu

TABLE 23-continued

Loop 6 - Double Mutation Variants

Ile208Leu + Gly222Glu
Gly215Gln + Thr217Gln
Ile208Thr + Ser219Asp
Gly205Ser + Gly214Asp
Ile208Ser + Arg218Glu
Ile208Ser + Ile220Val
Thr211Gly + Arg218Asp
Ile213Asp + Ile220Ser
Pro204Gln + Ser219Glu
Thr211Gly + Ile220Met
Ile208His + Leu209Ala
Gly205Asn + Ser207Glu
Thr206Ser + Gly215Asn
Gly205Asn + Gly222Ser
Gly203Pro + Ile213Cys
Thr206Gln + Gly215Ser
Ile208Ser + Gly214Glu
Thr217Gln + Ser219Glu
Pro204Ser + Ser216Asp
Gly214Asn + Ser216Asp
Ile208Leu + Thr211Asn
Pro204Gly + Ser207Glu
Ser219Asp + Gly222Asn
Trp212Tyr + Ile213Thr
Thr206Ser + Trp212Val
Ile220Asp + Thr223Pro
Ile208Pro + Trp212Pro
Ile208Leu + Thr217Asp
Pro204Ser + Gly214Ser
Gly203Ser + Gly222Pro
Gly205Ser + Arg218Glu
Gly203Pro + Ser207Asp
Ile208Val + Ser219Glu
Ser216Asp + Gly222Gln
Ser207Asp + Trp212Ala
Ile220Cys + Gly222Glu
Thr206Asn + Ile213Cys
Thr206Asp + Gly215Gln
Ser207Asp + Thr211Ser
Ile208Leu + Ser216Glu
Leu209Val + Gly214Asp
Thr206Glu + Ile213Asn
Pro204Ser + Thr211Ser
Ile213Asp + Gly215Pro
Gly214Asp + Thr223Ser
Gly205Asn + Leu209Cys
Gly205Gln + Ile208Ala
Ile208Leu + Ser219Asp
Leu209Glu + Thr211Pro
Ile208Cys + Thr217Gln
Pro204Asn + Leu209Asn
Gly214Pro + Ile220Pro
Giy203Gln + Thr211Gly
Pro204Gly + Thr223Asp
Gly215Ser + Thr217Pro
Thr206Gln + Thr211Asn
Gly205Pro + Gly215Pro
Gly203Pro + Ser207Glu
Ser207Glu + Ile208His
Pro204Ser + Thr223Gly
Gly205Asn + Gly215Asp
Leu209Gln + Ser219Glu
Gly215Pro + Thr223Ser
Ile208Gln + Ser221Asp
Gly203Gln + Arg218Asp
Gly203Asn + Ile220Asp
Gly205Pro + Arg218Asp
Thr211Asn + Arg218Glu
Gly205Asn + Thr223Glu
Thr206Glu + Leu209His
Thr206Pro + Gly215Asp
Trp212Gln + Ser221Asp
Ser216Glu + Ile220Met
Gly215Asn + Gly222Asp
Ile213Cys + Ser219Asp
Pro204Ser + Thr211Asn
Pro204Ser + Thr223Pro

TABLE 23-continued

Loop 6 - Double Mutation Variants

Pro204Gln + Ile213Glu
Gly214ser + Ser221Asp
Ile208Leu + Thr223Pro
Ser207Asp + Ile208Gly
Ile208Leu + Arg218Glu
Leu209Ser + Ile220His
Ile213Leu + Arg218Asp
Pro204Ser + Ser219Asp
Gly203Ser + Gly222Glu
Gly205Pro + Thr223Asn
Trp212Thr + Gly214Ser
Thr206Ser + Ser216Asp
Gly203Pro + Thr206Gly
Thr211Pro + Gly222Ser
Ile213Thr + Thr223Glu
Thr206Pro + Ile213Glu
Ser207Asp + Gly222Asn
Ile213Val + Gly214Asn
Thr211Asn + Thr223Asn
Ile213Cys + Thr223Pro
Pro204Ser + Gly222Gln
Gly205Gln + Gly215Glu
Leu209Pro + Gly222Gln
Gly205Ser + Gly222Asp
Pro204Ser + Ile208Leu
Pro204Gln + Thr211Gly
Leu209Ser + Ser219Asp
Thr217Glu + Thr223Asn
Gly203Gln + Thr217Ser
Gly205Pro + Ile213Gln
Leu209Glu + Thr217Ser
Ser216Asp + Thr217Ser
Trp212Gln + Ile213Ala
Arg218Glu + Ile220Gln
Leu209Ile + Thr223Asn
Ile208Met + Gly215Gln
Arg218Asp + Ile220Ala
Gly203Asn + Pro204Asn
Ile208His + Ser221Asp
Ile213Asn + Ser219Asp
Trp212Met + Ser219Glu
Thr206Pro + Ser216Glu
Pro204Gln + Thr206Asp
Thr206Gly + Gly215Pro
Pro204Asn + Gly222Gln
Ser219Glu + Gly222Ser
Ile220Asn + Gly222Asn
Gly205Asn + Ile213Asn
Gly203Ser + Ile213Leu
Ser207Asp + Thr211Asn
Leu209Pro + Ile213Glu
Ile208Pro + Thr223Asp
Thr211Ser + Gly222Asp
Thr206Ser + Thr217Asp
Gly203Gln + Gly214Glu
Gly205Ser + Gly215Ser
Gly203Gln + Leu209Ala
Gly203Gln + Gly222Asn
Ser207Asp + Thr211Gly
Gly205Gln + Ser219Glu
Trp212Cys + Ser216Asp
Gly203Gln + Thr217Glu
Arg218Glu + Ile220Cys
Thr211Gly + Ser221Glu
Pro204Asn + Ser216Asp
Arg218Asp + Gly222Pro
Gly205Pro + Ser221Glu
Arg218Glu + Thr223Ser
Leu209Asn + Ser216Glu
Gly205Pro + Ile220Met
Thr206Asn + Thr217Asp
Gly203Ser + Ile208Thr
Thr217Ser + Arg218Glu
Pro204Asn + Thr211Asn
Gly205Asn + Thr217Glu
Ser207Asp + Thr223Gly
Trp212Tyr + Ile213Pro TABLE 23-continued

| Loop 6 - Double Mutation Variants |
| --- |
| Gly214Gln + Ser216Asp |
| Thr206Asp + Ile208Thr |

TABLE 24

| Loop 6 - Triple Mutation Variants |
| --- |
| Gly203Gln + Thr206Gly + Ser219Glu |
| Ile213Ala + Gly215Asp + Thr217Gly |
| Gly203Asn + Ser219Asp + Thr223Ser |
| Gly215Pro + Ser216Glu + Thr223Ser |
| Gly203Gln + Trp212Pro + Gly222Asp |
| Pro204Ser + Gly205Ser + Ser207Glu |
| Gly205Pro + Ile208Met + Ser219Asp |
| Thr211Gly + Gly215Gln + Thr217Asn |
| Thr211Ser + Thr217Gln + Thr223Asp |
| Gly205Gln + Thr211Asn + Gly222Asn |
| Thr211Pro + Gly214Asn + Thr217Asn |
| Gly205Pro + Leu209Asn + Thr223Gln |
| Gly203Gln + Trp212Leu + Ile220Ala |
| Trp212Thr + Gly215Glu + Ile220Thr |
| Gly205Gln + Ser207Asp + Trp212Ala |
| Gly205Asn + Trp212Phe + Ser216Glu |
| Ser207Glu + Thr211Gly + Gly222Asn |
| Pro204Gln + Gly205Ser + Ser221Glu |
| Thr206Pro + Leu209Gly + Thr223Asn |
| Ile208Met + Thr217Gly + Thr223Gln |
| Thr211Ser + Gly215Pro + Gly222Glu |
| Ile208Pro + Trp212Pro + Ser216Glu |
| Gly203Ser + Thr211Gln + Gly222Pro |
| Gly203Pro + Ile208Val + Ser219Glu |
| Thr206Pro + Gly215Ser + Ser216Glu |
| Thr206Pro + Ile220Asn + Thr223Gly |
| Pro204Gln + Gly205Pro + Arg218Glu |
| Trp212His + Ile213Met + Gly215Asp |
| Ile208Ser + Gly222Gln + Thr223Gln |
| Gly205Gln + Trp212Leu + Arg218Asp |
| Gly214Gln + Ser216Glu + Gly222Ser |
| Gly203Asn + Ser216Glu + Gly222Gln |
| Leu209Asn + Gly222Glu + Thr223Ser |
| Thr206Asp + Thr211Asn + Gly214Ser |
| Pro204Asn + Thr211Gly + Trp212Thr |
| Gly203Ser + Ile208Ala + Ser216Glu |
| Thr211Ser + Gly214Pro + Gly222Glu |
| Gly215Gln + Arg218Asp + Ile220Val |
| Gly215Ser + Ser216Asp + Thr223Ser |
| Thr206Asn + Thr211Asn + Arg218Glu |
| Pro204Asn + Thr217Glu + Thr223Ser |
| Thr206Ser + Ile213Met + Gly215Ser |
| Pro204Gly + Gly205Ser + Trp212Gln |
| Thr211Pro + Trp212Ala + Thr223Asp |
| Gly215Glu + Ile220Ala + Thr223Gln |
| Thr206Gln + Ile208Ser + Leu209Asp |
| Thr211Ser + Trp212Val + Ser219Glu |
| Gly205Pro + Thr211Pro + Ser216Asp |
| Gly205Pro + Trp212His + Ser219Glu |
| Gly205Pro + Trp212Asn + Ser219Asp |
| Leu209Ser + Thr211Gln + Arg218Asp |
| Pro204Gly + Thr211Asn + Gly215Glu |
| Gly203Pro + Pro204Ser + Ser216Asp |
| Gly203Gln + Ile213Val + Arg218Glu |
| Ile208Gly + Thr217Asn + Gly222Ser |
| Pro204Ser + Gly205Gln + Trp212Ile |
| Pro204Gln + Gly214Glu + Gly215Gln |
| Trp212Cys + Gly215Gln + Ser221Glu |
| Gly203Asn + Leu209Val + Thr217Glu |
| Gly205Asn + Ser207Asp + Thr217Gly |
| Pro204Gln + Thr206Asp + Gly215Ser |
| Ile208Gln + Thr211Pro + Ser219Asp |
| Gly205Ser + Ile213His + Ser219Glu |
| Gly203Ser + Ile208Ser + Trp212Met |
| Thr211Pro + Trp212Tyr + Ser219Asp |
| Gly205Gln + Ile208His + Gly222Asn |
| Gly203Ser + Thr211Ser + Ile220Glu |

TABLE 24-continued

| Loop 6 - Triple Mutation Variants |
| --- |
| Pro204Gly + Leu209Ile + Arg218Glu |
| Trp212Tyr + Ile213Ser + Thr217Pro |
| Ile208Asn + Ile213Pro + Gly214Ser |
| Gly203Gln + Ile213His + Ser219Asp |
| Gly205Asn + Thr211Gln + Ser221Glu |
| Gly205Asn + Ser207Glu + Gly214Gln |
| Ile208Val + Gly214Glu + Gly222Gln |
| Gly203Ser + Thr206Gly + Ile213Leu |
| Pro204Gly + Ile208Pro + Gly215Asp |
| Thr206Glu + Thr217Gly + Ile220Pro |
| Ile213Ser + Thr217Asp + Gly222Gln |
| Ile208Val + Gly215Asn + Thr223Ser |
| Gly205Pro + Ser207Glu + Thr217Ser |
| Gly203Pro + Thr206Glu + Ile208His |
| Gly205Ser + Trp212Cys + Ser216Asp |
| Pro204Ser + Thr206Asp + Leu209Ile |
| Thr2G6Glu + Ile208Thr + Ile220Gly |
| Ile213Gln + Ile220Glu + Gly222Gln |
| Ile208Val + Gly214Gln + Gly215Pro |
| Leu209Pro + Ser216Glu + Thr217Asn |
| Pro204Gln + Trp212Met + Gly222Glu |
| Ile208Met + Thr211Asn + Thr223Gln |
| Pro204Gln + Leu209Ile + Arg218Asp |
| Ile208Leu + Ser216Glu + Ile220Pro |
| Pro204Gly + Gly205Gln + Thr206Glu |
| Ile208Ser + Leu209His + Gly214Pro |
| Gly203Pro + Ile208Gln + Trp212Ser |
| Gly205Asn + Gly215Glu + Gly222Pro |
| Gly203Ser + Thr217Gln + Ile220Leu |
| Leu209Ser + Gly214Ser + Gly222Gln |
| Ile208Gly + Leu209Pro + Ser221Asp |
| Gly205Asn + Thr2063er + Ile220Gly |
| Ser207Glu + Leu209Met + Gly222Asn |
| Gly203Ser + Trp212Gln + Ser216Asp |
| Gly205Asn + Ile208Cys + Thr211Gln |
| Thr211Gly + Trp212Gly + Thr223Glu |
| Gly205Asn + Gly214Pro + Ser221Glu |
| Gly205Ser + Trp212Ala + Ser216Asp |
| Gly203Gln + Arg218Glu + Ile220Leu |
| Ser207Asp + Thr211Asn + Thr223Gly |
| Trp212Cys + Gly215Asn + Thr223Pro |
| Gly205Asn + Gly214Ser + Arg218Glu |
| Gly214Pro + Thr217Glu + Gly222Asn |
| Thr206Gln + Ile208Asn + Thr211Ser |
| Gly203Gln + Gly214Pro + Ser219Glu |
| Trp212His + Ile213Gln + Arg218Glu |
| Ile208Ala + Ile213Ala + Ser221Glu |
| Pro204Asn + Ile208Leu + Trp212Pro |
| Gly205Asn + Ser219Asp + Ile220His |
| Gly205Gln + Ile208Leu + Thr211Gln |
| Trp212Tyr + Ile213Gly + Gly215Gln |
| Trp212Met + Gly215Glu + Gly222Asn |
| Thr206Ser + Thr211Ser + Thr217Asn |
| Ile208Leu + Ile213Ser + Ile220Pro |
| Ile208Ser + Gly214Pro + Gly222Asn |
| Thr211Ser + Ser216Glu + Thr223Pro |
| Gly203Ser + Thr217Pro + Thr223Gly |
| Gly203Ser + Trp212Ala + Gly214Asp |
| Gly205Asn + Ile208Val + Ser219Asp |
| Gly203Ser + Pro204Gln + Ser221Asp |
| Gly203Pro + Trp212Gly + Gly222Pro |
| Ile208Gln + Thr217Gly + Arg218Glu |
| Thr206Gln + Ser207Glu + Thr223Gly |
| Ser207Asp + Leu209His + Thr211Pro |
| Ile208Thr + Trp212Val + Ile220Met |
| Leu209Ala + Ser221Asp + Thr223Gln |
| Gly203Asn + Thr211Gly + Gly214Glu |
| Gly214Pro + Gly215Glu + Ile220Pro |
| Gly205Ser + Gly214Asn + Ser216Glu |
| Thr206Gln + Ile213Thr + Ser219Glu |
| Pro204Gly + Thr211Gly + Ser221Asp |
| Gly203Pro + Gly205Asn + Gly215Asp |
| Gly203Pro + Thr211Asn + Thr223Asn |
| Pro204Gly + Leu209Pro + Gly215Glu |
| Gly203Pro + Ile213Glu + Ile220Gly |
| Pro204Gln + Ile213Met + Ile220Pro |
| Gly214Pro + Thr217Gln + Gly222Glu |

TABLE 24-continued

| Loop 6 - Triple Mutation Variants |
|---|
| Ile208His + Ser221Glu + Thr223Asn |
| Gly203Pro + Gly214Asn + Arg218Asp |
| Ile213Ala + Ser216Asp + Gly222Ser |
| Gly203Asn + Thr211Gly + Thr217Asn |
| Leu209Met + Thr211Gln + Ser219Asp |
| Thr206Ser + Leu209Ile + Thr211Gly |
| Ile213Met + Gly215Gln + Ser221Asp |
| Pro204Asn + Ser207Asp + Ile220His |
| Gly203Gln + Ile208Val + Ser221Asp |
| Thr217Gln + Ile220Val + Thr223Glu |
| Gly205Asn + Ile208Val + Ile213His |
| Thr206Asn + Thr211Gly + Thr217Asp |
| Ser207Glu + Ile208Cys + Gly215Pro |
| Pro204Asn + Gly205Pro + Trp212Ile |
| Pro204Gly + Ile208Val + Thr223Asp |
| Pro204Gly + Gly215Asn + Ile220His |
| Gly205Asn + Thr211Asn + Trp212Pro |
| Pro204Ser + Thr206Glu + Ile213Val |
| Gly203Pro + Ser207Glu + Gly214Asn |
| Pro204Gln + Gly214Glu + Gly215Glu |
| Gly205Ser + Thr217Asp + Arg218Asp |
| Leu209Met + Thr217Asp + Arg218Asp |
| Thr217Asp + Arg218Asp + Ile220Cys |
| Thr211Gln + Ser221Glu + Gly222Asp |
| Gly205Pro + Thr206Asp + Ser207Glu |
| Pro204Gly + Thr206Asp + Ser207Glu |
| Thr211Gln + Ile220Glu + Ser221Asp |
| Trp212Tyr + Arg218Asp + Ser219Glu |
| Ile208Val + Arg218Glu + Ser219Glu |
| Gly205Gln + Gly215Asp + Ser216Asp |
| Leu209Glu + Trp212Phe + Ser219Asp |
| Thr206Glu + Ile208Ala + Ser221Asp |
| Gly205Asn + Ser207Glu + Ser221Glu |
| Ser207Glu + Thr211Asn + Ile220Asp |
| Gly203Pro + Ser207Glu + Ile220Glu |
| Ser207Asp + Trp212His + Ser219Asp |

TABLE 25

| Loop 6 - Quadruple Mutation Variants |
|---|
| Gly203Gln + Thr206Gly + Leu209Ser + Ser219Glu |
| Ile208Val + Thr217Ser + Ser219Asp + Gly222Pro |
| Gly203Asn + Ile213Thr + Gly214Pro + Ser219Glu |
| Gly203Gln + Trp212Phe + Gly214Asn + Gly215Asp |
| Ser207Asp + Leu209Thr + Thr211Pro + Trp212Gly |
| Gly205Pro + Trp212Asn + Ile213His + Ile220Asp |
| Gly203Gln + Pro204Ser + Trp212Ile + Ile220Ser |
| Pro204Gln + Thr211Gly + Ser219Glu + Ile220Met |
| Gly203Gln + Trp212Gly + Gly215Glu + Ile220Ala |
| Thr206Gln + Thr211Pro + Gly215Asn + Ile220Thr |
| Leu209Val + Thr211Ser + Arg218Asp + Ile220Ser |
| Gly203Gln + Ile208Cys + Leu209Ser + Gly214Glu |
| Gly205Gln + Ser207Glu + Gly215Gln + Ile220Ala |
| Ile208Ala + Leu209Val + Ser216Glu + Thr223Pro |
| Pro204Gly + Ile208His + Ser219Glu + Ile220Ser |
| Thr206Asp + Ile208Gly + Thr217Asn + Thr223Ser |
| Gly203Asn + Leu209Ser + Gly214Ser + Ser221Asp |
| Ile213Asp + Gly214Ser + Ile220Gln + Gly222Asn |
| Trp212Thr + Ile213Gly + Gly214Ser + Ile220Ala |
| Gly203Asn + Leu209Asp + Trp212Phe + Gly222Gln |
| Thr206Asn + Thr211Ser + Ile213Gly + Ser219Asp |
| Pro204Asn + Gly205Gln + Thr206Asn + Ser207Glu |
| Gly203Gln + Gly205Asn + Ser207Asp + Leu209Thr |
| Gly205Gln + Ile213Val + Gly214Pro + Arg218Glu |
| Thr206Pro + Ile213Pro + Gly222Pro + Thr223Asp |
| Gly203Asn + Gly214Asn + Ser221Asp + Thr223Gly |
| Ile213Asn + Ser216Asp + Ile220Asn + Gly222Asn |
| Pro204Ser + Leu209Pro + Ile213Glu + Ile220Pro |
| Gly203Gln + Gly205Ser + Leu209Ala + Gly215Ser |
| Gly203Gln + Ser207Asp + Thr211Gly + Gly222Asn |
| Pro204Gln + Leu209His + Thr217Gly + Ser219Glu |
| Thr206Asp + Ile208Thr + Leu209Ala + Thr217Asn |
| Ile208Thr + Leu209Gly + Arg218Asp + Ile220Leu |

TABLE 25-continued

| Loop 6 - Quadruple Mutation Variants |
|---|
| Pro204Asn + Ile208Val + Leu209His + Arg218Glu |
| Ile208Asn + Thr211Gln + Ser219Glu + Gly222Gln |
| Thr206Gly + Ser207Glu + Ile208Thr + Ile213Gly |
| Leu209Glu + Gly214Gln + Ile220Val + Gly222Gln |
| Gly205Gln + Gly214Asn + Thr217Gln + Thr223Glu |
| Gly203Gln + Leu209Val + Gly215Pro + Ile220Glu |
| Thr211Gln + Trp212Gln + Gly215Asn + Ser219Glu |
| Pro204Ser + Ile208Ser + Gly222Glu + Thr223Gln |
| Pro204Gly + Ile208Ser + Gly215Gln + Ser221Asp |
| Gly203Gln + Thr211Gly + Ile213Leu + Gly214Asn |
| Pro204Asn + Thr211Ser + Gly214Asp + Thr217Asn |
| Pro204Gly + Trp212Met + Gly215Glu + Gly222Asn |
| Thr206Glu + Ile208Leu + Ile213Ser + Ile220Pro |
| Thr206Gly + Trp212Leu + Gly214Asp + Gly222Ser |
| Gly203Ser + Gly214Asp + Thr217Pro + Thr223Gly |
| Gly203Ser + Pro204Asn + Ile208Ala + Gly215Glu |
| Gly203Ser + Thr211Ser + Ser219Glu + Gly222Asn |
| Ser207Glu + Ile208Gly + Thr211Pro + Ile220Pro |
| Gly203Asn + Gly205Pro + Leu209Ala + Gly222Glu |
| Leu209Asn + Thr211Gly + Ile213Thr + Thr223Gln |
| Gly203Pro + Pro204Asn + Ile213His + Thr217Gln |
| Ile208Asn + Thr217Pro + Ile220Leu + Ser221Glu |
| Thr206Ser + Thr211Gln + Ile213Gly + Ser221Asp |
| Gly205Pro + Gly215Asp + Ile220His + Thr223Gly |
| Pro204Gln + Ile208Thr + Ser219Asp + Gly222Asn |
| Gly203Pro + Leu209Met + Thr211Pro + Ile220Cys |
| Thr206Gly + Leu209Cys + Ile213His + Ser216Asp |
| Ile208Gly + Leu209Met + Thr217Gly + Ile220Pro |
| Gly203Asn + Thr206Ser + Gly214Gln + Ser221Glu |
| Ile208His + Thr211Ser + Trp212Pro + Arg218Asp |
| Thr206Ser + Ile208Pro + Leu209Ile + Gly214Asp |
| Gly205Pro + Thr206Glu + Ile213His + Gly222Asn |
| Thr211Asn + Ile213Gln + Thr217Asp + Thr223Ser |
| Thr206Asn + Trp212Val + Arg218Glu + Ile220Pro |
| Pro204Asn + Ser207Asp + Thr211Gln + Gly214Ser |
| Pro204Ser + Ile213Met + Gly214Asp + Thr217Gly |
| Gly203Pro + Ile208Ala + Ser216Glu + Thr217Pro |
| Ser207Asp + Trp212Cys + Gly215Pro + Thr217Gly |
| Pro204Asn + Gly214Gln + Ser216Glu + Ile220His |
| Pro204Ser + Trp212Ala + Gly214Asp + Gly215Pro |
| Pro204Asn + Leu209Gly + Thr211Gly + Ile213Thr |
| Pro204Ser + Gly205Gln + Ile208His + Ser219Asp |
| Gly203Asn + Gly205Ser + Leu209Ser + Arg218Glu |
| Thr206Pro + Thr211Gln + Ile213Glu + Gly214Asn |
| Ser207Asp + Gly214Asn + Ile220Val + Gly222Asn |
| Trp212Tyr + Ile213Val + Gly214Asn + Gly222Ser |
| Gly205Pro + Ile208Gly + Ser216Asp + Ile220His |
| Gly203Asn + Leu209Gly + Gly214Pro + Arg218Asp |
| Pro204Gln + Ile208Cys + Ile213Gly + Gly215Glu |
| Pro204Asn + Gly205Pro + Leu209Ala + Thr211Pro |
| Gly203Pro + Ile213Ala + Thr217Gly + Arg218Glu |
| Gly203Gln + Pro204Gly + Ile220Gly + Ser221Glu |
| Gly205Asn + Ile213Gly + Gly214Pro + Gly222Ser |
| Gly203Asn + Thr211Gln + Gly214Glu + Gly222Gln |
| Ile213Thr + Gly215Gln + Ser219Asp + Ile220Pro |
| Gly203Asn + Pro204Ser + Arg218Asp + Thr223Pro |
| Gly203Ser + Thr211Gln + Arg218Glu + Ile220Val |
| Gly203Ser + Pro204Ser + Ile208Ser + Thr211Gln |
| Pro204Gly + Gly214Asn + Gly215Glu + Thr223Asn |
| Ile208Cys + Thr211Pro + Trp212Ser + Gly215Pro |
| Pro204Asn + Ile213Met + Thr217Glu + Ile220Gln |
| Pro204Gly + Gly205Pro + Ile208Gly + Thr211Pro |
| Gly203Ser + Thr206Gly + Ile208Asn + Ser219Asp |
| Pro204Asn + Ile213Glu + Gly215Pro + Thr217Asn |
| Gly203Asn + Thr211Gln + Arg218Glu + Ile220Gly |
| Gly203Gln + Ile208Cys + Gly215Ser + Arg218Asp |
| Pro204Gln + Gly205Gln + Gly214Ser + Thr223Gly |
| Pro204Gln + Leu209Met + Trp212Phe + Ser219Glu |
| Gly205Asn + Ile208Cys + Leu209Ile + Ile220Asn |
| Gly203Pro + Leu209Cys + Thr217Gly + Ile220Gly |
| Gly205Asn + Thr206Gly + Ile208Asn + Ser216Glu |
| Pro204Gln + Thr206Pro + Ser207Glu + Gly214Asn |
| Gly203Gln + Ile208Met + Trp212His + Thr223Pro |
| Pro204Asn + Leu209Val + Thr211Asn + Gly215Ser |
| Gly203Asn + Ile208His + Ser221Asp + Gly222Ser |
| Pro204Asn + Leu209Pro + Ser219Glu + Ile220Glu |
| Thr211Pro + Ile213Asn + Gly214Glu + Gly215Asp |

TABLE 25-continued

Loop 6 - Quadruple Mutation Variants

Thr211Gln + Gly21SSer + Thr217Asp + Arg218Asp
Gly205Asn + Thr217Asp + Arg218Asp + Ile220Gln
Ile208Thr + Leu209Thr + Ser221Asp + Gly222Glu
Gly203Asn + Gly205Asn + Ser221Asp + Gly222Glu
Thr206Ser + Trp212Pro + Ser221Asp + Gly222Asp
Ile208Pro + Thr211Ser + Gly222Asp + Thr223Asp
Pro204Ser + Trp212Met + Gly222Glu + Thr223Asp
Gly203Gln + Thr206Glu + Ser207Glu + Thr211Gln
Gly203Asn + Thr206Glu + Ser207Asp + Thr211Asn
Thr206Asp + Ser207Asp + Ile220Thr + Thr223Pro
Gly203Gln + Thr217Ser + Ile220Glu + Ser221Asp
Gly205Ser + Thr211Gln + Arg218Glu + Ser219Asp
Leu209Gly + Gly214Ser + Arg218Glu + Ser219Glu
Ile208Gln + Gly214Pro + Ser216Asp + Thr217Glu
Ile208Gly + Ile213Met + Gly215Glu + Ser216Glu
Ile208Ser + Leu209Asp + Thr211Gly + Ser219Asp
Pro204Gln + Ile208Thr + Leu209Asp + Ser219Asp
Thr206Asp + Trp212Gln + Ser221Asp + Thr223Gly
Gly203Asn + Thr206Asp + Trp212Phe + Ser221Glu
Pro204Gln + Thr206Glu + Leu209Ile + Ser221Glu
Pro204Gln + Gly205Gln + Ser207Glu + Ser221Glu
Ser207Asp + Ile208Leu + Trp212Ile + Ser221Glu
Ser207Glu + Leu209Met + Ile220Glu + Thr223Ser
Thr217Asn + Arg218Asp + Ser219Asp + Ile220Asp
Pro204Asn + Ser207Asp + Ser219Glu + Gly222Gln
Pro204Gly + Gly205Pro + Ser207Glu + Ser219Glu
Gly205Gln + Ser207Asp + Trp212Val + Ser219Glu
Ser207Glu + Ile208Ser + Ser219Glu + Thr223Gly
Thr206Asp + Thr217Ser + Ile220Asp + Ser221Glu
Trp212Gln + Gly214Asp + Ser216Glu + Ile220Val
Gly214Asp + Gly215Gln + Ser216Glu + Thr223Asn
Gly203Gln + Leu209Asp + Thr211Asn + Arg218Glu
Pro204Ser + Leu209Glu + Arg218Asp + Ile220Cys
Ser207Asp + Ile208Gly + Ser221Glu + Gly222Asp
Pro204Asn + Ser207Glu + Ser221Asp + Gly222Asp
Pro204Ser + Gly20SSer + Ile213Asp + Ser216Asp
Thr206Asn + Ser219Glu + Ser221Glu + Thr223Asn
Thr206Pro + Trp212Pro + Ser216Glu + Arg218Glu
Gly203Ser + Gly215Asn + Ser216Asp + Arg218Glu
Thr206Gln + Trp212Asn + Ser216Asp + Arg218Glu
Leu209Val + Trp212Ile + Ser216Asp + Arg218Glu
Pro204Gly + Ile208Pro + Ser216Asp + Arg218Asp
Ile208Gly + Thr211Asn + Ser216Glu + Arg218Glu
Trp212His + Ile213Asn + Thr217Glu + Ser219Glu
Ile208Leu + Thr211Pro + Thr217Asp + Ser219Glu
Gly203Asn + Thr217Asp + Ser219Glu + Ile220Ala
Thr206Pro + Thr217Glu + Ser219Glu + Ile220Ala
Gly203Gln + Gly215Glu + Thr217Glu + Ile220Cys
Gly203Asn + Arg218Glu + Ser219Asp + Ser221Glu
Leu209Met + Ser219Asp + Ser221Glu + Gly222Asp
Thr211Ser + Ile213Glu + Ser216Asp + Arg218Asp
Thr211Asn + Ser216Asp + Arg218Asp + Ser219Asp
Ser216Glu + Arg218Asp + Ser219Glu + Thr223Ser
Gly203Pro + Thr206Glu + Leu209Asp + Ile220Asp
Ser207Asp + Leu209Gln + Gly222Asp + Thr223Ser
Gly205Gln + Ser207Glu + Ile213Gln + Gly222Asp
Gly205Asn + Ser207Glu + Ile213Leu + Gly222Asp
Gly205Gln + Ser207Glu + Gly222Asp + Thr223Glu
Ser207Asp + Trp212Gly + Ser219Glu + Gly222Glu
Trp212Thr + Gly214Glu + Ser216Asp + Arg218Asp
Ser207Asp + Arg218Asp + Ser221Asp + Gly222Asn
Ser207Asp + Trp212His + Arg218Glu + Ser221Glu
Pro204Asn + Thr206Asp + Thr211Ser + Ser219Asp
Thr206Asn + Ile213Pro + Gly214Glu + Thr217Asp
Thr211Gln + Gly214Glu + Gly215Ser + Thr217Glu
Leu209Asp + Gly214Pro + Ser221Glu + Gly222Asp
Ser207Glu + Leu209Ala + Ile213Ala + Arg218Glu
Pro204Gln + Ser207Glu + Trp212Leu + Arg218Asp
Pro204Gly + Ile213Glu + Arg218Glu + Ser219Glu
Pro204Gly + Thr206Glu + Leu209Asp + Thr223Gly

TABLE 26

Loop 6 - Quintuple Substitution Variants

Pro204Gln + Gly205Gln + Ile208Ala + Ser216Asp + Gly222Pro
Pro204Gln + Ser207Glu + Ile208Ser + Thr211Gly + Ile220Ala
Gly205Gln + Trp212Phe + Gly214Pro + Gly215Asp + Thr217Gly
Gly203Asn + Ile208Gln + Leu209Gln + Thr211Pro + Thr223Asp
Gly203Ser + Ile208Cys + Gly214Gln + Ser219Glu + Ile220Thr
Trp212Gln + Ile213Ser + Gly214Asn + Thr217Glu + Ile220Ser
Gly205Ser + Ile208Pro + Trp212Tyr + Gly214Gln + Ser221Asp
Gly205Gln + Thr206Glu + Ile208Thr + Leu209Thr + Trp212Cys
Gly203Asn + Gly205Pro + Ile208Val + Gly214Asn + Ser219Glu
Gly203Gln + Gly205Gln + Ile208Gly + Thr217Asn + Gly222Ser
Ile208Met + Thr211Gly + Ile213Cys + Gly214Pro + Ile220Leu
Thr211Pro + Ile213Ser + Thr217Asp + Ile220Pro + Gly222Gln
Pro204Asn + Gly205Ser + Thr211Gly + Ile220Thr + Gly222Asn
Gly203Asn + Gly205Asn + Leu209His + Ile220His + Thr223Gln
Pro204Gly + Ile208Asn + Thr217Gln + Gly222Glu + Thr223Gln
Gly205Gln + Ser207Asp + Ile208Met + Ile213Cys + Gly214Pro
Gly205Asn + Thr211Gln + Trp212Met + Thr217Glu + Gly222Asn
Gly205Gln + Thr206Pro + Leu209Glu + Ile213Thr + Ile220Gly
Thr211Asn + Gly214Gln + Gly215Ser + Thr217Ser + Gly222Ser
Pro204Gly + Gly205Gln + Thr211Gly + Ser221Glu + Thr223Gln
Gly203Ser + Ile208Thr + Ile220Val + Gly222Pro + Thr223Glu
Gly205Asn + Thr206Pro + Ser216Glu + Thr217Gln + Gly222Ser
Gly203Asn + Pro204Gln + Ile208Met + Gly215Gln + Ser219Asp
Gly205Gln + Thr206Pro + Trp212Ser + Ile213Gln + Ser221Glu
Leu209Gln + Gly214Gln + Thr217Ser + Ser221Asp + Thr223Asn
Ser207Glu + Trp212Tyr + Ile213Gly + Gly214Pro + Ile220Pro
Gly203Pro + Trp212Pro + Gly214Glu + Gly215Pro + Gly222Pro
Pro204Ser + Thr206Asn + Thr211Gly + Trp212Gln + Thr223Gln
Pro204Gly + Thr206Pro + Trp212Val + Gly214Pro + Arg218Glu
Gly203Gln + Thr211Gln + Gly215Asn + Thr217Glu + Ile220Val
Gly203Gln + Gly205Pro + Leu209Val + Thr211Gln + Gly214Asp
Pro204Asn + Ile213Thr + Gly215Gln + Ser219Asp + Ile220Pro
Pro204Gln + Thr206Asn + Ile208Met + Gly215Glu + Ile220Ala
Gly203Ser + Gly205Pro + Ile208Asn + Leu209Glu + Thr211Gln
Pro204Gly + Gly205Gln + Thr211Ser + Trp212Met + Thr217Pro
Gly205Ser + Thr206Gly + Ile208Val + Gly214Asp + Thr223Pro
Ser207Glu + Ile208Ala + Gly215Pro + Thr217Gln + Thr223Pro
Gly203Ser + Gly205Gln + Trp212Asn + Ile213Ser + Thr223Pro
Pro204Gln + Ile208Ala + Leu209Gln + Thr211Ser + Gly214Ser
Pro204Gln + Ile208His + Thr211Gln + Gly215Pro + Ser216Asp
Pro204Gln + Leu209Ile + Thr211Ser + Gly214Asp + Ile220Cys
Leu209Ile + Thr211Gln + Trp212Asn + Ile213Val + Thr217Asp
Pro204Asn + Ile208His + Leu209Val + Thr211Asn + Gly222Ser
Gly203Gln + Pro204Asn + Gly205Asn + Ile213Ala + Gly214Asp
Ser207Asp + Thr211Gln + Trp212Gly + Gly222Gln + Thr223Gly
Gly205Gln + Ile208Gly + Thr211Gln + Ile220Ser + Gly222Asp
Gly205Pro + Ile208Pro + Leu209Val + Ile220Leu + Gly222Glu
Pro204Gly + Thr206Glu + Leu209Cys + Ile213His + Ile220Met
Leu209Gly + Trp212Val + Ser216Asp + Ile220Cys + Thr223Ser
Gly205Gln + Leu209Val + Thr211Asn + Gly214Pro + Gly222Asp
Ile208Ala + Leu209His + Gly215Ala + Ile220Val + Gly222Glu
Ser207Glu + Ile208Pro + Thr211Asn + Ile213His + Gly222Ser
Ile208His + Leu209Cys + Thr217Pro + Ile220Glu + Gly222Gln
Pro204Gly + Gly205Ser + Ile208Ala + Trp212Leu + Thr223Asn
Gly203Pro + Gly205Pro + Trp212Ala + Gly215Ser + Arg218Glu
Pro204Ser + Trp212Ala + Ile213Thr + Gly215Asn + Ser216Glu
Thr211Asn + Trp212Thr + Ser216Glu + Gly222Gln + Thr223Pro
Thr206Gln + Ile208Pro + Thr211Gly + Ile213Leu + Gly215Asp
Gly203Asn + Ile208Met + Ser221Glu + Gly222Asp + Thr223Asn
Pro204Gln + Thr206Gly + Trp212Gly + Gly215Asp + Ile220Cys
Gly203Asn + Pro204Gln + Trp212Pro + Ile220Gly + Thr223Asp
Pro204Ser + Thr206Ser + Ile208Leu + Thr211Ser + Gly222Pro
Gly203Ser + Ile208Thr + Leu209His + Thr211Gln + Ile220Glu
Pro204Asn + Thr211Pro + Gly214Gln + Gly215Glu + Thr217Ser
Pro204Asn + Thr211Pro + Thr217Asp + Ile220Val + Thr223Gln
Gly203Ser + Ile208Gln + Leu209Asn + Thr211Ser + Trp212Asn
Pro204Asn + Ile208His + Thr211Gln + Ile220Gly + Gly222Asp
Gly205Pro + Trp212Val + Gly215Pro + Ser216Asp + Thr217Pro
Gly203Gln + Ile208Ala + Thr211Pro + Gly214Ser + Arg218Glu
Gly203Asn + Pro204Gln + Leu209Met + Trp212Ser + Thr217Glu
Gly205Pro + Ser207Glu + Ile208Met + Leu209Met + Ile220Asn
Thr211Gly + Trp212Asn + Ser219Glu + Ile220Asp + Thr223Pro
Ile208Met + Ile213Thr + Thr217Asp + Arg218Glu + Thr223Gly
Gly203Ser + Ile208Gln + Thr217Glu + Arg218Asp + Gly222Pro
Gly205Gln + Thr217Glu + Arg218Glu + Ile220His + Thr223Pro
Gly203Ser + Ile213Gln + Thr217Asp + Arg218Asp + Gly222Gln
Gly203Pro + Pro204Gly + Ile208Gly + Ser221Asp + Gly222Asp

TABLE 26-continued

| Loop 6 - Quintuple Substitution Variants |
|---|
| Gly203Asn + Thr211Gln + Ile213Asp + Gly214Glu + Gly222Gln |
| Thr206Glu + Ser207Glu + Leu209Asn + Thr211Gln + Thr217Asn |
| Gly203Gln + Leu209Met + Thr211Pro + Ile220Glu + Ser221Glu |
| Ile208Val + Leu209His + Thr211Gln + Arg218Glu + Ser219Glu |
| Gly203Pro + Pro204Asn + Leu209His + Arg218Asp + Ser219Asp |
| Ile208Ala + Trp212Gln + Arg218Glu + Ser219Glu + Ile220Thr |
| Leu209Gly + Thr211Pro + Gly215Asn + Ser216Glu + Thr217Asp |
| Ile208Asn + Leu209Thr + Ile213His + Ser216Glu + Thr217Glu |
| Leu209Asn + Gly215Glu + Ser216Asp + Ile220Asn + Thr223Asn |
| Gly203Ser + Pro204Gly + Gly215Glu + Ser216Asp + Thr223Ser |
| Pro204Gln + Ile208Cys + Ile213Cys + Gly215Glu + Ser216Glu |
| Pro204Gln + Gly205Asn + Thr206Asp + Ser207Glu + Ser221Glu |
| Gly203Gln + Pro204Asn + Thr206Asp + Ile208Cys + Ser221Glu |
| Pro204Gly + Thr206Glu + Ile208Gln + Trp212His + Ser221Glu |
| Thr206Asp + Ile208Met + Trp212Met + Ile213Met + Ser221Glu |
| Ser207Asp + Thr211Gln + Trp212Ala + Ile213Pro + Ser221Asp |
| Thr206Gln + Ser207Asp + Leu209Val + Thr211Gly + Ser221Asp |
| Pro204Ser + Ser207Glu + Ile208Thr + Trp212Ile + Ser221Asp |
| Ser207Glu + Leu209Ala + Thr217Gly + Ile220Ala + Ser221Asp |
| Ser207Asp + Thr211Pro + Trp212Cys + Gly215Pro + Ser221Glu |
| Gly205Pro + Ser207Glu + Trp212Asn + Ser221Glu + Thr223Ser |
| Gly205Gln + Ser207Glu + Thr211Gly + Thr217Gly + Ser221Glu |
| Thr206Gln + Ser207Glu + Ile208Ala + Leu209Cys + Ile220Glu |
| Thr211Gln + Arg218Glu + Ser219Asp + Ile220Asp + Gly222Ser |
| Gly205Asn + Thr206Pro + Ser207Asp + Ser219Glu + Gly222Gln |
| Pro204Ser + Ser207Asp + Ser219Asp + Ile220Met + Thr223Pro |
| Thr206Asn + Ser207Glu + Ile208Thr + Ile213Gly + Ser219Glu |
| Gly205Gln + Leu209Asn + Thr217Asp + Arg218Glu + Ser219Asp |
| Pro204Gly + Ile208Val + Ile213Asp + Gly214Glu + Ser216Asp |
| Pro204Ser + Ile220His + Ser221Glu + Gly222Glu + Thr223Glu |
| Thr206Asp + Trp212Val + Ile220Glu + Ser221Asp + Thr223Pro |
| Thr206Glu + Ser207Asp + Gly214Asn + Ile220Asp + Thr223Asn |
| Ile208Leu + Leu209Val + Thr211Ser + Gly214Asp + Ser216Glu |
| Thr211Ser + Ile213His + Gly214Asp + Ser216Asp + Ile220Gln |
| Gly205Pro + Thr206Ser + Leu209Glu + Thr217Asn + Arg218Glu |
| Gly205Ser + Leu209Asp + Gly214Ser + Gly215Ser + Arg218Asp |
| Ser207Glu + Leu209Gly + Trp212Phe + Ser219Glu + Ser221Glu |
| Gly203Pro + Pro204Asn + Thr211Ser + Ile213Glu + Ser216Glu |
| Thr206Glu + Ser207Asp + Ile208Ala + Gly215Pro + Ser219Glu |
| Thr206Glu + Leu209Ser + Trp212Ile + Ile220Thr + Gly222Glu |
| Thr206Asp + Ser207Asp + Ile208Leu + Ile213Pro + Gly222Glu |
| Gly203Ser + Thr206Asp + Ser207Glu + Ile220Gln + Gly222Glu |
| Thr211Gly + Ile213Ala + Gly214Glu + Ser216Glu + Thr217Asp |
| Ser207Asp + Thr211Gln + Arg218Glu + Ser219Glu + Ile220Val |
| Ser207Glu + Leu209Gln + Gly214Gln + Ile220Val + Gly222Gln |
| Ser207Glu + Leu209Glu + Thr211Gln + Gly214Gln + Thr217Gln |
| Gly205Gln + Ser207Glu + Thr211Ser + Arg218Asp + Ile220Glu |
| Leu209Glu + Thr217Pro + Ser219Asp + Ser221Glu + Gly222Ser |
| Thr211Gly + Gly214Asn + Ser219Glu + Ile220Leu + Ser221Asp |
| Gly203Pro + Ile208Gln + Gly214Pro + Ser219Asp + Ser221Glu |
| Pro204Asn + Leu209Ile + Ser219Glu + Ser221Asp + Gly222Ser |
| Thr211Ser + Trp212Gln + Gly214Gln + Ser219Asp + Ser221Asp |
| Leu209Ala + Gly214Pro + Ser219Glu + Ile220Met + Ser221Glu |
| Pro204Gly + Gly205Gln + Ile213Val + 3er216Asp + Arg218Glu |
| Pro204Gly + Thr206Pro + Thr211Asn + Ser216Glu + Arg218Glu |
| Thr206Asp + Ile208Thr + Leu209Ala + Thr217Asn + Ile220Asp |
| Pro204Gln + Thr206Glu + Ile208Pro + Trp212His + Ile220Glu |
| Thr206Gln + Thr211Ser + Thr217Asp + Ser219Asp + Thr223Pro |
| Gly203Ser + Pro204Ser + Gly205Pro + Gly215Asp + Thr217Glu |
| Gly203Pro + Pro204Gln + Gly215Glu + Thr217Glu + Gly222Gln |
| Pro204Ser + Leu209Met + Gly215Glu + Thr217Asp + Thr223Asn |
| Pro204Gly + Trp212Leu + Gly214Ser + Ser221Asp + Thr223Asp |
| Leu209Ser + Thr211Asn + Arg218Asp + Ile220Glu + Ser221Glu |
| Ile208Gly + Leu209Asn + Ser219Asp + Ser221Glu + Gly222Asp |
| Pro204Gly + Ile208Leu + Gly215Asp + Ser216Glu + Arg218Asp |
| Pro204Gln + Ile208Gly + Gly215Asp + Ser216Glu + Arg218Glu |
| Thr206Gly + Ile213Ser + Ser216Glu + Arg218Asp + Ser219Glu |
| Pro204Gln + Thr206Glu + Ser207Asp + Thr211Asn + Thr223Glu |
| Pro204Gly + Gly205Ser + Ser207Glu + Arg218Asp + Ser221Asp |
| Thr206Asp + Ile213Thr + Gly214Ser + Ser219Asp + Gly222Glu |
| Gly203Asn + Thr206Asn + Ile213Pro + Gly214Glu + Thr217Asp |
| Pro204Ser + Ile213Gly + Gly214Glu + Thr217Asp + Ile220Ala |
| Ser207Glu + Thr217Asp + Arg218Asp + Ile220Ala + Thr223Ser |
| Ser207Asp + Leu209Ser + Trp212Val + Gly215Ser + Arg218Glu |
| Pro204Asn + Ser207Glu + Leu209Val + Trp212Phe + Arg218Asp |
| Gly205Ser + Ser207Glu + Gly215Gln + Arg218Glu + Thr223Asn |
| Gly205Ser + Leu209Asp + Ile213Pro + Gly215Asn + Ser221Asp |
| Gly205Pro + Ser207Glu + Leu209Glu + Thr217Ser + Gly222Asp |
| Ser207Asp + Leu209Asp + Thr217Gly + Gly222Asp + Thr223Ser |
| Gly203Asn + Ile208Ser + Leu209Asp + Ser216Glu + Ser219Asp |
| Leu209Ala + Trp212Ser + Gly214Glu + Gly215Glu + Arg218Glu |
| Gly205Gln + Thr206Glu + Ile213Gln + Arg218Glu + Ser221Glu |
| Pro204Gly + Leu209Asn + Gly215Pro + Thr217Asp + Ile220Asp |
| Thr206Pro + Trp212Ala + Arg218Asp + Ser219Glu + Gly222Asp |
| Gly203Asn + Gly205Pro + Trp212Asn + Arg218Glu + Ser221Asp |
| Thr206Gly + Ile208Ala + Trp212Tyr + Arg218Asp + Ser221Glu |
| Gly205Gln + Thr211Ser + Arg218Asp + Ser221Glu + Thr223Pro |
| Gly205Pro + Thr211Pro + Trp212Pro + Arg218Glu + Ser221Glu |
| Gly203Ser + Arg218Asp + Ile220Asn + Ser221Asp + Thr223Ser |
| Trp212His + Ile213Asn + Gly214Glu + Thr217Glu + Ser219Glu |
| Gly205Pro + Ile213Pro + Gly215Asp + Arg218Glu + Ser219Asp |
| Pro204Ser + Gly215Asp + Arg218Glu + Ser219Glu + Gly222Asn |
| Ser207Glu + Gly214Gln + Ser216Asp + Arg218Glu + Gly222Gln |
| Ser207Asp + Gly215Pro + Ser216Glu + Thr217A5n + Arg218Asp |
| Gly205Ser + Ile208Cys + Leu209Ala + Gly215Asp + Arg218Asp |
| Gly203Asn + Ser207Asp + Ser216Glu + Ser219Asp + Gly222Pro |
| Ser207Glu + Leu209Ile + Ser216Glu + Thr217Gly + Ser219Glu |
| Leu209Asp + Trp212Pro + Gly214Glu + Ser216Glu + Ile220Cys |
| Gly203Gln + Thr206Gly + Leu209Ser + Ser216Glu + Ser219Glu |
| Ile208Leu + Gly214Asn + Ser216Glu + Thr217Ser + Ser219Glu |
| Leu209Ser + Ser216Glu + Thr217Ser + Ser219Glu + Ile220His |
| Pro204Gln + Leu209Pro + Gly214Ser + Ser216Glu + Ser219Asp |
| Thr206Gly + Ile208Met + Gly215Asp + Arg218Asp + Ile220Glu |

TABLE 27

| Loop 6 - Sextuple Substitution Variants |
|---|
| Gly203Asn + Thr206Asn + Ile208Asn + Trp212Asn + Ile213Leu + Ser221Glu |
| Pro204Gin + Gly205Gln + Ile208Ala + Leu209Pro + Ser216Asp + Gly222Pro |
| Gly203Gln + Gly205Asn + Gly215Ser + Thr217Ser + Ile220Met + Ser221Asp |
| Ile208Pro + Leu209Ala + Gly215Gln + Arg218Asp + Ile220Val + Thr223Ser |
| Gly203Ser + Leu209Cys + Trp212Tyr + Ser216Asp + Thr217Asn + Ile220Val |
| Gly203Gln + Gly205Ser + Leu209Ala + Ile213Met *+ Gly215Asn + Gly222Asn |
| Gly203Pro + Gly205Ser + Leu209Ala + Trp212Ala + Gly214Gln + Ser219Asp |
| Gly203Pro + Leu209Ile + Thr211Pro + Ile213Val + Gly215Pro + Ile220Pro |
| Thr206Ser + Ile208Asn + Thr211Gln + Ile213Gly + Ile220Leu + Ser221Asp |
| Pro204Ser + Gly205Pro + Ile208Thr + Gly215Asp + Ile220His + Thr223Gly |
| Gly203Pro + Pro204Gln + Leu209Met + Thr211Pro + Ser219Asp + Ile220Cys |
| Pro204Asn + Thr206Asn + Ser207Asp + Thr211Gln + Gly214Ser + Ile220Pro |
| Gly203Ser + Leu209Pro + Trp212Met + Ile213Cys + Thr217Pro + Arg218Glu |
| Pro204Asn + Gly205Ser + Ile208Ala + Ile213Pro + Gly215Ser + Ile220Gly |
| Gly203Ser + Gly205Asn + Ser207Glu + Thr211Ser + Trp212Val + Thr217Asn |
| Gly203Gln + Pro204Asn + Ile208His + Leu209Pro + Ile213Leu + Gly222Asn |
| Gly205Asn + Thr206Gly + Ile208Pro + Thr211Pro + Trp212Ile + Thr223Asn |
| Gly205Gln + Thr206Ser + Ile208Gln + Ser221Asp + Gly222Gln + Thr223Pro |
| Ile208Leu + Trp212Asn + Ile213Thr + Gly214Ser + Thr217Gln + Ser219Glu |
| Gly203Gln + Pro204Gln + Leu209His + Ser219Glu + Gly222Asn + Thr223Gln |
| Pro204Gln + Gly205Asn + Ile208Cys + Leu209Ile + Ile220Asn + Thr223Glu |

TABLE 27-continued

Loop 6 - Sextuple Substitution Variants

Gly203Pro + Gly205Gln + Thr206Gly + Thr211Gln + Trp212Pro + Gly215Glu
Thr206Gln + Ile208Leu + Thr211Gln + Gly214Asn + Ile220Asn + Thr223Asn
Ile208Val + Leu209Cys + Thr211Ser + Ile213Gly + Gly214Asp + Thr223Gly
Pro204Ser + Gly205Asn + Leu209Ser + Thr217Gly + Arg218Glu + Gly222Ser
Pro204Ser + Gly205Gln + Leu209His + Thr211Gln + Gly214Ser + Ser221Glu
Ile208His + Leu209Cys + Thr211Ser + Trp212Ser + Gly214Glu + Gly222Asn
Ile208Gln + Leu209Gly + Trp212Phe + Thr217Pro + Ile220Thr + Gly222Glu
Gly205Pro + Ser207Glu + Ile208Met + Leu209Met + Trp212Cys + Ile220Asn
Pro204Ser + Thr206Asn + Ile208Gln + Trp212Phe + Ser219Glu + Thr223Gly
Gly205Pro + Ile208Cys + Trp212Ile + Thr217Gln + Ile220Leu + Gly222Pro
Pro204Ser + Gly205Ser + Ile208Cys + Ile213Pro + Ser221Asp + Thr223Gln
Pro204Ser + Thr206Gln + Trp212Met + Gly214Ser + Ser221Asp + Thr223Ser
Gly205Ser + Ile208Gln + Ile213Cys + Gly215Pro + Thr217Gln + Thr223Asp
Pro204Asn + Gly205Pro + Ile208Ser + Ile213Asp + Ile220Thr + Gly222Gln
Pro204Asn + Ile208Ala + Leu209Ser + Thr211Gly + Gly215Ser + Ser219Glu
Gly203Gln + Gly205Gln + Thr206Gln + Ser207Glu + Ile208Ala + Ile220Ala
Leu209Ser + Thr211Gly + Trp212Tyr + Ile213His + Ser216Asp + Thr223Pro
Pro204Gln + Thr206Ser + Ile208Met + Leu209Cys + Thr211Ser + Gly214Asp
Gly203Asn + Leu209Gln + Thr211Ser + Gly215Pro + Ile220Cys + Gly222Pro
Leu209His + Thr211Asn + Trp212Ile + Ile213Ala + Ser219Glu + Thr223Gly
Pro204Gln + Ile208His + Trp212Gln + Gly215Ser + Ser221Asp + Thr223Gln
Ile208Cys + Leu209Met + Trp212Ser + Ile213Gln + Ser216Glu + Thr223Pro
Gly205Ser + Leu209Met + Trp212Gly + Arg218Glu + Ile220Gly + Gly222Asn
Pro204Asn + Trp212Gln + Gly215Ser + Ser216Glu + Thr217Asn + Ile220Asn
Gly203Pro + Ile208Val + Leu209Asp + Trp212Ala + Ile220Gln + Thr223Gly
Gly203Gln + Gly2o5Pro + Ile208Gly + Trp212Ser + Thr217Asp + Gly222Asn
Gly205Ser + Leu209Thr + Thr217Gln + Ile220Met + Gly222Gln + Thr223Glu
Gly203Asn + Pro204Ser + Gly205Pro + Trp212Pro + Gly215Gln + Thr217Glu
Pro204Ser + Gly205Ser + Leu209Asn + Ser216Glu + Ile220Leu + Gly222Asn
Gly203Gln + Leu209Thr + Trp212Leu + Ile213Gly + Ser219Glu + Ile220His
Ile208Gln + Trp212Gly + Ile213Asn + Thr217Pro + Gly222Ser + Thr223Asp
Pro204Ser + Ile208His + Thr211Gly + Ile213Met + Gly214Gln + Ser216Asp
Gly203Asn + Gly205Pro + Leu209Glu + Trp212Ile + Ile213Val + Gly215Pro
Gly203Asn + Pro204Gln + Leu209Met + Trp212Ser + Thr217Glu + Arg218Glu
Leu209Gln + Trp212Gln + Gly214Asn + Gly215Ser + Gly222Glu + Thr223Glu
Gly205Pro + Thr211Gly + Trp212Val + Arg218Glu + Ser219Asp + Ile220Pro
Gly203Asn + Pro204Gln + Gly205Gln + Gly214Pro + Arg218Glu + Ser219Asp
Gly205Pro + Thr211Gln + Gly215Asn + Thr217Ser + Arg218Glu + Ser219Glu
Pro204Asn + Gly205Ser + Ile208Gly + Thr217Ser + Arg218Glu + Ser219Asp
Thr206Pro + Gly214Ser + Thr217Gln + Arg218Glu + Ser219Glu + Thr223Asn
Thr206Gln + Leu209Glu + Thr211Asn + Trp212Ile + Gly215Ser + Ser219Asp
Leu209Glu + Thr211Gln + Ile213Val + Gly215Gln + Ser219Glu + Gly222Pro
Pro204Gln + Ser207Glu + Ile208Pro + Thr211Gly + Ile220Pro + Ser221Asp
Pro204Asn + Thr206Gln + Ser207Glu + Ile208Ala + Leu209Cys + Ile220Glu
Thr206Glu + Thr211Gln + Ile213Pro + Gly214Asn + Ser221Asp + Gly222Gln
Gly203Asn + Pro204Gln + Leu209Asp + Gly215Pro + Ser219Asp + Ile220Asp
Ser207Glu + Ile208Ala + Thr211Gly + Trp212Ser + Ser219Glu + Ile220Gln
Ser207Glu + Leu209Gly + Thr211Pro + Gly215Asn + Ser219Glu + Ile220Val
Ser207Glu + Ile208Asn + Leu209Cys + Gly215Asn + Ser219Glu + Thr223Ser
Gly203Asn + Gly205Ser + Ser207Asp + Thr217Ser + Ser219Asp + Ile220Leu
Gly203Asn + Pro204Asn + Ser207Asp + Leu209Thr + Ser219Asp + Thr223Gln
Gly203Pro + Ile208Pro + Thr211Ser + Ser221Asp + Gly222Asp + Thr223Asp
Gly205Ser + Ser207Glu + Leu209Glu + Thr217Ser + Ser219Glu + Gly222Asn
Thr206Pro + Leu209Ser + Thr211Pro + Ile213Glu + Gly215Glu + Ile220Ala
Gly203Ser + Ile208Ser + Leu209His + Trp212Gly + Gly214Asp + Ser216Glu
Gly203Ser + Gly205Ser + Trp212Ala + Gly214Glu + Gly215Ser + Ser216Asp
Gly205Gln + Ser207Glu + Ile208Ser + Leu209Gly + Ser219Asp + Ser221Glu
Thr206Pro + Ser207Glu + Ile208His + Trp212Ala + Ser219Glu + Ser221Asp
Gly205Ser + Ser207Asp + Leu209Cys + Thr217Pro + Ser221Asp + Gly222Glu
Ser207Glu + Leu209Asp + Thr211Gln + Trp212Gln + Thr217Gln + Ile220Glu
Leu209Asp + Thr211Gln + Gly214Pro + Thr217Glu + Ser219Glu + Thr223Gln
Gly203Ser + Thr206Glu + Ser207Glu + Gly215Ser + Ser219Asp + Ile220Thr
Gly205Ser + Thr206Glu + Ser207Glu + Thr211Gly + Ile220Val + Gly222Glu
Thr206Glu + Ser207Asp + Leu209Ser + Trp212Ile + Ile220Thr + Gly222Glu
Gly203Pro + Ser207Glu + Leu209Asn + Thr217Gln + Arg218Asp + Ser219Asp
Gly205Gln + Thr206Gln + Ser207Asp + Arg218Glu + Ser219Asp + Ile220Pro
Pro204Ser + Gly205Gln + Ser207Asp + Thr217Asn + Arg218Asp + Ser219Asp
Gly203Pro + Thr206Pro + Ser207Glu + Ile208Asn + Leu209Asp + Thr217Ser
Gly203Asn + Pro204Gln + Thr206Asp + Trp212Phe + Ser221Glu + Thr223Asp
Pro204Gln + Gly205Gln + Ser207Glu + Leu209Glu + Trp212Met + Ser221Glu
Gly203Asn + TrpIle + Gly214Ser + Ser219Asp + Ser221Glu + Thr223Gln
Gly205Gln + Thr206Gln + Ile208Pro + Thr217Pro + Ser219Asp + Ser221Asp
Gly203Asn + Thr211Asn + Gly215Pro + Ser219Asp + Ser221Asp + Gly222Asn
Pro204Ser + Trp212His + Gly214Gln + Ser219Glu + Ser221Glu + Gly222Glu
Gly203Pro + Thr211Gln + Ile213Met + Ser219Glu + Ser221Asp + Gly222Ser
Ile208Leu + Thr211Gly + Gly214Pro + Gly215Asn + Ser216Glu + Arg218Asp
Ile208Ala + Leu209Pro + Trp212Pro + Ser216Glu + Arg218Asp + Thr223Pro

TABLE 27-continued

| Loop 6 - Sextuple Substitution Variants |
|---|
| Gly205Gln + Ile208Asn + Gly215Ser + Ser216Glu + Arg218Glu + Thr223Asn |
| Gly203Ser + Thr206Gly + Gly214Pro + Gly215Gln + Ser216Asp + Arg218Asp |
| Gly203Ser + Thr206Pro + Trp212Pro + Gly215Asn + Ser216Glu + Arg218Glu |
| Gly203Asn + Gly205Asn + Leu209Val + Ile220Glu + Gly222Glu + Thr223Ser |
| Pro204Gly + Gly205Pro + Leu209Ile + Ile213Met + Ser221Asp + Thr223Glu |
| Gly205Ser + Trp212Tyr + Gly214Pro + Arg218Glu + Ser219Asp + Ser221Asp |
| Gly205Gln + Ile208Ala + Leu209Cys + Arg218Glu + Ser219Asp + Ser221Asp |
| Gly205Gln + Leu209Val + Trp212Cys + Ile220Asp + Ser221Glu + Thr223Asp |
| Pro204Gln + Thr211Gln + Gly215Glu + Thr217Asp + Arg218Glu + Thr223Asn |
| Gly203Gln + Leu209Asn + Ser216Asp + Arg218Glu + Ser219Asp + Thr223Pro |
| Ile208Ala + Leu209Pro + Gly214Ser + Ser216Asp + Arg218Glu + Ser219Asp |
| Pro204Asn + Ile208Gly + Thr211Gln + Ser216Asp + Arg218Glu + Ser219Glu |
| Gly203Ser + Ile208Ala + Trp212Ser + Ser216Glu + Arg218Asp + Ser219Glu |
| Gly205Pro + Thr211Ser + Ser216Glu + Thr217Asp + Ser219Asp + Gly222Asn |
| Pro204Gln + Leu209Ala + Gly215Gln + Ser216Glu + Thr217Asp + Ser219Asp |
| Pro204Asn + Ser207Glu + Thr211Gln + Gly214Ser + Gly222Glu + Thr223Asn |
| Gly205Asn + Ser207Asp + Trp212His + Gly214Ser + Gly222Glu + Thr223Glu |
| Gly203Ser + Ser207Glu + Thr211Ser + Ile213Ala + Arg218Asp + Ser221Asp |
| Gly203Gln + Thr206Glu + Trp212Ile + Ile213Asn + Ser219Asp + Gly222Glu |
| Ile208Ala + Leu209Met + Thr211Pro + Ile213Thr + Gly214Glu + Thr217Glu |
| Gly203Ser + Pro204Ser + Gly205Ser + Gly214Asp + Gly215Pro + Thr217Glu |
| Gly203Asn + Ile208Met + Ile213Cys + Gly214Asp + Thr217Glu + Thr223Asn |
| Pro204Asn + Leu209Ile + Trp212Val + Ile213Asp + Gly215Asp + Arg218Glu |
| Ser207Asp + Ile208Met + Thr211Pro + Trp212Ala + Gly215Asn + Arg218Glu |
| Pro204Asn + Thr206Gln + Ser207Glu + Gly214Asn + Gly215Gln + Arg218Glu |
| Gly203Gln + Gly205Pro + Ser207Asp + Ile208Gly + Arg218Glu + Gly222Gln |
| Gly205Pro + Thr206Asn + Ser207Asp + Trp212Tyr + Arg218Asp + Ile220Thr |
| Pro204Asn + Gly205Pro + Ser207Glu + Ile20GGln + Thr217Pro + Arg218Asp |
| Thr206Gln + Ser207Glu + Trp212Ser + Thr217Asn + Arg218Glu + Ile220Ala |
| Gly205Pro + Thr206Glu + Leu209Thr + Gly214Gln + Arg218Asp + Ser219Glu |
| Gly203Ser + Pro204Asn + Ser207Asp + Gly215Gln + Thr217Asp + Ile220Asp |
| Ile208Gly + Thr211Gln + Ile213Glu + Arg218Glu + Gly222Ser + Thr223Gln |
| Gly203Pro + Thr206Gly + Gly214Gln + Ser219Glu + Ser221Asp + Thr223Asp |
| Thr211Gly + Trp212Phe + Ser219Asp + Ile220Pro + Ser221Glu + Thr223Glu |
| Leu209Ala + Ile213Ala + Ser219Asp + Ile220Gln + Ser221Asp + Thr223Asp |
| Pro204Gln + Leu209Glu + Trp212Met + Gly214Ser + Gly215Asp + Thr217Glu |
| Ile208Met + Ile213Ser + Thr217Glu + Ile220Asp + Ser221Asp + Thr223Gln |
| Leu209Asp + Thr211Asn + Ile213Asp + Arg218Glu + Ile220Leu + Gly222Ser |
| Gly203Pro + Gly205Gln + Thr217Asp + Arg218Glu + Ile220Ala + Ser221Asp |
| Trp212Cys + Ile213Gly + Arg218Glu + Ser219Glu + Ile220Pro + Gly222Glu |
| Thr206Gln + Ile208Gly + Leu209Ile + Arg218Glu + Ser219Glu + Gly222Asp |
| Gly203Gln + Ile208Met + Ser219Glu + Ile220Glu + Gly222Pro + Thr223Glu |
| Gly203Gln + Gly205Asn + Thr211Gln + Ser219Asp + Ile220Glu + Thr223Glu |
| Pro204Asn + Gly205Pro + Leu209Ser + Gly214Ser + Arg218Glu + Ser221Glu |
| Ile208Thr + Leu209Asn + Trp212Asn + Arg218Asp + Ser221Glu + Gly222Asn |
| Gly203Ser + Pro204Gln + Gly205Asn + Thr211Gly + Arg218Asp + Ser221Glu |
| Pro204Asn + Thr206Pro + Gly214Pro + Arg218Glu + Ser221Glu + Thr223Asn |
| Thr206Asp + Ile213Gln + Gly215Asn + Thr217Asp + Ser219Asp + Thr223Ser |
| Ile213Met + Gly214Asp + Gly215Ser + Thr217Glu + Ser219Asp + Ile2205er |
| Pro204Asn + Gly205Gln + Ser207Asp + Gly215Pro + Ser219Glu + Thr223Glu |
| Pro204Ser + Thr206Gln + Ser207Glu + Thr217Gly + Ser219Asp + Thr223Asp |
| Pro204Gln + Trp212Leu + G1Y215Glu + Thr217Pro + Arg218Asp + Ser219Asp |
| Gly203Asn + Thr211Gly + Gly214Asn + Gly215Pro + Ser219Asp + Gly222Asp |
| Gly203Pro + Trp212Ile + Gly214Asn + Ser219Glu + Ile220Pro + Gly222Glu |
| Thr206Glu + Leu209Ile + Gly215Asn + Ser219Asp + Ile220Cys + Thr223Asp |
| Gly203Asn + Ser207Asp + Gly214Gln + Ser216Glu + Arg218Asp + Ile220Thr |
| Ser207Glu + Ile208Cys + Ile213His + Gly214Ser + Ser216Asp + Arg218Glu |
| Thr206Gln + Ile208Ser + Leu209Asp + Gly215Glu + Arg218Asp + Ile220Ala |
| Gly205Ser + Ile213Cys + Gly214Asp + Arg218Glu + Ser219Asp + Gly222Gln |
| Pro204Asn + Gly214Asp + Arg218Asp + Ser219Asp + Gly222Pro + Thr223Gln |
| Pro204Gly + Thr211Asn + Ile213Ala + Gly215Asp + Arg218Glu + Ile220Gly |
| Ser207Glu + Leu209Ile + Ser216Glu + Thr217Gly + Ser219Asp + Ile220Gly |
| Gly205Ser + Ser207Asp + Thr211Gly + Ser216Glu + Ser219Asp + Ile220Asn |
| Pro204Gln + Gly205Ser + Thr206Asn + Leu209Glu + Trp212Gly + Ser216Asp |
| Gly205Pro + Trp212Gly + Ile213His + Gly214Asp + Ser216Glu + Ser219Glu |
| Pro204Ser + Thr206Asn + Ile213Ala + Ser216Asp + Ser219Glu + Thr223Gln |
| 11e208Asn + Trp212Asn + Gly215Asn + Ser216Glu + Ser219Glu + Ile220Ser |
| Ile208Leu + Thr211Gly + Gly214Gln + Ser216Glu + Ser219Glu + Gly222Pro |
| Pro204Ser + Thr206Ser + Ser216Asp + Thr217Pro + Ser219Glu + Thr223Asn |
| Leu209Val + Trp212Cys + Gly214Ser +Arg218Glu + Ile220Glu + Thr223Asp |
| Gly205Gln + Trp212Met + Gly215Asp + Arg218Glu + Ile220Glu + Gly222Ser |
| Gly205Pro + Thr206Ser + Ser207Glu + Leu209Gly + Gly214Ser + Thr223Glu |
| Thr206Asp + Leu209Glu + Thr211Gln + Thr217Gln + Ile220Met + Thr223Glu |
| Pro204Gly + Ile208Cys + Thr217Ser + Arg218Glu + Ser221Glu + Thr223Asp |
| Ser207Glu + Leu209Val + Ile213Gly + Ser216Glu + Thr217Asp + Gly222Gln |
| Ile208Thr + Ser216Glu + Ser219Glu + Ile220Leu + Ser221Glu + Thr223Pro |
| Gly203Gln + Gly205Gln + Ile213Ala + Ser216Glu + Ser219Asp + Ser221Asp |

TABLE 27-continued

| Loop 6 - Sextuple Substitution Variants |
|---|
| Gly203Gln + Pro204Gln + Thr206Asp + Leu209Asn + Arg218Glu + Gly222Glu |
| Gly205Gln + Ile213Ala + Gly215Glu + Ser216Glu + Ile220Glu + Gly222Asn |
| Thr206Asn + Ile208Ala + Leu209Asp + Ile213Glu + Gly214Glu + Gly222Ser |
| Gly203Ser + Pro204Ser + Ile208Cys + Ile213Glu + Gly215Glu + Ser219Glu |
| Thr206Pro + Leu209Cys + Ile213Glu + Gly215Glu + Thr217Ser + Ser219Glu |

TABLE 28

| Loop 6 - Heptuple Subst1tut1on Mutation Variants |
|---|
| Pro204Asn + Leu209Thr + Thr211Gln + Trp212His + Gly215Asp + Ile220Val + Thr223Ser |
| Pro204Gly + Gly205Asn + Ile208Leu + Thr211Asn + Trp212Gly + Gly214Pro + Arg218Asp |
| Gly203Pro + Thr206Gly + Ile208Pro + Thr211Gln + Thr217Glu + Ile220Met + Thr223Asn |
| Pro204Gln + Ile208Ala + Leu209Gln + Thr211Ser + Gly214Ser + Ser219Glu + Thr223Pro |
| Pro204Gly + Gly205Pro + Thr206Glu + Ile208Pro + Leu209Val + Ile213His + Ile220Leu |
| Gly205Gln + Thr206Ser + Ile208Leu + Thr211Ser + Gly214Asn + Gly222Pro + Thr223Glu |
| Pro204Gly + Gly205Ser + Ile208Ala + Trp212Leu + Thr217Gln + Arg218Asp + Thr223Asn |
| Ile208Asn + Thr211Asn + Trp212Val + 11e213Asp + Ile220Ala + Gly222Pro + Thr223Pro |
| Pro204Gly + Ile208Cys + Trp212Cys + Ile213Gly + Thr217Gln + Ser219Asp + Ile220Ala |
| Gly205Pro + 11e208Asn + Thr211Pro + Trp212Phe + Ile220Met + Ser221Glu + Gly222Ser |
| Gly203Gln + Pro204Ser + Thr206Ser + Ile208Val + Trp212Tyr + Ile220Gly + Ser221Glu |
| Pro204Ser + Gly205Pro + Leu209Met + Trp212Leu + 11e213Asp + Gly215Gln + Gly222Ser |
| Gly205Pro + Ile208Pro + Leu209Thr + Thr211Ser + Trp212Asn + Ser216Glu + Ile220Ala |
| Gly203Gln + Gly205Ser + Thr206Gly + Trp212Ala + Gly215Pro + Thr217Ser + Ser221Glu |
| Gly203Ser + Ile208Cys + Leu209Met + Trp212Ser + Gly215Pro + Ser216Glu + Thr223Pro |
| Gly205Ser + Thr206Gly + Trp212Gly + Thr217Gly + Arg218Glu + Ile220Gly + Gly222Asn |
| Gly203Ser + Gly205Pro + Thr206Gly + Gly214Gln + Ser216Asp + Ile220Gly + Thr223Ser |
| Pro204Asn + Trp212Gln + Ile213Thr + Gly215Ser + Ser216Glu + Thr217Asn + Ile220Asn |
| Gly203Asn + Pro204Gly + Thr206Asn + Ile208Leu + Thr211Pro + Ile220Leu + Gly222Pro |
| Gly203Asn + Gly205Asn + Thr211Ser + Trp212Met + Ile213Glu + Gly214Asn + Thr223Asn |
| Pro204Asn + Gly205Pro + Ile208Ser + Thr211Gln + Ile213Gln + Gly215Gln + Arg218Glu |
| Gly203Gln + Gly205Gln + Thr206Ser + Ile208Val + Trp212Gln + Thr217Pro + Ile220Glu |
| Pro204Gly + Gly205Pro + Ile208Met + Thr211Ser + Ile213Gly + Gly215Pro + Ser216Glu |
| Gly203Gln + Gly205Ser + Thr206Ser + Ile208Ala + Ile213Ala + Ile220Met + Thr223Glu |
| Pro204Gly + Thr206Gln + Leu209Ala + Thr211Gln + Thr217Asn + Arg218Glu + Ile220Pro |
| Gly203Gln + Pro204Gly + Gly205Ser + Ser207Asp + Leu209Asn + Gly214Ser + Gly215Pro |
| Gly203Gln + Gly205Gln + Leu209Met + Trp212Thr + Gly214Gln + Ile220Asn + Gly222Glu |
| Gly203Ser + Thr206Asp + Ile208Leu + Thr211Pro + Gly214Ser + Gly215Ser + Gly222Gln |
| Pro204Gln + Thr206Gly + Ile208Asn + Trp212Gly + Ile213Pro + Thr217Pro + Arg218Asp |

TABLE 28-continued

| Loop 6 - Heptuple Subst1tut1on Mutation Variants |
|---|
| Gly205Asn + Ile208Thr + Thr211Gly + Ile213His + Thr217Gly + Arg218Glu + Thr223Asn |
| Gly205Asn + Thr206Pro + Ile208Ala + Leu209Ala + Trp212Leu + Gly215Pro + Gly222Asp |
| Gly203Pro + Thr206Gln + Ile208Asn + Leu209Cys + Gly215Glu + Gly222Pro + Thr223Ser |
| Pro204Gln + Ile208Ala + Trp212Asn + Ile213Ser + Gly215Ser + Ser219Asp + Ile220Asp |
| Gly203Ser + Thr211Ser + Trp212Met + Arg218Asp + Ser219Asp + Gly222Asn + Thr223Asn |
| Gly203Ser + Gly205Pro + Thr206Pro + Ile208Leu + Arg218Glu + Ser219Glu + Ile220Ala |
| Pro204Gly + Thr211Asn + Gly214Pro + Ser216Asp + Thr217Glu + Ile220Gln + Gly222Pro |
| Gly203Asn + Gly205Pro + Leu209Val + Thr211Pro + Gly215Asn + Ser216Glu + Thr217Asp |
| Pro204Gly + Gly205Gln + Thr211Ser + Trp212Met + Gly215Asp + Ser216Glu + Thr217Pro |
| Pro204Asn + Thr206Gly + Ile208Met + Leu209Asp + Ser219Glu + Ile220His + Thr223Pro |
| Gly205Gln + Thr206Glu + Ile208Thr + Leu209Thr + Thr211Gln + Trp212Cys + Ser221Asp |
| Pro204Gly + Thr206Glu + Leu209Ala + Trp212Met + Ile220Val + Ser221Asp + Gly222Ser |
| Gly205Gln + Thr206Glu + Thr211Asn + Trp212Ser + Thr217Gln + Ser221Asp + Thr223Gln |
| Ser207Glu + Leu209Thr + Ile213Gln + Gly214Gln + Gly215Asn + Ser219Glu + Ile220Glu |
| Thr206Gln + Ser207Glu + Leu209Ile + Ile213Ala + Gly214Ser + Ile220Thr + Ser221Asp |
| Pro204Asn + Thr206Gln + Ser207Glu + Ile208Ala + Leu209Cys + Thr211Gly + Ile220Glu |
| Thr206Pro + Ser207Glu + Thr211Gln + Gly214Pro + Gly215Ser + Thr217Gly + Ser219Glu |
| Pro204Asn + Ser207Glu + Leu209Gly + Thr211Asn + Gly215Asn + Ser219Glu + Ile220Val |
| Pro204Gln + Gly205Ser + Leu209Ser + Trp212Gly + Thr217Glu + Arg218Glu + Ser219Asp |
| Gly203Gln + Ser207Asp + Leu209His + Gly214Ser + Gly215Gln + Ser219Asp + Ser221Asp |
| Pro204Gln + Gly205Asn + Ser207Glu + Leu209Gln + Thr211Gly + Ser219Glu + Ser221Asp |
| Gly203Asn + Thr206Glu + Ile208Gln + Leu209Gln + Thr211Pro + Trp212Ile + G1y222Glu |
| Gly203Ser + Thr206Glu + Ser207Asp + Thr211Ser + Trp212Gly + Ile220Gly + Gly222Asp |
| Gly205Pro + Thr206Asp + Ser207Asp + Ile213Pro + Gly214Ser + Gly222Glu + Thr223Asn |
| Gly203Gln + Thr206Asp + Leu209Met + Trp212Leu + Gly214Asn + Gly222Asp + Thr223Glu |
| Pro204Asn + Thr206Gln + Leu209Ser + Ser216Glu + Thr217Asp + Arg218Glu + Ser219Asp |
| Pro204Asn + Thr206Gly + Ser207Glu + Ile208Thr + Gly215Gln + Ile220Asp + Gly222Glu |
| Gly203Pro + Gly205Gln + Thr206Ser + Leu209Asp + Thr211Ser + Ile213Cys + Thr217Asp |
| Gly205Gln + Ser207Glu + Thr211Ser + Trp212Ser + Ile213Gln + Arg218Asp + Ile220Glu |
| Gly203Ser + Pro204Gly + Thr206Glu + Ser207Glu + Ile208Ser + Leu209Asp + Trp212Ala |
| Gly203Ser + Ile208Thr + Leu209Glu + Trp212Tyr + Thr217Gln + Ser219Asp + Ser221Glu |
| Gly203Ser + Gly205Ser + Thr211Ser + Gly215Gln + Thr217Pro + Ser219Glu + Ser221Asp |
| Gly205Gln + Thr206Gly + Leu209Ser + 1le213Gly + Ser219Glu + Ser221Asp + Thr223Gln |
| Pro204Gln + Ser207Asp + Ile208Ser + Ile213Leu + Arg218Glu + Ser219Glu + Ser221Glu |
| Gly203Asn + Trp212Gln + Gly214Pro + Ser216Glu + Arg218Glu + Ile220Leu + Thr223Pro |
| Pro204Asn + Gly205Gln + Thr206Gly + Ile213His + Gly214Ser + Ser216Asp + Arg218Glu |
| Ile208Val + 11e213Met + Gly214Ser + Ser216Asp + Thr217Gly + Arg218Asp + Ile220Met |
| Pro204Ser + Gly205Asn + Ile208Leu + Leu209His + Ser216Asp + Arg218Glu + Thr223Pro |

TABLE 28-continued

Loop 6 - Heptuple Substitution Mutation Variants

Gly203Gln + Ile208Cys + Thr211Pro + Trp212Ser + Gly215Ser + Ser216Glu + Arg218Glu
Gly203Pro + Gly205Ser + Leu209Ile + Thr211Asn + Thr217Glu + Ser219Asp + Ile220His
Gly205Ser + Leu209Cys + Thr211Asn + Gly215Gln + Thr217Glu + Ser219Asp + Gly222Pro
Gly203Gln + Ile208Ala + Trp212Ile + Gly215Gln + Thr217Glu + Ser219Asp + Gly222Pro
Gly203Ser + Thr206Glu + Ser207Glu + Ile208Pro + Ile213Thr + Gly222Glu + Thr223Asp
Gly203Ser + Ile208Gln + Trp212Ser + Ile213Leu + Arg218Asp + Ser219Glu + Ser221Asp
Gly203Asn + Gly205Asn + Trp212Asn + Ile213Glu + Ser216Glu + Thr217Pro + Arg218Asp
Thr206Asn + Leu209Asp + Ile213Met + Ser216Glu + Thr217Glu + Ser219Glu + Ile220Gly
Gly205Pro + Thr211Pro + Trp212Val + Gly214Ser + Ser216Asp + Arg218Glu + Ser219Glu
Thr206Asn + Ser207Asp + Thr211Ser + Ile213Cys + Ile220Met + Ser221Asp + Thr223Asp
Gly203Asn + Ile213Ser + Thr217Asp + Arg218Glu + Ser219Asp + Ser221Asp + Thr223Gln
Thr206Asn + Ser207Glu + Leu209Cys + Trp212Ser + Arg218Glu + Ser221Asp + Gly222Pro
Gly203Gln + Ser207Asp + Gly214Pro + Gly215Pro + Arg218Asp + Ser221Asp + Gly222Ser
Gly203Asn + Thr206Glu + Leu209Gln + Arg218Glu + Ser219Asp + Ser221Glu + Gly222Pro
Gly203Pro + Ser207Glu + Trp212Ser + Gly214Pro + Ser219Glu + Ser221Asp + Thr223Asp
Gly205Gln + Thr211Gln + Ile213Glu + Ser216Glu + Arg218Asp + Ser219Asp + Ile220Ala
Gly203Asn + Pro204Ser + Ser207Glu + Gly215Gln + Thr217Asp + Ile220Asp + Ser221Asp
Gly203Gln + Gly205Asn + Ser207Asp + Leu209Ile + Thr211Gly + Thr217Asp + Arg218Glu
Pro204Gly + Trp212Met + Gly214Asp + Ser216Asp + Thr217Glu + Ser219Asp + Thr223Gln
Ser207Asp + Trp212Tyr + Gly215Asn + Ser216Asp + Arg218Glu + Ser219Glu + Thr223Pro
Thr206Gly + Ser207Asp + Ile208Gln + Ser216Glu + Arg218Glu + Ser219Asp + Ile220Gln
Ser207Glu + Leu209Gln + Thr211Pro + Gly215Pro + Ser216Asp + Arg218Glu + Ser219Asp
Gly205Asn + Ser207Asp + Ile208Val + Gly214Pro + Ser216Asp + Arg218Glu + Ser219Glu
Thr206Asp + Ile208His + Thr211Ser + Trp212Asn + Arg218Asp + Ser219Glu + Gly222Pro
Ile208Gly + Trp212Met + Ile213Gln + Ser216Glu + Arg218Asp + Ser219Asp + Ser221Asp
Gly203Asn + Thr206Glu + Leu209Asp + Thr217Pro + Ile220Ser + Gly222Glu + Thr223Asp
Gly203Asn + Thr206Asp + Ile208His + Thr211Ser + Trp212Phe + Arg218Asp + Ser221Glu
Pro204Asn + Gly214Asn + Gly215Pro + Ser216Glu + Thr217Asp + Arg218Asp + Ser221Asp
Pro204Gln + Gly205Pro + Thr211Asn + Gly215Gln + Ser219Glu + Ser221Asp + Thr223Glu
Ser207Asp + Leu209Val + Trp212Cys + Gly214Ser + Arg218Glu + Ile220Glu + Thr223Asp
Thr206Asn + Ser207Asp + Ile208Ala + Gly215Pro + Arg218Glu + Ser221Glu + Thr223Asp
Pro204Gln + Gly205Asn + Thr206Gln + Leu209Cys + Thr217Asp + Arg218Glu + Ser221Glu
Gly203Pro + Thr206Ser + Ile213His + Ser219Glu + Ile220Cys + Gly222Glu + Thr223Asp
Gly205Ser + Thr211Ser + Trp212Gln + Gly214Ser + Ser219Asp + Ile220Glu + Thr223Asp
Ser207Asp + Leu209Gln + Ile213Gly + Ser216Glu + Ser219Asp + Ile220Ser + Ser221Glu
Ser207Asp + Thr211Pro + Trp212Gln + Ile213Pro + Ser216Asp + Ser219Asp + Ser221Asp
Pro204Gly + Gly205Pro + Ile208Gly + Leu209Glu + Ile213Thr + Thr217Asp + Ser221Glu
Thr206Gln + Ser207Asp + Ile208Cys + Leu209Thr + Arg218Asp + Ser219Asp + Thr223Asp
Gly203Pro + Ile208Asn + Thr211Gln + Ile213Met + Thr217Gln +
Arg218Glu + Ser221Asp
Gly203Asn + Gly205Asn + Thr206Gln + Thr211Gly + Trp212Gln + Arg218Glu + Ser221Glu
Gly203Ser + Ile20aPro + Gly215Pro + Arg218Asp + Ile220Asn + Ser221Glu + Thr223Asn
Thr206Pro + Thr211Pro + Gly214Ser + Gly215Pro + Arg218Asp + Ser221Glu + Thr223Ser
Thr206Asp + Ser207Asp + Trp212Thr + Ile213Cys + Ser216Glu + Thr217Pro + Ser219Asp
Gly205Asn + Thr206Asp + Ser207Asp + Ile213Thr + Ser216Glu + Ser219Glu + Ile220Leu
Thr206Ser + Ile213Met + Gly214Asp + Gly215Ser + Thr217Glu + Ser219Asp + Ile220Glu
Pro204Asn + Thr206Pro + Leu209Glu + Thr217Gly + Arg218Glu + Ser219Asp + Thr223Asp
Pro204Gly + Ser207Glu + Thr211Pro + Gly214Asp + Arg218Asp + Ser219Asp + Thr223Gln
Gly205Pro + Leu209Glu + Thr211Asn + Gly214Asp + Thr217Asp + Ile220Met + Gly222Asn
Pro204Ser + Trp212His + Ile213Asn + Gly214Glu + Thr217Glu + Ser219Glu + Gly222Asn
Gly203Gln + Ser207Glu + Ile208Cys + Gly215Pro + Ser219Glu + Ile220Asn + Thr223Glu
Ser207Glu + Ile208Gly + Ile213Pro + Arg218Asp + Ile220Met + Gly222Asp + Thr223Glu
Thr206Asp + Ser207Glu + Ile208Gly + Thr211Gln + Ser216Asp + Ser221Glu + Thr223Asn
Gly203Asn + Ser207Glu + Trp212Ser + Ile213Asp + Gly215Asn + Ser216Glu + Arg218Glu
Gly203Asn + Leu209Ser + Ile213Val + Thr217Pro + Ser219Asp + Ile220Ala + Gly222Glu
Ile208Met + Thr211Gly + Trp212Leu + Gly214Pro + Gly215Pro + Ser219Asp + Gly222Glu
Ser207Glu + Leu209Ser + Ile213Ser + Gly214Asn + Ser216Asp + Arg218Glu + Ser221Asp
Gly203Ser + Ser207Asp + Ile208Asn + Thr211Asn + Gly214Glu + Ser219Asp + Ile220Asp
Ser207Asp + Thr211Asn + Ile213Ala + Gly215Asp + Thr217Ser + Ser219Glu + Ile220Glu
Pro204Ser + Gly205Asn + Thr211Pro + Thr217Glu + Ser221Asp + Gly222Glu + Thr223Glu
Ser207Glu + Leu209Ala + Gly214Pro + Ser216Glu + Thr217Ser + Arg218Glu + Ile220Leu
Ile208Val + Leu209Glu + Trp212Ser + Gly215Glu + Ser219Asp + Ile220Asp + Gly222Pro
Gly203Gln + Ile213Ser + Gly215Glu + Ser216Asp + Ser219Asp + Gly222Ser + Thr223Gln
Gly205Pro + Leu209Val + Gly214Asn + Ser216Glu + Ser219Asp + Ile220Glu + Gly222Asp
Pro204Asn + Leu209Asp + Ile213Met + Gly214Pro + Thr217Glu + Ser221Glu + Gly222Asp
Gly203Ser + Ser207Glu + Trp212Pro + Gly214Asp + Ser216Asp + Thr217Asp + Ile220Met
Thr206Glu + Thr211Gln + Ile213Pro + Gly214Asp + Thr217Gly + Ser221Asp + Gly222Asp
Ile208Cys + Leu209Ser + Thr211Asn + Ile213Ala + Gly215Asp + Arg218Glu + Ile220Gly
Ile208Thr + Leu209His + Ile213Met + Gly214Glu + Ser221Glu + Gly222Asp + Thr223Asp
Thr206Gln + Gly214Gln + Gly215Glu + Thr217Gly + Arg218Glu + Ser219Glu + Ser221Asp
Pro204Ser + Thr206Ser + Ile213Cys + Gly215Glu + Ser216Glu + Thr217Glu + Thr223Asp
Thr206Gln + Ile208Met + Trp212Gly + Gly214Asp + Ser216Asp + Thr217Pro + Ser219Asp
Ser207Glu + Ile208Thr + Thr211Gln + Trp212Gln + Gly215Asp + Ser219Asp + Ser221Asp
Gly203Gln + Pro204Gln + Ser207Glu + Ile208Cys + Gly214Glu + Ser219Asp + Ser221Glu
Ser207Asp + Ile208Thr + Thr211Asn + Gly215Glu + Ser219Glu + Ile220Met + Ser221Glu
Pro204Ser + Ser207Glu + Gly214Ser + Gly215Asp + Ser219Asp + Ile220Met + Ser221Glu
Ser207Asp + Ile208Leu + Trp212Ile + Ile213Asp + Thr217Asn + Arg218Glu + Ser221Glu
Thr206Glu + Trp212Ser + Ile213Cys + Thr217Gly + Arg218Glu + Ser219Glu + Thr223Glu

TABLE 28-continued

| Loop 6 - Heptuple Subst1tut1on Mutation Variants |
|---|
| Thr206Asp + Ser207Glu + Trp212Cys + Ile213Cys + Gly215Asn + Ser216Asp + Arg218Glu |
| Thr206Glu + Ser207Glu + Gly214Gln + Gly215Pro + Ser216Asp + Thr217Ser + Arg218Asp |
| Pro204Ser + Gly205Ser + Trp212Pro + Ser216Asp + Ser219Asp + Ile220Val + Thr223Ser |
| Gly203Gln + Leu209Gln + Trp212Ala + Gly215Asn + Arg218Glu + Ile220Glu + Thr223Glu |
| Gly203Gln + Leu209Asp + Thr211Asn + Gly214Glu + Arg218Glu + Ile220Leu + Gly222Ser |
| Gly203Ser + Pro204Gln + Thr211Pro + Gly215Asp + Arg218Glu + Ile220Glu + Thr223Asn |
| Thr206Asn + Ile208Gln + Ser216Glu + Thr217Gly + Arg218Asp + Ile220Gly + Ser221Asp |
| Pro204Ser + Ile208His + Gly214Pro + Ser216Glu + Arg218Glu + Ser221Glu + Thr223Ser |
| Pro204Gln + Leu209Ile + Trp212Ala + Ser216Asp + Thr217Ser + Arg218Asp + Ser221Asp |
| Gly203Pro + Pro204Asn + Ser207Asp + Ile208Cys + Thr217Gly + Ile220Gly + Thr223Glu |
| Pro204Ser + Ser207Asp + Leu209His + Thr211Ser + Gly215Asn + Gly222Ser + Thr223Glu |
| Ile208His + Thr211Pro + Trp212Leu + Thr217Ser + Arg218Asp + Ser221Asp + Thr223Glu |
| Gly205Asn + Thr206Asn + Ser107Asp + Ile213Thr + Ser216Asp + Ser219Asp + Gly222Glu |
| Thr206Asp + Ser207Glu + Ile208Leu + Trp212Gly + Ser216Glu + Thr217Gln + Gly222Asp |
| Gly205Asn + Thr206Asn + Ser207Asp + Ile208Gln + Trp212Cys + Ser216Glu + Tht217Glu |
| Ser207Glu + Ile208Asn + Trp212Thr + Ile213Gln + Ser216Asp + Thr217Glu + Thr223Gly |
| Ser207Asp + Ile208His + Thr211Asn + Gly215Asn + Ser216Asp + Thr217Glu + Thr223Gly |
| Gly203Ser + Pro204Ser + Ile213Thr + Ser216Glu + Thr217Gly + Ser219Asp + Ser221Glu |
| Gly203Asn + Ile208Ser + Thr211Asn + Ser216Asp + Ser219Glu + Ser221Asp + Thr223Gly |
| Gly203Ser + Thr206Pro + Thr211Gly + Trp212Thr + Ser216Glu + Ser219Glu + Ser221Asp |
| Trp212Ser + Gly214Pro + Gly215Asp + Thr217Asp + Ser219Glu + Ser221Asp + Thr223Pro |
| Thr206Ser + Ser207Asp + Ile208Pro + Leu209Glu + Gly215Asp + Ile220Thr + Ser221Glu |
| Gly203Asn + Trp212Tyr + Gly214Asp + Gly215Ser + Arg218Glu + Ile220Pro + Thr223Ser |
| Pro204Ser + Ile208Thr + Thr211Gly + Trp212His + Gly214Asp + Thr217Pro + Arg218Glu |
| Leu209Glu + Thr211Pro + Ile213Cys + Gly214Glu + Arg218Asp + Ile220Asn + Ser221Asp |
| Gly205Gln + Thr211Asn + Gly214Asp + Gly215Glu + Thr217Asp + Ile220Ala + Thr223Glu |
| Gly205Gln + Thr211Gln + Ile213Asn + Gly215Asp + Thr217Glu + Ile220Glu + Ser221Asp |
| Pro204Asn + Ile213Asp + Thr217Glu + Arg218Glu + Ile220Ser + Gly222Pro + Thr223Glu |
| Gly205Gln + Ser207Glu + Ile208Cys + Gly214Asp + Ser216Glu + Ser219Asp + Thr223Gly |
| Gly203Ser + Ser207Glu + Gly215Asn + Ser216Asp + Thr217Gly + Arg218Glu + Gly222Glu |
| Thr206Gln + Leu209Met + Gly214Glu + Gly215Asn + Ser219Glu + Ser221Asp + Gly222Glu |
| Leu209Met + Thr211Ser + Trp212Cys + Ser216Glu + Thr217Pro + Ile220Glu + Ser221Glu |
| Thr206Gly + Thr211Gln + Trp212Cys + Ser216Asp + Ile220Glu + Ser221Asp + Thr223Gln |
| Gly203Ser + Pro204Asn + Ser207Glu + Ile213Asp + Thr217Ser + Ser219Glu + Gly222Asn |
| Gly205Pro + Thr206Asp + Trp212Leu + Gly214Asn + Ser216Glu + Ser219Asp + Gly222Ser |
| Gly203Asn + Pro204Ser + Gly205Gln + Ser207Asp + Trp212Phe + Gly215Asp + Arg218Glu |

TABLE 29

| Multi-loop Double Mutation Variants | | |
|---|---|---|
| Leu96Gly | + | Leu209Pro |
| Tyr104Cys | + | Ile220Gln |
| Leu133Ile | + | Ser216Glu |
| Leu96Ala | + | Asn162Glu |
| Gln103Asp | + | Ile220Thr |
| Tyr169Ser | + | Ser190Asp |
| Val95Asp | + | Gly205Gln |
| Asp65Glu | + | Ile213Asn |
| Gly100Ser | + | Ile220Glu |
| Gly100Glu | + | Asn163Gln |
| Asn162Ser | + | Ser207Asp |
| Ser170Glu | + | Ile220Ser |
| Ser140Glu | + | Ile220Leu |
| Gln103Glu | + | Thrl06pro |
| Leu133Pro | + | Leu209Asn |
| Gly203Asn | + | Gly222Asp |
| Ser207Glu | + | Ile213Leu |
| Ser101Asp | + | Thr206Gly |
| Gly203Ser | + | Ser207Glu |
| Asn99Glu | + | Trp212Asn |
| Gly102Pro | + | Ser216Asp |
| Ser219Asp | + | Ile220Met |
| Gly70Asp | + | Leu133Ser |
| Gly136Asn | + | Ser216Asp |
| Arg167Glu | + | Leu209Pro |
| Asn194Glu | + | Leu209Gly |
| Leu209Gln | + | Ser216Glu |
| Gly68Asn | + | Ser221Glu |
| Asp65Glu | + | Ile107cys |
| Arg218Glu | + | Ile220Ala |
| Asp65Glu | + | Gly135Pro |
| Gly68Asp | + | Phe192His |
| Gly66Asn | + | Leu209Ser |
| Asn168Ser | + | Gly214Pro |
| Thr71Gly | + | Leu96Gly |
| Gly70Gln | + | Ile220Gly |
| Tyr169His | + | Leu209Ile |
| Thr217Pro | + | Ser219Asp |
| Gly70Pro | + | Ile220Asp |
| Leu96Gln | + | Asn99Glu |
| Asp65Glu | + | Gly136Ser |
| Asn99Glu | + | Ile213Met |
| Gly205Pro | + | Ser207Asp |
| Asn99Glu | + | Leu209Gln |
| Val95Gln | + | Ser207Asp |
| Val95Gln | + | Ser219Asp |
| Asn67Ser | + | Thr217Glu |
| Gly160Gln | + | Leu209Asp |
| Gly136Asn | + | Gly160Asn |
| Asn163Gln | + | Thr223Asn |
| Leu209Glu | + | Thr217Asn |
| Gly102Pro | + | Trp212Gln |
| Arg64Asp | + | Gly203Asn |
| Asn67Gln | + | Thr211Asn |
| Asp65Glu | + | Tyr137Pro |
| Gln103Asp | + | Leu133Ile |
| Leu96Glu | + | Ile213Gln |
| Asn161Gln | + | Arg218Glu |
| Leu209Asn | + | Gly214Pro |
| Gly68Ser | + | Thr206Asn |
| Arg167Asp | + | Phe192Ile |
| Asp65Glu | + | Thr211Ser |
| Ser207Asp | + | Thr223Gly |
| Ser207Asp | + | Gly222Ser |
| Tyr104Leu | + | Arg167Glu |
| Asp98Glu | + | Ile220Asn |
| Arg64Glu | + | Gly215Asn |
| Asn67Asp | + | Asn163Ser |
| Gly160Ser | + | Thr206Gln |
| Ile213Ser | + | Thr223Asp |
| Gly215Gln | + | Ser219Asp |
| Phe202Leu | + | Ser219Glu |
| Ser207Asp | + | Ile220Cys |
| Tyr137Ser | + | Ser219Asp |
| Gly100Asn | + | Leu209Thr |
| Tyr137His | + | Ser170Asp |
| Ser170Asp | + | Ile220Thr |

TABLE 29-continued

Multi-loop Double Mutation Variants

| | | |
|---|---|---|
| Thr106Gln | + | Ser207Asp |
| Arg167Asp | + | Leu209Pro |
| Ser105Asp | + | Gly136Asn |
| Ser139Asp | + | Phe192Thr |
| Ser190Glu | + | Pro204Ser |
| Asn67Glu | + | Leu209Ala |
| Trp212Ser | + | Ser216Glu |
| Tyr104Ala | + | Thr206Asp |
| Asn161Gln | + | Gly222Asn |
| Val95Thr | + | Leu133Ser |
| Gly160Ser | + | Asp165Glu |
| Asn163Ser | + | Leu209Val |
| Gly136Glu | + | Ile220Pro |
| Ser191Asp | + | Pro204Ser |
| Thr217Glu | + | Ile220Asn |
| Leu209Met | + | Gly214Asp |
| Thr71Pro | + | Ser191Glu |
| Ser101Glu | + | Trp212Phe |
| Gly70Ser | + | Ser219Glu |
| Gly66Gln | + | Asn99Ser |
| Asn163Gln | + | Ser190Glu |
| Ile107Ser | + | Ser190Asp |
| Ile208Thr | + | Ser219Asp |
| Ser216Asp | + | Ile220Leu |
| Ser140Asp | + | Ala164His |
| Asp65Glu | + | Val95Ser |
| Phe202Met | + | Leu209Ser |
| Asn67Gln | + | Tyr169Gly |
| Gly136Ser | + | Asn162Asp |
| Gly160Pro | + | Ser219Asp |
| Gly102Pro | + | Ser207Asp |
| Val95Asn | + | Ser207Asp |
| Asp97Glu | + | Ile107Gln |
| Thr206Glu | + | Ile220Pro |
| Ser216Glu | + | Thr223Gly |
| Asp97Glu | + | Leu133Cys |
| Gly134Gln | + | Gly135Asp |
| Thr206Gln | + | Ile220His |
| Gly100Asn | + | Thr223Asp |
| Gly66Pro | + | Ile220Val |
| Gly66Asn | + | Asn168Glu |
| Ser190Asp | + | Ile213Val |
| Gly135Pro | + | Asn162Glu |
| Leu133Ile | + | Gly134Pro |
| Asn163Ser | + | Arg167Glu |
| Gly134Gln | + | Ser216Glu |
| Asn194Gln | + | Leu209Gly |
| Asn99Gln | + | Ile213Met |
| Leu96Ile | + | Gly160Asp |
| Arg167Glu | + | Ile220Ala |
| Val95Ala | + | Ser139Asp |
| Gln103Ser | + | Gly214Ser |
| Asn67Glu | + | Thr71Gln |
| Gly135Pro | + | Ser191Glu |
| Ile107Ala | + | Ile220Glu |
| Gly214Gln | + | Ser219Glu |
| Gly160Asp | + | Phe192Met |
| Leu96Ala | + | Asp97Glu |
| Asn168Gln | + | Leu209Glu |
| Gln103Glu | + | Gly136Asn |
| Gly215Asp | + | Gly222Ser |
| Ser207Asp | + | Thr223Asn |
| Ser216Asp | + | Ile220cys |
| Val95Ser | + | Thr206Glu |
| Gly70Asn | + | Ser216Asp |
| Leu209Ser | + | Ile220Asp |
| Ala164Pro | + | Ile208Thr |
| Tyr137Thr | + | Leu209Glu |
| Thr106Asp | + | Tyr137Thr |
| Thr106Gly | + | Asp165Glu |
| Asn99Asp | + | Ile213Gly |
| Asn161Glu | + | Ile220Ser |
| Gly160Asp | + | Ile220Met |
| Gly135Asp | + | Asn163Gln |
| Tyr169Ser | + | Ser216Glu |
| Ser140Asp | + | Leu209Asn |
| Ser140Asp | + | Leu209Gln |
| Ser170Glu | + | Gly222Pro |
| Ile213His | + | Ser216Asp |
| Leu96Thr | + | Gly222Asn |
| Asp65Glu | + | Asn168Gln |
| Tyr104Leu | + | Ser219Glu |
| Thr106Pro | + | Gly134Pro |
| Asn99Asp | + | Gly215Asn |
| Thr206Glu | + | Ile220Val |
| Gly70Pro | + | Leu96Glu |
| Thr106Gly | + | Ser219Glu |
| Gly100Glu | + | Ile107Gly |
| Gly102Gln | + | Tyr169Gly |
| Arg64Glu | + | Pro204Gly |
| Leu133Gln | + | Ser207Asp |
| Gly100Gln | + | Leu133His |
| Thr106Asp | + | Leu209Ala |
| Gly68Ser | + | Ile220Gln |
| Asn67Asp | + | Gly68Gln |
| Leu96Glu | + | Ile220Leu |
| Thr206Gln | + | Ser219Asp |
| Ala164Gln | + | Gly222Gln |
| Gly66Glu | + | Gly68Pro |
| Ser140Asp | + | Ala166Asn |
| Asn67Ser | + | Gly100Asp |
| Ser219Asp | + | Ile220Thr |
| Ser170Gly | + | Gly215Ser |
| Thr71Gly | + | Phe192Ile |
| Gly100Ser | + | Ser219Asp |
| Gly215Pro | + | Ser219Asp |
| Leu209Met | + | Ser221Asp |
| Asn162Asp | + | Tyr169Met |
| Tyr104His | + | Asn162Glu |
| Asn67Gln | + | Leu96Ser |
| Leu209Asp | + | Ile220Ala |
| Gly70Ser | + | Ile220Gln |
| Gly66Ser | + | Gly70Glu |
| Tyr169His | + | Thr206Gly |
| Asn194Gln | + | Thr206Gly |
| Ile107Glu | + | Leu209Asn |
| Gly66Ser | + | Gly222Glu |
| Leu133Ile | + | Ser190Glu |
| Ser105Asp | + | Ile220His |
| Gly102Asp | + | Asn194Gln |
| Leu96Met | + | Ser216Asp |
| Asn161Asp | + | Gly203Gln |
| Gly136Gln | + | Asn161Asp |
| Phe202Ile | + | Ser219Asp |
| Gln103Asp | + | Ile107Thr |
| Gly100Gln | + | Ser216Asp |
| Phe192Ala | + | Ser207Glu |
| Gly136Pro | + | Ser138Asp |
| Asp98Glu | + | Leu209Thr |
| Asn194Ser | + | Ser216Glu |
| Val95Asp | + | Gly222Gln |
| Thr211Pro | + | Ile220Met |
| Arg167Glu | + | Tyr169Ala |
| Gly66Asn | + | Ser138Asp |
| Asn67Glu | + | Leu209Pro |
| Gly70Glu | + | Tyr169Pro |
| Gly102Pro | + | Leu209Asn |
| Gly68Ser | + | Ser207Asp |
| Ser101Glu | + | Ile220Ser |
| Tyr137Val | + | Ser191Glu |
| Thr211Gly | + | Arg218Asp |
| Asn161Gln | + | Asn194Gln |
| Thr106Asn | + | Leu209Gln |
| Val95Ser | + | Gly134Asp |
| Ser191Asp | + | Ile220Ser |
| Asn163Ser | + | Thr223Glu |
| Leu209Thr | + | Arg218Asp |
| Gly70Asp | + | Val95Gly |
| Leu209Met | + | Ser216Asp |
| Thr206Ser | + | Arg218Glu |
| Leu209Ile | + | Thr217Asp |
| Ile213Pro | + | Ser219Glu |
| Gly205Ser | + | Thr206Asp |
| Phe192Gln | + | Thr206Glu |

TABLE 29-continued

Multi-loop Double Mutation Variants

| | | |
|---|---|---|
| Gly68Asp | + | Leu209Ser |
| Gly160Gln | + | Thr206Gly |
| Gly214Asp | + | Ile220Leu |
| Gly70Asn | + | Arg218Asp |
| Gly70Glu | + | Gly136Asn |
| Leu133Glu | + | Gly203Pro |
| Gly135Gln | + | Ser207Glu |
| Ile107Gly | + | Ile213Gln |
| Ser140Asp | + | Ile220Leu |
| Ser191Asp | + | Gly214Gln |
| Leu209Ser | + | Gly214Asp |
| Asn67Glu | + | Ile220Gln |
| Ala166Pro | + | Ser219Asp |
| Gly102Ser | + | Ile220Val |
| Gln103Ser | + | Ser140Glu |
| Gly102Asp | + | Ile220Gly |
| Tyr104Ile | + | Gly134Gln |
| Ser101Glu | + | Ile220Cys |
| Asn162Gln | + | Ser207Asp |
| Val95Pro | + | Ser207Asp |
| Asn168Gln | + | Leu209Ala |
| Gly100Gln | + | Gly136Asn |
| Phe192Pro | + | Asn194Glu |
| Asn99Ser | + | Thr211Gln |
| Gly215Pro | + | Ile220Asp |
| Arg64Glu | + | Leu133Ile |
| Ser207Glu | + | Ile220Cys |
| Asp97Glu | + | Thr206Asn |
| Thr106Asp | + | Tyr137Met |
| Ser138Glu | + | Thr223Pro |
| Ser138Asp | + | Ile220Ala |
| Ser191Asp | + | Leu209Asn |
| Leu133Ile | + | Ser170Glu |
| Ile107cys | + | Ser139Glu |
| Asn161Gln | + | Ser207Asp |
| Thr206Asn | + | Ser216Glu |
| Asn67Gln | + | Ser207Asp |
| Leu209Met | + | Ser219Glu |
| Gly68Ser | + | Asp97Glu |
| Gly136Glu | + | Gly222Asn |
| Thr106Pro | + | Leu209Val |
| Gln103Glu | + | Ile213Ala |
| Leu96Gln | + | Ser219Glu |
| Ile107Asp | + | Ala164Gln |
| Tyr169Asp | + | Thr211Pro |
| Leu133Glu | + | Leu209Val |
| Asp97Glu | + | Asn161Ser |
| Ile213Gly | + | Ser216Asp |
| Thr206Pro | + | Ser207Asp |
| Ala164Gln | + | Leu209Cys |
| Ser170Glu | + | Leu209Ala |
| Gly160Pro | + | Leu209Cys |
| Asn67Asp | + | Asn163Gln |
| Thr206Gly | + | Ser216Asp |
| Leu133Thr | + | Ser216Glu |
| Asn163Asp | + | Leu209Thr |
| Val95Met | + | Phe202Ser |
| Gly136Ser | + | Gly222Ser |
| Leu209Met | + | Ile220Met |
| Gln103Ser | + | Asn163Glu |
| Ile107His | + | Arg218Asp |
| Phe192Ala | + | Gly215Gln |
| Leu209Thr | + | Ser216Glu |
| Tyr169Glu | + | Thr217Ser |
| Ser101Asp | + | Leu209Ala |
| Leu209Ala | + | Ser221Asp |
| Gly66Asp | + | Thr106Gln |
| Val95Glu | + | Ile213Cys |
| Ser105Asp | + | Thr211Gln |
| Asp165Glu | + | Asn168Ser |
| Gly66Asn | + | Ile220Thr |
| Ser219Glu | + | Ile220Pro |
| Gly68Glu | + | Ile220Met |
| Val95His | + | Leu209Met |
| Gly66Ser | + | Leu209Met |
| Ser140Glu | + | Gly214Gln |
| Gly160Asn | + | Leu209Asp |
| Thr206Asp | + | Ile220Met |
| Gly102Asn | + | Thr206Glu |
| Gly134Pro | + | Phe192Pro |
| Leu133Asp | + | Phe202Ser |
| Asn162Glu | + | Ile220His |
| Leu133Gly | + | Leu209Met |
| Asn194Ser | + | Ser219Asp |
| Gly70Gln | + | Thr217Pro |
| Asp97Glu | + | Thr217Gln |
| Gly100Asp | + | Leu209Cys |
| Ser216Asp | + | Ile220Thr |
| Arg167Glu | + | Asn194Ser |
| Gly66Gln | + | Ser170Glu |
| Ser101Asp | + | Tyr137Ala |
| Asn67Gln | + | Asn161Asp |
| Asn168Asp | + | Leu209Ile |
| Asn67Gln | + | Gly68Glu |
| Asn161Asp | + | Thr217Pro |
| Thr206Asp | + | Leu209Met |
| Asp97Glu | + | Leu209Met |
| Asp97Glu | + | Tyr104His |
| Asp98Glu | + | Gly102Pro |
| Tyr104Ala | + | Ser191Glu |
| Gly100Ser | + | Arg167Glu |
| Ser207Asp | + | Leu209Ser |
| Asn194Ser | + | Ser207Asp |
| Leu96Val | + | Ile220Cys |
| Asn163Gln | + | Ser191Asp |
| Asn162Gln | + | Asp165Glu |
| Gly66Gln | + | Thr71Asn |
| Tyr137Leu | + | Phe192Asn |
| Gly66Asn | + | Ser207Glu |
| Asp97Glu | + | Leu133Ser |
| Thr206Gln | + | Ser216Asp |
| Leu96Pro | + | Ile213Glu |
| Asp165Glu | + | Gly214Asn |
| Ser190Glu | + | Thr217Gly |
| Tyr104Met | + | Ile220Glu |
| Asp65Glu | + | Thr223Ser |
| Gly100Asn | + | Ser170Glu |
| Gly134Ser | + | Leu209Cys |
| Ala164Gly | + | Ser207Asp |
| Thr71Asn | + | Ile220Asp |
| Ile107Cys | + | Ser219Asp |
| Thr106Gly | + | Asn162Asp |
| Asn161Glu | + | Leu209Thr |
| Gly214Gln | + | Ser221Asp |
| Ala164Gln | + | Ser207Glu |
| Asn67Ser | + | Ser216Asp |
| Leu209Ala | + | Thr217Ser |
| Ala166Gln | + | Ser216Asp |
| Leu209Gln | + | Ile220Glu |

TABLE 30

Multi-loop Triple Mutation Variants

| | | | | | |
|---|---|---|---|---|---|
| Leu96Gly | + | Leu209Pro | + | Ser216Glu |
| Arg64Glu | + | Tyr104Cys | + | Ile220Gln |
| Tyr169Ser | + | Ser190Asp | + | Ile220Thr |
| Gly100Glu | + | Asn162Ser | + | Asn163Gln |
| Gln103Glu | + | Leu133Pro | + | Leu209Asn |
| Gly70Asp | + | Leu133Ser | + | Gly136Asn |
| Gly68Asn | + | Leu209Gln | + | Ser216Gln |
| Asp65Glu | + | Gly135Pro | + | Ile220Ala |
| Gly66Asn | + | Asn67Glu | + | Leu209Ser |
| Thr71Gly | + | Leu96Gly | + | Gly214Pro |
| Gly70Gln | + | Leu209Ile | + | Ile220Gly |
| Tyr169His | + | Thr217Pro | + | Ser219Asp |
| Asn67Ser | + | Val95Gln | + | Thr217Glu |
| Gly136Asn | + | Gly160Gln | + | Leu209Asp |
| Gly136Glu | + | Asn163Gln | + | Thr223Asn |
| Arg64Asp | + | Gly203Asn | + | Trp212Gln |
| Gly68Ser | + | Leu209Asn | + | Gly214Pro |

TABLE 30-continued

Multi-loop Triple Mutation Variants

| | | | | | |
|---|---|---|---|---|---|
| Arg167Asp | + | Phe192Ile | + | Thr206Asn |
| Ser207Asp | + | Gly222Ser | + | Thr223Gly |
| Gly160Ser | + | Asn163Ser | + | Thr206Gln |
| Gly100Asn | + | Tyr137Ser | + | Ser219Asp |
| Asn67Asp | + | Gly100Asn | + | Tyr137His |
| Ser105Asp | + | Gly136Asn | + | Phe192Thr |
| Val95Thr | + | Leu133Ser | + | Asn161Gln |
| Ser140Glu | + | Asn163Ser | + | Leu209Val |
| Pro204Ser | + | Thr217Gln | + | Ile220Asn |
| Ile107Ser | + | Ile208Thr | + | Ser219Asp |
| Asp65Glu | + | Val95Ser | + | Leu209Ser |
| Asn67Gln | + | Tyr169Gly | + | Phe202Met |
| Gly136Ser | + | Gly160Pro | + | Asn162Asp |
| Val95Asn | + | Ile107Gln | + | Ser207Asp |
| Gly135Asp | + | Thr206Gln | + | Ile220His |
| Gly66Pro | + | Gly100Asn | + | Ile220Val |
| Gly135Pro | + | Asn162Gln | + | Ile213Val |
| Leu133Ile | + | Gly134Pro | + | Arg167Glu |
| Gly134Gln | + | Asn163Ser | + | Ser216Glu |
| Asn194Gln | + | Ser207Glu | + | Leu209Gly |
| Arg64Glu | + | Asn99Gln | + | Ile213Met |
| Tyr104Ser | + | Arg167Glu | + | Ile220Ala |
| Val95Ala | + | Gln103Ser | + | Ser139Asp |
| Ile107Ala | + | Gly214Gln | + | Ile220Glu |
| Gln103Glu | + | Gly136Asn | + | Asn168Gln |
| Thr206Pro | + | Ser216Glu | + | Ile220cys |
| Asn67Asp | + | Ala164Pro | + | Ile208Thr |
| Asp65Glu | + | Asn168Gln | + | Gly222Asn |
| Tyr104Leu | + | Leu209Ser | + | Ser219Glu |
| Ile107Pro | + | Asn194Glu | + | Thr206Gly |
| Leu133Asn | + | Leu209Ile | + | Ile213Asp |
| Gly70Pro | + | Thr106Gly | + | Ser219Glu |
| Asp65Glu | + | Gly102Gln | + | Tyr169Gly |
| Gly100Asn | + | Leu133Gln | + | Gly160Asp |
| Ala164Ser | + | Ser216Asp | + | Thr217Gly |
| Gly68Glu | + | Leu209Ala | + | Ile220Gln |
| Gly66Glu | + | Ala164Gln | + | Gly222Gln |
| Thr71Gly | + | Phe192Ile | + | Gly215Ser |
| Asn67Gln | + | Leu96Ser | + | Leu209Asp |
| Arg64Glu | + | Gly70Ser | + | Ile220Gln |
| Gly66Ser | + | Tyr169His | + | Thr206Gly |
| Ser170Glu | + | Thr206Gly | + | Gly215Ser |
| Gly66Ser | + | Ile107Glu | + | Leu209Asn |
| Ser105Asp | + | Asn194Gln | + | Ile220His |
| Leu96Met | + | Asn161Asp | + | Gly203Gln |
| Gly136Gln | + | Asn161Asp | + | Phe202Ile |
| Gly100Gln | + | Phe192Ala | + | Ser216Asp |
| Thr211Pro | + | Ile220Met | + | Gly222Gln |
| Gly68Ser | + | Thr106Gln | + | Ser207Asp |
| Asn161Gln | + | Thr211Gly | + | Arg218Asp |
| Thr106Asn | + | Asn194Gln | + | Leu209Gln |
| Asp65Glu | + | Tyr169Val | + | Ile220Val |
| Gly70Asp | + | Val95Gly | + | Leu209Met |
| Gly205Ser | + | Thr206Asp | + | Ile213Pro |
| Phe192Gln | + | Thr206Glu | + | Leu209Ser |
| Gly160Gln | + | Thr206Gly | + | Gly214Asp |
| Gly70Asn | + | Arg218Asp | + | Ile220Leu |
| Gly70Glu | + | Gly136Asn | + | Gly203Pro |
| Ile107Gly | + | Ile213Gly | + | Ser219Asp |
| Gly102Ser | + | Ala166Pro | + | Ile220Val |
| Tyr104Ile | + | Gly134Gln | + | Ile220Cys |
| Val95Pro | + | Asn162Gln | + | Ser207Asp |
| Gly100Gln | + | Gly136Asn | + | Asn194Glu |
| Asn99Ser | + | Thr211Gln | + | Ile220Asp |
| Arg64Glu | + | Leu133Ile | + | Ile220Ser |
| Asp97Glu | + | Thr206Asn | + | Ile220Cys |
| Ile107Asn | + | Thr206Asn | + | Ser207Glu |
| Asn67Gln | + | Leu96Gln | + | Ile213Asp |
| Gly68Ser | + | Leu209Met | + | Ser219Glu |
| Tyr169Asp | + | Leu209Val | + | Thr211Pro |
| Thr206Pro | + | Ile213Gly | + | Ser216Asp |
| Ala164Ser | + | Ser207Asp | + | Leu209Cys |
| Asn67Asp | + | Gly160Pro | + | Leu209Cys |
| Asn163Gln | + | Thr206Gly | + | Ser216Asp |
| Val95Met | + | Phe202Ser | + | Leu209Thr |
| Gly136Ser | + | Ile220Met | + | Gly222Ser |
| Gln103Ser | + | Asn163Glu | + | Leu209Met |
| Ile107His | + | Phe192Ala | + | Arg218Asp |
| Ser101Asp | + | Leu209Ala | + | Thr217Ser |
| Gly66Asn | + | Asp165Glu | + | Asn168Ser |
| Gly66Ser | + | Leu209Met | + | Gly214Gln |
| Gly134Pro | + | Ser140Glu | + | Phe192Pro |
| Leu133Gly | + | Ser207Glu | + | Leu209Met |
| Gly70Gln | + | Asn163Asp | + | Asn194Ser |
| Gly100Asp | + | Leu209Cys | + | Thr217Gln |
| Gly66Gln | + | Ser101Asp | + | Tyr137Ala |
| Asn67Gln | + | Asn168Asp | + | Leu209Ile |
| Asn161Asp | + | Leu209Met | + | Thr217Pro |
| Gly100Ser | + | Ser207Asp | + | Leu209Ser |
| Leu96Val | + | Asn194Ser | + | Ser207Asp |
| Asn163Gln | + | Ser191Asp | + | Ile220Cys |
| Gly66Gln | + | Thr71Asn | + | Ser216Asp |
| Gly66Asn | + | Tyr137Leu | + | Phe192Asn |
| Asp97Glu | + | Leu133Ser | + | Ile220Met |
| Leu96Pro | + | Thr206Gln | + | Ile213Glu |
| Asp165Glu | + | Gly214Asn | + | Thr217Gly |
| Asp65Glu | + | Gly100Asn | + | Thr223Ser |
| Gly134Ser | + | Ser170Glu | + | Leu209Cys |
| Thr71Asn | + | Ile107Cys | + | Ser219Asp |
| Thr106Gly | + | Asn162Asp | + | Leu209Thr |
| Asn67Ser | + | Ala164Gln | + | Ser207Glu |
| Ala166Gln | + | Leu209Ala | + | Ser216Asp |
| Leu96Gly | + | Leu133Ser | + | Ser190Glu |
| Ser207Asp | + | Leu209Thr | + | Ile220Pro |
| Tyr137Thr | + | Ser139Glu | + | Gly215Pro |
| Thr206Gly | + | Leu209Asp | + | Thr211Asn |
| Thr206Asp | + | Ile208Val | + | Ile220Leu |
| Leu96Cys | + | Ser207Glu | + | Ile220Leu |
| Ile107Leu | + | Gly136Glu | + | Ile220Gly |
| Thr106Asn | + | Ser139Glu | + | Ala164Thr |
| Ser191Glu | + | Leu209Ser | + | Ile220Gly |
| Ser140Glu | + | Gly215Ser | + | Gly222Pro |
| Leu96Ser | + | Ala164Gly | + | Ile220His |
| Asp97Glu | + | Tyr104Asn | + | Tyr137Gln |
| Gly70Pro | + | Asp98Glu | + | Leu133Thr |
| Gly66Ser | + | Thr71Gly | + | Phe202Ser |
| Ser101Asp | + | Thr206Gly | + | Ile213Gly |
| Tyr169Ile | + | Ser170Glu | + | Thr211Gly |
| Gly160Ser | + | Ile213Val | + | Ser219Glu |
| Leu209Gly | + | Ile220Gly | + | Thr223Pro |
| Thr106Gln | + | Ala164Gln | + | Phe192Glu |
| Asn99Glu | + | Leu209Gln | + | Ile220Met |
| Gly160Gln | + | Asn194Glu | + | Gly215Gln |
| Ser105Asp | + | Phe202Pro | + | Leu209Gln |
| Gly66Glu | + | Leu133Thr | + | Leu209Asn |
| Ala164Thr | + | Leu209Met | + | Ile220Thr |
| Thr71Gly | + | Gly214Asp | + | Gly222Asn |
| Val95Pro | + | Thr206Gly | + | Ile213Asp |
| Leu96Asn | + | Gly100Asn | + | Asn194Ser |
| Arg64Glu | + | Gly100Asn | + | Ile220Met |
| Gly66Ser | + | Arg218Asp | + | Gly222Ser |
| Asp65Glu | + | Asn162Gln | + | Ile220Thr |
| Asn99Asp | + | Thr206Ser | + | Ile220Ser |
| Leu96Ser | + | Tyr169His | + | Ser216Asp |
| Asp98Glu | + | Tyr169His | + | Gly215Asn |
| Tyr104Leu | + | Ser207Asp | + | Leu209Ser |
| Asn161Ser | + | Phe192His | + | Thr206Pro |
| Leu96Ser | + | Ser170Asp | + | Leu209Ile |
| Thr106Gln | + | Asn163Gln | + | Ser207Asp |
| Gly70Gln | + | Ala164Asp | + | Asn161Ser |
| Asn99Ser | + | Ala164Asp | + | Thr217Pro |
| Ser139Glu | + | Thr206Asn | + | Ile213Leu |
| Leu96Asn | + | Thr217Asn | + | Ile220His |
| Gln103Ser | + | Leu209Pro | + | Ser219Glu |
| Asp65Glu | + | Leu96Cys | + | Gln103Asn |
| Asn67Gln | + | Ser207Asp | + | Gly214Asn |
| Gly68Pro | + | Thr211Ser | + | Thr223Asp |
| Tyr137Gln | + | Ser138Glu | + | Ile220Asn |
| Asp65Glu | + | Phe192Val | + | Gly215Ser |
| Thr71Gln | + | Gly203Gln | + | Thr206Asp |
| Arg64Asp | + | Asn99Ser | + | Thr106Ser |
| Gly135Gln | + | Asn168Ser | + | Phe192Asp |
| Leu133Ala | + | Leu209Ala | + | Ser219Glu |
| Ala164Thr | + | Asn168Ser | + | Ile213Pro |

TABLE 30-continued

Multi-loop Triple Mutation Variants

| | | | | | |
|---|---|---|---|---|---|
| Ser207Glu | + | Gly214Gln | + | Ile220Asn | |
| Phe192Tyr | + | Leu209Pro | + | Gly215Gln | |
| Asn163Gln | + | Thr206Gly | + | Leu209Asn | |
| Leu96Pro | + | Asp98Glu | + | Asn163Gln | |
| Ser101Asp | + | Asn168Gln | + | Tyr169Val | |
| Gly136Pro | + | Asn162Glu | + | Ile220Thr | |
| Leu209Cys | + | Gly214Gln | + | Ile220cys | |
| Arg64Asp | + | Leu209Ile | + | Ile220His | |
| Gly134Pro | + | Gly135Ser | + | Ser219Glu | |
| Ala164Thr | + | Leu209Thr | + | Ser219Glu | |
| Trp212Phe | + | Ser219Glu | + | Ile220Glu | |
| Leu96Glu | + | Asp97Glu | + | Ile220Leu | |
| Leu96Glu | + | Asp97Glu | + | Gly222Pro | |
| Asn161Asp | + | Asn162Glu | + | Gly214Ser | |
| Gly160Asp | + | Asn161Glu | + | Ile220Ser | |
| Tyr137Val | + | Thr206Glu | + | Ser207Asp | |
| Gly68Pro | + | Arg218Glu | + | Ser219Glu | |
| Leu209Thr | + | Arg218Glu | + | Ser219Asp | |
| Tyr104Gln | + | Ser216Asp | + | Thr217Asp | |
| Leu209Glu | + | Thr217Asn | + | Ser219Asp | |
| Leu209Asp | + | Ser219Glu | + | Ile220Ser | |
| Asn194Gln | + | Ser207Asp | + | Ser221Glu | |
| Ala164Gly | + | Ser207Asp | + | Ile220Asp | |
| Leu96Val | + | Ser207Asp | + | Ile220Asp | |
| Leu96Glu | + | Gly102Glu | + | Ile213Gln | |
| Gly68Asn | + | Ser207Asp | + | Ser219Glu | |
| Ser207Asp | + | Ser219Glu | + | Ile220cys | |
| Leu96Gln | + | Ser207Asp | + | Ser219Glu | |
| Gly102Pro | + | Ser207Asp | + | Ser219Asp | |
| Gln103Ser | + | Ser207Asp | + | Ser219Glu | |
| Val95Gln | + | Ser207Asp | + | Ser219Asp | |
| Ser207Asp | + | Ile213Pro | + | Ser219Glu | |
| Asp65Glu | + | Asn67Asp | + | Ala164His | |
| Asp65Glu | + | Asn67Glu | + | Gly136Ser | |
| Asn162Gln | + | Asp165Glu | + | Arg167Glu | |
| Leu209Met | + | Gly214Asp | + | Ser216Glu | |
| Ser138Asp | + | Ser170Asp | + | Ile220Met | |
| Ser138Glu | + | Asn168Gln | + | Ser170Glu | |
| Arg64Glu | + | Gly66Asp | + | Thr217Pro | |
| Asp165Glu | + | Asn168Asp | + | Thr211Asn | |
| Leu96Glu | + | Asp98Glu | + | Gly222Ser | |
| Thr206Ser | + | Ser216Asp | + | Arg218Glu | |
| Ala164Ser | + | Ser216Glu | + | Arg218Glu | |
| Asn161Asp | + | Asn162Asp | + | Thr223Asp | |
| Leu209Ile | + | Thr217Asp | + | Ser219Glu | |
| Ser101Asp | + | Gln103Asp | + | Leu133Ile | |
| Asn67Glu | + | Asp97Glu | + | Leu209Ala | |
| Leu133Ile | + | Ser190Glu | + | Gly222Glu | |
| Ser207Asp | + | Ser219Glu | + | Gly222Asp | |
| Ala164Asp | + | Asn168Glu | + | Leu209Pro | |
| Asp65Glu | + | Gly68Glu | + | Asp97Glu | |
| Asn163Ser | + | Thr206Asp | + | Ser219Glu | |
| Arg64Glu | + | Asn67Asp | + | Gly215Asn | |
| Tyr137Asp | + | Ser139Glu | + | Arg167Asp | |
| Ser140Asp | + | Ser170Glu | + | Gly222Ser | |
| Tyr137Glu | + | Ser140Asp | + | Leu209Gln | |
| Arg64Glu | + | Asp97Glu | + | Tyr104His | |
| Val95Glu | + | Ser105Asp | + | Thr211Gln | |
| Gly100Asn | + | Asn161Glu | + | Ser221Asp | |
| Asp65Glu | + | Asn99Glu | + | Trp212Asn | |
| Asp65Glu | + | Asn99Glu | + | Thr217Ser | |
| Ser190Glu | + | Ser207Glu | + | Ile220Glu | |
| Gly68Glu | + | Gly136Pro | + | Ser216Glu | |
| Val95Glu | + | Asp98Glu | + | Gly102Pro | |
| Asn162Asp | + | Asp165Glu | + | Ser191Glu | |
| Val95Cys | + | Ser138Asp | + | Arg167Glu | |
| Leu209Asp | + | Ser216Glu | + | Ile220Ala | |
| Gly100Glu | + | Gln103Asp | + | Ile107Gly | |
| Gly100Asp | + | Gly102Pro | + | Gln103Glu | |
| Ser216Asp | + | Ser219Glu | + | Ile220Thr | |
| Gly102Pro | + | Ser216Asp | + | Ser219Asp | |
| Tyr104Gln | + | Ser216Glu | + | Ser219Glu | |
| Asn99Gln | + | Ser216Glu | + | Ser219Asp | |
| Thr206Gln | + | Ser216Asp | + | Ser219Asp | |
| Ser207Asp | + | Ser216Asp | + | Thr217Asp | |
| Gly134Asp | + | Asn162Glu | + | Phe192Glu | |
| Gly102Glu | + | Ser105Asp | + | Leu133Glu | |
| Ser216Asp | + | Ser219Asp | + | Ser221Asp | |
| Asn163Asp | + | Ser170Glu | + | Asn194Asp | |
| Tyr137Glu | + | Asn162Glu | + | Arg167Glu | |
| Ser105Asp | + | Gly135Asp | + | Tyr169Asp | |
| Val95Asp | + | Asp98Glu | + | Ser105Glu | |
| Gly136Asp | + | Ser140Asp | + | Gly203Gln | |
| Ser207Asp | + | Ser216Glu | + | Ile220Asp | |
| Thr106Gly | + | Tyr137Asp | + | Asp165Glu | |
| Asp65Glu | + | Gly100Glu | + | Gln103Asp | |
| Ser101Glu | + | Arg167Glu | + | Asn168Glu | |
| Asn67Asp | + | Ser191Asp | + | Phe192Glu | |
| Asp98Glu | + | Asn99Glu | + | Ser216Asp | |
| Asp98Glu | + | Asn99Asp | + | Ser216Asp | |
| Arg64Glu | + | Asp65Glu | + | Asp165Glu | |
| Gly102Glu | + | Gln103Glu | + | Ser221Glu | |
| Leu133Glu | + | Thr206Asp | + | Ser207Glu | |
| Ser139Glu | + | Ser216Asp | + | Thr217Asp | |
| Asp165Glu | + | Gly215Asp | + | Ser216Asp | |
| Asp97Glu | + | Leu209Glu | + | Ser219Glu | |
| Ser191Glu | + | Leu209Glu | + | Ser219Glu | |
| Thr106Asp | + | Leu209Asp | + | Ser219Glu | |
| Asn99Glu | + | Ile213Asp | + | Ser216Glu | |
| Ser207Glu | + | Leu209Glu | + | Ile213Asp | |
| Asn67Glu | + | Asp98Glu | + | Leu209Asp | |
| Ser101Asp | + | Ser207Asp | + | Ser221Asp | |
| Gly135Asp | + | Ser207Asp | + | Ser219Glu | |
| Asn162Glu | + | Ser207Asp | + | Ser219Glu | |
| Ser139Glu | + | Ser207Glu | + | Ser219Glu | |
| Gly134Glu | + | Ser170Glu | + | Ser216Asp | |
| Asp165Glu | + | Arg167Glu | + | Ser207Asp | |
| Asp165Glu | + | Arg167Asp | + | Ser219Asp | |
| Asp65Glu | + | Ser138Glu | + | Ser140Asp | |
| Asp97Glu | + | Arg167Glu | + | Tyr169Asp | |
| Ser207Glu | + | Ile213Glu | + | Ser216Glu | |
| Thr71Pro | + | Ser191Glu | + | Ser207Glu | |
| Ser191Asp | + | Ser207Asp | + | Gly214Gln | |
| Gly66Glu | + | Gly70Glu | + | Ser216Glu | |
| Asn163Asp | + | Ser191Asp | + | Ile220Glu | |
| Asp97Glu | + | Ser207Glu | + | Leu209Glu | |
| Tyr104Asp | + | Ser207Glu | + | Leu209Glu | |
| Ser190Asp | + | Thr206Glu | + | Ser216Asp | |
| Asp97Glu | + | Leu133Glu | + | Asn161Ser | |
| Asn168Asp | + | Ser170Asp | + | Ser190Asp | |
| Asp98Glu | + | Ser221Asp | + | Thr223Glu | |
| Asn67Asp | + | Asp97Glu | + | Gly135Glu | |
| Asn67Asp | + | Asp97Glu | + | Ser219Asp | |
| Ser105Glu | + | Gly160Asp | + | Gly222Asp | |
| Asp98Glu | + | Gly160Asp | + | Asn163Glu | |
| Ser139Glu | + | Ser170Glu | + | Arg218Asp | |
| Gln103Glu | + | Ser207Asp | + | Gly222Glu | |
| Ser207Asp | + | Ser216Asp | + | Gly222Asp | |
| Gly135Glu | + | Gly160Glu | + | Ser216Glu | |
| Tyr104Glu | + | Asn163Asp | + | Ser190Glu | |
| Ser190Glu | + | Asn194Asp | + | Ser219Asp | |
| Tyr104Met | + | Ser190Glu | + | Ile220Glu | |
| Asn67Asp | + | Ser216Asp | + | Ser219Glu | |
| Leu133Asp | + | Asn162Glu | + | Phe202Ser | |
| Asn162Glu | + | Ser191Asp | + | Leu209Glu | |
| Asp65Glu | + | Leu96Asp | + | Asn162Asp | |
| Arg64Asp | + | Gly136Glu | + | Arg167Glu | |
| Asn67Asp | + | Gly68Gln | + | Ser216Glu | |
| Asn67Glu | + | Ser216Glu | + | Ile220Cys | |
| Ser101Glu | + | Thr206Asp | + | Leu209Glu | |
| Asp65Glu | + | Leu209Glu | + | Ser216Glu | |
| Ser101Glu | + | Ile107Glu | + | Ser219Glu | |
| Gly68Asp | + | Ser170Glu | + | Ser216Asp | |
| Gly136Asp | + | Ser139Glu | + | Ser216Asp | |
| Gly135Asp | + | Leu209Ser | + | Thr223Asp | |
| Leu133Glu | + | Asn161Glu | + | Gly214Glu | |
| Arg64Glu | + | Ser191Glu | + | Ser221Asp | |
| Asn67Asp | + | Gly214Asp | + | Ser219Glu | |
| Thr106Glu | + | Ser219Glu | + | Gly222Glu | |
| Asp98Glu | + | Ile220Asp | + | Thr223Glu | |
| Arg167Asp | + | Gly215Glu | + | Arg218Asp | |
| Tyr104Glu | + | Ser139Glu | + | Ser219Asp | |
| Ile107Gly | + | Asn161Asp | + | Ile220Asp | |
| Gly160Glu | + | Ser216Asp | + | Ser219Asp | |

TABLE 30-continued

Multi-loop Triple Mutation Variants

| | | | | | |
|---|---|---|---|---|---|
| Asp165Glu | + | Ser216Glu | + | Ser219Asp |
| Asp98Glu | + | Ser207Asp | + | Thr223Asp |
| Ser139Asp | + | Asn168Glu | + | Ser207Glu |
| Ser105Asp | + | Ser138Glu | + | Ile220Glu |
| Ser105Asp | + | Ser138Asp | + | Ser219Asp |
| Ser105Asp | + | Ser138Asp | + | Gly222Asp |
| Ile213Pro | + | Ser216Glu | + | Ile220Glu |
| Ser101Glu | + | Gly214Glu | + | Arg218Glu |
| Gly136Glu | + | Asp165Glu | + | Ser190Asp |
| Asp65Glu | + | Leu209Cys | + | Ser216Asp |
| Ser138Asp | + | Asn161Glu | + | Thr206Glu |
| Gly136Asp | + | Ser140Asp | + | Ser219Glu |
| Gly68Glu | + | Gly134Glu | + | Ser219Asp |
| Gly68Asp | + | Asn194Glu | + | Ser219Asp |
| Gly68Glu | + | Asn161Glu | + | Ser219Asp |
| Gly68Asp | + | Ile107Asp | + | Ser219Glu |
| Gly68Glu | + | Ser139Asp | + | Ser219Asp |
| Asp98Glu | + | Gly135Asp | + | Ser139Glu |
| Gly135Glu | + | Ser139Glu | + | Leu209Glu |
| Ala164Glu | + | Ser190Asp | + | Ser219Glu |
| Gln103Asp | + | Tyr137Asp | + | Gly160Ser |
| Gly70Glu | + | Gly102Asp | + | Tyr169Pro |
| Gly70Glu | + | Ser219Glu | + | Gly222Asn |
| Gly70Glu | + | Leu209Met | + | Ser221Asp |
| Ile213Ser | + | Ser219Asp | + | Thr223Asp |
| Gly135Asp | + | Ser140Glu | + | Gly215Asp |
| Gly102Glu | + | Ser170Glu | + | Thr206Asn |
| Gly100Glu | + | Gly135Asp | + | Thr206Glu |
| Gly70Glu | + | Asp165Glu | + | Ile220Asp |
| Phe192Asp | + | Ser207Asp | + | Ile213Glu |
| Ala164Glu | + | Arg218Asp | + | Thr223Asp |
| Gly135Asp | + | Ser190Glu | + | Ile220Glu |
| Asn99Glu | + | Leu133Asp | + | Asp165Glu |
| Asp165Glu | + | Ser219Glu | + | Thr223Asp |
| Asn67Glu | + | Asn162Asp | + | Ser216Glu |

TABLE 31

Multi-loop Quadruple Mutation Variants

| | | | |
|---|---|---|---|
| Tyr104Cys + | Leu133Ile + | Ser216Glu + | Ile220Gln |
| Gly102Asn + | Gly160Ser + | Ala164Gly + | Arg218Asp |
| Asn 67Glu + | Thr206Gln + | Leu209Met + | Ile220Met |
| Gln103Glu + | Thr106Pro + | Leu133Pro + | Leu209Asn |
| Val 95His + | Gly136Asn + | Gly160Gln + | Gly222Glu |
| Arg 64Asp + | Gly102Pro + | Gly203Asn + | Trp212Gln |
| Val 95Thr + | Leu133Ser + | Asn161Gln + | Gly222Asn |
| Gly 66Gln + | Gly 70Ser + | Asn 99Ser + | Ser219Asp |
| Asp 65Glu + | Gly 68Asn + | Tyr169Val + | Ile220Val |
| Phe192Gln + | Gly205Ser + | Thr206Glu + | Leu209Ser |
| Leu133Val + | Asn162Asp + | Leu209Val + | Ile220Ala |
| Leu 96Thr + | Leu209Ile + | Ile220Val + | Thr223Ser |
| Gly100Glu + | Gly102Asn + | Gly134Ser + | Ile208Pro |
| Gly100Ser + | Asn194Gln + | Ser207Glu + | Ile220Thr |
| Asn 67Gln + | Ala164Gln + | Tyr169Asp + | Ile220Thr |
| Gly160Ser + | Ser191Glu + | Ile220Ser + | Gly222Ser |
| Thr206Pro + | Ser207Asp + | Leu209Cys + | Ile213Gly |
| Val 95Met + | Gly136Ser + | Phe202Ser + | Gly222Ser |
| Gln103Ser + | Asn163Glu + | Leu209Met + | Ile220Met |
| Ile107His + | Phe192Ala + | Gly215Gln + | Arg218Asp |
| Gly 66Asn + | Asp165Glu + | Asn168Ser + | Ile220Thr |
| Gly100Asn + | Ser140Glu + | Leu209Met + | Gly214Gln |
| Gly 70Gln + | Asn163Asp + | Asn194Ser + | Thr217Pro |
| Asn161Ser + | Phe192His + | Thr206Pro + | Ser219Asp |
| Val 95Cys + | Leu 96Ser + | Ser138Asp + | Leu209Ile |
| Gly 68Gln + | Ser101Asp + | Thr106Pro + | Ile220Met |
| Gly100Pro + | Gly102Gln + | Leu209Cys + | Gly215Asp |
| Gly100Asn + | Gln103Ser + | Ser207Asp + | Leu209Val |
| Thr106Gln + | Ile107Asn + | Phe192Val + | Thr223Gly |
| Tyr137Gln + | Ser138Asp + | Leu209Val + | Trp212Asn |
| Leu133Ala + | Asn162Asp + | Tyr169Val + | Leu209Ile |
| Gly102Ser + | Gly134Gln + | Gly136Asn + | Ser207Glu |
| Gly100Gln + | Gly134Pro + | Gly160Asn + | Ser219Glu |
| Tyr137Met + | Asn194Gln + | Ser207Asp + | Gly215Pro |

TABLE 31-continued

Multi-loop Quadruple Mutation Variants

| | | | |
|---|---|---|---|
| Ala164Asn + | Ser190Asp + | Phe202Ser + | Ile213Asn |
| Gly 68Pro + | Asp 98Glu + | Ala166His + | Asn168Ser |
| Ile107Pro + | Gly136Pro + | Ser207Glu + | Gly222Gln |
| Arg 64Asp + | Tyr169Gly + | Phe192Pro + | Gly205Ser |
| Val 95Thr + | Tyr104Cys + | Gly134Asp + | Ile208Asn |
| Ile107His + | Gly135Glu + | Phe192Gly + | Thr217Pro |
| Ile107Gly + | Ser191Glu + | Leu209Met + | Thr223Gln |
| Gly 68Gln + | Val 95Ala + | Ser207Glu + | Leu209Asn |
| Gly 66Asn + | Asp 97Glu + | Asn161Ser + | Gly214Asn |
| Tyr137Met + | Leu209Ser + | Ser216Asp + | Ile220Pro |
| Val 95Asn + | Leu209Val + | Ser219Asp + | Thr223Pro |
| Gly135Asn + | Ser140Glu + | Ala164Thr + | Ile220Leu |
| Gly 70Ser + | Gly135Asp + | Thr217Pro + | Ile220Thr |
| Gly 66Ser + | Ser140Asp + | Leu209Pro + | Ile213Leu |
| Val 95Asn + | Leu 96Ile + | Thr217Pro + | Ile220Gly |
| Leu 96Met + | Gly203Asn + | Ser219Glu + | Ile220Gly |
| Tyr104Cys + | Tyr169Ser + | Leu209Pro + | Ser216Glu |
| Gly 70Gln + | Ser138Asp + | Thr206Asn + | Ile220Gln |
| Asn163Gln + | Gly214Pro + | Ile220Asn + | Thr223Glu |
| Gly 68Asn + | Ser138Asp + | Asn168Ser + | Ile220Met |
| Asn161Gln + | Phe192His + | Thr217Asp + | Ile220Ala |
| Gln103Ser + | Phe192Asn + | Arg218Glu + | Ile220Thr |
| Ala164Gly + | Asn168Gln + | Ser207Asp + | Ile208Met |
| Thr106Gly + | Ser139Asp + | Phe192Thr + | Gly215Asn |
| Leu209His + | Ile213Ser + | Gly214Asn + | Ser219Glu |
| Gly 66Asn + | Asn 99Ser + | Ser101Glu + | Asn194Gln |
| Tyr137Glu + | Thr206Pro + | Trp212Thr + | Ile220His |
| Gly135Glu + | Tyr169Cys + | Thr206Gln + | Ile220Ser |
| Thr206Pro + | Leu209Ser + | Ser216Glu + | Ile220Val |
| Gly 66Asn + | Gly 68Asn + | Ser105Asp + | Leu209Pro |
| Ser170Glu + | Thr206Gly + | Leu209Gln + | Ile220Cys |
| Tyr104Thr + | Asn163Ser + | Leu209His + | Gly222Asn |
| Thr106Glu + | Tyr137Gln + | Asn162Ser + | Leu209Ala |
| Leu 96Thr + | Ser207Asp + | Gly214Ser + | Ile220Gly |
| Asn 99Ser + | Phe192Pro + | Trp212Val + | Ser216Asp |
| Gly136Ser + | Tyr137Asp + | Leu209Val + | Ile220Gly |
| Gly 66Ser + | Gly203Asn + | Ser219Glu + | Ile220Met |
| Ala164Thr + | Thr206Asn + | Thr217Ser + | Ser219Glu |
| Gly102Pro + | Thr106Asn + | Asn161Glu + | Tyr169Ser |
| Thr106Gly + | Gly134Gln + | Thr206Asn + | Ser207Glu |
| Gly 66Asn + | Gln103Asn + | Thr106Gln + | Ile220Gln |
| Arg 64Asp + | Asn 67Gln + | Ile107Ala + | Asn162Ser |
| Thr 71Gly + | Thr106Ser + | Asn163Ser + | Ile220Asn |
| Asn 67Gln + | Ala164Ser + | Ser207Asp + | Ile220Thr |
| Gly 68Ser + | Asn163Gln + | Arg167Asp + | Ile208Thr |
| Tyr137Ser + | Asn168Glu + | Leu209Asn + | Ile213Ala |
| Gly134Ser + | Gly135Pro + | Ala164His + | Asn168Ser |
| Asn163Gln + | Ala164Asp + | Leu209Gly + | Gly215Pro |
| Gly102Pro + | Gly136Pro + | Leu209Ser + | Ile220Pro |
| Tyr104Cys + | Gly136Asn + | Ala164Asn + | Leu209His |
| Asp 65Glu + | Leu 96Val + | Gly136Asn + | Tyr169Pro |
| Asn 67Asp + | Gly100Pro + | Tyr104Leu + | Leu209Ala |
| Val 95His + | Gly135Gln + | Ser191Glu + | Ile220Ala |
| Asn163Ser + | Asn194Ser + | Ser207Glu + | Leu209Ser |
| Gly 66Asn + | Leu 96Ile + | Tyr104Thr + | Ile213Ala |
| Gln103Asn + | Ser138Glu + | Gly160Ser + | Phe202Cys |
| Gly 68Pro + | Thr106Ser + | Asn194Asp + | Thr211Ser |
| Gly100Gln + | Tyr169Thr + | Thr211Pro + | Thr217Ser |
| Gly 66Asn + | Val 95Cys + | Ser139Asp + | Asn194Gln |
| Gly135Pro + | Asn161Glu + | Asn162Ser + | Leu209Ala |
| Gly 66Ser + | Thr 71Ser + | Val 95Thr + | Ile107Asn |
| Asn168Gln + | Leu209Pro + | Ser219Glu + | Ile220Gln |
| Gly 66Pro + | Tyr137Asn + | Tyr169Ile + | Thr223Asp |
| Ser101Glu + | Ile107Pro + | Leu133Cys + | Leu209Pro |
| Asn 67Asp + | Gly 68Ser + | Asn161Ser + | Thr223Ser |
| Asn 99Gln + | Gly102Asn + | Ile107Met + | Trp212Gly |
| Tyr137Ala + | Asn194Gln + | Ile213Asp + | Gly214Asn |
| Leu 96Ala + | Leu209Met + | Gly222Asn + | Thr223Gln |
| Leu 96Val + | Asn162Ser + | Asn163Gln + | Ser170Glu |
| Asn 67Ser + | Leu133Gln + | Leu209Gln + | Ser221Asp |
| Val 95Glu + | Ala164Thr + | Ser207Glu + | Leu209His |
| Gly100Gln + | Asn168Gln + | Ser219Asp + | Ile220Asp |
| Asp 97Glu + | Asp 98Glu + | Ile213Ala + | Thr217Gly |
| Gln103Asn + | Gly135Ser + | Gly215Glu + | Ser216Glu |
| Asn194Ser + | Leu209Gly + | Gly215Glu + | Ser216Glu |
| Gly 70Gln + | Tyr104Cys + | Leu209Glu + | Ser219Glu |
| Ile107Val + | Thr206Asp + | Ser207Glu + | Ser221Glu |

TABLE 31-continued

Multi-loop Quadruple Mutation Variants

| | | | |
|---|---|---|---|
| Leu133Gly + | Ser207Glu + | Leu209Met + | Ser221Glu |
| Val 95Thr + | Tyr137His + | Ser207Glu + | Ser219Glu |
| Gly 68Gln + | Asn162Ser + | Ser207Asp + | Ser219Glu |
| Tyr137Ala + | Ser207Glu + | Ile213Pro + | Ser219Asp |
| Gly100Asn + | Ser207Asp + | Ser207Asp + | Ser219Asp |
| Tyr137Gly + | Tyr137Ser + | Gly215Asn + | Ser219Glu |
| Asp 65Glu + | Asn 67Asp + | Phe202Ser + | Thr206Gly |
| Gly160Ser + | Asn161Glu + | Asn194Glu + | Thr217Asn |
| Asn 67Gln + | Ser207Asp + | Ser219Asp + | Ser221Glu |
| Gly102Asn + | Gly134Gln + | Ser138Glu + | Ser170Asp |
| Asp 65Glu + | Gly 68Asp + | Gly135Pro + | Phe192His |
| Phe192Asn + | Thr206Glu + | Ser207Glu + | Ser219Glu |
| Gly160Pro + | Thr206Asp + | Ser207Glu + | Ser219Asp |
| Leu 96Asn + | Thr206Glu + | Ser207Asp + | Gly222Glu |
| Asp 65Glu + | Asp 98Glu + | Phe192Leu + | Ile213Gln |
| Gly 66Gln + | Asn162Ser + | Ser207Glu + | Leu209Asp |
| Gly 66Ser + | Gly136Glu + | Ser190Asp + | Thr206Asp |
| Asn 67Gln + | Ile107His + | Asp165Glu + | Asn168Asp |
| Phe202Thr + | Ser207Asp + | Ile220Glu + | Gly222Glu |
| Asn 67Ser + | Val 95Gln + | Leu209Asp + | Thr217Glu |
| Asn163Asp + | Ser191Asp + | Asn194Glu + | Ile220Met |
| Ser207Glu + | Leu209Glu + | Ile213Met + | Ser221Asp |
| Asn 67Glu + | Leu 96Asp + | Asp 97Glu + | Leu209Ala |
| Thr206Asp + | Leu209Asp + | Ser219Asp + | Ile220Pro |
| Ser216Glu + | Thr217Glu + | Ser219Glu + | Gly222Gln |
| Ser139Glu + | Ser170Glu + | Phe192His + | Leu209Gln |
| Gly102Asn + | Pro204Ser + | Ser207Asp + | Gly222Glu |
| Thr106Gln + | Ser207Asp + | Leu209Ser + | Gly222Asp |
| Gly100Ser + | Ser207Asp + | Ile220Asn + | Gly222Asp |
| Thr106Asn + | Ser190Glu + | Ser207Asp + | Ser221Glu |
| Leu209Met + | Gly214Asp + | Thr217Glu + | Ile220Asn |
| Ala164Gln + | Ser207Asp + | Arg218Asp + | Ile220Val |
| Tyr169Gly + | Leu209Asp + | Ser216Glu + | Ser219Glu |
| Arg167Glu + | Asn194Asp + | Leu209Ser + | Ile220Pro |
| Gly102Pro + | Ile213Asp + | Arg218Asp + | Ser219Glu |
| Asp 98Glu + | Gly102Asp + | Asn161Gln + | Leu209Ser |
| Ile107Gly + | Gly134Asp + | Ser138Asp + | Tyr169Ser |
| Gly 68Asp + | Gly134Asp + | Phe192Pro + | Ser216Glu |
| Asp 65Glu + | Gly214Glu + | Ile220Thr + | Gly222Pro |
| Ser190Asp + | Ser207Asp + | Ile208Met + | Ile220Val |
| Gly134Asn + | Phe202His + | Arg218Asp + | Ser221Asp |
| Leu 96Ala + | Ile213Glu + | Ser216Glu + | Ser219Asp |
| Gly160Gln + | Ser207Asp + | Arg218Glu + | Gly222Asp |
| Gly 70Glu + | Ile107His + | Leu133Glu + | Phe192Thr |
| Gly136Asp + | Ser170Asp + | Asn194Asp + | Gly222Ser |
| Tyr104Gly + | Leu133Asp + | Ile213Ser + | Gly215Gln |
| Gly100Gln + | Ser207Glu + | Ser216Asp + | Ser219Glu |
| Gly100Asn + | Tyr137Ala + | Leu209Asp + | Ser216Glu |
| Asn162Ser + | Ser216Glu + | Ser219Asp + | Ile220Asn |
| Val 95Ser + | Leu 96Pro + | Ser216Asp + | Ser219Asp |
| Gly102Pro + | Ser216Asp + | Ser219Asp + | Ile220Met |
| Gly135Glu + | Gly136Gln + | Arg167Asp + | Asn194Glu |
| Asn 99Gln + | Ser207Glu + | Ser216Asp + | Thr217Asp |
| Asp 65Glu + | Ser101Glu + | Gly102Glu + | Leu133Thr |
| Asn163Glu + | Ser216Glu + | Ser219Asp + | Ser221Asp |
| Gly 66Gln + | Asn163Asp + | Ser170Glu + | Asn194Asp |
| Gly 66Pro + | Gly134Asp + | Asn161Glu + | Ser191Asp |
| Leu133Thr + | Asn161Asp + | Ser219Asp + | Ile220Asp |
| Ser105Asp + | Gly135Asp + | Gly136Ser + | Tyr169Asp |
| Asn 67Gln + | Asn163Glu + | Asn194Glu + | Ser221Asp |
| Ser207Glu + | Ile213Pro + | Ser216Glu + | Ile220Glu |
| Gly 68Asp + | Leu 96Glu + | Thr206Gly + | Gly214Glu |
| Asn 99Glu + | Ser101Glu + | Gly136Glu + | Asn163Gln |
| Ser138Glu + | Ser139Asp + | Asn163Asp + | Ile220Met |
| Ser101Glu + | Trp212Phe + | Ser219Glu + | Ile220Glu |
| Ala164Glu + | Asn168Gln + | Ser219Glu + | Ile220Asp |
| Ser101Glu + | Gly160Glu + | Arg167Glu + | Asn168Glu |
| Arg167Glu + | Asn168Glu + | Asn194Ser + | Ser207Asp |
| Arg167Glu + | Asn168Asp + | Asn194Ser + | Ile220Glu |
| Leu 96Thr + | Arg167Asp + | Asn168Glu + | Ser216Glu |
| Thr106Asp + | Leu209Asn + | Ser221Asp + | Gly222Asp |
| Asp 65Glu + | Tyr137His + | Asn161Glu + | Asn162Asp |
| Asn 67Asp + | Ser191Asp + | Phe192Glu + | Pro204Ser |
| Arg 64Asp + | Gly 68Ser + | Gly222Asp + | Thr223Glu |
| Ser139Glu + | Ser140Glu + | Arg218Asp + | Thr223Pro |
| Leu 96Met + | Asp 98Glu + | Asn 99Asp + | Ser219Asp |
| Arg 64Asp + | Asp 65Glu + | Gln103Asp + | Leu209Ile |
| Tyr137Glu + | Ser138Glu + | Ser216Asp + | Thr217Asn |
| Gly136Asp + | Thr206Asp + | Ser207Glu + | Ile220Met |
| Ser101Asp + | Ala164Ser + | Thr206Asp + | Ser207Glu |
| Gly 66Gln + | Tyr104Asp + | Ser105Asp + | Ser219Asp |
| Ser138Asp + | Thr217Glu + | Arg218Glu + | Ser219Asp |
| Arg 64Asp + | Leu209Gln + | Ser216Glu + | Thr217Glu |
| Ser105Glu + | Leu209Asp + | Ser219Glu + | Thr223Gln |
| Ser101Asp + | Leu209Asp + | Ser219Glu + | Ile220Ser |
| Asn163Asp + | Phe192Leu + | Asn194Glu + | Ser207Glu |
| Asn163Asp + | Asn194Glu + | Ser207Glu + | Trp212His |
| Ala164Asp + | Asn194Glu + | Ser207Asp + | Ile220Leu |
| Ala164Glu + | Asn194Glu + | Ser207Glu + | Ile220Ser |
| Gly100Asp + | Ala164Glu + | Asn194Asp + | Thr206Ser |
| Leu 96Pro + | Ser207Glu + | Ser216Glu + | Ser221Asp |
| Val 95Asp + | Phe192Tyr + | Ser207Asp + | Ser221Asp |
| Ala164Asp + | Ser207Asp + | Gly215Gln + | Ser221Asp |
| Asp 65Glu + | Leu209Gln + | Ser216Glu + | Arg218Asp |
| Ile107Cys + | Ser139Asp + | Ser207Glu + | Ser219Asp |
| Tyr137Glu + | Ser207Asp + | Ser219Glu + | Ile220Ser |
| Val 95Gln + | Tyr104Asp + | Ser207Asp + | Ser219Asp |
| Asn163Glu + | Ser207Glu + | Ser219Glu + | Gly222Ser |
| Asn168Glu + | Ser207Glu + | Ser219Glu + | Gly222Asn |
| Gly135Asp + | Gly203Ser + | Ser207Glu + | Ser219Glu |
| Leu 96Thr + | Ser139Glu + | Ser207Asp + | Ser219Asp |
| Gly100Glu + | Ser207Asp + | Ser219Glu + | Ile220Cys |
| Gln103Glu + | Tyr104Pro + | Gly136Glu + | Ile220Asn |
| Gln103Glu + | Ser105Asp + | Ser219Asp + | Ile220Cys |
| Gln103Glu + | Ser105Asp + | Tyr137Thr + | Thr206Glu |
| Gly160Asn + | Ser207Asp + | Gly214Glu + | Ser216Asp |
| Asp 97Glu + | Ser101Asp + | Ser207Asp + | Ile220Thr |
| Thr106Asp + | Tyr137Met + | Leu209Glu + | Arg218Glu |
| Gly136Gln + | Ser138Asp + | Ser170Glu + | Ser216Glu |
| Gly 70Asp + | Leu133Ser + | Ser138Asp + | Ser170Asp |
| Asn163Glu + | Tyr169Cys + | Ser219Asp + | Gly222Asp |
| Arg 64Glu + | Gly 66Asp + | Asn168Gln + | Arg218Asp |
| Ser105Asp + | Gly136Asn + | Ser139Asp + | Phe192Thr |
| Tyr137Leu + | Ser191Glu + | Ser207Glu + | Gly222Ser |
| Ser191Asp + | Ser207Asp + | Leu209His + | Ile220Thr |
| Asn 99Ser + | Ser191Glu + | Ser207Asp + | Ile220Asn |
| Gly 66Asp + | Asn 99Asp + | Thr106Gln + | Ser216Asp |
| Asp 97Glu + | Phe202Thr + | Arg218Glu + | Ile220Asp |
| Gly 70Asp + | Asn 99Asp + | Ser207Glu + | Leu209Glu |
| Thr106Glu + | Ser207Glu + | Leu209Asp + | Gly214Gln |
| Asp 65Glu + | Tyr137Pro + | Asp165Glu + | Asn168Asp |
| Asn 99Gln + | Asp165Glu + | Asn168Asp + | Gly215Glu |
| Asn 67Glu + | Asn161Glu + | Ile220Ala + | Gly222Glu |
| Gly 66Asp + | Leu 96Gly + | Leu209Glu + | Ile220Asp |
| Asp 98Glu + | Leu209Ala + | Ser219Glu + | Ser221Asp |
| Asn 67Glu + | Ala164Gln + | Ser219Glu + | Ser221Asp |
| Gly100Glu + | Gly136Asn + | Ser216Asp + | Arg218Glu |
| Ile107Asp + | Thr206Ser + | Ser216Asp + | Arg218Asp |
| Ala164Gly + | Asn194Asp + | Thr217Asp + | Ser219Glu |
| Asp 98Glu + | Asn163Asp + | Asp165Glu + | Trp212Tyr |
| Ser139Glu + | Gly215Glu + | Thr217Asp + | Gly222Pro |
| Ser101Glu + | Ser105Glu + | Phe192Val + | Leu209His |
| Tyr104Asn + | Leu209Glu + | Ser216Asp + | Gly222Asp |
| Gly 70Glu + | Tyr104Ala + | Thr206Asp + | Ser219Glu |
| Leu 96Glu + | Asn 99Asp + | Ala164Gln + | Gly214Glu |
| Ser139Asp + | Asn161Glu + | Ala164Glu + | Ile220Gly |
| Asn 67Ser + | Gly 70Asp + | Leu 96Glu + | Ser221Glu |
| Asn 67Asp + | Asp 97Glu + | Asn163Ser + | Ser221Glu |
| Ser170Glu + | Ser207Asp + | Ile220Ser + | Gly222Asp |
| Leu 96Gly + | Asn163Asp + | Thr206Asp + | Ser219Glu |
| Asn 67Asp + | Ser190Asp + | Gly215Ser + | Gly222Asp |
| Tyr137Cys + | Arg167Asp + | Ser170Asp + | Ser219Asp |
| Gly135Glu + | Ser138Asp + | Gly214Glu + | Gly222Ser |
| Asp 65Glu + | Asp 97Glu + | Asn194Glu + | Gly205Asn |
| Gly102Ser + | Ser105Asp + | Leu133Glu + | Thr223Glu |
| Gly 70Asp + | Asp 98Glu + | Leu209Met + | Ser216Asp |
| Ser138Glu + | Ala164Ser + | Thr206Glu + | Ser219Glu |
| Gly 68Pro + | Asp 97Glu + | Thr206Asp + | Ser219Asp |
| Ser105Asp + | Ser140Glu + | Arg218Glu + | Thr223Gln |
| Asn 99Asp + | Gly102Glu + | Ile213Val + | Ser219Glu |
| Asn 99Asp + | Gly102Asp + | Gly136Ser + | Ser138Asp |
| Gly 70Glu + | Val 95Glu + | Gly100Asn + | Gly222Glu |
| Asn 67Glu + | Ser216Glu + | Ser219Asp + | Ile220Cys |
| Asn 67Asp + | Ala164Pro + | Ser216Glu + | Ser219Asp |

TABLE 31-continued

Multi-loop Quadruple Mutation Variants

| | | | |
|---|---|---|---|
| Asn 99Asp + | Asn161Glu + | Ser190Asp + | Gly215Asn |
| Val 95Asp + | Asn161Gln + | Ser190Glu + | Ser221Asp |
| Gly 68Asp + | Gly100Glu + | Gly222Ser + | Thr223Glu |
| Gly134Glu + | Tyr169Leu + | Ser207Glu + | Arg218Glu |
| Thr106Asp + | Ser207Glu + | Arg218Asp + | Ile220Cys |
| Arg 64Glu + | Asn163Ser + | Ser207Asp + | Arg218Asp |
| Ser139Asp + | Ser207Asp + | Arg218Asp + | Ile220Thr |
| Leu133Asp + | Gly134Pro + | Asn162Asp + | Tyr169Asn |
| Val 95Asp + | Gly134Glu + | Asn194Glu + | Thr211Gly |
| Ile107Asn + | Ser140Glu + | Ser170Glu + | Ser219Asp |
| Tyr137Cys + | Ser140Glu + | Ser170Asp + | Ser219Glu |
| Tyr137Thr + | Ser140Glu + | Ser170Glu + | Thr206Glu |
| Tyr137Asn + | Gly160Glu + | Asp165Glu + | Ser216Glu |
| Asn 99Glu + | Gly160Asp + | Asp165Glu + | Leu209Gln |
| Asp 97Glu + | Tyr104Glu + | Leu133Ser + | Ile220Leu |
| Asn 67Glu + | Val 95Gly + | Pro204Ser + | Ser216Asp |
| Asn 99Asp + | Asn162Gln + | Ser191Asp + | Gly222Glu |
| Gly100Glu + | Thr106Gly + | Asn162Asp + | Tyr169Glu |
| Asp 65Glu + | Asn 99Asp + | Gly135Asn + | Gly160Asp |
| Asp 65Glu + | Asn 99Glu + | Trp212Asn + | Ser219Asp |
| Gly134Glu + | Asn161Asp + | Thr217Pro + | Ser219Asp |
| Asp 97Glu + | Gln103Asp + | Asn163Gln + | Ile220Glu |
| Asn161Glu + | Asp165Glu + | Ser207Asp + | Thr223Gln |
| Ser140Glu + | Ala164His + | Thr217Asp + | Ile220Asp |
| Gly 70Ser + | Gly102Asp + | Leu133Asp + | Ser191Asp |
| Ser101Glu + | Ile107Glu + | Thr217Pro + | Ser219Glu |
| Tyr137Glu + | Asn162Glu + | Ser190Asp + | Ile213Gln |
| Gly 68Asp + | Ser170Glu + | Ser216Asp + | Ile220Val |
| Gln103Asp + | Gly135Asp + | Leu209Met + | Ser216Asp |
| Tyr104Val + | Gly136Glu + | Ser139Glu + | Ser190Asp |
| Gly102Pro + | Asn161Glu + | Asp165Glu + | Gly214Glu |
| Gly 70Glu + | Tyr169Cys + | Ser190Glu + | Ser207Glu |
| Asn168Glu + | Ser190Glu + | Pro204Ser + | Ser207Glu |
| Ser190Asp + | Ser207Asp + | Leu209Ser + | Ser216Glu |
| Asn 67Glu + | Ser101Glu + | Tyr137Asp + | Gly215Gln |
| Arg 64Glu + | Ser191Glu + | Ile220His + | Ser221Asp |
| Arg167Asp + | Ser191Asp + | Ile213Ala + | Ser221Glu |
| Arg167Glu + | Thr206Ser + | Ser219Asp + | Gly222Glu |
| Ser101Glu + | Asn161Gln + | Asn162Asp + | Ser190Asp |
| Ser101Asp + | Gly136Pro + | Ser216Asp + | Ser219Glu |
| Tyr104Gln + | Thr106Glu + | Ser216Glu + | Ser219Glu |
| Gly 68Pro + | Leu133Glu + | Ser216Glu + | Ser219Glu |
| Gly160Glu + | Leu209Val + | Ser216Glu + | Ser219Glu |
| Ser191Glu + | Leu209Gln + | Ser216Asp + | Ser219Asp |
| Asn 67Gln + | Arg167Glu + | Ser216Glu + | Ser219Asp |
| Asn 99Gln + | Ser170Asp + | Ser216Glu + | Ser219Asp |
| Ser138Glu + | Asn162Glu + | Ser216Glu + | Ser219Glu |
| Gly135Gln + | Asn168Glu + | Ser216Asp + | Ser219Asp |
| Gly100Glu + | Thr206Ser + | Ser207Glu + | Thr223Glu |
| Asn163Gln + | Gly214Asn + | Ser216Glu + | Ile220Asp |
| Gly100Pro + | Thr211Asn + | Ser216Glu + | Ile220Asp |
| Thr206Pro + | Leu209Thr + | Ser216Asp + | Ile220Asp |
| Gly102Asp + | Gly160Asp + | Ser190Glu + | Trp212Ser |
| Leu133Cys + | Gly134Asp + | Asn162Asp + | Ser216Asp |
| Asp 65Glu + | Thr106Gln + | Ser216Glu + | Gly222Gln |
| Asp 98Glu + | Gly100Ser + | Asn168Asp + | Ile213Glu |
| Ser101Asp + | Tyr137Ala + | Asn161Glu + | Thr206Glu |
| Gly 70Asp + | Gly136Glu + | Ser140Glu + | Ile220Pro |
| Gly 68Glu + | Tyr104Glu + | Leu209Val + | Ser219Asp |
| Gly 68Asp + | Gly160Gln + | Asn194Glu + | Ser219Asp |
| Asn163Gln + | Ser190Glu + | Ser216Glu + | Ile220Glu |
| Arg 64Asp + | Gln103Asn + | Leu133Asp + | Gly214Glu |
| Arg 64Asp + | Tyr104Ser + | Leu209Glu + | Gly214Asp |
| Gly 70Asp + | Ser101Asp + | Ser140Glu + | Ile220Val |
| Gly 70Asp + | Leu 96Thr + | Leu209Asn + | Ser216Glu |
| Ile107Asp + | Ser138Glu + | Ala166Gln + | Ser219Asp |
| Asn161Glu + | Ser207Asp + | Leu209Ile + | Thr217Asp |
| Gly 68Asn + | Asn163Glu + | Arg167Glu + | Ser219Asp |
| Asn 99Ser + | Gln103Asp + | Gly136Glu + | Thr206Glu |
| Gln103Glu + | Leu133Gln + | Gly136Glu + | Ser216Glu |
| Gly102Asp + | Leu133Thr + | Ser207Asp + | Thr217Glu |
| Asp 97Glu + | Ser207Asp + | Thr217Glu + | Thr223Asn |
| Ser101Glu + | Ser191Asp + | Ser207Asp + | Leu209Cys |
| Ile107Ser + | Ser191Glu + | Ser207Asp + | Ser216Asp |
| Thr 71Pro + | Ser191Glu + | Ser207Glu + | Ser216Glu |
| Ala164Gln + | Ser191Glu + | Ser207Asp + | Ser216Asp |
| Ser170Glu + | Asn194Asp + | Ser207Glu + | Ile220Val |
| Ser170Asp + | Asn194Glu + | Trp212Ser + | Ser216Glu |
| Arg 64Glu + | Asn 99Glu + | Ser170Asp + | Leu209Thr |
| Asp 97Glu + | Leu133Glu + | Asn161Ser + | Ser216Asp |
| Tyr137Pro + | Ser140Asp + | Phe192Asp + | Ser207Glu |
| Asn 99Ser + | Gln103Glu + | Ser170Asp + | Ser219Asp |
| Gln103Glu + | Asn163Glu + | Ser170Glu + | Ile220His |
| Asp 65Glu + | Asn 99Ser + | Ser101Glu + | Ser191Asp |
| Ser105Glu + | Gly135Asp + | Thr206Asp + | Thr217Gln |
| Leu 96Cys + | Asn161Glu + | Arg167Glu + | Arg218Asp |
| Arg 64Glu + | Gly100Glu + | Asn161Ser + | Leu209Glu |
| Val 95Met + | Asp 97Glu + | Ser105Glu + | Ile220Asn |
| Gly 68Glu + | Val 95Glu + | Asn168Ser + | Leu209Ala |
| Asn 67Glu + | Asn161Asp + | Ser216Asp + | Gly222Asn |
| Asn 67Asp + | Leu133His + | Arg167Glu + | Ser216Glu |
| Ser105Asp + | Gly160Ser + | Ser170Asp + | Thr206Glu |
| Gly 66Pro + | Asn162Asp + | Ser170Glu + | Ser219Glu |
| Gly100Glu + | Gly102Asn + | Tyr104Asp + | Ser207Asp |
| Gly100Glu + | Tyr104Asp + | Gly160Glu + | Gly215Gln |

TABLE 32

Multi-loop Quintuple Mutation Variants

| | | | | |
|---|---|---|---|---|
| Leu133Gln + | Gly136Glu + | Thr206Gln + | Leu209Met + | Ile220Met |
| Gly203Asn + | Gly205Gln + | Ser216Glu + | Thr217Gly + | Ile220Gly |
| Val 95His + | Ala164Ser + | Ser170Glu + | Phe192Met + | Thr223Gly |
| Leu133Asn + | Asn161Gln + | Asn163Gln + | Leu209Met + | Ile220Leu |
| Asn 67Gln + | Gly136Ser + | Asn162Asp + | Tyr169Gly + | Phe202Met |
| Ile107Asn + | Leu209Gln + | Ile213Gly + | Ser219Glu + | Ile220His |
| Gly 66Ser + | Thr 71Gly + | Tyr169His + | Phe202Ser + | Ile220Asp |
| Gly135Ser + | Ala166Ser + | Ser207Glu + | Ile213Gly + | Gly222Ser |
| Asp 98Glu + | Thr106Pro + | Tyr137Cys + | Trp212Ile + | Ile220Val |
| Gly134Asn + | Ala166Pro + | Phe192Met + | Thr206Gly + | Ser219Glu |
| Thr106Glu + | Gly205Asn + | Leu209Cys + | Gly215Pro + | Ile220Thr |
| Asn163Gln + | Asn168Gln + | Phe192Cys + | Thr206Gln + | Leu209Ser |
| Leu 96Gly + | Ile107Gly + | Ser140Asp + | Leu209Ala + | Thr223Gly |
| Asn 67Ser + | Val 95His + | Gly135Gln + | Ser191Glu + | Ile220Ala |
| Ile107Gly + | Tyr169Ser + | Asn194Ser + | Ser207Glu + | Leu209Ser |
| Tyr137His + | Leu209Met + | Ile220Val + | Gly222Asn + | Thr223Gly |
| Val 95Ala + | Tyr137Pro + | Ala164Glu + | Asn168Gln + | Thr206Asn |
| Leu 96Gln + | Tyr137Leu + | Tyr169His + | Leu209Asp + | Ile220Pro |
| Gly 66Pro + | Gly 70Asn + | Leu133Pro + | Phe202Pro + | Ser207Glu |
| Val 95Ala + | Leu 96Met + | Tyr104Asn + | Ile107Ala + | Ser216Asp |
| Gly 70Ser + | Ile107Gly + | Leu133Met + | Phe192His + | Asn194Asp |
| Gly 68Pro + | Val 95Ser + | Gly100Asn + | Tyr137Cys + | Ile220Pro |
| Gly 66Ser + | Gly102Gln + | Ala164Gln + | Ser219Glu + | Gly222Asn |
| Gly135Gln + | Ser190Glu + | Leu209Cys + | Gly215Gln + | Ile220Val |
| Gly 68Pro + | Asn163Asp + | Phe192Pro + | Leu209Gly + | Ile220Thr |
| Asn 67Gln + | Gly 70Asn + | Ile107Leu + | Gly136Asn + | Asn162Glu |
| Gly 70Pro + | Ile107His + | Ser190Glu + | Pro204Asn + | Leu209Gln |
| Leu 96Ile + | Asp165Glu + | Phe202Gly + | Leu209Asn + | Thr211Gly |
| Gly 66Pro + | Gly 70Asp + | Tyr169Asn + | Leu209His + | Gly215Ser |
| Tyr104Met + | Asn194Glu + | Leu209Cys + | Thr217Pro + | Ile220Gln |
| Gly 70Asn + | Leu 96Ile + | Tyr104His + | Asn161Asp + | Ile220Gln |
| Val 95Thr + | Gly102Pro + | Thr206Ser + | Gly214Glu + | Gly222Ser |
| Thr106Gln + | Asn163Ser + | Ile213Pro + | 3er216Glu + | Ile220Ser |
| Leu 96Cys + | Gly136Asn + | Ser170Glu + | Thr206Gln + | Ile220Glu |
| Gly 66Gln + | Ser105Glu + | Gly135Pro + | Gly205Asn + | Thr206Ser |
| Gly102Pro + | Tyr104Ile + | Thr211Gly + | Ser216Glu + | Thr223Gln |
| Tyr104Ala + | Gly203Asn + | Gly205Gly + | Arg218Asp + | Ile220Cys |
| Gly 66Pro + | Val 95Thr + | Asn161Ser + | Asn162Gln + | Ile220Cys |
| Gly102Asn + | Gly136Gln + | Phe202Met + | Ile208Val + | Ile213Glu |
| Gly 66Ser + | Gly 68Ser + | Gly134Gln + | Ala164Gly + | Asp165Glu |
| Gly 66Pro + | Ala164Asp + | Tyr169Ser + | Thr206Gln + | Thr217Asn |
| Leu 96Ile + | Gly136Asn + | Asn161Ser + | Thr206Gln + | Ser207Asp |
| Asn 67Asp + | Tyr104Asn + | Gly135Gln + | Tyr169Ile + | Leu209His |
| Gly 70Pro + | Gly136Pro + | Ser190Asp + | Leu209Ser + | Gly214Pro |
| Asp 65Glu + | Tyr137Val + | Ala164Asn + | Phe192Ala + | Thr206Asp |
| Leu 96Thr + | Gln103Ser + | Tyr104Asn + | Asp165Glu + | Ile220His |
| Gly 68Asp + | Gly 70Pro + | Asn 99Ser + | Gly214Ser + | Thr223Ser |
| Leu 96Ser + | Leu133Ala + | Tyr137Met + | Leu209Ile + | Ser221Asp |
| Gly134Gln + | Asn194Gln + | Thr206Ser + | Leu209Met + | Ile213Leu |
| Gly 70Glu + | Leu133Cys + | Gly135Gln + | Thr206Gly + | Gly222Asn |
| Gly134Ser + | Ala166Gln + | Tyr169Cys + | Thr206Gly + | Ser221Asp |

TABLE 32-continued

Multi-loop Quintuple Mutation Variants

| | | | | |
|---|---|---|---|---|
| Gly160Ser + | Thr206Asp + | Ile213Gln + | Ile220Pro + | Thr223Gly |
| Tyr104Asn + | Gly135Pro + | Leu209Ile + | Ser219Glu + | Ile220Val |
| Asn 67Gln + | Thr106Asn + | Gly160Glu + | Tyr169Asn + | Leu209Ala |
| Val 95Glu + | Gly100Pro + | Thr206Asn + | Leu209Thr + | Ile220Ala |
| Asp 98Glu + | Gly102Ser + | Ala164Asp + | Thr206Ser + | Ile220Asn |
| Gln103Asn + | Gly136Pro + | Ser138Asp + | Leu209Gly + | Ile220Gln |
| Asn 67Gln + | Thr106Asn + | Gly136Gln + | Thr206Ser + | Ile220Asn |
| Asn 67Gln + | Gly134Gln + | Tyr169Cys + | Ser219Asp + | Ile220Asp |
| Ala166His + | Thr206Glu + | Ser207Asp + | Ile213Cys + | Ile220His |
| Gly 70Pro + | Ile107Gly + | Leu209Gln + | Ile220Glu + | Ser221Asp |
| Asn 99Ser + | Gly160Ser + | Gly215Glu + | Ser216Glu + | Thr217Gln |
| Gly102Gln + | Ile107Cys + | Ala164Ser + | Leu209Asp + | Ser219Asp |
| Gly134Asn + | Tyr137Gln + | Leu209Glu + | Ser219Asp + | Ile220Met |
| Gly102Gln + | Gly160Gln + | Leu209Asp + | Arg218Asp + | Ser219Glu |
| Gly 70Asn + | Ser207Glu + | Leu209Val + | Ser219Glu + | Ile220Glu |
| Ala164Asn + | Ser207Asp + | Thr217Pro + | Ser219Glu + | Ile220Asp |
| Val 95Thr + | Ala164Pro + | Ser219Glu + | Ile213Val + | Ser221Asp |
| Val 95Asn + | Gly102Pro + | Gly160Pro + | Ser207Asp + | Ser219Asp |
| Asn 67Gln + | Ser207Glu + | Leu209Val + | Ser219Asp + | Ile220Ala |
| Asn 67Gln + | Gly136Gln + | Ser138Glu + | Ser140Asp + | Leu209Met |
| Tyr104Asn + | Ser138Glu + | Leu209Glu + | Ser219Thr + | Ile220Val |
| Asp 97Glu + | Asn 99Asp + | Gly102Gln + | Tyr137Ser + | Ile220Cys |
| Asn161Asp + | Asn163Gln + | Tyr169Ala + | Asn194Asp + | Leu209Ala |
| Thr206Glu + | Ser207Asp + | Leu209His + | Ser219Asp + | Thr223Gly |
| Gly102Ser + | Gly136Asn + | Thr206Asp + | Leu209Thr + | Gly222Asp |
| Thr 71Gly + | Gly102Asn + | Ser219Asp + | Ile220Cys + | Ser221Glu |
| Thr106Ser + | Gly160Asp + | Gly205Asn + | Ser219Asp + | Ser221Asp |
| Val 95Gln + | Leu133Gln + | Gly215Asn + | Thr217Asp + | Ser219Asp |
| Leu209Ser + | Ser219Glu + | Ile220Gly + | Ser221Glu + | Gly222Asp |
| Gln103Ser + | Gly203Pro + | Ser216Glu + | Arg218Glu + | Ser219Asp |
| Val 95Ser + | Gly135Gln + | Ser138Asp + | Tyr169Glu + | Ile213Thr |
| Asn 67Gln + | Gly160Pro + | Ser207Glu + | Leu209Cys + | Gly222Glu |
| Gly135Asp + | Ser138Glu + | Gly203Gln + | Ile213Met + | Gly222Asn |
| Asn162Gln + | Ser207Asp + | Leu209Pro + | Ser219Glu + | Gly222Asp |
| Tyr137Asn + | Ala164Asp + | Arg167Asp + | Leu209Ile + | Ile220Met |
| Leu 96Gln + | Gly102Asn + | Gly135Asp + | Asn168Asp + | Ile220Ala |
| Val 95Pro + | Asn 99Asp + | Gly102Asp + | Gly160Gln + | Leu209Asn |
| Asn 99Ser + | Ile107Gly + | Asn162Gln + | Leu209Asp + | Ser221Glu |
| Gly 66Pro + | Asn162Asp + | Ser191Asp + | Thr206Asn + | Thr223Asn |
| Gln103Asp + | Tyr104Asn + | Ser105Glu + | Ser140Asp + | Leu209Cys |
| Leu 96Ser + | Gly136Ser + | Asn168Glu + | Asn194Asp + | Thr206Asn |
| Gly 68Ala + | Val 95Ala + | Gly136Asn + | Gly203Asn + | Ser216Asp |
| Asp 65Glu + | Thr106Asn + | Gly134Gln + | Gly214Asp + | Ser216Glu |
| Gly 68Gln + | Val 95Pro + | Asn162Gln + | Ser190Glu + | Ser207Asp |
| Ala166Thr + | Ser190Glu + | Ser207Glu + | Leu209Gln + | Thr217Gly |
| Gly100Pro + | Gly160Glu + | Ser190Glu + | Ser207Asp + | Leu209Pro |
| Asn 67Glu + | Ser101Glu + | Tyr104His + | Phe192Ser + | Leu209Thr |
| Ser191Glu + | Phe202His + | Leu209Met + | Ser221Asp + | Thr223Gln |
| Gly134Asp + | Ser139Asp + | Ser140Glu + | Ile213Met + | Thr223Asn |
| Tyr137Asn + | Tyr169Ile + | Thr206Asp + | Ser219Asp + | Thr223Asp |
| Tyr104Cys + | Leu133Ile + | Ser207Glu + | Ser216Glu + | Arg218Asp |
| Gly 68Asn + | Tyr137Ser + | Ser207Asp + | Ser216Asp + | Ser219Glu |
| Tyr137Ser + | Asn168Ser + | Gly214Asp + | Ser216Asp + | Ser219Glu |
| Ile107His + | Asn162Ser + | Ser216Glu + | Ser219Asp + | Ile220Asn |
| Asn 67Gln + | Asn163Ser + | Ser216Asp + | Ser219Glu + | Thr223Ser |
| Leu 96Asn + | Leu133Pro + | Thr206Gln + | Ser216Asp + | Ser219Asp |
| Ser191Glu + | Thr206Asp + | Gly214Asn + | Ser219Asp + | Thr223Asn |
| Gly 66Ser + | Ser105Glu + | Thr106Pro + | Ser138Glu + | Leu209Ile |
| Gly136Asp + | Gly160Glu + | Asn163Ser + | Ile220Ser + | Gly222Asp |
| Ile107Met + | Asn162Asp + | Ser190Asp + | Ser221Asp + | Gly222Ser |
| Gly 70Gln + | Gly214Ser + | Ser216Glu + | Ser219Glu + | Ser221Glu |
| Gly136Glu + | Asn162Glu + | Gly214Ser + | Gly215Asn + | Ile220Leu |
| Gly 68Asp + | Leu209Thr + | Arg218Glu + | Ser221Asp + | Thr223Pro |
| Gly100Ser + | Phe192Glu + | Gly215Asn + | Ser219Asp + | Ile220Glu |
| Gly134Gln + | Phe192Glu + | Ile213Gly + | Ser219Asp + | Ile220Glu |
| Thr106Gly + | Asn162Ser + | Asn194Asp + | Thr206Asp + | Ser221Asp |
| Gln103Asp + | Asn161Asp + | Ser207Asp + | Thr217Ser + | Ile220Glu |
| Gly 68Asn + | Phe192Asp + | Leu209Asp + | Ser219Asp + | Ile220Asn |
| Gly 68Asp + | Phe192Tyr + | Leu209Gly + | Ser219Asp + | Ile220Gln |
| Arg 64Asp + | Asp 98Glu + | Tyr137Val + | Phe192Val + | Gly214Asp |
| Tyr104Gly + | Ile107Gly + | Gly160Glu + | Ser170Asp + | Leu209Cys |
| Val 95Thr + | Ile107Gly + | Ser191Glu + | Ser219Glu + | Ile220Asp |
| Asp 65Glu + | Gly 66Asp + | Gly100Asn + | Gly102Ser + | Ser190Glu |
| Asp 65Glu + | Gly 66Asp + | Gly134Gln + | Ile220Asp + | Thr223Gln |
| Asp 65Glu + | Gly 66Asp + | Leu209Glu + | Ile213Ala + | Ile220Ala |
| Asn 99Gln + | Ser190Glu + | Ser191Asp + | Ser219Glu + | Ile220His |
| Gly 70Asp + | Ser101Asp + | Tyr137Cys + | Gly160Ser + | Ile220His |
| Tyr137Ser + | Ser138Asp + | Ser139Glu + | Ile213Met + | Ser216Asp |
| Gly135Ser + | Ser138Glu + | Asn194Ser + | Ser219Glu + | Ile220Glu |
| Thr 71Pro + | Asp 97Glu + | Thr106Ser + | Ser219Glu + | Ile220Glu |
| Arg 64Asp + | Gly 66Gln + | Thr206Gly + | Ser219Glu + | Ile220Asp |
| Val 95Ala + | Gln103Ser + | Ser139Asp + | Arg167Glu + | Ile220Ala |
| Ser101Asp + | Gly102Glu + | Ile213Val + | Thr217Ser + | Thr223Glu |
| Asn 99Asp + | Gly100Glu + | Tyr137Thr + | Asn163Glu + | Gly215Gln |
| Gly 66Ser + | Ile197Glu + | Leu209Asn + | Ser221Glu + | Gly222Glu |
| Asn 67Gln + | Thr 71Gln + | Asn161Asp + | Asn162Glu + | Gly214Ser |
| Gly100Asp + | Ser101Glu + | Thr106Gln + | Ile213Cys + | Ser221Asp |
| Arg 64Asp + | Asp 65Glu + | Gly 68Ser + | Leu 96Gln + | Asn168Asp |
| Gly160Pro + | Thr206Glu + | Ser207Glu + | Gly215Glu + | Gly222Pro |
| Gly102Ser + | Tyr137Asp + | Tyr169His + | Thr206Glu + | Ser207Asp |
| Gly 70Asp + | Asn 99Ser + | Tyr104Glu + | Ser105Asp + | Thr217Gln |
| Leu 96Glu + | Gly135Ser + | Thr217Ser + | Ile220Glu + | Ser221Glu |
| Asp 97Glu + | Asp 98Glu + | Gly205Pro + | Gly215Ser + | Ser219Glu |
| Gly 68Gln + | Ser138Asp + | Leu209Ile + | Arg218Asp + | Ser219Asp |
| Asn 67Ser + | Gly136Asp + | Gly215Pro + | Ser216Glu + | Thr217Asp |
| Asn 99Gln + | Ser101Glu + | Asn161Gln + | Asn162Asp + | Asn163Asp |
| Tyr137Gln + | Tyr169Thr + | Ser207Asp + | Gly215Asp + | Ser216Asp |
| Leu 96Cys + | Ser190Asp + | Gly215Glu + | Ser216Glu + | Ile220Cys |
| Gly160Pro + | Phe192Asn + | Ser207Glu + | Gly215Asp + | Ser216Glu |
| Thr 71Asn + | Phe192Val + | Ser207Asp + | Gly215Asp + | Ser216Asp |
| Gly134Glu + | Asn168Asp + | Trp212Ile + | Ile220Asn + | Thr223Glu |
| Gln103Asp + | Gly134Ser + | Ser139Glu + | Asn162Ser + | Ser170Asp |
| Gln103Asp + | Thr106Ser + | Ser138Glu + | Leu209Val + | Gly215Gln |
| Asn 67Gln + | Gln103Asp + | Gly135Gln + | Ser138Glu + | Leu209Asn |
| Asp 97Glu + | Ile107Gln + | Gly136Ser + | Ser207Asp + | Ser221Asp |
| Tyr137Ile + | Ser138Glu + | Asn194Ser + | Ser207Asp + | Ser221Asp |
| Gln103Asp + | Gly135Asn + | Gly136Pro + | Ser207Glu + | Ile220Glu |
| Gly102Gln + | Gly135Glu + | Gly203Ser + | Ser207Asp + | Ile220Glu |
| Tyr104Ile + | Asn163Asp + | Arg167Glu + | Tyr169Cys + | Ile208Cys |
| Gly 66Glu + | Asp 97Glu + | Tyr104Glu + | Gly136Gln + | Leu209Met |
| Gly102Ser + | Ile107Cys + | Arg167Asp + | Ser207Asp + | Ser219Asp |
| Gly100Asn + | Gly134Asp + | Ser207Asp + | Gly214Ser + | Ser219Asp |
| Arg 64Asp + | Val 95Ser + | Thr206Ser + | Ser207Asp + | Ser219Glu |
| Asn194Asp + | Ser207Glu + | Ser219Asp + | Ile220Met + | Thr223Asn |
| Ser140Glu + | Ser207Glu + | Leu209Ala + | Gly215Gln + | Ser219Glu |
| Tyr104Ser + | Gly160Glu + | Ser207Asp + | Gly215Ser + | Ser219Asp |
| Asp 65Glu + | Thr206Ser + | Ser207Asp + | Gly215Ser + | Ser219Asp |
| Gln103Ser + | Asn168Glu + | Pro204Gln + | Ser207Glu + | Ser219Glu |
| Leu133Thr + | Ser140Glu + | Asn161Ser + | Ser207Asp + | Ser219Glu |
| Leu 96Pro + | Ser140Glu + | Ser207Asp + | Leu209Thr + | Ser219Glu |
| Asn161Asp + | Asn168Gln + | Ser170Asp + | Ser191Asp + | Phe192Gln |
| Gln103Glu + | Thr106Glu + | Leu209Gly + | Ile213His + | Ser219Glu |
| Asp 65Glu + | Asn 67Asp + | Thr106Asn + | Asn194Glu + | Ile208Asn |
| Asp 65Glu + | Asn 67Glu + | Leu 96Ala + | Gly102Ser + | Tyr169Asp |
| Asn 99Ser + | Asp165Glu + | Arg167Asp + | Ile213Gly + | Ser219Asp |
| Tyr104Ile + | Tyr137Ile + | Asp165Glu + | Arg167Glu + | Ser219Asp |
| Ser190Glu + | Phe192Glu + | Leu209Cys + | Ser219Glu + | Ile220Ala |
| Ser138Glu + | Ser140Glu + | Thr206Gly + | Ile220His + | Ser221Glu |
| Val 95Pro + | Ile107Ser + | Ser138Asp + | Ser140Glu + | Ser219Glu |
| Asp 65Glu + | Gly102Ser + | Ser138Asp + | Ser140Asp + | Ala166Gly |
| Val 95Cys + | Ser101Glu + | Ser138Glu + | Ser140Asp + | Phe192Ser |
| Asp 97Glu + | Asn 99Asp + | Ser139Asp + | Ile213Thr + | Thr223Gly |
| Asp 97Glu + | Asn 99Asp + | Ser140Glu + | Ala166Gln + | Phe192Thr |
| Leu 96Met + | Gly136Glu + | Asn161Asp + | Asn168Gln + | Ile220Pro |
| Gln103Asp + | Ser105Glu + | Asn162Ser + | Ser207Glu + | Thr223Gln |
| Arg 64Asp + | Gln103Glu + | Ser105Asp + | Asn163Gln + | Leu209Cys |
| Tyr137Ala + | Ser170Glu + | Phe192Met + | Gly214Glu + | Ser216Asp |
| Gly 70Ser + | Ser105Glu + | Gly214Glu + | Ser216Glu + | Thr223Asn |
| Gln103Ser + | Asn168Asp + | Gly205Ser + | Gly214Asp + | Ser216Asp |
| Gly135Glu + | Tyr169Glu + | Ser207Asp + | Leu209Met + | Ile220Cys |
| Asn 99Gln + | Gly136Asp + | Gly160Ser + | Ser170Asp + | Ser216Asp |
| Gly136Asp + | Tyr169Ser + | Ser170Asp + | Ile213Glu + | Thr217Asn |
| Asp 97Glu + | Ser101Asp + | Ser139Glu + | Asn162Ser + | Ile220Val |
| Asp 97Glu + | Ser101Glu + | Ile213Met + | Thr217Gly + | Arg218Asp |
| Thr106Asn + | Ile107Pro + | Asn194Glu + | Ser219Asp + | Ser221Glu |
| Leu 96Met + | Asn 99Asp + | Ser101Glu + | Ser139Asp + | Leu209Thr |
| Asn 99Asp + | Ser101Glu + | Gln103Ser + | Ser139Asp + | Ile220Pro |
| Gly 68Glu + | Asp 97Glu + | Gly160Asn + | Asn163Ser + | Ile220Asp |
| Arg 64Asp + | Gly 66Asp + | Ile107Gly + | Ser207Asp + | Ile220Val |
| Gly 70Gln + | Gln103Asp + | Leu133Ile + | Ser140Asp + | Leu209Thr |
| Asn 67Glu + | Gly 70Glu + | Asn 99Gln + | Tyr104Met + | Leu209Asp |
| Tyr104Gln + | Ile107His + | Ser191Asp + | Thr206Glu + | Arg218Asp |
| Asn161Glu + | Ala164Gln + | Ile213Asp + | Ser216Asp + | Thr217Asn |
| Thr106Gln + | Gly136Pro + | Thr206Ser + | Ser207Glu + | Thr217Glu |

TABLE 32-continued

Multi-loop Quintuple Mutation Variants

Asp 65Glu + Leu 96Gly + Asp 98Glu + Thr106Asp + Ile220Gln
Asp 65Glu + Asp 98Glu + Ile107Gly + Gly135Asn + Gly136Asp
Gly136Asp + Ser138Asp + Ser207Glu + Leu209Asn + Gly222Asn
Thr106Gln + Gly136Asp + Ser138Asp + Leu209Cys + Ser216Glu
Val 95Ala + Asp 97Glu + Asn168Ser + Ser207Asp + Leu209Glu
Ile107Glu + Thr206Ser + Ser207Asp + Leu209Glu + Thr211Gly
Gly 70Pro + Leu 96Val + Gly102Glu + Ser207Glu + Leu209Asp
Val 95His + Asn194Asp + Ser207Asp + Leu209Asp + Thr217Asn
Ser140Asp + Ala164Pro + Ser207Asp + Leu209Asp + Thr211Gly
Gln103Asp + Tyr104Gln + Gly160Ser + Asp165Glu + Asn168Asp
Asp 65Glu + Gly 66Ser + Gly 70Glu + Gly136Asn + Ser207Asp
Gly 68Asp + Phe192Asn + Gly205Asn + Thr217Asp + Ser221Asp
Gly134Asp + Gly136Asp + Ser207Glu + Leu209Ile + Ile220Cys
Gly100Asn + Gly136Glu + Gly160Gln + Ser219Asp + Ser221Glu
Gly102Ser + Ser170Glu + Gly215Asn + Ser219Glu + Ser221Glu
Gly 66Ser + Asn163Gln + Arg167Glu + Ser219Glu + Ser221Asp
Gly100Glu + Gly136Asn + Leu209Ser + Ser219Glu + Ser221Asp
Leu133Ala + Gly134Asp + Ile213Cys + Ser219Glu + Ser221Glu
Gly102Asn + Gln103Glu + Thr206Ser + Ser216Glu + Arg218Asp
Asp 98Glu + Thr206Gly + Ile213Ala + Ser216Asp + Arg218Glu
Asn163Asp + Ile208Asn + Ile213Asn + Ser216Asp + Arg218Asp
Gly 66Ser + Gly 70Glu + Tyr169His + Thr206Gly + Ile220Asp
Arg 64Glu + Asn 67Glu + Ile107Gly + Leu209Val + Ile220Glu
Gln103Glu + Gly134Ser + Ser138Glu + Arg167Asp + Thr223Asn
Gly100Pro + Tyr104Pro + Leu133Gln + Phe192Asp + Ser207Glu
Gly 68Asn + Ser138Asn + Asn163Glu + Arg167Asp + Thr206Gly
Gly 70Ser + Gln103Asp + Asn162Ser + Ser170Asp + Leu209Met
Asp 98Glu + Gly100Ser + Ser101Asp + Asn161Ser + Ile220Asp
Tyr137Pro + Ser139Asp + Asn161Glu + Ala164Glu + Ile220Gly
Gly 66Asp + Asn 99Glu + Tyr104Met + Ser207Glu + Leu209Pro
Gly 66Asp + Asp 97Glu + Tyr104Gln + Ile208Val + Leu209Asp
Ile107Asp + Phe192Met + Ser207Asp + Gly222Glu + Thr223Gln
Arg 64Glu + Leu 96Ala + Ala164Asn + Ser207Glu + Gly222Asp
Leu 96His + Ser207Glu + Ser216Glu + Thr217Asn + Gly222Asp
Tyr169His + Ser170Glu + Ser207Asp + Ile220Ser + Gly222Asp
Gly 68Pro + Leu133Glu + Leu209Asp + Gly214Gln + Ser221Glu
Ser101Asp + Arg167Asp + Ser170Glu + Gly215Asn + Thr223Gly
Asp 6SGlu + Asp 97Glu + Ser207Asp + Gly222Ser + Thr223Ser
Asp 6SGlu + Asp 97Glu + Asn 99Gln + Gly135Glu + Thr206Gly
Tyr104Met + Gly160Asp + Ala164Glu + Leu209Asp + Ile220Thr
Leu 96Ser + Asn162Glu + Asp165Glu + Tyr169Cys + Arg218Glu
Asp 65Glu + Ile107Thr + Asn162Glu + Asp165Glu + Thr217Pro
Val 95Glu + Ser101Asp + Asn162Glu + Phe192Thr + Gly215Gln
Gln103Asn + Tyr104His + Thr206Glu + Ser216Glu + Thr223Glu
Gly135Asp + Asn168Asp + Tyr169Asn + Ser191Glu + Gly205Pro
Gly102Glu + Ser105Glu + Asn161Gln + Ser207Glu + Ile220Met
Leu133Glu + Phe192Pro + Thr206Glu + Thr217Pro + Ser219Glu
Asn 99Asp + Ser105Glu + Leu133Val + Ser140Glu + Gly214Ser
Asn 99Glu + Gly102Asp + Asn162Gln + Phe192Pro + Ser219Asp
Ile107Val + Ser190Glu + Asn194Glu + Leu209Thr + Ser216Glu
Gly100Glu + Leu133Glu + Ala166Thr + Ser216Asp + Thr217Pro
Arg 64Asp + Ala164Gln + SeT191ASp + Thr206Glu + Leu209Cys
Leu 96Val + Gly134Asp + Gly136Pro + Ser191Asp + Thr206Glu
Tyr104Asn + Asp165Glu + Phe192Asp + Ser207Asp + Ile220Gln
Ser101Asp + Ala164Ser + Thr206Pro + Ser207Glu + Arg218Asp
Asp165Glu + Ser207Glu + Leu209Asn + Trp212Gly + Arg218Asp
Gly100Asn + Tyr104Pro + Ser138Glu + Ser207Asp + Arg218Glu
Ser140Glu + Ser170Glu + Thr211Gln + Gly215Asn + Ser221Asp
Gly100Glu + Ser140Asp + Ser170Asp + Thr206Ser + Leu209His
Ser140Glu + Tyr169Pro + Ser170Asp + Arg218Asp + Ile220Pro
Gln103Ser + Tyr104Asp + Leu209Glu + Ser221Asp + Gly222Ser
Asp 97Glu + Ile107Cys + Asn162Asp + Ser191Asp + Leu209Ala
Asp 97Glu + Tyr104Glu + Ile107Gly + Leu133Ser + Ile220Leu
Leu 96Glu + Leu133Asp + Gly134Asn + Gly215Ser + Ser216Glu
Asn 67Glu + Leu 96Glu + Thr106Pro + Ile107Cys + Ser207Glu
Arg 64Glu + Asp 97Glu + Gly102Asp + Asp165Glu + Phe192Tyr
Gly 66Ser + Gly134Asp + Asn161Asp + Ser207Glu + Thr217Gly
Asp 65Glu + Gly 70Asn + Gly100Asp + Leu209Asp + Ser216Glu
Gly 68Asp + Ser101Asp + Leu209Thr + Trp212Ala + Ser219Asp
Thr106Gly + Asn163Asp + Leu209Pro + Ser219Glu + Thr223Glu
Asp 65Glu + Gln103Ser + Gly134Gly + Gly136Asn + Ser138Glu
Gln103Ser + Ile107His + Asn161Asp + Asp165Glu + Ser207Glu
Gly 66Pro + Ser140Glu + Ala164His + Thr217Glu + Ile220Asp
Arg 64Asp + Ser101Asp + Tyr104Leu + Ile107Glu + Ile220Asn
Arg 64Glu + Val 95Met + Gly136Ser + Ser190Glu + Ile213Asp
Gly135Glu + Gly160Pro + Leu209Gln + Ile220Leu + Thr223Glu
Asp 65Glu + Val 95Gln + Ser170Glu + Phe192Met + Gly214Glu
Gly100Asn + Ser190Asp + Ser207Asp + Leu209Ser + Ser216Glu
Val 95Gly + Arg167Asp + Ser190Asp + Ser207Glu + Ile220Asn
Asn 67Glu + Ser101Glu + Leu133Ser + Asn163Asp + Thr223Ser
Asn 67Glu + Asn 99Ser + Ser101Glu + Tyr104Ala + Ser207Glu
Gly134Asn + Ser138Asp + Arg218Asp + Ile220His + Ser221Glu
Gly 66Gln + Val 95Pro + Ser138Glu + Arg218Glu + Ser221Asp
Asn 67Asp + Thr 71Ser + Gly135Glu + Asn161Asp + Ala164His
Asp 65Glu + Gly 66Pro + Ser191Glu + Ile213Ser + Ser221Glu
Gly 70Pro + Gly134Pro + Ser191Asp + Ser216Asp + Ser221Asp
Gly100Glu + Tyr104Glu + Asn153Gln + Ile213Pro + Ile220Ser
Gly134Glu + Gly136Pro + Asn162Gln + Ser216Asp + Thr223Asp
Thr 71Asn + Ser105Asp + Leu209Met + Ser219Asp + Gly222Glu
Gly 66Asn + Gly102Asn + Tyr169Asp + Ser216Asp + Ser219Asp
Gly136Pro + Asn161Glu + Ser216Glu + Ser219Glu + Ile220Ser
Ser140Glu + Ile208Met + Ser216Glu + Ser219Glu + Ile220Asn
Gly160Asp + Thr206Gln + Gly214Ser + Ser216Glu + Ser219Glu
Asn 99Ser + Ser190Glu + Ser216Glu + Ser219Glu + Ile220His
Ser139Asp + Thr206Gln + Ser216Glu + Ser219Asp + Gly222Asn
Gly102Asn + Ser190Asp + Ser216Glu + Ser219Asp + Gly222Gln
Gln103Ser + Asn163Asp + Trp212Met + Ser216Asp + Ser219Asp
Thr 71Gly + Gly136Glu + Asn194Gln + Ser216Asp + Ser219Glu
Asp 97Glu + Leu209Met + Ser216Glu + Ser219Asp + Ile220Val
Asn 99Gln + Asp165Glu + Leu209Met + Ser216Glu + Ser219Glu
Thr106Glu + Asn168Gln + Leu209Met + Ser216Glu + Ser219Glu
Leu 96Gln + Asn161Gln + Tyr169Asp + Ser216Asp + Ser219Glu
Leu 96Met + Asn161Asp + Gly203Glu + Ser216Asp + Ser219Glu
Asn 99Glu + Thr206Ser + Ser207Glu + Leu209Val + Thr223Glu
Ser207Glu + Leu209Met + Ser216Asp + Ile220Leu + Thr223Asp
Val 95Ala + Gly214Asn + Ser216Asp + Ile220Asp + Gly222Pro
Ser101Asp + Tyr104Glu + Gly136Asn + Gly160Glu + Ser190Asp
Gly 70Asp + Gly135Glu + Arg167Asp + Asn168Gln + Ile220Gln
Asp 65Glu + Leu 96Met + Gly136Glu + Asn162Asp + Leu209Ala
Val 95Asp + Asn 99Glu + Asn194Ser + Gly214Pro + Thr223Asp
Gly136Glu + Ala164Ser + Asp165Glu + Tyr169Pro + Ser216Asp
Arg 64Glu + Gly135Asn + Asn162Asp + Ser191Asp + Gly214Asp
Arg 64Asp + Asn162Gln + Thr206Gln + Ser207Asp + Gly214Glu
Leu 96Ala + Gln103Ser + Asn162Glu + Arg167Asp + Gly215Glu
Asn161Ser + Asn162Glu + Arg167Glu + Thr206Pro + Ser219Asp
Ala164His + Asp165Glu + Tyr169Pro + Ser170Asp + Gly215Glu
Val 95Ala + Gln103Glu + Ser138Asp + Gly160Asn + Ser219Asp
Ile107Glu + Leu133Asn + Ser138Asp + Ala164Gly + Ser191Glu
Ile107Glu + Leu133Ser + Asn163Glu + Arg167Glu + Leu209His
Ser101Glu + Leu209Asp + Gly215Gln + Ile220Asn + Gly222Glu
Ser139Asp + Asn162Gln + Tyr169Gln + Leu209Asp + Gly222Asp
Thr106Glu + Gly136Ser + Ser170Glu + Asn194Glu + Thr206Gln
Tyr104Ala + Leu133Asn + Asn162Asp + Ser207Asp + Thr217Asp
Tyr169Cys + Ser191Glu + Ser207Glu + Ser216Asp + Gly222Gln
Val 95Gln + Tyr104Leu + Tyr137Glu + Ser191Glu + Ser207Glu
Gly 66Asp + Gly100Asn + Ser101Glu + Ser139Glu + Tyr169Gln
Gly 66Gln + Val 95Ser + Ser101Glu + Asn163Ser + Ser191Asp
Arg 64Glu + Val 95Ala + Asn 99Glu + Ala164Glu + Gly214Ser
Arg 64Glu + Asn 99Glu + Ser105Asp + Gly160Pro + Leu209Gly
Asn 67Asp + Val 95Asp + Gly102Pro + Ser207Glu + Gly214Ser
Ser101Asp + Ser105Asp + Asn162Glu + Tyr169Gln + Ile220Ser
Ser139Asp + Gly160Ser + Ala166Thr + Phe192Glu + Ser207Asp
Val 95Gly + Gly136Pro + Asn161Glu + Arg167Asp + Ser207Asp
Asp 65Glu + Ser101Glu + Gly102Asn + Leu133Thr + Ser170Asp
Gly136Gln + Asn161Asp + Arg167Asp + Asn194Ser + Ser216Glu
Gly135Asp + Ala164Asp + Ser216Glu + Ile220Leu + Gly222Asn
Asp 97Glu + Asn 99Gln + Gln103Asn + Ser105Glu + Ala166Ser
Asn 99Gln + Asn163Glu + Ile213Leu + Ile220His + Ser221Glu
Gly135Glu + Asp165Glu + Phe192Gln + Ser207Glu + Gly215Ser
Asn162Asp + Ser170Glu + Asn194Ser + Leu209Gln + Ser219Glu
Gly100Asp + Thr106Asp + Ala164Glu + Phe192Thr + Asn194Gln
Ser105Glu + Asn162Glu + Leu209His + Ser221Glu + Gly222Gln
Gly 68Asn + Gly135Glu + Gly160Gln + Ser216Glu + Ile220Asp
Asp 97Glu + Ala164Gly + Leu209Met + Ser216Asp + Ile220Glu
Gly 68Asp + Tyr137Asp + Asn194Glu + Leu209Cys + Ser221Asp
Ile107Asp + Gly136Gln + Ser139Asp + Ser216Asp + Ile220Thr
Gly100Pro + Ser101Glu + Gly136Glu + Ser191Asp + Phe192Ala
Gly 70Glu + Gly160Pro + Ala164Thr + Ser170Glu + Ser216Glu
Arg 64Asp + Tyr104His + Asp165Glu + Leu209Gln + Thr223Glu
Leu133Ala + Ser138Asp + Leu209Cys + Thr217Glu + Ser221Asp
Ser140Glu + Gly203Asn + Thr217Glu + Ile220Met + Ser221Asp
Asp 97Glu + Thr106Asn + Gly134Glu + Asp165Glu + Thr211Gln
Gly102Pro + Ser140Asp + Asn194Asp + Gly215Pro + Ser221Asp
Arg167Asp + Leu209Asn + Ser219Asp + Ile220Val + Thr223Glu

TABLE 32-continued

Multi-loop Quintuple Mutation Variants

Gly 68Asp + Gly102Asp + Gly136Ser + Ser170Asp + Phe192Leu

TABLE 33

Multi-loop Sextuple Mutation Variants

Val95His + Ala164Ser + Ser170Glu + Phe192Met + Leu209Thr + Ile220Pro
Leu133Asn + Asn161Gln + Asn163Gln + Leu209Met + Ile220Leu + Thr223Gly
Gly134Asn + Tyr169Ala + Thr211Pro + Ser216Asp + Ile220Met + Gly222Gln
Gly136Glu + Gly203Gln + Thr206Pro + Leu209Thr + Gly215Pro + Ile220Met
Gly100Ser + Gly135Asn + Ala164Thr + Gly214Glu + Thr217Gln + Ile220Leu
Thr106Ser + Thr206Pro + Ile208Cys + Leu209Ser + Ser216Asp + Ile220Ser
Gly68Asn + Leu96His + Gly102Asn + Leu209Cys + Trp212Ala + Ile220Val
Gly70Pro + Val95Gln + Gly102Gln + Asn162Asp + Gly214Gln + Ile220His
Asn67Gln + Leu96Val + Leu133Ala + Ala164Thr + Leu209Ala + Ser219Asp
Gly100Asn + Leu133Asp + Asn161Gln + Thr206Gly + Ile213Leu + Gly222Gln
Leu96Asn + Gly100Gln + Thr106Asn + Ser140Glu + Tyr169His + Ile220Asn
Gly70Pro + Asn99Ser + Gly135Gln + Tyr169Gly + Thr206Ser + Ser216Asp
Ser101Glu + Gly102Glu + Tyr169Met + Thr206Asn + Leu209Ile + Ile220Gln
Val95Ala + Asn168Gln + Gly214Asp + Gly215Glu + Ser216Glu + Ile220Pro
Leu96Pro + Thr106Gly + Ile107Gln + Asn163Glu + Phe192Glu + Leu209Gly
Asn194Ser + Phe202Gly + Ser207Glu + Arg218Glu + Ser219Asp + Ile220Asp
Asp65Glu + Asp97Glu + Asp98Glu + Asn168Ser + Tyr169Thr + Thr211Ser
Asn67Gln + Gly215Ser + Ser219Glu + Ile220Pro + Ser221Glu + Gly222Gln
Gly102Asn + Gln103Ser + Tyr169Ile + Thr206Gly + Ser216Glu + Arg218Asp
Asn67Glu + Gly70Glu + Leu96Pro + Asn99Ser + Asn162Gln + Phe192Pro
Asn67Asp + Gly68Gln + Gly70Asp + Leu133Val + Leu209Gly + Thr217Asn
Gly68Ser + Leu133Glu + Gly135Asp + Ser170Glu + Ile213Asn + Ile220Ser
Val95Asp + Asp97Glu + Gly100Asp + Gly135Gln + Leu209Gln + Thr223Ser
Leu96Cys + Gly134Asp + Gly160Glu + Asn161Glu + Asn162Glu + Leu209Pro
Asp65Glu + Leu96Glu + Asp97Glu + Asn99Asp + Ile220Ser + Gly222Pro
Val95Pro + Leu209Ser + Ser219Glu + Ile220Gly + Ser221Glu + Gly222Asp
Gly66Asn + Asp98Glu + Ser101Asp + Tyr104Cys + Asn194Gln + Ile220Asn
Ile107Thr + Tyr137His + Phe202Leu + Ser216Glu + Arg218Asp + Ser219Glu
Gly134Pro + Tyr137Pro + Ser207Glu + Leu209Cys + Ser219Asp + Gly222Glu
Leu133Thr + Asn163Ser + Ser207Asp + Ile213Met + Arg218Asp + Ser221Asp
Arg64Asp + Asp98Glu + Thr106Ser + Gly160Asp + Ile213Pro + Ile220Asn
Gly70Gln + Leu96Asn + Tyr169Met + Thr206Glu + Leu209Cys + Thr223Asp
Gly68Pro + Ala164Glu + Arg167Glu + Pro204Asn + Thr206Gln + Ile220Ser
Asn99Ser + Gly135Asp + Tyr137Met + Ser138Glu + Asn168Asp + Thr211Asn

TABLE 33-continued

Multi-loop Sextuple Mutation Variants

Gly68Pro + Tyr104Glu + Ser138Glu + Thr217Ser + Ile220Gln + Thr223Pro
Gly66Ser + Asn163Gln + Thr206Asp + Leu209Gly + Ser219Asp + Ile220Met
Gly68Asp + Thr106Pro + Thr206Gly + Leu209Glu + Ser219Glu + Ile220Asp
Tyr137Leu + Tyr169Cys + Phe192Asn + Ser207Asp + Arg218Glu + Ile220Leu
Gly68Asn + Val95Glu + Gly100Glu + Leu133Cys + Gly134Pro + Thr217Ser
Gly68Asp + Gly100Glu + Thr206Pro + Ser219Glu + Ile220Glu + Ser221Glu
Tyr137Asn + Ala164Gln + Ser207Glu + Leu209Glu + Arg218Asp + Gly222Glu
Gly135Pro + Ser191Asp + Asn194Gln + Thr206Glu + Ser207Glu + Ser219Glu
Val95Asp + Ser105Asp + Gly160Asn + Leu209Gly + Gly215Pro + Ile220Ala
Gly68Asp + Gly100Ser + Gly134Asn + Ser207Glu + Ser219Glu + Ser221Glu
Asn67Gln + Gln103Ser + Thr206Glu + Leu209Glu + Ser216Glu + Ser219Asp
Tyr104Ile + Thr206Glu + Ser216Asp + Arg218Asp + Ser219Glu + Thr223Ser
Gly68Gln + Val95Pro + Leu133Ala + Asn162Gln + Ser190Glu + Ser207Asp
Asn163Ser + Thr206Asp + Ser207Glu + Leu209Ser + Ser216Glu + Ser219Asp
Asn161Ser + Thr206Ser + Gly214Asp + Gly215Asp + Thr217Glu + Ile220Glu
Asn99Ser + Ser138Asp + Ser139Asp + Ser140Asp + Ile213Gly + Ser216Asp
Gly70Glu + Leu96Asn + Thr206Asn + Ser207Glu + Ser219Asp + Ser221Asp
Tyr104His + Asn161Asp + Ser170Asp + Phe192His + Asn194Asp + Gly222Pro
Leu96Glu + Asp97Glu + Ser101Asp + Leu209Thr + Ser219Asp + Ile220Asn
Ser207Asp + Ile208Ala + Leu209Thr + Ser216Asp + Ser219Glu + Ile220Leu
Gly100Glu + Leu133Glu + Gly135Glu + Asn161Glu + Ala164Gly + Leu209Thr
Leu96Asn + Gly136Ser + Leu209His + Gly214Glu + Ser216Asp + Ser219Glu
Tyr104Leu + Ile107Glu + Tyr137Glu + Ser138Asp + Asn168Gln + Leu209Ile
Tyr137Glu + Phe192Met + Ser207Asp + Ser219Asp + Ser221Glu + Thr223Pro
Tyr137Asp + Asn168Asp + Ser170Glu + Phe192Asn + Ser207Asp + Ile220Asn
Val95Ser + Gly102Ser + Asn162Gln + Leu209Ser + Ser216Glu + Ser219Asp
Gly66Ser + Gly102Gln + Ser216Glu + Ser219Asp + Ile220Val + Gly222Asn
Asp97Glu + Asp98Glu + Ser101Glu + Gly134Pro + Asn162Glu + Thr206Gln
Val95Pro + Ser101Asp + Gly135Asn + Ser207Asp + Leu209Asp + Ile220Asp
Asp98Glu + Gly203Ser + Ser207Glu + Leu209Pro + Arg218Glu + Ser219Asp
Thr106Pro + Gly135Asp + Ser140Asp + Asn162Glu + Ser170Glu + Gly214Gln
Gly68Gln + Ile107Asn + Asn162Ser + Ser191Asp + Ser207Asp + Ser219Glu
Gly102Ser + Gly136Asn + Thr206Glu + Leu209Thr + Arg218Asp + Gly222Asp
Asp65Glu + Gln103Ser + Ser207Glu + Leu209Gln + Arg218Asp + Ile220Glu
Gly66Pro + Asn99Gln + Gly136Asp + Arg218Asp + Ile220Glu + Ser221Asp
Tyr104Asp + Gly134Glu + Gly135Asp + Thr211Ser + Ser219Glu + Ile220Val
Gly100Gln + Tyr104Ser + Ser139Glu + Ser191Glu + Phe192Asp + Thr206Glu
Ser138Glu + Thr206Pro + Leu209Thr + Ser216Glu + Arg218Asp + Ser219Asp
Asp97Glu + Leu209Gln + Ser216Asp + Arg218Asp + Ser219Glu +

TABLE 33-continued

Multi-loop Sextuple Mutation Variants

Ile220Ala
Gly102Asp + Leu133Thr + Asn163Gln + Ser216Glu + Thr217Glu + Ser219Asp
Asp98Glu + Asn99Asp + Gly102Asp + Thr106Ser + Ile107Gln + Ser138Asp
Asn67Asp + Gly70Glu + Ser170Asp + Phe192Pro + Leu209Thr + Ile213Glu
Gln103Asp + Gly134Asn + Asn162Glu + Phe192Glu + Ile220Leu + Gly222Asp
Asp65Glu + Asp97Glu + Gly100Asp + Tyr169Met + Ser191Glu + Ile220Cys
Asn67Asp + Asp98Glu + Ala164Pro + Ile208Thr + Leu209Ser + Ile220Asp
Gly136Asn + Ser191Asp + Thr206Pro + Arg218Asp + Ser219Asp + Gly222Asp
Asp98Glu + Gly136Asp + Ser138Glu + Ser140Asp + Gly203Gln + Ile220Met
Leu133Ile + Gly134Pro + Gly135Pro + Asn162Glu + Arg167Glu + Ile213Val
Gly102Asn + Ser140Asp + Asn161Glu + Asn162Asp + Ser190Glu + Gly205Asn
Ser139Glu + Gly160Glu + Asn161Gln + Thr206Pro + Ser221Glu + Gly222Glu
Gly66Asp + Asn67Asp + Ile107Gly + Asn194Gln + Ser207Asp + Ile220Glu
Tyr104Gly + Gly136Asp + Ser170Asp + Ser190Glu + Asn194Asp + Gly222Ser
Gly68Asp + Ile107Asp + Gly135Asn + Gly215Glu + Ser216Glu + Ile220Gly
Ser101Glu + Ser207Asp + Leu209Met + Gly215Pro + Thr217Glu + Ser219Glu
Asp65Glu + Gly100Glu + Gln103Asp + Asn161Gln + Phe192His + Ile220Ser
Gly68Gln + Ser138Asp + Ser139Glu + Ala164Gly + Asn194Glu + Phe202Gln
Asn99Glu + Thr106Gln + Gly214Gln + Gly215Asn + Ser219Asp + Ile220Glu
Gly66Pro + Asn163Glu + Ala164Gln + Phe192His + Ser219Asp + Ile220Asp
Gly100Gln + Tyr104Pro + Tyr137His + Arg167Asp + Asn168Asp + Ser207Asp
Asn99Ser + Gly100Ser + Asn161Asp + Asn162Asp + Leu209Asn + Ser216Glu
Gly100Asp + Ser101Glu + Asn168Gln + Leu209Met + Ile213Ser + Ser219Asp
Val95His + Gly100Gln + Ser139Glu + Ser140Asp + Ser207Glu + Thr217Ser
Gly100Asp + Gly134Gln + Ser139Asp + Ser140Asp + Asn161Ser + Leu209Val
Val95Cys + Gly100Glu + Thr106Asn + Ser139Asp + Ser140Glu + Gly222Ser
Ser105Asp + Asn194Gln + Thr206Asp + Ser207Asp + Leu209Val + Gly215Ser
Asn163Glu + Phe192Pro + Trp212Val + Ser216Asp + Thr217Asp + Gly222Pro
Val95Asn + Gln103Asn + Leu209Gln + Gly215Asp + Ser216Glu + Ser221Asp
Gly66Gln + Gly134Glu + Ser170Asp + Leu209Thr + Ile220Asp + Gly222Asp
Gly66Gln + Thr106Glu + Ile107Glu + Asn163Asp + Asn194Glu + Pro204Asn
Gly102Glu + Gln103Asp + Phe192Ile + Ser207Glu + Leu209Pro + Ile220Asp
Arg64Glu + Asp65Glu + Ala164Asn + Ser207Glu + Leu209His + Ser219Asp
Arg64Asp + Asp65Glu + Gly135Pro + Tyr137Met + Ser207Glu + Ser219Asp
Tyr104Gly + Ser105Glu + Phe192Gln + Ser207Asp + Ser221Asp + Gly222Gln
Ser105Glu + Tyr137Ile + Ala164His + Thr206Asn + Ser207Glu + Ser221Glu
Asn67Gln + Asp98Glu + Asn161Gln + Asn168Ser + Ser207Glu + Ile220Asp
Gly134Ser + Ser139Asp + Thr206Asp + Ile213Ala + Arg218Glu + Ser219Asp
Asp98Glu + Gly100Gln + Gln103Asn + Gly134Asp + Ser139Glu + Ser170Glu
Leu96Gly + Asp98Glu + Thr106Asn + Leu209Glu + Ser216Asp + Ser219Asp
Gly70Glu + Asp97Glu + Asn99Glu + Gly135Ser + Asn194Glu + Leu209Thr
Thr106Gly + Arg167Glu + Ser207Glu + Gly214Gln + Gly215Pro + Ser219Glu
Ala164Glu + Thr206Gly + Ser207Asp + Leu209His + Ser219Asp + Ile220Gln
Gly160Ser + Asn162Gln + Ser170Glu + Thr206Pro + Ser207Asp + Ser219Asp
Tyr104Cys + Asn162Gln + Tyr169Asp + Ser207Glu + Leu209Ala + Ser219Asp
Asn67Gln + Asp165Glu + Ser207Glu + Leu209Val + Ser219Asp + Ile220Ala
Gly66Gln + Thr106Gln + Phe192Asp + Asn194Ser + Thr206Glu + Ser207Asp
Gly134Asp + Ala164Ser + Ser170Asp + Ser207Asp + Ile208Met + Ser219Asp
Gly66Gln + Gly102Asn + Gly136Asp + Ser139Glu + Asn168Asp + Ser219Asp
Asp97Glu + Asn99Asp + Thr206Asn + Ser207Asp + Ser219Asp + Ile220Met
Ile107Val + Asn162Asp + Ser191Asp + Ser207Asp + Ser219Glu + Gly222Pro
Gly66Ser + Asn67Glu + Ser138Asp + Ser140Glu + Leu209Cys + Ile213Ala
Gly70Ser + Asp98Glu + Gly100Asp + Asn162Gln + Ser207Glu + Ser219Glu
Asp97Glu + Asn99Glu + Tyr104Gly + Thr206Glu + Leu209Ala + Thr217Gln
Arg64Glu + Gly66 Glu + Asn162Asp + Tyr169Ser + Leu209His + Gly214Glu
Gly70Gln + Leu133Asp + Gly136Glu + Asn194Asp + Ile213Cys + Gly222Asp
Gly70Gln + Gln103Asp + Ser105Glu + Thr106Pro + Ser219Asp + Ile220Ser
Gln103Glu + Ser105Glu + Asn162Gln + Gly205Pro + Trp212Asn + Arg218Glu
Asp97Glu + Asn99Gln + Gly136Asp + Gly160Ser + Ser170Asp + Leu209Met
Ser105Glu + Ile107Glu + Ser207Glu + Ile213Thr + Gly215Ser + Ile220Asn
Ser190Asp + Phe192Ile + Ser216Glu + Ser219Glu + Ile220Glu + Gly222Ser
Asp65Glu + Gly102Gln + Ser207Asp + Ile213Asp + Ser216Glu + Ile220Asn
Gln103Asp + Leu133Asn + Phe192Asp + Ile213Val + Ile220Asp + Ser221Asp
Leu96Cys + Ile107Gly + Asn162Asp + Asn194Asp + Ser216Asp + Ile220His
Ser101Asp + Ser105Glu + Thr106Asn + Ser138Asp + Ser170Glu + Leu209Ser
Gly70Ser + Tyr169Val + Phe192Asp + Ser216Glu + Ser219Glu + Ile220Asp
Gly136Gln + Asn161Asp + Asn163Gln + Arg167Asp + Asn194Glu + Ser216Glu
Asp97Glu + Asp98Glu + Asn161Glu + Ala164Asp + Ile213Ala + Thr217Gly
Ile107Cys + Arg167Asp + Asn168Glu + Ser207Glu + Ile220Thr + Gly222Glu
Arg167Asp + Tyr169His + Ser170Glu + Leu209Val + Ser219Asp + Ile220Glu
Gly70Gln + Phe192Asp + Ser216Glu + Arg218Glu + Ile220Val + Gly222Glu
Arg64Asp + Gly70Asn + Phe192Ala + Ser207Asp + Leu209Glu + Thr223Gly
Gly68Asn + Asp98Glu + Ser207Asp + Leu209Asp + Ile220Asn + Thr223Gln
Gly100Gln + Leu133Ile + Asp165Glu + Ala166His + Tyr169Asp + Ser191Glu
Asn163Asp + Ser191Asp + Thr206Gly + Leu209Asp + Thr211Asn + Ile220Asp
Asn99Gln + Gly160Glu + Tyr169Val + Ser191Asp + Ser216Asp + Gly222Asp
Asn67Glu + Asp97Glu + Ser105Asp + Ala164Thr + Thr206Ser + Ile220Val
Arg64Asp + Gly70Glu + Val95Thr + Asp97Glu + Asn162Asp +

TABLE 33-continued

Multi-loop Sextuple Mutation Variants

Thr223Gln
Leu96Ser + Gln103Glu + Ser105Glu + Gly134Asp + Asn194Ser + Ser219Asp
Gly100Gln + Leu133Gln + Ala164Gln + Arg167Glu + Ser219Asp + Ser221Glu
Val95Gln + Tyr137Asn + Ser140Glu + Pro204Asn + Ser219Asp + Ser221Asp
Gly134Ser + Ser190Glu + Ser207Glu + Leu209Gln + Thr217Glu + Ile220His
Gly70Ser + Gly134Ser + Asn162Ser + Ser170Asp + Ser216Glu + Arg218Asp
Asp97Glu + Tyr137Thr + Tyr169Gln + Ser216Glu + Arg218Glu + Gly222Gln
Asn67Glu + Gly70Glu + Asn99Gln + Tyr104Met + Gly136Asp + Ala164Asn
Asn67Glu + Gly68Asp + Gly70Gln + Ser191Glu + Ile213Ser + Ile220Glu
Thr106Gly + Asn162Glu + Gly215Glu + Thr217Asp + Ser219Glu + Ile220Asn
Arg64Asp + Asp65Glu + Ile208Gln + Leu209Asp + Ser216Asp + Ile220Val
Ser101Glu + Leu133Glu + Thr206Asn + Ser207Glu + Thr217Asn + Ser219Asp
Tyr104Glu + Ser138Glu + Asn162Glu + Asn194Glu + Thr211Ser + Trp212Ser
Asn98Glu + Asn99Gln + Gly102Glu + Ser190Glu + Ser191Glu + Ile220Pro
Val95Asp + Gly134Gln + Tyr169Pro + Phe192Asn + Ser221Glu + Thr223Asp
Asn67Glu + Leu96Glu + Gly160Ser + Asn162Ser + Thr206Gly + Thr217Asp
Gly68Asp + Val95Glu + Asn99Glu + Tyr169Ala + Gly215Asp + Thr217Ser
Val95Ser + Gly135Ser + Asn161Asp + Ile213Asp + Ser216Asp + Ser219Asp
Arg64Glu + Asp98Glu + Gly136Ser + Gly160Gln + Leu209Asp + Ile220Asp
Asp65Glu + Gly66Ser + Asn194Gln + Ser207Asp + Ser216Asp + Ser219Asp
Asn99Ser + Ser101Asp + Tyr104Asp + Gly134Ser + Ser207Asp + Ile220Asp
Arg64Glu + Asp98Glu + Ile107Asn + Thr206Ser + Ser219Asp + Ser221Glu
Val95Pro + Ala164Asp + Asp165Glu + Ser170Asp + Ile213Asp + Ile220Val
Gly135Ser + Asn161Gln + Asn162Asp + Tyr169Asp + Gly215Gln + Ser221Glu
Tyr137His + Ser140Asp + Asn161Gln + Ser170Asp + Ser207Asp + Leu209Asp
Leu96Ile + Ser138Glu + Ala164His + Asn194Asp + Thr206Asp + Gly222Glu
Asn161Glu + Ser207Asp + Gly214Asn + Ser216Asp + Arg218Glu + Gly222Gln
Leu96Asn + Ser170Asp + Ile208Asn + Gly215Glu + Arg218Glu + Ser219Asp
Gly134Asp + Ser139Asp + Ser140Glu + Thr206Asp + Ile213Met + Thr223Asn
Asp65Glu + Asp165Glu + Phe192Pro + Leu209Gly + Gly215Glu + Ser216Asp
Asn99Asp + Ser101Glu + Ile107Glu + Ser191Glu + Asn194Gln + Ile220Leu
Asp65Glu + Ser190Glu + Asn194Gln + Ser207Glu + Gly215Pro + Ser219Glu
Gly134Asn + Ser138Glu + Ser139Glu + Ser216Glu + Ser219Asp + Ile220Pro
Tyr137Cys + Ala164Thr + Ser190Glu + Ile208His + Ser216Glu + Gly222Glu
Asp165Glu + Ser207Asp + Ser216Asp + Arg218Asp + Ile220Pro + Gly222Pro
Val95Met + Ser139Glu + Ser140Asp + Ala164Asn + Ser216Asp + Ser219Asp
Val95Gly + Gly102Ser + Ser105Asp + Ser138Glu + Asn163Glu + Ala164Glu
Asp65Glu + Val95Gly + Asp97Glu + Gly160Ser + Asp165Glu + Ile220Ser
Thr71Gln + Ser101Asp + Thr106Glu + Tyr169Pro + Ser207Glu + Ser219Asp
Tyr137Ile + Asp165Glu + Tyr169Cys + Gly214Asp + Arg218Glu + Ser219Asp
Asn99Ser + Ala164Asp + Ser170Asp + Asn194Glu + Thr206Gln + Ser216Asp
Asp65Glu + Gly134Asp + Gly160Asn + Asn161Glu + Asn168Asp + Ile220Asn
Asp65Glu + Phe192Ser + Ser216Glu + Ser219Asp + Ile220Met + Ser221Glu
Gly68Asn + Leu133Gln + Asn168Asp + Ser207Glu + Ser216Glu + Ser219Asp
Gly135Glu + Ser207Glu + Ser216Asp + Thr217Asn + Ser219Glu + Ile220Pro
Gly68Asn + Asn163Glu + Ser207Asp + Ser216Glu + Ser219Glu + Ile220Asn
Gly102Glu + Tyr137Cys + Thr206Ser + Ser207Glu + Ser216Asp + Ser219Asp
Leu133Ser + Arg167Glu + Ser170Asp + Ser191Asp + Thr206Asp + Leu209His
Gly66Gln + Gly136Glu + Ser138Glu + Thr206Gln + Arg218Glu + Ser221Asp
Asn67Glu + Ser139Asp + Ile208Val + Leu209Ser + Ser216Asp + Thr217Asp
Arg64Asp + Val95His + Gly134Glu + Ser138Glu + Arg167Glu + Leu209Cys
Arg64Asp + Phe192Val + Thr206Asp + Leu209Ala + Ser219Glu + Gly222Ser
Leu96Ala + Ser140Asp + Phe202Gln + Thr206Asp + Leu209Ala + Ser219Glu
Leu96Ile + Gly102Pro + Gly134Asp + Thr206Asp + Leu209Ala + Ser219Glu
Gly102Glu + Ser105Asp + Ile107Cys + Ser140Asp + Asn194Asp + Ile220Ala
Gly100Glu + Ser105Asp + Tyr137Pro + Ser140Glu + Gly203Asn + Gly222Pro
Thr106Asn + Asn162Glu + Asn168Asp + Ser216Glu + Arg218Asp + Ile220Asn
Asp98Glu + Leu133Gly + Gly136Asp + Ser140Glu + Asn168Glu + Phe192Ser
Val95Ala + Asp165Glu + Asn168Ser + Ser207Asp + Leu209Glu + Ser216Asp
Gly134Glu + Ala164Asp + Asn168Glu + Phe192Cys + Ser219Glu + Ile220Pro
Gly68Asn + Ser191Asp + Phe192Asn + Gly215Glu + Ser219Glu + Ser221Glu
Gln103Glu + Ile107Asn + Ser140Glu + Ser190Glu + Ser191Glu + Leu209Thr
Tyr104Ala + Leu133Asn + Asn162Asp + Thr206Glu + Ser207Asp + Thr217Asp
Gly160Asn + Asn194Asp + Ser207Asp + Ile213Val + Ser216Asp + Thr217Asp
Leu96Ile + Ala164Gln + Asp165Glu + Ser207Glu + Arg218Glu + Ile220Met
Gly66Glu + Ile107Ala + Gly160Asn + Phe192Val + Ser207Glu + Arg218Glu
Gly100Gln + Tyr104Asp + Gly134Asp + Ala164Ser + Phe192Leu + Ser216Asp
Arg167Glu + Leu209Thr + Ser216Glu + Ser219Glu + Ser221Glu + Gly222Asn
Gly68Asn + Asp98Glu + Leu209Gly + Ser216Asp + Ser219Asp + Ser221Glu
Asp65Glu + Ser207Glu + Leu209Asp + Gly215Asp + Gly222Ser + Thr223Asn
Gly134Ser + Ser140Glu + Asn168Gln + Ser191Glu + Asn194Glu + Ser221Asp
Leu96Ile + Thr106Glu + Gly160Asp + Ser219Glu + Gly222Glu + Thr223Ser
Ser101Asp + Ser105Glu + Asn161Gln + Ser207Glu + Ile213Asn + Ser221Glu
Gln103Ser + Gly135Asp + Ser190Glu + Thr206Ser + Ser219Glu + Ile220Glu
Asp65Glu + Gly100Asp + Ser105Asp + Ser140Glu + Phe192Thr + Ile220His
Asp65Glu + Ser101Glu + Ala164Thr + Ile213Glu + Thr217Asn + Ser219Glu
Ser105Asp + Gly134Asp + Asn168Ser + Ser191Asp + Phe192Glu + Ile220Cys
Leu96Asp + Ile107Asp + Gly214Ser + Ser216Glu + Ser219Glu +

TABLE 33-continued

Multi-loop Sextuple Mutation Variants

Ile220Val
Asn162Gln + Asp165Glu + Arg218Asp + Ser219Glu + Ile220Thr + Thr223Asp
Thr71Gly + Asn161Asp + Asn168Asp + Ser207Glu + Leu209Asp + Thr223Gln
Asp65Glu + Asp98Glu + Leu133Ser + Asp165Glu + Leu209Met + Gly215Glu
Arg64Asp + Asn99Glu + Asp165Glu + Ala166Asn + Asn194Glu + Ile220Cys
Asn99Ser + Gly136Asp + Asn163Asp + Asp165Glu + Phe202Cys + Ser216Glu
Val95Pro + Leu133Thr + Gly136Glu + Asp165Glu + Ser216Asp + Arg218Glu
Leu133Pro + Gly134Asn + Asn194Asp + Thr206Glu + Gly214Glu + Ser221Asp
Gly70Asp + Asp97Glu + Tyr104Asn + Pro204Gly + Leu209Asp + Ser216Glu
Gln103Asp + Gly135Asp + Ser140Asp + Asn168Gln + Gly214Asp + Ile220Leu
Asp65Glu + Thr71Ser + Asn99Glu + Ser138Asp + Phe192Tyr + Leu209Gly
Tyr104Val + Ile107Glu + Thr206Asp + Ser216Asp + Ser219Glu + Ile220Leu
Leu133Ala + Arg167Glu + Leu209Gln + Ser216Glu + Thr217Glu + Ser221Glu
Asn67Glu + Asp98Glu + Tyr137Ala + Asp165Glu + Thr206Pro + Ile220Asp
Ser101Glu + Ile107Asp + Asn161Glu + Asp165Glu + Ile220Thr + Thr223Gln
Tyr104Asp + Thr106Asn + Tyr137Glu + Gly160Gln + Asn162Asp + Gly215Ser
Asn67Asp + Asp97Glu + Tyr104Thr + Leu133Asp + Ala164Glu + Ile220Ala
Asp97Glu + Asn99Ser + Ser105Asp + Thr206Asp + Ser207Glu + Trp212Thr
Asn67Gln + Tyr104Ile + Ser105Glu + Asn163Glu + Ile220Glu + Ser221Glu
Asp98Glu + Asn99Gln + Leu133Asp + Phe192Glu + Asn194Glu + Gly205Pro
Asn99Asp + Ile107Ser + Tyr137Met + Asn161Glu + Asp165Glu + Ile213Asn
Gly70Asn + Gln103Ser + Ser138Glu + Ala164Asp + Ser170Glu + Ser219Asp
Ser101Glu + Thr106Asn + Gly135Glu + Leu209Ser + Thr217Asn + Ser219Glu
Gly68Glu + Gly102Gln + Gly135Ser + Ser190Asp + Ser207Asp + Ile220Ala
Asp65Glu + Val95Glu + Gly100Gln + Ser105Asp + Asn194Ser + Leu209Glu
Asp65Glu + Tyr137His + Asn161Glu + Asn162Asp + Tyr169Thr + Ser207Asp
Asn67Ser + Gly134Pro + Asn194Asp + Gly214Asp + Arg218Asp + Ser211Glu
Asp65Glu + Tyr137Asn + Thr211Pro + Arg218Asp + Ile220Val + Ser221Asp
Asp65Glu + Gly100Ser + Tyr104Ala + Ser207Glu + Thr217Asp + Gly222Asp
Asp98Glu + Asn99Gln + Gln103Glu + Gly136Ser + Leu209Asp + Arg218Glu
Asp65Glu + Val95Pro + Ser101Asp + Gln103Glu + Asn168Ser + Ser219Glu
Tyr104Val + Gly134Pro + Tyr137Asp + Ala164Glu + Thr211Gly + Gly215Ser
Ser101Asp + Gly135Pro + Ser190Asp + Ser191Asp + Ser216Asp + Gly222Gln
Asn99Glu + Ser101Glu + Gln103Ser + Gly160Pro + Ile213Asp + Gly222Glu
Gly68Ser + Ser138Glu + Ser139Glu + Gly160Glu + Asn163Ser + Ser219Glu
Arg64Glu + Ser101Glu + Ser138Glu + Ser139Glu + Asn161Ser + Thr206Asn
Gly66Asn + Gly68Asp + Tyr104Leu + Ser138Asp + Ser139Asp + Ser207Asp
Asp65Glu + Gln103Glu + Tyr137Cys + Thr206Asn + Ser219Glu + Ile220Glu
Leu96Asp + Tyr137Asp + Leu209Thr + Ile213Gly + Ser219Asp + Ile220Glu
Leu96Asp + Asp97Glu + Ser140Glu + Phe192Ala + Thr217Asp + Gly222Pro
Ser101Glu + Leu133Cys + Arg167Asp + Asn168Glu + Leu209Ala + Ser216Glu
Val95Gly + Thr106Glu + Arg167Asp + Asn168Glu + Ser191Asp + Ile220Val
Gly66Ser + Asp97Glu + Tyr169Thr + Ser170Asp + Thr217Glu + Arg218Asp
Arg64Asp + Ile107His + Gly135Asp + Gly136Asp + Ile213Thr + Ser219Asp
Asp97Glu + Leu133Thr + Gly134Glu + Arg218Glu + Ser219Asp + Thr223Ser
Asp98Glu + Gly102Ser + Leu133Met + Ser139Asp + Ser140Asp + Ser216Glu
Tyr137Ile + Ser139Glu + Ser140Glu + Gly160Gln + Leu209Asp + Gly214Asp
Leu96Ala + Asp98Glu + Asn99Glu + Asp165Glu + Leu209Thr + Ser216Glu
Asn99Gln + Ser138Asp + Asn161Glu + Gly215Glu + Ser216Asp + Ile220Gly
Ser105Asp + Thr106Pro + Gly136Pro + Gly160Glu + Leu209Asp + Ser219Asp
Gln103Glu + Ala166Thr + Asn194Glu + Leu209Asp + Ser219Glu + Ile220Cys
Tyr104Met + Thr106Ser + Ser139Asp + Thr206Pro + Ser219Asp + Gly222Glu
Ile107Gln + Asp165Glu + Asn168Glu + Ser191Asp + Leu209Met + Ser219Glu
Gly68Ser + Thr106Glu + Ile107Gly + Asn162Glu + Ser207Asp + Ile220Asp
Arg64Asp + Gly160Asp + Ser207Glu + Ile208Gly + Ile213Leu + Ile220Asp
Tyr137Asp + Ser170Asp + Phe192Ser + Ser207Glu + Leu209Pro + Gly214Glu
Tyr104Cys + Gly135Asp + Ser138Asp + Thr206Asp + Gly214Glu + Arg218Glu
Arg64Asp + Asp97Glu + Ser139Asp + Asn168Gln + Thr206Asn + Gly214Asp
Asp65Glu + Leu133Asn + Ser170Glu + Ile208Thr + Ser216Glu + Arg218Asp
Ser101Asp + Ser138Glu + Thr206Pro + Ser207Glu + Ser219Glu + Ile220Cys
Gly134Glu + Ser207Glu + Leu209Ser + Gly214Glu + Ser219Glu + Ile220Ala
Arg64Asp + Gly68Asn + Gly135Asp + Gly136Gln + Ser207Asp + Ser219Glu
Ser101Asp + Ser138Glu + Ser207Asp + Leu209Ile + Ser219Glu + Gly222Gln
Gly66Asp + Ser105Asp + Ala164Gln + Phe192Ala + Ser207Glu + Ser219Asp
Arg64Glu + Gly66Asn + Asn99Ser + Ser138Glu + Ser207Asp + Ser219Glu
Arg64Asp + Ile107Thr + Ile213Gly + Ser216Asp + Arg218Asp + Gly222Glu
Gln103Glu + Ile107His + Gly135Pro + Gly136Asp + Arg167Asp + Ser219Glu
Gly68Glu + Asp97Glu + Thr106Glu + Phe192Met + Ser207Glu + Ile213Ala
Ala164Glu + Asn168Ser + Ser191Glu + Ser216Asp + Ser219Asp + Ile220Thr
Gly68Gln + Asn162Glu + Ser190Asp + Leu209Thr + Ser219Asp + Gly222Gln
Val95Cys + Ile107Asp + Tyr137Ala + Asn194Glu + Gly214Asp + Ser216Glu
Asp65Glu + Gly70Gln + Leu209Gly + Ser216Glu + Ser221Asp + Thr223Glu
Ser101Glu + Gly205Gln + Leu209Glu + Ser216Asp + Thr217Ser + Ile220Thr
Tyr137Thr + Ser139Glu + Leu209Asp + Gly215Pro + Ser216Glu + Thr217Gln
Asn99Glu + Gly136Pro + Ser140Glu + Ser170Glu + Asn194Glu + Ile220Met
Gly66Gln + Asp98Glu + Gly100Glu + Ser105Glu + Ile220Asp + Thr223Asn
Asp98Glu + Gly100Glu + Ser105Asp + Gly136Ser + Asn168Glu + Gly214Pro
Val95Asn + Asp97Glu + Ser101Asp + Asp165Glu + Phe192His +

TABLE 33-continued

Multi-loop Sextuple Mutation Variants

Ile220Glu
Gly135Glu + Asn163Asp + Phe192Tyr + Asn194Gln + Ser219Glu + Ser221Glu
Asn99Glu + Ser101Asp + Ser140Asp + Asn161Gln + Ser190Asp + Gly215Asn
Gly68Gln + Gly100Asp + Gln103Asp + Tyr137Gly + Gly160Asp + Leu209Cys
Gly100Asp + Gln103Asp + Gly160Gln + Leu209Asn + Trp212Ser + Ser221Glu
Gly135Asp + Ser138Asp + Asn162Gln + Leu209Val + Ser216Glu + Thr223Asp
Arg64Asp + Gly66Glu + Leu96Thr + Thr106Ser + Asn161Glu + Arg218Glu
Tyr137Ser + Asn161Asp + Ser170Asp + Ser190Glu + Leu209Asp + Gly215Gln
Leu133Ala + Ser139Asp + Thr206Gln + Leu209Ala + Ser216Asp + Ser219Glu
Asn67Ser + Val95Thr + Ser140Glu + Thr206Pro + Ser216Glu + Ser219Asp
Val95Asn + Ser138Glu + Ile208Gln + Leu209Val + Ser216Glu + Ser219Asp
Gly70Asp + Asn99Gln + Ser101Glu + Leu133Asn + Leu209Gln + Ser216Asp
Tyr104Gln + Ile107His + Ser138Asp + Ser191Asp + Thr206Glu + Arg218Asp
Thr106Glu + Ser138Glu + Thr206Gly + Ser219Glu + Ile220Thr + Ser221Glu
Tyr137Glu + Asn161Glu + Leu209Thr + Ile213Asp + Ser216Asp + Thr217Asn
Arg64Glu + Asn67Glu + Ser170Asp + Trp212His + Ile213Ala + Arg218Glu
Val95Asp + Ile107Gly + Gly134Asp + Ser138Asp + Asn161Gln + Ser190Glu
Asp65Glu + Asp98Glu + Gly160Ser + Asp165Glu + Phe192Gly + Ser219Glu
Asp97Glu + Leu133His + Gly136Glu + Ser138Asp + Leu209Gly + Ser216Asp
Asp65Glu + Ser138Glu + Tyr169Met + Ser207Asp + Leu209Glu + Gly215Pro
Leu96Gln + Asp97Glu + Ser138Glu + Thr206Pro + Ser207Glu + Leu209Asp
Gly70Gln + Asp97Glu + Ser190Asp + Thr206Glu + Ser216Asp + Ile220Asn
Arg64Glu + Gly66Pro + Gly70Ser + Asp165Glu + Tyr169Glu + Ser191Asp
Gly136Asp + Asn163Asp + Phe192Pro + Ser216Glu + Arg218Asp + Ile220Val
Gly66Asp + Tyr137Gly + Asn162Ser + Ala164Glu + Arg167Asp + Ser216Glu
Gly100Asn + Gly102Asp + Tyr104His + Asp165Glu + Ser216Asp + Arg218Asp
Gly102Glu + Leu133Val + Ser140Glu + Thr206Glu + Ile220Glu + Thr223Pro
Ser105Glu + Leu133Asn + Ala164Asn + Asp165Glu + Thr217Glu + Ser219Asp
Gly70Asp + Val95Thr + Gly134Asp + Ser139Glu + Asn161Glu + Asn194Ser
Gly100Ser + Gly135Glu + Ser140Glu + Asn161Asp + Ile213Cys + Arg218Glu
Gly136Asp + Tyr137Gly + Ser140Asp + Asn162Glu + Thr211Gly + Gly214Asp
Val95Gly + Tyr104Ala + Ser138Glu + Asn163Asp + Arg167Asp + Ser219Asp
Asp65Glu + Gly70Asn + Val95Ser + Ser191Asp + Thr206Glu + Ser216Asp
Tyr104Leu + Leu133Cys + Gly134Asp + Asn162Asp + Tyr169Pro + Ser216Asp
Val95Glu + Asn99Asp + Tyr104Ala + Tyr137Ala + Leu209Asp + Ile220Cys
Gly66Glu + Thr106Ser + Leu209Gly + Gly215Asn + Ser216Asp + Ile220His
Thr71Pro + Gly102Glu + Gly134Asp + Ser139Asp + Ile220Pro + Ser221Asp
Leu96Ser + Asp98Glu + Ser101Asp + Gln103Ser + Gly160Asp + Ser216Glu
Leu96Cys + Ala164Asn + Tyr169Pro + Thr217Asn + Arg218Asp + Gly222Asp
Tyr104Asn + Gly136Glu + Tyr137His + Ser140Glu + Ser216Glu + Ile220Cys
Asp98Glu + Gly135Asp + Ser138Glu + Asn163Glu + Phe192Cys + Ile220Ser
Gly66Glu + Asn99Glu + Gly102Pro + Thr106Asn + Ser139Glu + Ser221Asp
Gly68Glu + Tyr104Ala + Ala164Gln + Asn168Asp + Ser219Glu + Thr223Asn
Asn99Glu + Gly102Pro + Ser140Asp + Ser207Glu + Leu209Asn + Gly222Asp
Ser105Asp + Thr106Gln + Gly160Asp + Ser191Asp + Phe192His + Gly202Gln
Asp98Glu + Tyr104Thr + Asn162Gln + Arg167Asp + Ser170Glu + Ser216Glu
Asn99Asp + Gly102Ser + Tyr137Asp + Asp165Glu + Ile220Ala + Thr223Gly
Asp98Glu + Thr106Pro + Gly135Asp + Ser138Glu + Phe192Asp + Ile220Gln
Arg64Glu + Val95Ala + Leu96Asn + Ala164Glu + Leu208Ala + Gly214Glu
Arg64Glu + Gly136Asn + Ala166Ser + Leu209His + Gly214Asp + Ser221Glu
Asn67Asp + Gly102Asn + Ala164Glu + Asn168Glu + Ser207Asp + Ile220Leu
Gly135Glu + Gly136Gln + Ser139Asp + Gly160Asn + Ala164Ser + Thr206Glu
Ser105Asp + Asn163Gln + Thr206Glu + Gly215Glu + Arg218Glu + Ile220Cys
Gly68Gln + Ser101Asp + Ser139Glu + Asn162Asp + Asp165Glu + Leu209Gln
Gly100Ser + Ser140Asp + Asn162Glu + Asp165Glu + Pro204Gln + Ser207Glu
Thr106Glu + Ile107Ala + Gly136Glu + Ser140Asp + Asn168Gln + Ser219Asp
Arg64Glu + Val95Thr + Asp98Glu + Tyr104Thr + Ser140Glu + Ser191Asp

II. Cleaning Compositions

In another embodiment of the present invention, an effective amount of one or more of the enzyme variants are included in compositions useful for cleaning a variety of surfaces in need of proteinaceous stain removal. Such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form); oral cleaning compositions, unlimited in form (e.g., dentifrice, toothpaste and mouthwash formulations); denture cleaning compositions, unlimited in form (e.g., liquid, tablet); and contact lens cleaning compositions, unlimited in form (e.g., liquid, tablet).

The cleaning compositions also comprise, in addition to the Proteinase K variants described hereinbefore, one or more cleaning composition materials compatible with the protease enzyme. the term "cleaning composition material", as used herein, means any liquid, solid or gaseous material selected for the particular type of cleaning composition desired and the form of the product (e.g., liquid, granule, bar, spray, stick, paste, gel), which materials are also compatible with the Proteinase K variant used in the composition. the specific selection of cleaning composition materials are readily made by considering the surface material to be cleaned, the desired form of the composition for the cleaning condition during use (e.g., through the wash detergent use). The term "compatible", as used herein, means the cleaning composition materials do not reduce the proteolytic activity of the Proteinase K variant to such an extent that the protease is not effective as desired during normal use situations. Specific cleaning composition materials are exemplified in detail hereinafter.

As used herein, "effective amount of enzyme variant" refers to the quantity of enzyme variant necessary to achieve the enzymatic activity necessary in the specific cleaning composition. Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like. Preferably the cleaning compositions comprise from about 0.0001% to about 10% of one or more enzyme variants of the present invention, more preferably from about 0.001% to about 1%, more preferably still from about 0.01% to about 0.1%. Several examples of various cleaning compositions wherein the enzyme variants may be employed are discussed in further detail below. All parts, percentages and ratios used herein are by weight unless otherwise specified.

As used herein, "non-fabric cleaning compositions" include hard surface cleaning compositions, dishwashing compositions, oral cleaning compositions, denture cleaning compositions and contact lens cleaning compositions.

A. Cleaning Compositions for Hard Surfaces, Dishes and Fabrics

The enzyme variants of the present invention can be used in a variety of detergent compositions where high sudsing and good insoluble substrate removal are desired. Thus the enzyme variants can be used with various conventional ingredients to provide fully-formulated hard-surface cleaners, dishwashing compositions, fabric laundering compositions and the like. Such compositions can be in the form of liquids, granules, bars and the like. Such compositions can be formulated as modern "concentrated" detergents which contain as much as 30%–60% by weight of surfactants.

The cleaning compositions herein can optionally, and preferably, contain various anionic, nonionic, zwitterionic, etc., surfactants. Such surfactants are typically present at levels of from about 5% to about 35% of the compositions.

Nonlimiting examples of surfactants useful herein include the conventional $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)x(CHOSO_3)^-$ $M^+)CH_3$ and $CH_3(CH_2)y(CHOSO_3^-M^+)$ $CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. (Use of such surfactants in combination with the aforesaid amine oxide and/or betaine or sultaine surfactants is also preferred, depending on the desires of the formulator.) Other conventional useful surfactants are listed in standard texts. Particularly useful surfactants include the $C_{10}$–$C_{18}$ N-methyl glucamides disclosed in U.S. Pat. No. 5,194,639, Connor et al., issued Mar. 16, 1993, incorporated herein by reference.

A wide variety of other ingredients useful in detergent cleaning compositions can be included in the compositions herein, including other active ingredients, carriers, hydrotropes, processing aids, dyes or pigments, solvents for liquid formulations, etc. If an additional increment of sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additionally sudsing.

The liquid detergent compositions herein can contain water and other solvents as carriers. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11.0. Finished products thus are typically formulated at this range. Techniques for controlling pH at recommended usage levels include the use of buffers, alkalis, acids, etc., and are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases and proteases in such compositions, typically at levels of from about 0.001% to about 1% by weight. Various detersive and fabric care enzymes are well-known in the laundry detergent art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various suds suppressors, especially silicones and secondary alcohols, various fabric softeners, especially smectite clays, and the like can all be used in such compositions at levels ranging from about 1% to about 35% by weight. Standard formularies and published patents contain multiple, detailed descriptions of such conventional materials.

Enzyme stabilizers may also be used in the cleaning compositions. Such enzyme stabilizers include propylene glycol (preferably from about 1% to about 10%), sodium formate (preferably from about 0.1% to about 1%) and calcium formate (preferably from about 0.1% to about 1%).

1. Hard Surface Cleaning Compositions

As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more enzyme variants of the present invention, preferably from about 0.001% to about 10%, more preferably from about 0.01% to about 5%, more preferably still from about 0.05% to about 1% by weight of active enzyme of the composition. In addition to comprising one or more of the enzyme variants, such hard surface cleaning compositions typically comprise a surfactant and a water-soluble sequestering builder. In certain specialized products such as spray window cleaners, however, the surfactants are sometimes not used since they may produce a filmy/streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%.

Preferably the pH should be in the range of about 8 to 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3-pentanediol and 2-ethyl-1,3-hexanediol. When used, such solvents are typically present at levels of from about 0.5% to about 15%, preferably from about 3% to about 11%.

Additionally, highly volatile solvents such as isopropanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

The hard surface cleaning composition embodiment of the present invention is illustrated by the following examples.

EXAMPLES 7–12

Examples 7–12
Liquid Hard Surface Cleaning Compositions

| Component | Example No. | | | | | |
|---|---|---|---|---|---|---|
| | 7 | 8 | 9 | 10 | 11 | 12 |
| Asn67Ser | 0.05 | 0.50 | 0.02 | 0.03 | 0.10 | 0.03 |
| Val95His | — | — | — | — | 0.20 | 0.02 |
| Na$_2$DIDA* | | | | | | |
| EDTA** | — | — | 2.90 | 2.90 | — | — |
| Na Citrate | — | — | — | — | 2.90 | 2.90 |
| NaC$_{12}$ Alkyl-benzene sulfonate | 1.95 | — | 1.95 | — | 1.95 | — |

-continued

Examples 7–12
Liquid Hard Surface Cleaning Compositions

| Component | Example No. | | | | | |
|---|---|---|---|---|---|---|
| | 7 | 8 | 9 | 10 | 11 | 12 |
| NaC$_{12}$ Alkylsulfate | — | 2.20 | — | 2.20 | — | 2.20 |
| NaC$_{12}$ (ethoxy)*** sulfate | — | 2.20 | — | 2.20 | — | 2.20 |
| C$_{12}$ Dimethylamine oxide | — | 0.50 | — | 0.50 | — | 0.50 |
| Na Cumene sulfonate | 1.30 | — | 1.30 | — | 1.30 | — |
| Hexyl Carbitol*** | 6.30 | 6.30 | 6.30 | 6.30 | 6.30 | 6.30 |
| Water**** | balance to 100% | | | | | |

*Disodium N-diethyleneglycol-N,N-iminodiacetate
**Na$_4$ ethylenediamine diacetic acid
***Diethyleneglycol monohexyl ether
****All formulas adjusted to pH 7

In Examples 7–10, the Proteinase K variants recited in Tables 2–36, among others, are substituted for Asn 67Ser, with substantially similar results.

In Examples 11–12, any combination of the Proteinase K variants recited in Tables 2–36, among others, are substituted for Asn67Ser and Val95His, with substantially similar results.

EXAMPLES 13–18

Examples 13–18
Spray Compositions for Cleaning Hard Surfaces
and Removing Household Mildew

| Component | Example No. | | | | | |
|---|---|---|---|---|---|---|
| | 13 | 14 | 15 | 16 | 17 | 18 |
| Gly134Asn + Ser140Asp | 0.50 | 0.05 | 0.60 | 0.30 | 0.20 | 0.30 |
| Leu96Gly + Leu209Pro | — | — | — | — | 0.30 | 0.10 |
| Sodium octyl sulfate | 2.00 | 2.00 | 2.00 | 2.00 | 2.00 | 2.00 |
| Sodium dodecyl sulfate | 4.00 | 4.00 | 4.00 | 4.00 | 4.00 | 4.00 |
| Sodium hydroxide | 0.80 | 0.80 | 0.80 | 0.80 | 0.80 | 0.80 |
| Silicate (Na) | 0.04 | 0.04 | 0.04 | 0.04 | 0.04 | 0.04 |
| Perfume | 0.35 | 0.35 | 0.35 | 0.35 | 0.35 | 0.35 |
| Water | balance to 100% | | | | | |

Product pH is about 7.

In Examples 13–16, the Proteinase K variants recited in Tables 2–36, among others, are substituted for Gly134Asn+Ser140Asp, with substantially similar results.

In Examples 17–18, any combination of the Proteinase K variants recited in Tables 2–36, among others, are substituted for Gly134Asn+Ser140Asp and Leu96Gly+Leu209Pro, with substantially similar results.

2. Dishwashing Compositions

In another embodiment of the present invention, dishwashing compositions comprise one or more enzyme variants of the present invention. As used herein, "dishwashing composition" refers to all forms for compositions for cleaning dishes, including but not limited to, granular and liquid forms. The dishwashing composition embodiment of the present invention is illustrated by the following examples.

EXAMPLES 19–24

Examples 19–24
Dishwashing Composition

| Component | 19 | 20 | 21 | 22 | 23 | 24 |
|---|---|---|---|---|---|---|
| Ala164Asp | 0.05 | 0.50 | 0.02 | 0.40 | 0.10 | 0.03 |
| Ser191Asp + Phe192Met + Asn194Gln | — | — | — | — | 0.40 | 0.02 |
| $C_{12}$—$C_{14}$ N-methyl-glucamide | 0.90 | 0.90 | 0.90 | 0.90 | 0.90 | 0.90 |
| $C_{12}$ ethoxy (1) sulfate | 12.00 | 12.00 | 12.00 | 12.00 | 12.00 | 12.00 |
| 2-methyl undecanoic acid | 4.50 | 4.50 | 4.50 | 4.50 | 4.50 | 4.50 |
| $C_{12}$ ethoxy (2) carboxylate | 4.50 | 4.50 | 4.50 | 4.50 | 4.50 | 4.50 |
| $C_{12}$ alcohol ethoxylate (4) | 3.00 | 3.00 | 3.00 | 3.00 | 3.00 | 3.00 |
| $C_{12}$ amine oxide | 3.00 | 3.00 | 3.00 | 3.00 | 3.00 | 3.00 |
| Sodium cumene sulfonate | 2.00 | 2.00 | 2.00 | 2.00 | 2.00 | 2.00 |
| Ethanol | 4.00 | 4.00 | 4.00 | 4.00 | 4.00 | 4.00 |
| $Mg^{++}$ (as $MgCl_2$) | 0.20 | 0.20 | 0.20 | 0.20 | 0.20 | 0.20 |
| $Ca^{++}$ (as $CaCl_2$) | 0.40 | 0.40 | 0.40 | 0.40 | 0.40 | 0.40 |
| Water | balance to 100% | | | | | |

Product pH is adjusted to 7.

In Examples 19–22, the Proteinase K variants recited in Tables 2–36, among others, are substituted for Ala164Asp, with substantially similar results.

In Examples 23–24, any combination of the Proteinase K variants recited in Tables 2–36, among others, are substituted for Ala164Asp and Ser191Asp+Phe192Met+Asn194Gln, with substantially similar results.

3. Fabric Cleaning Compositions

In another embodiment of the present invention, fabric cleaning compositions comprise one or more enzyme variants of the present invention. As used herein, "fabric cleaning composition" refers to all forms for detergent compositions for cleaning fabrics, including but not limited to, granular, liquid and bar forms. Preferred fabric cleaning compositions are those in the liquid form.

a. Granular Fabric Cleaning Compositions

The granular fabric cleaning compositions of the present invention contain an effective amount of one or more enzyme variants of the present invention, preferably from about 0.001% to about 10%, more preferably from about 0.005% to about 5%, more preferably from about 0.01% to about 1% by weight of active enzyme of the composition. In addition to one or more enzyme variants, the granular fabric cleaning compositions typically comprise at least one surfactant, one or more builders, and, in some cases, a bleaching agent.

The granular fabric cleaning composition embodiment of the present invention is illustrated by the following examples.

EXAMPLES 25–28

Granular Fabric Cleaning Composition

| Component | 25 | 26 | 27 | 28 |
|---|---|---|---|---|
| Ile208Ala | 0.10 | 0.20 | 0.03 | 0.05 |
| Trp212Phe | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 25–26, the Proteinase K variants recited in Tables 2–36, among others, are substituted for Ile208Ala, with substantially similar results.

In Examples 27–28, any combination of the Proteinase K variants recited in Tables 2–36, among others, are substituted for Ile208Ala and Trp212Phe, with substantially similar results.

EXAMPLES 29–32

Granular Fabric Cleaning Composition

| Component | 29 | 30 | 31 | 32 |
|---|---|---|---|---|
| Asn194Glu + Leu209Gly | 0.10 | 0.20 | 0.03 | 0.05 |
| Gly100Asn + Gln103Ser + Ser207Asp + Leu209Val | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 29–30, the Proteinase K variants recited in Tables 2–36, among others, are substituted for Asn194Glu+Leu209Gly, with substantially similar results.

In Examples 31–32, any combination of the Proteinase K variants recited in Tables 2–36, among others, are substituted for Asn194Glu+Leu209Gly and Gly100Asn+Gln103Ser+Ser207Asp+Leu209Valo, with substantially similar results.

EXAMPLES 33–36

Granular Fabric Cleaning Composition

| Component | 33 | 34 | 35 | 36 |
|---|---|---|---|---|
| Arg64Asp + Gly70Gln + Thr71Gly | 0.10 | 0.20 | 0.03 | 0.05 |
| Phe192Asp + Asn194Ser | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |

-continued

Granular Fabric Cleaning Composition

| Component | Example No. 33 | 34 | 35 | 36 |
|---|---|---|---|---|
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 33–34, the Proteinase K variants recited in Tables 2–36, among others, are substituted for Arg64Asp+Gly70Gln+Thr71Gly, with substantially similar results.

In Examples 35–36, any combination of the Proteinase K variants recited in Tables 2–36, among others, are substituted for Arg64Asp+Gly70Gln+Thr71Gly and Phe192Asp+Asn194Ser, with substantially similar results.

EXAMPLES 37–40

Granular Fabric Cleaning Composition

| Component | Example No. 37 | 38 | 39 | 40 |
|---|---|---|---|---|
| Ala164His + Ala166Gly | 0.10 | 0.20 | 0.03 | 0.05 |
| Ile213Pro + Ser216Glu + Ile220Glu | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 37–38, the Proteinase K variants recited in Tables 2–36, among others, are substituted for Ala164His+Ala166Gly, with substantially similar results.

In Examples 39–40, any combination of the Proteinase K variants recited in Tables 2–36, among others, are substituted for Ala164His+Ala166Gly and Ile213Pro+Ser216Glu+Ile220Glu, with substantially similar results.

EXAMPLES 41–42

Granular Fabric Cleaning Composition

| Component | Example No. 41 | 42 |
|---|---|---|
| Linear alkyl benzene sulphonate | 11.4 | 10.70 |
| Tallow alkyl sulphate | 1.80 | 2.40 |
| $C_{14–15}$ alkyl sulphate | 3.00 | 3.10 |
| $C_{14–15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| Diethylene triamine penta methylene phosphonic acid | 1.00 | 0.20 |
| Gly203Gln + Thr211Gly + Ile213Leu + Gly214Asn | 0.30 | 0.30 |
| Lipase | 0.36 | 0.40 |
| Amylase | 0.30 | 0.30 |
| Sodium silicate | 2.00 | 2.50 |
| Sodium sulphate | 3.50 | 5.20 |
| Polyvinyl pyrrolidone | 0.30 | 0.50 |
| Perborate | 0.5 | 1 |
| Phenol sulphonate | 0.1 | 0.2 |
| Peroxidase | 0.1 | 0.1 |
| Minors | Up to 100 | Up to 100 |

EXAMPLES 43–44

Granular Fabric Cleaning Composition

| Component | Example No. 43 | 44 |
|---|---|---|
| Sodium linear $C_{12}$ alkyl benzene-sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Polyvinyl pyrrolidone | 0.5 | 0.7 |
| Tetraacetylethylene diamine | 3.0 | 3.0 |
| Boric acid | 4.0 | — |
| Perborate | 0.5 | 1 |
| Phenol sulphonate | 0.1 | 0.2 |
| Asp98Glu + Tyr104Leu | 0.4 | 0.4 |
| Fillers (e.g., silicates; carbonates; perfumes; water) | Up to 100 | Up to 100 |

EXAMPLE 45

Compact Granular Fabric Cleaning Composition

| Component | Weight % |
|---|---|
| Alkyl Sulphate | 8.0 |
| Alkyl Ethoxy Sulphate | 2.0 |
| Mixture of $C_{25}$ and $C_{45}$ alcohol 3 and 7 times ethoxylated | 6.0 |
| Polyhydroxy fatty acid amide | 2.5 |
| Zeolite | 17.0 |
| Layered silicate/citrate | 16.0 |
| Carbonate | 7.0 |
| Maleic acid acrylic acid copolymer | 5.0 |
| Soil release polymer | 0.4 |
| Carboxymethyl cellulose | 0.4 |
| Poly (4-vinylpyridine)-N-oxide | 0.1 |
| Copolymer of vinylimidazole and vinylpyrrolidone | 0.1 |
| PEG2000 | 0.2 |
| Gly136Ser + Tyr137Met + Ser138Glu | 0.5 |
| Lipase | 0.2 |
| Cellulase | 0.2 |
| Tetracetylethylene diamine | 6.0 |
| Percarbonate | 22.0 |
| Ethylene diamine disuccinic acid | 0.3 |

-continued

| Compact Granular Fabric Cleaning Composition | |
|---|---|
| Component | Weight % |
| Suds Suppressor | 3.5 |
| Disodium-4,4'-bis (2-morpholino-4-anilino-s-triazin-6-ylamino) stilbene-2,2'-disulphonate | 0.25 |
| Disodium-4,4'-bis (2-sulfostyril) biphenyl | 0.05 |
| Water, Perfume and Minors | Up to 100 |

EXAMPLE 46

| Granular Fabric Cleaning Composition | |
|---|---|
| Component | Weight % |
| Linear alkyl benzene sulphonate | 7.6 |
| $C_{16}$–$C_{18}$ alkyl sulfate | 1.3 |
| $C_{14-15}$ alcohol 7 times ethoxylated | 4.0 |
| Coco-alkyl-dimethyl hydroxyethyl ammonium chloride | 1.4 |
| Dispersant | 0.07 |
| Silicone fluid | 0.8 |
| Trisodium citrate | 5.0 |
| Zeolite 4A | 15.0 |
| Maleic acid acrylic acid copolymer | 4.0 |
| Diethylene triamine penta methylene phosphonic acid | 0.4 |
| Perborate | 15.0 |
| Tetraacetylethylene diamine | 5.0 |
| Smectite clay | 10.0 |
| Poly (oxy ethylene) (MW 300,000) | 0.3 |
| Ser219Asp | 0.4 |
| Lipase | 0.2 |
| Amylase | 0.3 |
| Cellulase | 0.2 |
| Sodium silicate | 3.0 |
| Sodium carbonate | 10.0 |
| Carboxymethyl cellulose | 0.2 |
| Brighteners | 0.2 |
| Water, perfume and minors | Up to 100 |

EXAMPLE 47

| Granular Fabric Cleaning Composition | |
|---|---|
| Component | Weight % |
| Linear alkyl benzene sulfonate | 6.92 |
| Tallow alkyl sulfate | 2.05 |
| $C_{14-15}$ alcohol 7 times ethoxylated | 4.4 |
| $C_{12-15}$ alkyl ethoxy sulfate - 3 times ethoxylated | 0.16 |
| Zeolite | 20.2 |
| Citrate | 5.5 |
| Carbonate | 15.4 |
| Silicate | 3.0 |
| Maleic acid acrylic acid copolymer | 4.0 |
| Carboxymethyl cellulase | 0.31 |
| Soil release polymer | 0.30 |
| Ser190Glu + Ser191Glu + Phe192Leu + Asn194Ser | 0.2 |
| Lipase | 0.36 |
| Cellulase | 0.13 |
| Perborate tetrahydrate | 11.64 |
| Perborate monohydrate | 5.7 |
| Tetraacetylethylene diamine | 5.0 |
| Diethylene triamine penta methyl phosphonic acid | 0.38 |
| Magnesium sulfate | 0.40 |
| Brightener | 0.19 |
| Perfume, silicone, suds suppressors | 0.85 |
| Minors | Up to 100 | b. Liquid Fabric Cleaning Compositions

Liquid fabric cleaning compositions of the present invention comprise an effective amount of one or more enzyme variants of the present invention, preferably from about 0.005% to about 5%, more preferably from about 0.01% to about 1%, by weight of active enzyme of the composition. Such liquid fabric cleaning compositions typically additionally comprise an anionic surfactant, a fatty acid, a water-soluble detergency builder and water.

The liquid fabric cleaning composition embodiment of the present invention is illustrated by the following examples.

EXAMPLES 48–52

| Liquid Fabric Cleaning Compositions | | | | | |
|---|---|---|---|---|---|
| | Example No. | | | | |
| Component | 48 | 49 | 50 | 51 | 52 |
| Ile220Asp | 0.05 | 0.03 | 0.30 | 0.03 | 0.10 |
| Th206Asp + Ile220Met | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In Examples 48–50 the Proteinase K variants recited in Tables 2–36, among others, are substituted for Ile220Asp, with substantially similar results.

In Examples 51–52, any combination of the Proteinase K variants recited in Tables 2–36, among others, are substituted for Ile220Asp and Thr206Asp+Ile220Met, with substantially similar results.

EXAMPLES 53–57

| Liquid Fabric Cleaning Compositions | | | | | |
|---|---|---|---|---|---|
| | Example No. | | | | |
| Component | 53 | 54 | 55 | 56 | 57 |
| Gly136Ser | 0.05 | 0.03 | 0.30 | 0.03 | 0.10 |
| Gly215Pro | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In Examples 53–55 the Proteinase K variants recited in Tables 2–36, among others, are substituted for Gly136Ser, with substantially similar results.

In Examples 56–57, any combination of the Proteinase K variants recited in Tables 2–36, among others, are substituted for Gly136Ser and Gly215Pro, with substantially similar results.

EXAMPLES 58–59

| Liquid Fabric Cleaning Composition | | |
|---|---|---|
| | Example No. | |
| Component | 58 | 59 |
| $C_{12-14}$ alkenyl succinic acid | 3.0 | 8.0 |
| Citric acid monohydrate | 10.0 | 15.0 |
| Sodium $C_{12-15}$ alkyl sulphate | 8.0 | 8.0 |
| Sodium sulfate of $C_{12-15}$ alcohol 2 times ethoxylated | — | 3.0 |
| $C_{12-15}$ alcohol 7 times ethoxylated | — | 8.0 |
| $C_{12-15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Pro204Asn + Thr211Pro + Gly214Gln + Gly215Glu + Thr217Ser | 0.2 | 0.2 |
| Polyvinyl pyrrolidone | 1.0 | 2.0 |
| Suds suppressor | 0.15 | 0.15 |
| NaOH | up to pH 7.5 | |
| Perborate | 0.5 | 1 |
| Phenol sulphonate | 0.1 | 0.2 |
| Peroxidase | 0.4 | 0.1 |
| Waters and minors | up to 100 parts | |

In each of Examples 58 and 59 herein, the Proteinase K variants recited in Tables 2–36, among others, are substituted for Pro204Asn+Thr211Pro+Gly214Gln+Gly215Glu+Thr217Ser, with substantially similar results.

EXAMPLES 60–62

| Liquid Fabric Cleaning Composition | | | |
|---|---|---|---|
| | Example No. | | |
| Component | 60 | 61 | 62 |
| Citric Acid | 7.10 | 3.00 | 3.00 |
| Fatty Acid | 2.00 | — | 2.00 |
| Ethanol | 1.93 | 3.20 | 3.20 |
| Boric Acid | 2.22 | 3.50 | 3.50 |
| Monoethanolamine | 0.71 | 1.09 | 1.09 |
| 1,2 Propanediol | 7.89 | 8.00 | 8.00 |
| NaCumene Sulfonate | 1.80 | 3.00 | 3.00 |
| NaFormate | 0.08 | 0.08 | 0.08 |
| NaOH | 6.70 | 3.80 | 3.80 |
| Silicon anti-foam agent | 1.16 | 1.18 | 1.18 |
| Leu96Met + Asn99Ser + Ser105Asp | 0.0145 | — | — |
| Thr211Ser + Gly222Asp | — | 0.0145 | — |
| Tyr169Ser + Ser190Asp + Ile220Thr | — | — | 0.0145 |
| Lipase | 0.200 | 0.200 | 0.200 |
| Cellulase | — | 7.50 | 7.50 |
| Soil release polymer | 0.29 | 0.15 | 0.15 |
| Anti-foaming agents | 0.06 | 0.085 | 0.085 |
| Brightener 36 | 0.095 | — | — |
| Brightener 3 | — | 0.05 | 0.05 |
| $C_{12}$ alkyl benzenesulfonic acid | 9.86 | — | — |
| $C_{12-15}$ alkyl polyethoxylate (2.5) sulfate | 13.80 | 18.00 | 18.00 |
| $C_{12}$ glucose amide | — | 5.00 | 5.00 |
| $C_{12-13}$ alkyl polyethoxylate (9) | 2.00 | 2.00 | 2.00 |
| Water, perfume and minors | balance to 100% | | | c. Bar Fabric Cleaning Compositions

Bar fabric cleaning compositions of the present invention suitable for hand-washing soiled fabrics contain an effective amount of one or more enzyme variants of the present invention, preferably from about 0.001% to about 10%, more preferably from about 0.01% to about 1% by weight of the composition.

The bar fabric cleaning composition embodiment of the present invention is illustrated by the following examples.

EXAMPLES 63–66

| Bar Fabric Cleaning Compositions | | | | |
|---|---|---|---|---|
| | Example No. | | | |
| Component | 63 | 64 | 65 | 66 |
| Leu96Ala + Asp97Glu + Ser101Asp + Ile107Asp | 0.3 | — | 0.1 | 0.02 |
| Ser193Asp | — | — | 0.4 | 0.03 |
| $C_{12}-C_{16}$ alkyl sulfate, Na | 20.0 | 20.0 | 20.0 | 20.00 |
| $C_{12}-C_{14}$ N-methyl glucamide | 5.0 | 5.0 | 5.0 | 5.00 |
| $C_{11}-C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10µ) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

*Can be selected from convenient materials such as $CaCO_3$, talc, clay, silicates, and the like.

In Examples 63–64 the Proteinase K variants recited in Tables 2–36, among others, are substituted for Leu 96Ala+Asp 97Glu+Ser101Asp+Ile107Asp, with substantially similar results.

In Examples 65–66, any combination of the Proteinase K variants recited in Tables 2–36, among others, are substituted for Leu96Ala+Asp97Glu+Ser101Asp+Ile107Asp and Ser193Asp, with substantially similar results.

EXAMPLES 67–70

| Bar Fabric Cleaning Compositions | | | | |
|---|---|---|---|---|
| | Example No. | | | |
| Component | 67 | 68 | 69 | 70 |
| Arg64Asp + Gly68Gln | 0.3 | — | 0.1 | 0.02 |
| Tyr137Gln | — | 0.3 | 0.4 | 0.03 |
| $C_{12}-C_{16}$ alkyl sulfate, Na | 20.0 | 20.0 | 20.0 | 20.00 |
| $C_{12}-C_{14}$ N-methyl glucamide | 5.0 | 5.0 | 5.0 | 5.00 |
| $C_{11}-C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10µ) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

*Can be selected from convenient materials such as $CaCO_3$, talc, clay, silicates, and the like.

In Example 67, the Proteinase K variants recited in Tables 2–36, among others, are substituted for Arg64Asp+

Gly68Gln, with substantially similar results.

In Example 68, the Proteinase K variants recited in Tables 2–36, among others, are substituted for Tyr137Gln, with substantially similar results.

In Examples 69–70, any combination of the Proteinase K variants recited in Tables 2–36, among others, are substituted for Arg64Asp+Gly68Glnand Tyr137Gln, with substantially similar results.

B. Additional Cleaning Compositions

In addition to the hard surface cleaning, dishwashing and fabric cleaning compositions discussed above, one or more enzyme variants of the present invention may be incorporated into a variety of other cleaning compositions where hydrolysis of an insoluble substrate is desired. Such additional cleaning compositions include but are not limited to, oral cleaning compositions, denture cleaning compositions, and contact lens cleaning compositions.

1. Oral Cleaning Compositions

In another embodiment of the present invention, a pharmaceutically-acceptable amount of one or more enzyme variants of the present invention are included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral cleaning compositions comprise from about 0.0001% to about 20% of one or more enzyme variants of the present invention, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in U.S. Pat. No. 5,096,700, Seibel, issued Mar. 17, 1992; U.S. Pat. No. 5,028,414, Sampathkumar, issued Jul. 2, 1991; and U.S. Pat. No. 5,028,415, Benedict, Bush and Sunberg, issued Jul. 2, 1991; all of which are incorporated herein by reference.

The oral cleaning composition embodiment of the present invention is illustrated by the following examples.

EXAMPLES 71–74

Dentifrice Composition

| Component | Example No. | | | |
|---|---|---|---|---|
| | 71 | 72 | 73 | 74 |
| Gly160Pro | 2.000 | 3.500 | 1.500 | 2.000 |
| Sorbitol (70% aqueous solution) | 35.000 | 35.000 | 35.000 | 35.000 |
| PEG-6* | 1.000 | 1.000 | 1.000 | 1.000 |
| Silica dental abrasive** | 20.000 | 20.000 | 20.000 | 20.000 |
| Sodium fluoride | 0.243 | 0.243 | 0.243 | 0.243 |
| Titanium dioxide | 0.500 | 0.500 | 0.500 | 0.500 |
| Sodium saccharin | 0.286 | 0.286 | 0.286 | 0.286 |
| Sodium alkyl sulfate (27.9% aqueous solution) | 4.000 | 4.000 | 4.000 | 4.000 |
| Flavor | 1.040 | 1.040 | 1.040 | 1.040 |
| Carboxyvinyl Polymer*** | 0.300 | 0.300 | 0.300 | 0.300 |
| Carrageenan**** | 0.800 | 0.800 | 0.800 | 0.800 |
| Water | balance to 100% | | | |

*PEG-6 = Polyethylene glycol having a molecular weight of 600.
**Precipitated silica identified as Zeodent 119 offered by J. M. Huber.
***Carbopol offered by B. F. Goodrich Chemical Company.
****Iota Carrageenan offered by Hercules Chemical Company.

In Examples 71–74 the Proteinase K variants recited in Tables 2–36, among others, are substituted for Gly160Pro, with substantially similar results.

EXAMPLES 75–78

Mouthwash Composition

| Component | Example No. | | | |
|---|---|---|---|---|
| | 75 | 76 | 77 | 78 |
| Ala166Gln + Ser216Asp | 3.00 | 7.50 | 1.00 | 5.00 |
| SDA 40 Alcohol | 8.00 | 8.00 | 8.00 | 8.00 |
| Flavor | 0.08 | 0.08 | 0.08 | 0.08 |
| Emulsifier | 0.08 | 0.08 | 0.08 | 0.08 |
| Sodium Fluoride | 0.05 | 0.05 | 0.05 | 0.05 |
| Glycerin | 10.00 | 10.00 | 10.00 | 10.00 |
| Sweetener | 0.02 | 0.02 | 0.02 | 0.02 |
| Benzoic acid | 0.05 | 0.05 | 0.05 | 0.05 |
| Sodium hydroxide | 0.20 | 0.20 | 0.20 | 0.20 |
| Dye | 0.04 | 0.04 | 0.04 | 0.04 |
| Water | balance to 100% | | | |

In Examples 75–78, the Proteinase K variants recited in Tables 2–36, among others, are substituted for Ala166Gln+Ser216Asp, with substantially similar results.

EXAMPLES 79–82

Lozenge Composition

| Component | Example No. | | | |
|---|---|---|---|---|
| | 79 | 80 | 81 | 82 |
| Gly70Ser + Ile107Gly + Leu133Met + Phe192His + Asn194Asp | 0.01 | 0.03 | 0.10 | 0.02 |

-continued

Lozenge Composition

| Component | Example No. | | | |
|---|---|---|---|---|
| | 79 | 80 | 81 | 82 |
| Sorbitol | 17.50 | 17.50 | 17.50 | 17.50 |
| Mannitol | 17.50 | 17.50 | 17.50 | 17.50 |
| Starch | 13.60 | 13.60 | 13.60 | 13.60 |
| Sweetener | 1.20 | 1.20 | 1.20 | 1.20 |
| Flavor | 11.70 | 11.70 | 11.70 | 11.70 |
| Color | 0.10 | 0.10 | 0.10 | 0.10 |
| Corn Syrup | balance to 100% | | | |

In Examples 79–82, the Proteinase K variants recited in Tables 2–36, among others, are substituted for Gly70Ser+Ile107Gly+Leu133Met+Phe192His+Asn194Asp, with substantially similar results.

EXAMPLES 83–86

Chewing Gum Composition

| Component | Example No. | | | |
|---|---|---|---|---|
| | 83 | 84 | 85 | 86 |
| Gly214Asn | 0.03 | 0.02 | 0.10 | 0.05 |
| Sorbitol crystals | 38.44 | 38.40 | 38.40 | 38.40 |
| Paloja-T gum base* | 20.00 | 20.00 | 20.00 | 20.00 |
| Sorbitol (70% aqueous solution) | 22.00 | 22.00 | 22.00 | 22.00 |
| Mannitol | 10.00 | 10.00 | 10.00 | 10.00 |
| Glycerine | 7.56 | 7.56 | 7.56 | 7.56 |
| Flavor | 1.00 | 1.00 | 1.00 | 1.00 |

*Supplied by L.A. Dreyfus Company.

In Examples 83–86, the Proteinase K variants recited in Tables 2–36, among others, are substituted for Gly214Asn, with substantially similar results.

2. Denture Cleaning Compositions

In another embodiment of the present invention, denture cleaning compositions for cleaning dentures outside of the oral cavity comprise one or more enzyme variants of the present invention. Such denture cleaning compositions comprise an effective amount of one or more of the enzyme variants, preferably from about 0.0001% to about 50% of one or more of the enzyme variants, more preferably from about 0.001% to about 35%, more preferably still from about 0.01% to about 20%, by weight of the composition, and a denture cleansing carrier. Various denture cleansing composition formats such as effervescent tablets and the like are well known in the art (see for example U.S. Pat. No. 5,055,305, Young, incorporated herein by reference), and are generally appropriate for incorporation of one or more of the enzyme variants for removing proteinaceous stains from dentures.

The denture cleaning composition embodiment of the present invention is illustrated by the following examples.

EXAMPLES 87–90

Two-layer Effervescent Denture Cleansing Tablet

| Component | Example No. | | | |
|---|---|---|---|---|
| | 87 | 88 | 89 | 90 |
| Acidic Layer | | | | |
| Tyr137Leu + Tyr169Cys + Phe192Asn + Ser207Asp + Arg218Glu + Ile220Leu | 1.0 | 1.5 | 0.01 | 0.05 |
| Tartaric acid | 24.0 | 24.0 | 24.00 | 24.00 |
| Sodium carbonate | 4.0 | 4.0 | 4.00 | 4.00 |
| Sulphamic acid | 10.0 | 10.0 | 10.00 | 10.00 |
| PEG 20,000 | 4.0 | 4.0 | 4.00 | 4.00 |
| Sodium bicarbonate | 24.5 | 24.5 | 24.50 | 24.50 |
| Potassium persulfate | 15.0 | 15.0 | 15.00 | 15.00 |
| Sodium acid pyrophosphate | 7.0 | 7.0 | 7.00 | 7.00 |
| Pyrogenic silica | 2.0 | 2.0 | 2.00 | 2.00 |
| TAED* | 7.0 | 7.0 | 7.00 | 7.00 |
| Ricinoleylsulfosuccinate | 0.5 | 0.5 | 0.50 | 0.50 |
| Flavor | 1.0 | 1.0 | 1.00 | 1.00 |
| Alkaline Layer | | | | |
| Sodium perborate monohydrate | 32.0 | 32.0 | 32.00 | 32.00 |
| Sodium bicarbonate | 19.0 | 19.0 | 19.00 | 19.00 |
| EDTA | 3.0 | 3.0 | 3.00 | 3.00 |
| Sodium tripolyphosphate | 12.0 | 12.0 | 12.00 | 12.00 |
| PEG 20,000 | 2.0 | 2.0 | 2.00 | 2.00 |
| Potassium persulfate | 26.0 | 26.0 | 26.00 | 26.00 |
| Sodium carbonate | 2.0 | 2.0 | 2.00 | 2.00 |
| Pyrogenic silica | 2.0 | 2.0 | 2.00 | 2.00 |
| Dye/flavor | 2.0 | 2.0 | 2.00 | 2.00 |

In Examples 87–90, the Proteinase K variants recited in Tables 2–36, among others, are substituted for Tyr137Leu+Tyr169Cys+Phe192Asn+Ser207Asp+Arg218Glu+Ile220Leu, with substantially similar results.

3. Contact Lens Cleaning Compositions

In another embodiment of the present invention, contact lens cleaning compositions comprise one or more enzyme variants of the present invention. Such contact lens cleaning compositions comprise an effective amount of one or more of the enzyme variants, preferably from about 0.01% to about 50% of one or more of the enzyme variants, more preferably from about 0.01% to about 20%, more preferably still from about 1% to about 5%, by weight of the composition, and a contact lens cleaning carrier. Various contact lens cleaning composition formats such as tablets, liquids and the like are well known in the art (see for example U.S. Pat. No. 4,863,627, Davies, Meaken and Rees, issued Sep. 5, 1989; U.S. Pat. No. Re. 32,672, Huth, Lam and Kirai, reissued May 24, 1988; U.S. Pat. No. 4,609,493, Schafer, issued Sep. 2, 1986; U.S. Pat. No. 4,690,793, Ogunbiyi and Smith, issued Sep. 1, 1987; U.S. Pat. No. 4,614,549, Ogunbiyi, Riedhammer and Smith, issued Sep. 30, 1986; and U.S. Pat. No. 4,285,738, Ogata, issued Aug. 25, 1981; each of which are incorporated herein by reference), and are generally appropriate for incorporation of one or more enzyme variants of the present invention for removing proteinaceous stains from contact lens.

The contact lens cleaning composition embodiment of the present is invention is illustrated by the following examples.

EXAMPLES 91–94

Enzymatic Contact Lens Cleaning Solution

| Component | Example No. | | | |
|---|---|---|---|---|
| | 91 | 92 | 93 | 94 |
| Gly102Gln | 0.01 | 0.5 | 0.1 | 2.0 |
| Glucose | 50.00 | 50.0 | 50.0 | 50.0 |
| Nonionic surfactant (polyoxyethlene-polyoxypropylene copolymer) | 2.00 | 2.0 | 2.0 | 2.0 |
| Anionic surfactant (polyoxyethylene-alkylphenylether sodium sulfricester) | 1.00 | 1.0 | 1.0 | 1.0 |
| Sodium chloride | 1.00 | 1.0 | 1.0 | 1.0 |
| Borax | 0.30 | 0.3 | 0.3 | 0.3 |
| Water | balance to 100% | | | |

In Examples 91–94, the Proteinase K variants recited in Tables 2–36, among others, are substituted for Gly 102Gln, with substantially similar results.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A Proteinase K variant having a modified amino acid sequence of the Proteinase K wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at one or more positions in one of the loop regions; wherein A. when the substitution occurs in the first loop region, the substitution occurs at one of positions 65, 66, 68, 70 or 71; wherein
  a. when a substitution occurs at position 65, the substituting amino acid is Glu;
  b. when a substitution occurs at position 66, the substituting amino acid is Asn, Asp, Gln, Glu, Pro or Ser;
  c. when a substitution occurs at position 68, the substituting amino acid is Asn, Asp, Gln, Glu, Pro or Ser;
  d. when a substitution occurs at position 70, the substituting amino acid is Asn, Asp, Gln, Glu, Pro or Ser; and
  e. when a substitution occurs at position 71, the substituting amino acid is Asn, Asp, Gln, Glu, Pro or Ser;

B. when the substitution occurs in the second loop region, the substitution occurs at one of positions 95, 96, or 106; wherein
  a. when a substitution occurs at position 95, the substituting amino acid is Ala, Asn, Asp, Gln, Glu, Gly, His, Met, Pro, Ser or Thr;
  b. when a substitution occurs at position 96, the substituting amino acid is Ala, Asn, Asp, Cys, Gln, Glu, Gly, His, Ile, Met, Pro, Ser, Thr or Val; and
  c. when a substitution occurs at position 106, the substituting amino acid is Asn, Gln, Gly, Pro or Ser;

C. when the substitution occurs in the third loop region, the substitution occurs at one of positions 137, 139 or 140; wherein
  a. when a substitution occurs at position 137, the substituting amino acid is Asp, His, Ile, Leu, Met or Pro;
  b. when a substitution occurs at position 139, the substituting amino acid is Asp or Glu; and
  c. when a substitution occurs at position 140, the substituting amino acid is Asp or Glu;

D. when the substitution occurs in the fourth loop region, the substitution occurs at position 162; wherein the substituting amino acid is Asp, or Glu;

E. when the substitution occurs in the fifth loop region, the substitution occurs at position 193; wherein the substituting amino acid is Asp or Glu; and F. when the substitution occurs in the sixth loop region, the substitution occurs at one of positions 203, 204, 205, 206, 208, 209, 210, 260, 212, 213, 214, 215, 219, or 223; wherein a. when a substitution occurs at position 203, the substituting amino acid is Asn, Asp, Gln, Glu, Pro or Ser;
b. when a substitution occurs at position 204, the substituting amino acid is Asn, Asp, Gln, Glu, Gly or Ser;
c. when a substitution occurs at position 205, the substituting amino acid is Asn, Asp, Gln, Glu, Pro or Ser;
d. when a substitution occurs at position 206, the substituting amino acid is Asn, Asp, Gln, Glu, Gly, Pro or Ser;
e. when a substitution occurs at position 208, the substituting amino acid is Ala, Asn, Asp, Cys, Gln, Glu, Gly, His, Leu, Met, Pro, Ser, Thr or Val;
f. when a substitution occurs at position 209, the substituting amino acid is Ala, Asn, Asp, Cys, Gln, Glu, Gly, His, Ile, Met, Pro, Ser, Thr or Val;
g. when a substitution occurs at position 210, the substituting amino acid is Asp or Glu;
h. when a substitution occurs at position 211, the substituting amino acid is Asn, Asp, Gln, Glu, Pro or Ser;
i. when a substitution occurs at position 212, the substituting amino acid is Asp or Glu;
j. when a substitution occurs at position 213, the substituting amino acid is Ala, Asn, Asp, Cys, Gln, Glu, Gly, His, Leu, Met, Pro, Ser, Thr or Val;
k. when a substitution occurs at position 214, the substituting amino acid is Asn, Gln, Pro or Ser;
l. when a substitution occurs at position 215, the substituting amino acid is Asn, Asp, Gln, Glu, Pro or Ser;
n. when a substitution occurs at position 219, the substituting amino acid is Asp or Glu; and
o. when a substitution occurs at position 223, the substituting amino acid is Asn, Asp, Gln, Glu, Pro or Ser;

whereby the Proteinase K variant has decreased adsorption to, and increased hydrolysis of, an insoluble substrate as compared to wild-type Proteinase K and wherein amino acid substitutions at proteinase K position 162 or proteinase K positions 95 and 96 or substitutions of aspartate, cysteine and glutamate at proteinase K position 209 or 211 are combined with at least one further substitution at a corresponding position selected from the proteinase K positions: 65, 66, 68, 70, 71, 105, 106, 137, 139, 140, 191, 193, 203 to 206, 208 to 215, 219 and 223.

2. The Proteinase K variant of claim 1, wherein the substitution occurs in the first loop region.

3. The Proteinase K variant of claim 1, wherein the substitution occurs in the second loop region.

4. The Proteinase K variant of claim 1, wherein the substitution occurs in the third loop region.

5. The Proteinase K variant of claim 1, wherein the substitution occurs in the fourth loop region.

6. The Proteinase K variant of claim 1, wherein the substitutions occurs in the fifth loop region.

7. The Proteinase K variant of claim 1, wherein the substitution occurs in the sixth loop region.

8. A Proteinase K variant having a modified amino acid sequence of the Proteinase K wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 50, 65, 66, 67, 68, 70 or 71; wherein
a. when a substitution occurs at position 64, the substituting amino acid is Asp or Glu;
b. when a substitution occurs at position 65, the substituting amino acid is Glu;
c. when a substitution occurs at position 66, the substituting amino acid is Asn, Asp, Gln, Glu, Pro or Ser;
d. when a substitution occurs at position 67, the substituting amino acid is Asp, Gln, Glu or Ser;
e. when a substitution occurs at position 68, the substituting amino acid is Asn, Asp, Gln, Glu, Pro or Ser;
f. when a substitution occurs at position 70, the substituting amino acid is Asn, Asp, Gln, Glu, Pro or Ser; and
g. when a substitution occurs at position 71, the substituting amino acid is Asn, Asp, Gln, Glu, Gly, Pro or Ser;

B. when a substitution occurs in the second loop region, the substitution occurs at one or more of positions 95, 96, 97, 98, 99, 100, 101, 102, 103, 104, 105, 106 or 107; wherein
a. when a substitution occurs at position 95, the substituting amino acid is Ala, Asn, Asp, Cys, Gln, Glu, Gly, His, Met, Pro, Ser or Thr;
b. when a substitution occurs at position 96, the substituting amino acid is Ala, Asn, Asp, Cys, Gln, Glu, Gly, His, Ile, Met, Pro, Ser, Thr or Val;
c. when a substitution occurs at position 97, the substituting amino acid is Glu; but when position 97 is substituted the variant is not a double, triple, quadruple, quintuple, sextuple, or septuple mutation variant having substitutions at positions selected from the group consisting of 104, 161, 162, 170, 192, and 220;
d. when a substitution occurs at position 98, the substituting amino acid is Glu; but when position 98 is substituted the variant is not a double, triple, quadruple, quintuple, or sextuple mutation variant having substitutions at positions selected from the group consisting of 104, 162, 170, 192, and 220;
e. when a substitution occurs at position 99, the substituting amino acid is Asp, Gln, Glu or Ser; but when position 99 is substituted the variant is not a double, triple, quadruple, quintuple, or sextuple mutation variant having substitutions at positions selected from the group consisting of 104, 162, 170, 192, and 220;
f. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 104, 162, 170, 192, and 220;
g. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 104, 162, 170, 192, and 220;
h. when a substitution occurs at position 102, the substituting amino acid is Asn, Asp, Gln, Glu, Pro or Ser; but when position 102 is substituted the variant is not a double, triple, quadruple, quintuple, or sextuple mutation variant having substitutions at positions selected from the group consisting of 104, 162, 170, 192, and 220;

i. when a substitution occurs at position 103, the substituting amino acid is Asn, Asp, Glu or Ser; but when position 103 is substituted the variant is not a double, triple, quadruple, quintuple, or sextuple mutation variant having substitutions at positions selected from the group consisting of 104, 162, 170, 192, and 220;

j. when a substitution occurs at position 104, the substituting amino acid is Ala, Asn, Asp, Cys, Gln, Glu, Gly, His, Ile, Leu, Met, Pro, Ser, Thr or Val;

k. when a substitution occurs at position 105, the substituting amino acid is Asp or Glu;

l. when a substitution occurs at position 106, the substituting amino acid is Asn, Asp, Gln, Glu, Gly, Pro or Ser; and m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, quintuple, sextuple, or septuple mutation variant having substitutions at positions selected from the group consisting of 104, 161, 162, 170, 192, and 220;

C. when a substitution occurs in the third loop region, the substitution occurs at one or more of positions 133, 134, 135, 122, 137, 138, 139 or 140; wherein a. when a substitution occurs at position 133, the substituting amino acid is Ala, Asn, Asp, Cys, Gln, Glu, Gly, His, Ile, Met, Pro, Ser, Thr or Val; but when position 133 is substituted the variant is not a double, triple, quadruple, quintuple, sextuple, or septuple mutation variant having substitutions at positions selected from the group consisting of 104, 161, 162, 170, 192, and 220;

b. when a substitution occurs at position 134, the substituting amino acid is Asn, Asp, Gln, Glu, Pro or Ser; but when position 134 is substituted the variant is not a double, triple, quadruple, quintuple, sextuple, or septuple mutation variant having substitutions at positions selected from the group consisting of 104, 161, 162, 170, 192, and 220;

c. when a substitution occurs at position 135, the substituting amino acid is Asn, Asp, Gln, Glu, Pro or Ser; but when position 135 is substituted the variant is not a double, triple, quadruple, quintuple, sextuple, or septuple mutation variant having substitutions at positions selected from the group consisting of 104, 161, 162, 170, 192, and 220;

d. when a substitution occurs at position 136, the substituting amino acid is Asn, Asp, Gln, Glu, Pro or Ser; but when position 136 is substituted the variant is not a double, triple, quadruple, quintuple, sextuple, or septuple mutation variant having substitutions at positions selected from the group consisting of 104, 161, 162, 170, 192, and 220;

e. when a substitution occurs at position 137, the substituting amino acid is Ala, Asn, Asp, Cys, Gln, Glu, Gly, His, Ile, Leu, Met, Pro, Ser, Thr or Val;

f. when a substitution occurs at position 138, the substituting amino acid is Asp or Glu;

g. when a substitution occurs at position 139, the substituting amino acid is Asp or Glu; and h. when a substitution occurs at position 140, the substituting amino acid is Asp or Glu;

D. when a substitution occurs in the fourth loop region, the substitution occurs at one or more of positions 160, 161, 162, 163, 150, 165, 166, 167, 168, 169 or 170; wherein a. when a substitution occurs at position 160, the substituting amino acid is Asn, Asp, Gln, Glu, Pro or Ser; but when position 160 is substituted the variant is not a double, triple, quadruple, quintuple, or sextuple mutation variant having substitutions at positions selected from the group consisting of 104, 162, 170, 192, and 220;

b. when a substitution occurs at position 161, the substituting amino acid is Asp, Gln, Glu or Ser;

c. when a substitution occurs at position 162, the substituting amino acid is Asp, Gln, Glu or Ser;

d. when a substitution occurs at position 163, the substituting amino acid is Asp, Gln, Glu or Ser; but when position 163 is substituted the variant is not a double, triple, quadruple, quintuple, or sextuple mutation variant having substitutions at positions selected from the group consisting of 104, 162, 170, 192, and 220;

e. when a substitution occurs at position 164, the substituting amino acid is Asn, Asp, Gln, Glu, Gly, His, Pro, Ser or Thr; but when position 164 is substituted the variant is not a double, triple, quadruple, quintuple, or sextuple mutation variant having substitutions at positions selected from the group consisting of 104, 162, 170, 192, and 220;

f. when a substitution occurs at position 165, the substituting amino acid is Glu; but when position 165 is substituted the variant is not a double, triple, quadruple, quintuple, or sextuple mutation variant having substitutions at positions selected from the group consisting of 104, 162, 170, 192, and 220;

g. when a substitution occurs at position 166, the substituting amino acid is Asn, Asp, Gln, Glu, Gly, His, Pro, Ser or Thr; but when position 166 is substituted the variant is not a double, triple, quadruple, quintuple, or sextuple mutation variant having substitutions at positions selected from the group consisting of 104, 162, 170, 192, and 220;

h. when a substitution occurs at position 167, the substituting amino acid is Asp or Glu; but when position 167 is substituted the variant is not a double, triple, quadruple, quintuple, or sextuple mutation variant having substitutions at positions selected from the group consisting of 104, 162, 170, 192, and 220;

i. when a substitution occurs at position 168, the substituting amino acid is Asp, Gln, Glu or Ser; but when position 168 is substituted the variant is not a double, triple, quadruple, quintuple, or sextuple mutation variant having substitutions at positions selected from the group consisting of 104, 162, 170, 192, and 220;

j. when a substitution occurs at position 169, the substituting amino acid is Ala, Asn, Asp, Cys, Gln, Glu, Gly, His, Ile, Leu, Met, Pro, Ser, Thr or Val; but when position 169 is substituted the variant is not a double, triple, quadruple, quintuple, or sextuple mutation variant having substitutions at positions selected from the group consisting of 104, 162, 170, 192, and 220; and k. when a substitution occurs at position 170, the substituting amino acid is Asp or Glu; but when position 170 is substituted the variant is not a double, triple, quadruple, or quintuple mutation variant having substitutions at positions selected from the group consisting of 104, 162, 192, and 220;

E. when a substitution occurs in the fifth loop region, the substitution occurs at one or more of positions 190, 191, 192, 193 or 194; wherein
   a. when a substitution occurs at position 190, the substituting amino acid is Asp or Glu;
   b. when a substitution occurs at position 191, the substituting amino acid is Asp or Giu;
   c. when a substitution occurs at position 192, the substituting amino acid is Ala, Asn, Asp, Cys, Gln, Glu, Gly, His, Ile, Leu, Met, Pro, Ser, Thr, Tyr or Val;
   d. when a substitution occurs at position 193, the substituting amino acid is Asp or Glu; and
   e. when a substitution occurs at position 194, the substituting amino acid is Asp, Gln, Glu or Ser; and F. when a substitution occurs in the sixth loop region, the substitution occurs at one or more of positions 203, 204, 205, 206, 207, 208, 209, 210, 260, 212, 213, 214, 215, 216, 217, 2143, 219, 220, 221, 222 or 223; wherein
   a. when a substitution occurs at position 203, the substituting amino acid is Asn, Asp, Gln, Glu, Pro or Ser;
   b. when a substitution occurs at position 204, the substituting amino acid is Asn, Asp, Gln, Glu, Gly or Ser;
   c. when a substitution occurs at position 205, the substituting amino acid is Asn, Asp, Gln, Glu, Pro or Ser;
   d. when a substitution occurs at position 206, the substituting amino acid is Asn, Asp, Gln, Glu, Gly, Pro or Ser;
   e. when a substitution occurs at position 207, the substituting amino acid is Asp or Glu;
   f. when a substitution occurs at position 208, the substituting amino acid is Ala, Asn, Asp, Cys, Gln, Glu, Gly, His, Leu, Met, Pro, Ser, Thr or Val;
   g. when a substitution occurs at position 209, the substituting amino acid is Ala, Asn, Asp, Cys, Gln, Glu, Gly, His, Ile, Met, Pro, Ser, Thr or Val;
   h. when a substitution occurs at position 210, the substituting amino acid is Asp or Glu;
   i. when a substitution occurs at position 211, the substituting amino acid is Asn, Asp, Gln, Glu, Gly, Pro or Ser;
   j. when a substitution occurs at position 212, the substituting amino acid is Ala, Asn, Asp, Cys, Gln, Glu, Gly, His, Ile, Leu, Met, Phe, Pro, Ser, Thr, Tyr or Val;
   k. when a substitution occurs at position 213, the substituting amino acid is Ala, Asn, Asp, Cys, Gln, Giu, Gly, His, Leu, Met, Pro, Ser, Thr or Val;
   l. when a substitution occurs at position 214, the substituting amino acid is Asn, Asp, Gln, Glu, Pro or Ser;
   m. when a substitution occurs at position 215, the substituting amino acid is Asn, Asp, Gln, Glu, Pro or Ser;
   n. when a substitution occurs at position 216, the substituting amino acid is Asp or Glu; but when position 216 is substituted the variant is not a double, triple, quadruple, quintuple, sextuple, or septuple mutation variant having substitutions at positions selected from the group consisting of 104, 161, 162, 170, 192, and 220;
   o. when a substitution occurs at position 217, the substituting amino acid is Asn, Asp, Gln, Glu, Gly, Pro or Ser; but when position 217 is substituted the variant is not a double, triple, quadruple, quintuple, sextuple, or septuple mutation variant having substitutions at positions selected from the group consisting of 104, 161, 162, 170, 192, and 220;
   p. when a substitution occurs at position 218, the substituting amino acid is Asp or Glu; but when position 218 is substituted the variant is not a double, triple, quadruple, quintuple, sextuple, or septuple mutation variant having substitutions at positions selected from the group consisting of 104, 161, 162, 170, 192, and 220;
   q. when a substitution occurs at position 219, the substituting amino acid is Asp or Glu;
   r. when a substitution occurs at position 220, the substituting amino acid is Ala, Asn, Asp, Cys, Gln, Glu, Gly, His, Leu, Met, Pro, Ser, Thr or Val;
   s. when a substitution occurs at position 221, the substituting amino acid is Asp or Glu;
   t. when a substitution occurs at position 222, the substituting amino acid is Asn, Asp, Gln, Glu, Pro or Ser; and
   u. when a substitution occurs at position 223, the substituting amino acid is Asn, Asp, Gln, Glu, Gly, Pro or Ser;

whereby the Proteinase K variant has decreased adsorption to, and increased hydrolysis of, an insoluble substrate as compared to wild-type Proteinase K and wherein glutamate and aspartate substitutions at positions 67 and 169 are combined with at least one further substitution at a proteinase K position selected from: 65, 66, 68, 70, 71, 105, 106,137, 139, 140, 191, 193, 203 to 206, 208 to 215, 219, 223.

9. The Proteinase K variant of claim 8, wherein two or more substitutions occur in the first loop region.

10. The Proteinase K variant of claim 8, wherein two or more substitutions occur in the second loop region.

11. The Proteinase K variant of claim 8, wherein two or more substitutions occur in the third loop region.

12. The Proteinase K variant of claim 8, wherein two or more substitutions occur in the fourth loop region.

13. The Proteinase K variant of claim 8, wherein two or more substitutions occur in the fifth loop region.

14. The Proteinase K variant of claim 8, wherein two or more substitutions occur in the sixth loop region.

15. Proteinase K variant having a modified amino acid sequence of the Proteinase K wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
   A. when a substitution occurs in the first loop region, the substitution occurs at one or more of positions 50, 65, 66, 68, 70 or 71; wherein
      a. when a substitution occurs at position 64, the substituting amino acid is Asp or Glu;
      b. when a substitution occurs at position 65, the substituting amino acid is Glu;
      c. when a substitution occurs at position 66, the substituting amino acid is Asn, Asp, Gln, Glu, Pro or Ser;
      d. when a substitution occurs at position 68, the substituting amino acid is Asn, Asp, Gln, Glu, Pro or Ser;

e. when a substitution occurs at position 70, the substituting amino acid is Asn, Asp, Gln, Glu, Pro or Ser; and f. when a substitution occurs at position 71, the substituting amino acid is Asn, Asp, Gln, Glu, Pro or Ser;

B. when a substitution occurs in the second loop region, the substitution occurs at one or more of positions 95, 96, 97, 98, 99, 100, 101, 102, 103, 104, 105, 106 or 107; wherein a. when a substitution occurs at position 95, the substituting amino acid is Ala, Asn, Asp, Cys, Gln, Glu, Gly, His, Met, Pro, Ser or Thr;

b. when a substitution occurs at position 96, the substituting amino acid is Ala, Asn, Asp, Cys, Gln, Glu, Gly, His, Ile, Met, Pro, Ser, Thr or Val;

c. when a substitution occurs at position 97, the substituting amino acid is Glu; but when position 97 is substituted the variant is not a double, triple, quadruple, quintuple, sextuple, or septuple mutation variant having substitutions at positions selected from the group consisting of 104, 161, 162, 170, 192, and 220;

d. when a substitution occurs at position 98, the substituting amino acid is Glu; but when position 98 is substituted the variant is not a double, triple, quadruple, quintuple, or sextuple mutation variant having substitutions at positions selected from the group consisting of 104, 162, 170, 192, and 220;

e. when a substitution occurs at position 99, the substituting amino acid is Asp, Gln, Glu or Ser; but when position 99 is substituted the variant is not a double, triple, quadruple, quintuple, or sextuple mutation variant having substitutions at positions selected from the group consisting of 104, 162, 170, 192, and 220;

f. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 104, 162, 170, 192, and 220;

g. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 104, 162, 170, 192, and 220;

h. when a substitution occurs at position 102, the substituting amino acid is Asn, Asp, Gln, Glu, Pro or Ser; but when position 102 is substituted the variant is not a double, triple, quadruple, quintuple, or sextuple mutation variant having substitutions at positions selected from the group consisting of 104, 162, 170, 192, and 220;

i. when a substitution occurs at position 103, the substituting amino acid is Asn, Asp, Glu or Ser; but when position 103 is substituted the variant is not a double, triple, quadruple, quintuple, or sextuple mutation variant having substitutions at positions selected from the group consisting of 104, 162, 170, 192, and 220;

j. when a substitution occurs at position 104, the substituting amino acid is Ala, Asn, Asp, Cys, Gln, Glu, Gly, His, Ile, Leu, Met, Pro, Ser, Thr or Val;

k. when a substitution occurs at position 105, the substituting amino acid is Asp or Glu;

l. when a substitution occurs at position 106, the substituting amino acid is Asn, Asp, Gln, Glu, Gly, Pro or Ser; and m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, quintuple, sextuple, or septuple mutation variant having substitutions at positions selected from the group consisting of 104, 161, 162, 170, 192, and 220;

C. when a substitution occurs in the third loop region, the substitution occurs at one or more of positions 133, 134, 135, 122, 137, 138, 139 or 140; wherein a. when a substitution occurs at position 133, the substituting amino acid is Ala, Asn, Asp, Cys, Gln, Glu, Gly, His, Ile, Met, Pro, Ser, Thr or Val; but when position 133 is substituted the variant is not a double, triple, quadruple, quintuple, sextuple, or septuple mutation variant having substitutions at positions selected from the group consisting of 104, 161, 162, 170, 192, and 220;

b. when a substitution occurs at position 134, the substituting amino acid is Asn, Asp, Gln, Glu, Pro or Ser; but when position 134 is substituted the variant is not a double, triple, quadruple, quintuple, sextuple, or septuple mutation variant having substitutions at positions selected from the group consisting of 104, 161, 162, 170, 192, and 220;

c. when a substitution occurs at position 135, the substituting amino acid is Asn, Asp, Gln, Glu, Pro or Ser; but when position 135 is substituted the variant is not a double, triple, quadruple, quintuple, sextuple, or septuple mutation variant having substitutions at positions selected from the group consisting of 104, 161, 162, 170, 192, and 220;

d. when a substitution occurs at position 136, the substituting amino acid is Asn, Asp, Gln, Glu, Pro or Ser; but when position 136 is substituted the variant is not a double, triple, quadruple, quintuple, sextuple, or septuple mutation variant having substitutions at positions selected from the group consisting of 104, 161, 162, 170, 192, and 220;

e. when a substitution occurs at position 137, the substituting amino acid is Ala, Asn, Asp, Cys, Gln, Glu, Gly, His, Ile, Leu, Met, Pro, Ser, Thr or Val;

f. when a substitution occurs at position 138, the substituting amino acid is Asp or Glu;

g. when a substitution occurs at position 139, the substituting amino acid is Asp or Glu; and h. when a substitution occurs at position 140, the substituting amino acid is Asp or Glu;

D. when a substitution occurs in the fourth loop region, the substitution occurs at one or more of positions 160, 161, 162, 163, 150, 165, 166, 167, 168, 169 or 170; wherein a. when a substitution occurs at position 160, the substituting amino acid is Asn, Asp, Gln, Glu, Pro or Ser; but when position 160 is substituted the variant is not a double, triple, quadruple, quintuple, or sextuple mutation variant having substitutions at positions selected from the group consisting of 104, 162, 170, 192, and 220;

b. when a substitution occurs at position 161, the substituting amino acid is Asp, Gln, Glu or Ser;

c. when a substitution occurs at position 162, the substituting amino acid is Asp, Gln, Glu or Ser;
d. when a substitution occurs at position 163, the substituting amino acid is Asp, Gln, Glu or Ser; but when position 163 is substituted the variant is not a double, triple, quadruple, quintuple, or sextuple mutation variant having substitutions at positions selected from the group consisting of 104, 162, 170, 192, and 220;
e. when a substitution occurs at position 164, the substituting amino acid is Asn, Asp, Gln, Glu, Gly, His, Pro, Ser or Thr; but when position 164 is substituted the variant is not a double, triple, quadruple, quintuple, or sextuple mutation variant having substitutions at positions selected from the group consisting of 104, 162, 170, 192, and 220;
f. when a substitution occurs at position 165, the substituting amino acid is Glu; but when position 165 is substituted the variant is not a double, triple, quadruple, quintuple, or sextuple mutation variant having substitutions at positions selected from the group consisting of 104, 162, 170, 192, and 220;
g. when a substitution occurs at position 166, the substituting amino acid is Asn, Asp, Gln, Glu, Gly, His, Pro, Ser or Thr; but when position 166 is substituted the variant is not a double, triple, quadruple, quintuple, or sextuple mutation variant having substitutions at positions selected from the group consisting of 104, 162, 170, 192, and 220;
h. when a substitution occurs at position 167, the substituting amino acid is Asp or Glu; but when position 167 is substituted the variant is not a double, triple, quadruple, quintuple, or sextuple mutation variant having substitutions at positions selected from the group consisting of 104, 162, 170, 192, and 220;
i. when a substitution occurs at position 168, the substituting amino acid is Asp, Gln, Glu or Ser; but when position 168 is substituted the variant is not a double, triple, quadruple, quintuple, or sextuple mutation variant having substitutions at positions selected from the group consisting of 104, 162, 170, 192, and 220;
j. when a substitution occurs at position 169, the substituting amino acid is Ala, Asn, Asp, Cys, Gln, Glu, Gly, His, Ile, Leu, Met, Pro, Ser, Thr or Val; but when position 169 is substituted the variant is not a double, triple, quadruple, quintuple, or sextuple mutation variant having substitutions at positions selected from the group consisting of 104, 162, 170, 192, and 220; and
k. when a substitution occurs at position 170, the substituting amino acid is Asp or Glu; but when position 170 is substituted the variant is not a double, triple, quadruple, or quintuple mutation variant having substitutions at positions selected from the group consisting of 104, 162, 192, and 220;
E. when a substitution occurs in the fifth loop region, the substitution occurs at one or more of positions 190, 191, 192, 193 or 194; wherein
a. when a substitution occurs at position 190, the substituting amino acid is Asp or Glu;
b. when a substitution occurs at position 191, the substituting amino acid is Asp or Glu;
c. when a substitution occurs at position 192, the substituting amino acid is Ala, Asn, Asp, Cys, Gln, Glu, Gly, His, Ile, Leu, Met, Pro, Ser, Thr, Tyr or Val;
d. when a substitution occurs at position 193, the substituting amino acid is Asp or Glu; and
e. when a substitution occurs at position 194, the substituting amino acid is Asp, Gln, Glu or Ser; and
F. when a substitution occurs in the sixth loop region, the substitution occurs at one or more of positions 203, 204, 205, 206, 207, 208, 209, 210, 260, 212, 213, 214, 215, 216, 217, 218, 219, 220, 221, 222 or 223; wherein
a. when a substitution occurs at position 203, the substituting amino acid is Asn, Asp, Gln, Glu, Pro or Ser;
b. when a substitution occurs at position 204, the substituting amino acid is Asn, Asp, Gln, Glu, Gly or Ser;
c. when a substitution occurs at position 205, the substituting amino acid is Asn, Asp, Gln, Glu, Pro or Ser;
d. when a substitution occurs at position 206, the substituting amino acid is Asn, Asp, Gln, Glu, Gly, Pro or Ser;
e. when a substitution occurs at position 207, the substituting amino acid is Asp or Glu;
f. when a substitution occurs at position 208, the substituting amino acid is Ala, Asn, Asp, Cys, Gln, Glu, Gly, His, Leu, Met, Pro, Ser, Thr or Val;
g. when a substitution occurs at position 209, the substituting amino acid is Ala, Asn, Asp, Cys, Gln, Glu, Gly, His, Ile, Met, Pro, Ser, Thr or Val;
h. when a substitution occurs at position 210, the substituting amino acid is Asp or Glu;
i. when a substitution occurs at position 211, the substituting amino acid is Asn, Asp, Gln, Glu, Gly, Pro or Ser;
j. when a substitution occurs at position 212, the substituting amino acid is Ala, Asn, Asp, Cys, Gln, Glu, Gly, His, Ile, Leu, Met, Phe, Pro, Ser, Thr, Tyr or Val;
k. when a substitution occurs at position 213, the substituting amino acid is Ala, Asn, Asp, Cys, Gln, Glu, Gly, His, Leu, Met, Pro, Ser, Thr or Val;
l. when a substitution occurs at position 214, the substituting amino acid is Asn, Asp, Gln, Glu, Pro or Ser;
m. when a substitution occurs at position 215, the substituting amino acid is Asn, Asp, Gln, Glu, Pro or Ser;
n. when a substitution occurs at position 216, the substituting amino acid is Asp or Glu; but when position 216 is substituted the variant is not a double, triple, quadruple, quintuple, sextuple, or septuple mutation variant having substitutions at positions selected from the group consisting of 104, 161, 162, 170, 192, and 220;
o. when a substitution occurs at position 217, the substituting amino acid is Asn, Asp, Gln, Glu, Gly, Pro or Ser; but when position 217 is substituted the variant is not a double, triple, quadruple, quintuple, sextuple, or septuple mutation variant having substitutions at positions selected from the group consisting of 104, 161, 162, 170, 192, and 220;
p. when a substitution occurs at position 218, the substituting amino acid is Asp or Glu; but when position 218 is substituted the variant is not a double, triple, quadruple, quintuple, sextuple, or septuple mutation variant having substitutions at positions selected from the group consisting of 104, 161, 162, 170, 192, and 220;

q. when a substitution occurs at position 219, the substituting amino acid is Asp or Glu;
r. when a substitution occurs at position 220, the substituting amino acid is Ala, Asn, Asp, Cys, Gln, Glu, Gly, His, Leu, Met, Pro, Ser, Thr or Val;
s. when a substitution occurs at position 221, the substituting amino acid is Asp or Glu;
t. when a substitution occurs at position 222, the substituting amino acid is Asn, Asp, Gln, Glu, Pro or Ser; and
u. when a substitution occurs at position 223, the substituting amino acid is Asn, Asp, Gln, Glu, Gly, Pro or Ser;

whereby the Proteinase K variant has decreased adsorption to, and increased hydrolysis of, an insoluble substrate as compared to wild-type Proteinase K.

16. The Proteinase K variant of claim 15, wherein two or more substitutions occur in the first loop region.

17. The Proteinase K variant of claim 15, wherein two or more substitutions occur in the second loop region.

18. The Proteinase K variant of claim 15, wherein two or more substitutions occur in the third loop region.

19. The Proteinase K variant of claim 15, wherein two or more substitutions occur in the fourth loop region.

20. The Proteinase K variant of claim 15, wherein two or more substitutions occur in the fifth loop region.

21. The Proteinase K variant of claim 15, wherein two or more substitutions occur in the sixth loop region.

22. A Proteinase K variant having a modified amino acid sequence of the Proteinase K wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 50, 65, 66, 67, 68, 70 or 71; wherein
   a. when a substitution occurs at position 64, the substituting amino acid is Asp or Glu;
   b. when a substitution occurs at position 65, the substituting amino acid is Glu;
   c. when a substitution occurs at position 66, the substituting amino acid is Asn, Asp, Gln, Glu, Pro or Ser;
   d. when a substitution occurs at position 67, the substituting amino acid is Asp, Gln, Glu or Ser;
   e. when a substitution occurs at position 68, the substituting amino acid is Asn, Asp, Gln, Glu, Pro or Ser;
   f. when a substitution occurs at position 70, the substituting amino acid is Asn, Asp, Gln, Glu, Pro or Ser; and
   g. when a substitution occurs at position 71, the substituting amino acid is Asn, Asp, Gln, Glu, Gly, Pro or Ser;

B. when a substitution occurs in the second loop region, the substitution occurs at one or more of positions 95, 96, 97, 98, 100, 102, 103, 104, 106 or 107; wherein
   a. when a substitution occurs at position 95, the substituting amino acid is Ala, Asn, Asp, Cys, Gln, Glu, Gly, His, Met, Pro, Ser or Thr;
   b. when a substitution occurs at position 96, the substituting amino acid is Ala, Asn, Asp, Cys, Gln, Glu, Gly, His, Ile, Met, Pro, Ser, Thr or Val;
   c. when a substitution occurs at position 97, the substituting amino acid is Glu; but when position 97 is substituted the variant is not a double, triple, quadruple, quintuple, sextuple, or septuple mutation variant having substitutions at positions selected from the group consisting of 104, 161, 162, 170, 192, and 220;
   d. when a substitution occurs at position 98, the substituting amino acid is Glu; but when position 98 is substituted the variant is not a double, triple, quadruple, quintuple, or sextuple mutation variant having substitutions at positions selected from the group consisting of 104, 162, 170, 192, and 220;
   e. when a substitution occurs at position 100, the substituting amino acid is Asn, Gln, Pro or Ser; but when position 100 is substituted the variant is not a double, triple, quadruple, quintuple, or sextuple mutation variant having substitutions at positions selected from the group consisting of 104, 162, 170, 192, and 220;
   f. when a substitution occurs at position 102, the substituting amino acid is Asn, Gln, Glu, Pro or Ser; but when position 102 is substituted the variant is not a double, triple, quadruple, quintuple, or sextuple mutation variant having substitutions at positions selected from the group consisting of 104, 162, 170, 192, and 220;
   g. when a substitution occurs at position 103, the substituting amino acid is Asn or Ser; but when position 103 is substituted the variant is not a double, triple, quadruple, quintuple, or sextuple mutation variant having substitutions at positions selected from the group consisting of 104, 162, 170, 192, and 220;
   h. when a substitution occurs at position 104, the substituting amino acid is Asp, His, Ile, Leu, Met, Pro or Val;
   i. when a substitution occurs at position 106, the substituting amino acid is Asn, Gln, Gly, Pro or Ser; and
   j. when a substitution occurs at position 107, the substituting amino acid is Ala, Asn, Cys, Gln, Gly, His, Leu, Met, Pro, Ser, Thr or Val; but when position 107 is substituted the variant is not a double, triple, quadruple, quintuple, sextuple, or septuple mutation variant having substitutions at positions selected from the group consisting of 104, 161, 162, 170, 192, and 220;

C. when a substitution occurs in the third loop region, the substitution occurs at one or more of positions 133, 134, 135, 136, 137, 138, 139 or 140; wherein
   a. when a substitution occurs at position 133, the substituting amino acid is Ala, Asn, Asp, Cys, Gln, Glu, Gly, His, Ile, Met, Pro, Ser, Thr or Val; but when position 133 is substituted the variant is not a double, triple, quadruple, quintuple, sextuple, or septuple mutation variant having substitutions at positions selected from the group consisting of 104, 161, 162, 170, 192, and 220;
   b. when a substitution occurs at position 134, the substituting amino acid is Asn, Asp, Gln, Glu, Pro or Ser; but when position 134 is substituted the variant is not a double, triple, quadruple, quintuple, sextuple, or septuple mutation variant having substitutions at positions selected from the group consisting of 104, 161, 162, 170, 192, and 220;
   c. when a substitution occurs at position 135, the substituting amino acid is Asn, Asp, Gln, Glu, Pro or Ser; but when position 135 is substituted the variant is not a double, triple, quadruple, quintuple, sextuple, or septuple mutation variant having substitutions at positions selected from the group consisting of 104, 161, 162, 170, 192, and 220;
  d. when a substitution occurs at position 136, the substituting amino acid is Asn, Asp, Gln, Glu, Pro or Ser; but when position 136 is substituted the variant is not a double, triple, quadruple, quintuple, sextuple, or septuple mutation variant having substitutions at positions selected from the group consisting of 104, 161, 162, 170, 192, and 220;
  e. when a substitution occurs at position 137, the substituting amino acid is Ala, Asn, Asp, Cys, Gln, Glu, Gly, His, Ile, Leu, Met, Pro, Ser, Thr or Val;
  f. when a substitution occurs at position 138, the substituting amino acid is Asp or Glu;
  g. when a substitution occurs at position 139, the substituting amino acid is Asp or Glu; and
  h. when a substitution occurs at position 140, the substituting amino acid is Asp or Glu;
D. when a substitution occurs in the fourth loop region, the substitution occurs at one or more of positions 160, 161, 162, 163, 150, 165, 166, 167, 168, 169 or 170; wherein
  a. when a substitution occurs at position 160, the substituting amino acid is Asn, Asp, Gln, Glu, Pro or Ser; but when position 160 is substituted the variant is not a double, triple, quadruple, quintuple, or sextuple mutation variant having substitutions at positions selected from the group consisting of 104, 162, 170, 192, and 220;
  b. when a substitution occurs at position 161, the substituting amino acid is Asp, Gln, Glu or Ser;
  c. when a substitution occurs at position 162, the substituting amino acid is Asp, Gln, Glu or Ser;
  d. when a substitution occurs at position 163, the substituting amino acid is Asp, Gln, Glu or Ser; but when position 163 is substituted the variant is not a double, triple, quadruple, quintuple, or sextuple mutation variant having substitutions at positions selected from the group consisting of 104, 162, 170, 192, and 220;
  e. when a substitution occurs at position 164, the substituting amino acid is Asn, Asp, Gln, Glu, Gly, His, Pro, Ser or Thr; but when position 164 is substituted the variant is not a double, triple, quadruple, quintuple, or sextuple mutation variant having substitutions at positions selected from the group consisting of 104, 162, 170, 192, and 220;
  f. when a substitution occurs at position 165, the substituting amino acid is Glu; but when position 165 is substituted the variant is not a double, triple, quadruple, quintuple, or sextuple mutation variant having substitutions at positions selected from the group consisting of 104, 162, 170, 192, and 220;
  g. when a substitution occurs at position 166, the substituting amino acid is Asn, Asp, Gln, Glu, Gly, His, Pro, Ser or Thr; but when position 166 is substituted the variant is not a double, triple, quadruple, quintuple, or sextuple mutation variant having substitutions at positions selected from the group consisting of 104, 162, 170, 192, and 220;
  h. when a substitution occurs at position 167, the substituting amino acid is Asp or Glu; but when position 167 is substituted the variant is not a double, triple, quadruple, quintuple, or sextuple mutation variant having substitutions at positions selected from the group consisting of 104, 162, 170, 192, and 220;
  i. when a substitution occurs at position 168, the substituting amino acid is Asp, Gln, Glu or Ser; but when position 168 is substituted the variant is not a double, triple, quadruple, quintuple, or sextuple mutation variant having substitutions at positions selected from the group consisting of 104, 162, 170, 192, and 220;
  j. when a substitution occurs at position 169, the substituting amino acid is Ala, Asn, Asp, Cys, Gln, Glu, Gly, His, Ile, Leu, Met, Pro, Ser, Thr or Val; but when position 169 is substituted the variant is not a double, triple, quadruple, quintuple, or sextuple mutation variant having substitutions at positions selected from the group consisting of 104, 162, 170, 192, and 220; and
  k. when a substitution occurs at position 170, the substituting amino acid is Asp or Glu; but when position 170 is substituted the variant is not a double, triple, quadruple, or quintuple mutation variant having substitutions at positions selected from the group consisting of 104, 162, 192, and 220;
E. when a substitution occurs in the fifth loop region, the substitution occurs at one or more of positions 190, 191, 192, 193 or 194; wherein
  a. when a substitution occurs at position 190, the substituting amino acid is Asp or Glu;
  b. when a substitution occurs at position 191, the substituting amino acid is Asp or Glu;
  c. when a substitution occurs at position 192, the substituting amino acid is Ala, Asn, Asp, Cys, Gln, Glu, Gly, His, Ile, Leu, Met, Pro, Ser, Thr, Tyr or Val;
  d. when a substitution occurs at position 193, the substituting amino acid is Asp or Glu; and
  e. when a substitution occurs at position 194, the substituting amino acid is Asp, Gln, Glu or Ser; and
F. when a substitution occurs in the sixth loop region, the substitution occurs at one or more of positions 203, 204, 205, 206, 207, 208, 209, 210, 260, 212, 213, 214, 215, 216, 217, 218, 219, 220, 221, 222 or 223; wherein
  a. when a substitution occurs at position 203, the substituting amino acid is Asn, Asp, Gln, Glu, Pro or Ser;
  b. when a substitution occurs at position 204, the substituting amino acid is Asn, Asp, Gln, Glu, Gly or Ser;
  c. when a substitution occurs at position 205, the substituting amino acid is Asn, Asp, Gln, Glu, Pro or Ser;
  d. when a substitution occurs at position 206, the substituting amino acid is Asn, Asp, Gln, Glu, Gly, Pro or Ser;
  e. when a substitution occurs at position 207, the substituting amino acid is Asp or Glu;
  f. when a substitution occurs at position 208, the substituting amino acid is Ala, Asn, Asp, Cys, Gln, Glu, Gly, His, Leu, Met, Pro, Ser, Thr or Val;
  g. when a substitution occurs at position 209, the substituting amino acid is Ala, Asn, Asp, Cys, Gln, Glu, Gly, His, Ile, Met, Pro, Ser, Thr or Val;
  h. when a substitution occurs at position 210, the substituting amino acid is Asp or Glu;
  i. when a substitution occurs at position 211, the substituting amino acid is Asn, Asp, Gln, Glu, Gly, Pro or Ser;
  j. when a substitution occurs at position 212, the substituting amino acid is Ala, Asn, Asp, Cys, Gln, Glu, Gly, His, Ile, Leu, Met, Phe, Pro, Ser, Thr, Tyr or Val;

k. when a substitution occurs at position 213, the substituting amino acid is Ala, Asn, Asp, Cys, Gln, Glu, Gly, His, Leu, Met, Pro, Ser, Thr or Val;

l. when a substitution occurs at position 214, the substituting amino acid is Asn, Asp, Gln, Glu, Pro or Ser;

m. when a substitution occurs at position 215, the substituting amino acid is Asn, Asp, Gln, Glu, Pro or Ser;

n. when a substitution occurs at position 216, the substituting amino acid is Asp or Glu; but when position 216 is substituted the variant is not a double, triple, quadruple, quintuple, sextuple, or septuple mutation variant having substitutions at positions selected from the group consisting of 104, 161, 162, 170, 192, and 220;

o. when a substitution occurs at position 217, the substituting amino acid is Asn, Asp, Gln, Glu, Gly, Pro or Ser; but when position 217 is substituted the variant is not a double, triple, quadruple, quintuple, sextuple, or septuple mutation variant having substitutions at positions selected from the group consisting of 104, 161, 162, 170, 192, and 220;

p. when a substitution occurs at position 218, the substituting amino acid is Asp or Glu; but when position 218 is substituted the variant is not a double, triple, quadruple, quintuple, sextuple, or septuple mutation variant having substitutions at positions selected from the group consisting of 104, 161, 162, 170, 192, and 220;

q. when a substitution occurs at position 219, the substituting amino acid is Asp or Glu;

r. when a substitution occurs at position 220, the substituting amino acid is Ala, Asn, Asp, Cys, Gln, Glu, Gly, His, Leu, Met, Pro, Ser, Thr or Val;

s. when a substitution occurs at position 221, the substituting amino acid is Asp or Glu;

t. when a substitution occurs at position 222, the substituting amino acid is Asn, Asp, Gln, Glu, Pro or Ser; and u. when a substitution occurs at position 223, the substituting amino acid is Asn, Asp, Gln, Glu, Gly, Pro or Ser;

whereby the Proteinase K variant has decreased adsorption to, and increased hydrolysis of, an insoluble substrate as compared to wild-type Proteinase K and wherein glutamate and asparate substitutions at positions 67 and 169 are combined with at least one further substitution at a proteinase K position selected from: 65, 66, 68, 70, 71, 105, 106, 137, 139, 140, 191, 193, 203 to 206, 208 to 215, 219, 223.

23. The Proteinase K variant of claim 22, wherein two or more substitutions occur in the first loop region.

24. The Proteinase K variant of claim 22, wherein two or more substitutions occur in the second loop region.

25. The Proteinase K variant of claim 22, wherein two or more substitutions occur in the third loop region.

26. The Proteinase K variant of claim 22, wherein two or more substitutions occur in the fourth loop region.

27. The Proteinase K variant of claim 22, wherein two or more substitutions occur in the fifth loop region.

28. The Proteinase K variant of claim 22, wherein two or more substitutions occur in the sixth loop region.

29. A Proteinase K variant having a modified amino acid sequence of the Proteinase K wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 50, 65, 66, 67, 68, 70 or 71; wherein a. when a substitution occurs at position 64, the substituting amino acid is Asp or Glu;

b. when a substitution occurs at position 65, the substituting amino acid is Glu;

c. when a substitution occurs at position 66, the substituting amino acid is Asn, Asp, Gln, Glu, Pro or Ser;

d. when a substitution occurs at position 67, the substituting amino acid is Asp, Gln, Glu or Ser;

e. when a substitution occurs at position 68, the substituting amino acid is Asn, Asp, Gln, Glu, Pro or Ser;

f. when a substitution occurs at position 70, the substituting amino acid is Asn, Asp, Gln, Glu, Pro or Ser; and g. when a substitution occurs at position 71, the substituting amino acid is Asn, Asp, Gln, Glu, Gly, Pro or Ser;

B. when a substitution occurs in the second loop region, the substitution occurs at one or more of positions 95, 96, 97, 98, 99, 100, 101, 102, 103, 104, 105, 106 or 107; wherein a. when a substitution occurs at position 95, the substituting amino acid is Ala, Asn, Asp, Cys, Gln, Glu, Gly, His, Met, Pro, Ser or Thr;

b. when a substitution occurs at position 96, the substituting amino acid is Ala, Asn, Asp, Cys, Gln, Glu, Gly, His, Ile, Met, Pro, Ser, Thr or Val;

c. when a substitution occurs at position 97, the substituting amino acid is Glu; but when position 97 is substituted the variant is not a double, triple, quadruple, quintuple, sextuple, or septuple mutation variant having substitutions at positions selected from the group consisting of 104, 161, 162, 170, 192, and 220;

d. when a substitution occurs at position 98, the substituting amino acid is Glu; but when position 98 is substituted the variant is not a double, triple, quadruple, quintuple, or sextuple mutation variant having substitutions at positions selected from the group consisting of 104, 162, 170, 192, and 220;

e. when a substitution occurs at position 99, the substituting amino acid is Asp, Gln, Glu or Ser; but when position 99 is substituted the variant is not a double, triple, quadruple, quintuple, or sextuple mutation variant having substitutions at positions selected from the group consisting of 104, 162, 170, 192, and 220;

f. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 104, 162, 170, 192, and 220;

g. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 104, 162, 170, 192, and 220;

h. when a substitution occurs at position 102, the substituting amino acid is Asn, Asp, Gln, Glu, Pro or Ser; but when position 102 is substituted the variant is not a double, triple, quadruple, quintuple, or sextuple mutation variant having substitutions at positions selected from the group consisting of 104, 162, 170, 192, and 220;

i. when a substitution occurs at position 103, the substituting amino acid is Asn, Asp, Glu or Ser; but when position 103 is substituted the variant is not a double, triple, quadruple, quintuple, or sextuple mutation variant having substitutions at positions selected from the group consisting of 104, 162, 170, 192, and 220;

when a substitution occurs at position 104, the substituting amino acid is Ala, Asn, Asp, Cys, Gln, Glu, Gly, His, Ile, Leu, Met, Pro, Ser, Thr or Val;

k. when a substitution occurs at position 105, the substituting amino acid is Asp or Glu;

l. when a substitution occurs at position 106, the substituting amino acid is Asn, Asp, Gln, Glu, Gly, Pro or Ser; and m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, quintuple, sextuple, or septuple mutation variant having substitutions at positions selected from the group consisting of 104, 161, 162, 170, 192, and 220;

C. when a substitution occurs in the third loop region, the substitution occurs at one or more of positions 133, 134, 136, 137, 138, 139 or 140; wherein a. when a substitution occurs at position 133, the substituting amino acid is Ala, Asn, Cys, Gln, Gly, His, Met, Pro, Ser, Thr or Val; but when position 133 is substituted the variant is not a double, triple, quadruple, quintuple, sextuple, or septuple mutation variant having substitutions at positions selected from the group consisting of 104, 161, 162, 170, 192, and 220;

b. when a substitution occurs at position 134, the substituting amino acid is Asn, Asp, Gln, Glu, Pro or Ser; but when position 134 is substituted the variant is not a double, triple, quadruple, quintuple, sextuple, or septuple mutation variant having substitutions at positions selected from the group consisting of 104, 161, 162, 170, 192, and 220;

c. when a substitution occurs at position 136, the substituting amino acid is Asn, Asp, Gln, Glu, Pro or Ser;

d. when a substitution occurs at position 137, the substituting amino acid is Asp, His, Ile, Leu, Met or Pro;

e. when a substitution occurs at position 138, the substituting amino acid is Asp or Glu;

f. when a substitution occurs at position 139, the substituting amino acid is Asp or Glu; and g. when a substitution occurs at position 140, the substituting amino acid is Asp or Glu;

D. when a substitution occurs in the fourth loop region, the substitution occurs at one or more of positions 160, 161, 162, 163, 164, 165, 166, 167, 168, 169 or 170; wherein a. when a substitution occurs at position 160, the substituting amino acid is Asn, Asp, Gln, Glu, Pro or Ser; but when position 160 is substituted the variant is not a double, triple, quadruple, quintuple, or sextuple mutation variant having substitutions at positions selected from the group consisting of 104, 162, 170, 192, and 220;

b. when a substitution occurs at position 161, the substituting amino acid is Asp, Gln, Glu or Ser;

c. when a substitution occurs at position 162, the substituting amino acid is Asp, Gln, Glu or Ser;

d. when a substitution occurs at position 163, the substituting amino acid is Asp, Gln, Glu or Ser; but when position 163 is substituted the variant is not a double, triple, quadruple, quintuple, or sextuple mutation variant having substitutions at positions selected from the group consisting of 104, 162, 170, 192, and 220;

e. when a substitution occurs at position 164, the substituting amino acid is Asn, Asp, Gln, Glu, Gly, His, Pro, Ser or Thr; but when position 164 is substituted the variant is not a double, triple, quadruple, quintuple, or sextuple mutation variant having substitutions at positions selected from the group consisting of 104, 162, 170, 192, and 220;

f. when a substitution occurs at position 165, the substituting amino acid is Glu; but when position 165 is substituted the variant is not a double, triple, quadruple, quintuple, or sextuple mutation variant having substitutions at positions selected from the group consisting of 104, 162, 170, 192, and 220;

g. when a substitution occurs at position 166, the substituting amino acid is Asn, Asp, Gln, Glu, Gly, His, Pro, Ser or Thr; but when position 166 is substituted the variant is not a double, triple, quadruple, quintuple, or sextuple mutation variant having substitutions at positions selected from the group consisting of 104, 162, 170, 192, and 220;

h. when a substitution occurs at position 167, the substituting amino acid is Asp or Glu; but when position 167 is substituted the variant is not a double, triple, quadruple, quintuple, or sextuple mutation variant having substitutions at positions selected from the group consisting of 104, 162, 170, 192, and 220;

i. when a substitution occurs at position 168, the substituting amino acid is Asp, Gln, Glu or Ser; but when position 168 is substituted the variant is not a double, triple, quadruple, quintuple, or sextuple mutation variant having substitutions at positions selected from the group consisting of 104, 162, 170, 192, and 220;

j. when a substitution occurs at position 169, the substituting amino acid is Ala, Asn, Asp, Cys, Gln, Glu, Gly, His, Ile, Leu, Met, Pro, Ser, Thr or Val; but when position 169 is substituted the variant is not a double, triple, quadruple, quintuple, or sextuple mutation variant having substitutions at positions selected from the group consisting of 104, 162, 170, 192, and 220; and k. when a substitution occurs at position 170, the substituting amino acid is Asp or Glu; but when position 170 is substituted the variant is not a double, triple, quadruple, or quintuple mutation variant having substitutions at positions selected from the group consisting of 104, 162, 192, and 220;

E. when a substitution occurs in the fifth loop region, the substitution occurs at one or more of positions 190, 191, 192, 193 or 194; wherein a. when a substitution occurs at position 190, the substituting amino acid is Asp or Glu;

b. when a substitution occurs at position 191, the substituting amino acid is Asp or Glu;
c. when a substitution occurs at position 192, the substituting amino acid is Ala, Asn, Asp, Cys, Gln, Glu, Gly, His, Ile, Leu, Met, Pro, Ser, Thr, Tyr or Val;
d. when a substitution occurs at position 193, the substituting amino acid is Asp or Glu; and
e. when a substitution occurs at position 194, the substituting amino acid is Asp, Gln, Glu or Ser; and F. when a substitution occurs in the sixth loop region, the substitution occurs at one or more of positions 203, 204, 205, 206, 207, 208, 209, 210, 260, 212, 213, 214, 215, 216, 217, 218, 219, 220, 221, 222 or 223; wherein
  a. when a substitution occurs at position 203, the substituting amino acid is Asn, Asp, Gln, Glu, Pro or Ser;
  b. when a substitution occurs at position 204, the substituting amino acid is Asn, Asp, Gln, Glu, Gly or Ser;
  c. when a substitution occurs at position 205, the substituting amino acid is Asn, Asp, Gln, Glu, Pro or Ser;
  d. when a substitution occurs at position 206, the substituting amino acid is Asn, Asp, Gln, Glu, Gly, Pro or Ser;
  e. when a substitution occurs at position 207, the substituting amino acid is Asp or Glu;
  f. when a substitution occurs at position 208, the substituting amino acid is Ala, Asn, Asp, Cys, Gln, Glu, Gly, His, Leu, Met, Pro, Ser, Thr or Val;
  g. when a substitution occurs at position 209, the substituting amino acid is Ala, Asn, Asp, Cys, Gln, Glu, Gly, His, Ile, Met, Pro, Ser, Thr or Val;
  h. when a substitution occurs at position 210, the substituting amino acid is Asp or Glu;
  i. when a substitution occurs at position 211, the substituting amino acid is Asn, Asp, Gln, Glu, Gly, Pro or Ser;
  j. when a substitution occurs at position 212, the substituting amino acid is Ala, Asn, Asp, Cys, Gln, Glu, Gly, His, Ile, Leu, Met, Phe, Pro, Ser, Thr, Tyr or Val;
  k. when a substitution occurs at position 213, the substituting amino acid is Ala, Asn, Asp, Cys, Gln, Giu, Gly, His, Leu, Met, Pro, Ser, Thr or Val;
  l. when a substitution occurs at position 214, the substituting amino acid is Asn, Asp, Gln, Glu, Pro or Ser;
  m. when a substitution occurs at position 215, the substituting amino acid is Asn, Asp, Gln, Glu, Pro or Ser;
  n. when a substitution occurs at position 216, the substituting amino acid is Asp or Glu; but when position 216 is substituted the variant is not a double, triple, quadruple, quintuple, sextuple, or septuple mutation variant having substitutions at positions selected from the group consisting of 104, 161, 162, 170, 192, and 220;
  o. when a substitution occurs at position 217, the substituting amino acid is Asn, Asp, Gln, Glu, Gly, Pro or Ser; but when position 217 is substituted the variant is not a double, triple, quadruple, quintuple, sextuple, or septuple mutation variant having substitutions at positions selected from the group consisting of 104, 161, 162, 170, 192, and 220;
  p. when a substitution occurs at position 218, the substituting amino acid is Asp or Glu; but when position 218 is substituted the variant is not a double, t riple, quadruple, quintuple, sextuple, or septuple mutation variant having substitutions at positions s elected from the group con sisting of 104, 161, 162, 170, 192, and 220;
  q. when a substitution occurs at position 219, the substituting amino acid is Asp or Glu;
  r. when a substitution occurs at position 220, the substituting amino acid is Ala, Asn, Asp, Cys, Gln, Glu, Gly, His, Leu, Met, Pro, Ser, Thr or Val;
  c. when a substitution occurs at position 221, the substituting amino acid is Asp or Gl u;
  t. when a substitution occurs at position 222, the substituting amino acid is Asn, Asp, Gln, Glu, Pro or Ser; and
  u. when a substitution occurs at position 223, the substituting amino acid is Asn, Asp, Gln, Glu, Gly, Pro or Ser;

whereby the Proteinase K variant has decreased adsorption to, and increased hydrolysis of, an insoluble substrate as compared to wild-type Proteinase K and wherein glutamate and asparate substitutions at positions 67 and 169 are combined with at least one further substitution at a proteinase K position selected from: 65, 66, 68, 70, 71, 105, 106, 137, 139, 140, 191, 193, 203 to 206, 208 to 215, 219, 223.

30. The Proteinase K variant of claim 29, wherein two or more substitutions occur in the first loop region.

31. The Proteinase K variant of claim 29, wherein two or more substitutions occur in the second loop region.

32. The Proteinase K variant of claim 29, wherein two or more substitutions occur in the third loop region.

33. The Proteinase K variant of claim 29, wherein two or more substitutions occur in the fourth loop region.

34. The Proteinase K variant of claim 29, wherein two or more substitutions occur in the fifth loop region.

35. The Proteinase K variant of claim 29, wherein two or more substitutions occur in the sixth loop region.

36. A Proteinase K variant having a modified amino acid sequence of the Proteinase K wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
  A. when a substitution occurs in the first loop region, the substitution occurs at one or more of positions 64, 65, 66, 67, 68, 70 or 71; wherein
    a. when a substitution occurs at position 64, the substituting amino acid is Asp or Glu;
    b. when a substitution occurs at position 65, the substituting amino acid is Glu;
    c. when a substitution occurs at position 66, the substituting amino acid is Asn, Asp, Gln, Glu, Pro or Ser;
    d. when a substitution occurs at position 67, the substituting amino acid is Asp, Gln, Glu or Ser;
    e. when a substitution occurs at position 68, the substituting amino acid is Asn, Asp, Gln, Glu, Pro or Ser;
    f. when a substitution occurs at position 70, the substituting amino acid is Asn, Asp, Gln, Glu, Pro or Ser; and
    g. when a substitution occurs at position 71, the substituting amino acid is Asn, Asp, Gln, Glu, Gly, Pro or Ser;
  B. when a substitution occurs in the second loop region, the substitution occurs at one or more of positions 95, 96, 97, 98, 99, 100, 101, 102, 103, 104, 105, 106 or 107; wherein a. when a substitution occurs at position 95, the substituting amino acid is Ala, Asn, Asp, Cys, Gln, Glu, Gly, His, Met, Pro, Ser or Thr;
b. when a substitution occurs at position 96, the substituting amino acid is Ala, Asn, Asp, Cys, Gln, Glu, Gly, His, Ile, Met, Pro, Ser, Thr or Val;
c. when a substitution occurs at position 97, the substituting amino acid is Glu; but when position 97 is substituted the variant is not a double, triple, quadruple, quintuple, sextuple, or septuple mutation variant having substitutions at positions selected from the group consisting of 104, 161, 162, 170, 192, and 220;
d. when a substitution occurs at position 98, the substituting amino acid is Glu; but when position 98 is substituted the variant is not a double, triple, quadruple, quintuple, or sextuple mutation variant having substitutions at positions selected from the group consisting of 104, 162, 170, 192, and 220;
e. when a substitution occurs at position 99, the substituting amino acid is Asp, Gln, Glu or Ser; but when position 99 is substituted the variant is not a double, triple, quadruple, quintuple, or sextuple mutation variant having substitutions at positions selected from the group consisting of 104, 162, 170, 192, and 220;
f. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 104, 162, 170, 192, and 220;
g. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 104, 162, 170, 192, and 220;
h. when a substitution occurs at position 102, the substituting amino acid is Asn, Asp, Gln, Glu, Pro or Ser; but when position 102 is substituted the variant is not a double, triple, quadruple, quintuple, or sextuple mutation variant having substitutions at positions selected from the group consisting of 104, 162, 170, 192, and 220;
i. when a substitution occurs at position 103, the substituting amino acid is Asn, Asp, Glu or Ser; but when position 103 is substituted the variant is not a double, triple, quadruple, quintuple, or sextuple mutation variant having substitutions at positions selected from the group consisting of 104, 162, 170, 192, and 220;
j. when a substitution occurs at position 104, the substituting amino acid is Ala, Asn, Asp, Cys, Gln, Glu, Gly, His, Ile, Leu, Met, Pro, Ser, Thr or Val;
k. when a substitution occurs at position 105, the substituting amino acid is Asp or Glu;
l. when a substitution occurs at position 106, the substituting amino acid is Asn, Asp, Gln, Glu, Gly, Pro or Ser; and
m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, quintuple, sextuple, or septuple mutation variant having substitutions at positions selected from the group consisting of 104, 161, 162, 170, 192, and 220;

C. when a substitution occurs in the third loop region, the substitution occurs at one or more of positions 133, 134, 135, 136, 137, 138, 139 or 140; wherein
a. when a substitution occurs at position 133, the substituting amino acid is Ala, Asn, Asp, Cys, Gln, Glu, Gly, His, Ile, Met, Pro, Ser, Thr or Val; but when position 133 is substituted the variant is not a double, triple, quadruple, quintuple, sextuple, or septuple mutation variant having substitutions at positions selected from the group consisting of 104, 161, 162, 170, 192, and 220;
b. when a substitution occurs at position 134, the substituting amino acid is Asn, Asp, Gln, Glu, Pro or Ser; but when position 134 is substituted the variant is not a double, triple, quadruple, quintuple, sextuple, or septuple mutation variant having substitutions at positions selected from the group consisting of 104, 161, 162, 170, 192, and 220;
c. when a substitution occurs at position 135, the substituting amino acid is Asn, Asp, Gln, Glu, Pro or Ser; but when position 135 is substituted the variant is not a double, triple, quadruple, quintuple, sextuple, or septuple mutation variant having substitutions at positions selected from the group consisting of 104, 161, 162, 170, 192, and 220;
d. when a substitution occurs at position 136, the substituting amino acid is Asn, Asp, Gln, Glu, Pro or Ser; but when position 136 is substituted the variant is not a double, triple, quadruple, quintuple, sextuple, or septuple mutation variant having substitutions at positions selected from the group consisting of 104, 161, 162, 170, 192, and 220;
e. when a substitution occurs at position 137, the substituting amino acid is Ala, Asn, Asp, Cys, Gln, Glu, Gly, His, Ile, Leu, Met, Pro, Ser, Thr or Val;
f. when a substitution occurs at position 138, the substituting amino acid is Asp or Glu;
g. when a substitution occurs at position 139, the substituting amino acid is Asp or Glu; and
h. when a substitution occurs at position 140, the substituting amino acid is Asp or Glu;

D. when a substitution occurs in the fourth loop region, the substitution occurs at one or more of positions 161, 162, 163, 164, 165, 166, 167, 168, 169 or 170; wherein
a. when a substitution occurs at position 161, the substituting amino acid is Gln;
b. when a substitution occurs at position 162, the substituting amino acid is Asp, Gln, Glu or Ser;
c. when a substitution occurs at position 163, the substituting amino acid is Asp, Gln, Glu or Ser; but when position 163 is substituted the variant is not a double, triple, quadruple, quintuple, or sextuple mutation variant having substitutions at positions selected from the group consisting of 104, 162, 170, 192, and 220;
d. when a substitution occurs at position 164, the substituting amino acid is Asn, Asp, Gln, Glu, Gly, His, Pro, Ser or Thr; but when position 164 is substituted the variant is not a double, triple, quadruple, quintuple, or sextuple mutation variant having substitutions at positions selected from the group consisting of 104, 162, 170, 192, and 220;
e. when a substitution occurs at position 165, the substituting amino acid is Glu; but when position 165 is substituted the variant is not a double, triple, quadruple, quintuple, or sextuple mutation variant having substitutions at positions selected from the group consisting of 104, 162, 170, 192, and 220;

f. when a substitution occurs at position 166, the substituting amino acid is Asn, Asp, Gln, Glu, Gly, His, Pro, Ser or Thr; but when position 166 is substituted the variant is not a double, triple, quadruple, quintuple, or sextuple mutation variant having substitutions at positions selected from the group consisting of 104, 162, 170, 192, and 220;

g. when a substitution occurs at position 167, the substituting amino acid is Asp or Glu; but when position 167 is substituted the variant is not a double, triple, quadruple, quintuple, or sextuple mutation variant having substitutions at positions selected from the group consisting of 104, 162, 170, 192, and 220;

h. when a substitution occurs at position 168, the substituting amino acid is Asp, Gln, Glu or Ser; but when position 168 is substituted the variant is not a double, triple, quadruple, quintuple, or sextuple mutation variant having substitutions at positions selected from the group consisting of 104, 162, 170, 192, and 220;

i. when a substitution occurs at position 169, the substituting amino acid is Asp, His, Ile, Leu, Met or Pro; but when position 169 is substituted the variant is not a double, triple, quadruple, quintuple, or sextuple mutation variant having substitutions at positions selected from the group consisting of 104, 162, 170, 192, and 220; and j. when a substitution occurs at position 170, the substituting amino acid is Asp or Glu; but when position 170 is substituted the variant is not a double, triple, quadruple, or quintuple mutation variant having substitutions at positions selected from the group consisting of 104, 162, 192, and 220;

E. when a substitution occurs in the fifth loop region, the substitution occurs at one or more of positions 190, 191, 192, 193 or 194; wherein a. when a substitution occurs at position 190, the substituting amino acid is Asp or Glu;

b. when a substitution occurs at position 191, the substituting amino acid is Asp or Glu;

c. when a substitution occurs at position 192, the substituting amino acid is Ala, Asn, Asp, Cys, Gln, Glu, Gly, His, Ile, Leu, Met, Pro, Ser, Thr, Tyr or Val;

d. when a substitution occurs at position 193, the substituting amino acid is Asp or Glu; and e. when a substitution occurs at position 194, the substituting amino acid is Asp, Gln, Glu or Ser; and F. when a substitution occurs in the sixth loop region, the substitution occurs at one or more of positions 203, 204, 205, 206, 207, 208, 209, 210, 260, 212, 213, 214, 215, 216, 217, 218, 219, 220, 221, 222 or 223; wherein a. when a substitution occurs at position 203, the substituting amino acid is Asn, Asp, Gln, Glu, Pro or Ser;

b. when a substitution occurs at position 204, the substituting amino acid is Asn, Asp, Gln, Glu, Gly or Ser;

c. when a substitution occurs at position 205, the substituting amino acid is Asn, Asp, Gln, Glu, Pro or Ser;

d. when a substitution occurs at position 206, the substituting amino acid is Asn, Asp, Gln, Glu, Gly, Pro or Ser;

e. when a substitution occurs at position 207, the substituting amino acid is Asp or Glu;

f. when a substitution occurs at position 208, the substituting amino acid is Ala, Asn, Asp, Cys, Gln, Glu, Gly, His, Leu, Met, Pro, Ser, Thr or Val;

g. when a substitution occurs at position 209, the substituting amino acid is Ala, Asn, Asp, Cys, Gln, Glu, Gly, His, Ile, Met, Pro, Ser, Thr or Val;

h. when a substitution occurs at position 210, the substituting amino acid is Asp or Glu;

i. when a substitution occurs at position 211, the substituting amino acid is Asn, Asp, Gln, Glu, Gly, Pro or Ser;

j. when a substitution occurs at position 212, the substituting amino acid is Ala, Asn, Asp, Cys, Gln, Glu, Gly, His, Ile, Leu, Met, Phe, Pro, Ser, Thr, Tyr or Val;

k. when a substitution occurs at position 213, the substituting amino acid is Ala, Asn, Asp, Cys, Gln, Glu, Gly, His, Leu, Met, Pro, Ser, Thr or Val;

l. when a substitution occurs at position 214, the substituting amino acid is Asn, Asp, Gln, Glu, Pro or Ser;

m. when a substitution occurs at position 215, the substituting amino acid is Asn, Asp, Gln, Glu, Pro or Ser;

n. when a substitution occurs at position 216, the substituting amino acid is Asp or Glu; but when position 216 is substituted the variant is not a double, triple, quadruple, quintuple, sextuple, or septuple mutation variant having substitutions at positions selected from the group consisting of 104, 161, 162, 170, 192, and 220;

o. when a substitution occurs at position 217, the substituting amino acid is Asn, Asp, Gln, Glu, Gly, Pro or Ser; but when position 217 is substituted the variant is not a double, triple, quadruple, quintuple, sextuple, or septuple mutation variant having substitutions at positions selected from the group consisting of 104, 161, 162, 170, 192, and 220;

p. when a substitution occurs at position 218, the substituting amino acid is Asp or Glu; but when position 218 is substituted the variant is not a double, triple, quadruple, quintuple, sextuple, or septuple mutation variant having substitutions at positions selected from the group consisting of 104, 161, 162, 170, 192, and 220;

q. when a substitution occurs at position 219, the substituting amino acid is Asp or Glu;

r. when a substitution occurs at position 220, the substituting amino acid is Ala, Asn, Asp, Cys, Gln, Glu, Gly, His, Leu, Met, Pro, Ser, Thr or Val;

s. when a substitution occurs at position 221, the substituting amino acid is Asp or Glu;

t. when a substitution occurs at position 222, the substituting amino acid is Asn, Asp, Gln, Glu, Pro or Ser; and u. when a substitution occurs at position 223, the substituting amino acid is Asn, Asp, Gln, Glu, Gly, Pro or Ser;

whereby the Proteinase K variant has decreased adsorption to, and increased hydrolysis of, an insoluble substrate as compared to wild-type Proteinase K.

37. The Proteinase K variant of claim 36, wherein two or more substitutions occur in the first loop region.

38. The Proteinase K variant of claim 36, wherein two or more substitutions occur in the second loop region.

39. The Proteinase K variant of claim 36, wherein two or more substitutions occur in the third loop region.

40. The Proteinase K variant of claim 36, wherein two or more substitutions occur in the fourth loop region.

41. The Proteinase K variant of claim 36, wherein two or more substitutions occur in the fifth loop region.

42. The Proteinase K variant of claim 36, wherein two or more substitutions occur in the sixth loop region.

43. A Proteinase K variant having a modified amino acid sequence of the Proteinase K wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
   A. when a substitution occurs in the first loop region, the substitution occurs at one or more of positions 64, 65, 66, 67, 68, 70 or 71; wherein
      a. when a substitution occurs at position 64, the substituting amino acid is Asp or Glu;
      b. when a substitution occurs at position 65, the substituting amino acid is Glu;
      c. when a substitution occurs at position 66, the substituting amino acid is Asn, Asp, Gln, Glu, Pro or Ser;
      d. when a substitution occurs at position 67, the substituting amino acid is Asp, Gln, Glu or Ser;
      e. when a substitution occurs at position 68, the substituting amino acid is Asn, Asp, Gln, Glu, Pro or Ser;
      f. when a substitution occurs at position 70, the substituting amino acid is Asn, Asp, Gln, Glu, Pro or Ser; and
      g. when a substitution occurs at position 71, the substituting amino acid is Asn, Asp, Gln, Glu, Gly, Pro or Ser;
   B. when a substitution occurs in the second loop region, the substitution occurs at one or more of positions 95, 96, 97, 98, 99, 100, 101, 102, 103, 104, 105, 106 or 107; wherein
      a. when a substitution occurs at position 95, the substituting amino acid is Ala, Asn, Asp, Cys, Gln, Glu, Gly, His, Met, Pro, Ser or Thr;
      b. when a substitution occurs at position 96, the substituting amino acid is Ala, Asn, Asp, Cys, Gln, Glu, Gly, His, Ile, Met, Pro, Ser, Thr or Val;
      c. when a substitution occurs at position 97, the substituting amino acid is Glu; but when position 97 is substituted the variant is not a double, triple, quadruple, quintuple, sextuple, or septuple mutation variant having substitutions at positions selected from the group consisting of 104, 161, 162, 170, 192, and 220;
      d. when a substitution occurs at position 98, the substituting amino acid is Glu; but when position 98 is substituted the variant is not a double, triple, quadruple, quintuple, or sextuple mutation variant having substitutions at positions selected from the group consisting of 104, 162, 170, 192, and 220;
      e. when a substitution occurs at position 99, the substituting amino acid is Asp, Gln, Glu or Ser; but when position 99 is substituted the variant is not a double, triple, quadruple, quintuple, or sextuple mutation variant having substitutions at positions selected from the group consisting of 104, 162, 170, 192, and 220;
      f. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 104, 162, 170, 192, and 220;
      g. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 104, 162, 170, 192, and 220;
      h. when a substitution occurs at position 102, the substituting amino acid is Asn, Asp, Gln, Glu, Pro or Ser; but when position 102 is substituted the variant is not a double, triple, quadruple, quintuple, or sextuple mutation variant having substitutions at positions selected from the group consisting of 104, 162, 170, 192, and 220;
      i. when a substitution occurs at position 103, the substituting amino acid is Asn, Asp, Glu or Ser; but when position 103 is substituted the variant is not a double, triple, quadruple, quintuple, or sextuple mutation variant having substitutions at positions selected from the group consisting of 104, 162, 170, 192, and 220;
      j. when a substitution occurs at position 104, the substituting amino acid is Ala, Asn, Asp, Cys, Gln, Glu, Gly, His, Ile, Leu, Met, Pro, Ser, Thr or Val;
      k. when a substitution occurs at position 105, the substituting amino acid is Asp or Glu;
      l. when a substitution occurs at position 106, the substituting amino acid is Asn, Asp, Gln, Glu, Gly, Pro or Ser; and
      m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, quintuple, sextuple, or septuple mutation variant having substitutions at positions selected from the group consisting of 104, 161, 162, 170, 192, and 220;
   C. when a substitution occurs in the third loop region, the substitution occurs at one or more of positions 133, 134, 135, 136, 137, 138, 139 or 140; wherein
      a. when a substitution occurs at position 133, the substituting amino acid is Ala, Asn, Asp, Cys, Gln, Glu, Gly, His, Ile, Met, Pro, Ser, Thr or Val; but when position 133 is substituted the variant is not a double, triple, quadruple, quintuple, sextuple, or septuple mutation variant having substitutions at positions selected from the group consisting of 104, 161, 162, 170, 192, and 220;
      b. when a substitution occurs at position 134, the substituting amino acid is Asn, Asp, Gln, Glu, Pro or Ser; but when position 134 is substituted the variant is not a double, triple, quadruple, quintuple, sextuple, or septuple mutation variant having substitutions at positions selected from the group consisting of 104, 161, 162, 170, 192, and 220;
      c. when a substitution occurs at position 135, the substituting amino acid is Asn, Asp, Gln, Glu, Pro or Ser; but when position 135 is substituted the variant is not a double, triple, quadruple, quintuple, sextuple, or septuple mutation variant having substitutions at positions selected from the group consisting of 104, 161, 162, 170, 192, and 220;
  d. when a substitution occurs at position 136, the substituting amino acid is Asn, Asp, Gln, Glu, Pro or Ser; but when position 136 is substituted the variant is not a double, triple, quadruple, quintuple, sextuple, or septuple mutation variant having substitutions at positions selected from the group consisting of 104, 161, 162, 170, 192, and 220;
  e. when a substitution occurs at position 137, the substituting amino acid is Ala, Asn, Asp, Cys, Gln, Glu, Gly, His, Ile, Leu, Met, Pro, Ser, Thr or Val;
  f. when a substitution occurs at position 138, the substituting amino acid is Asp or Glu;
  g. when a substitution occurs at position 139, the substituting amino acid is Asp or Glu; and
  h. when a substitution occurs at position 140, the substituting amino acid is Asp or Glu;
D. when a substitution occurs in the fourth loop region, the substitution occurs at one or more of positions 160, 161, 162, 163, 164, 165, 166, 167, 168, 169 or 170; wherein
  a. when a substitution occurs at position 160, the substituting amino acid is Asn, Asp, Gln, Glu, Pro or Ser; but when position 160 is substituted the variant is not a double, triple, quadruple, quintuple, or sextuple mutation variant having substitutions at positions selected from the group consisting of 104, 162, 170, 192, and 220;
  b. when a substitution occurs at position 161, the substituting amino acid is Asp, Gln, Glu or Ser;
  c. when a substitution occurs at position 162, the substituting amino acid is Asp, Gln, Glu or Ser;
  d. when a substitution occurs at position 163, the substituting amino acid is Asp, Gln, Glu or Ser; but when position 163 is substituted the variant is not a double, triple, quadruple, quintuple, or sextuple mutation variant having substitutions at positions selected from the group consisting of 104, 162, 170, 192, and 220;
  e. when a substitution occurs at position 164, the substituting amino acid is Asn, Asp, Gln, Glu, Gly, His, Pro, Ser or Thr; but when position 164 is substituted the variant is not a double, triple, quadruple, quintuple, or sextuple mutation variant having substitutions at positions selected from the group consisting of 104, 162, 170, 192, and 220;
  f. when a substitution occurs at position 165, the substituting amino acid is Glu; but when position 165 is substituted the variant is not a double, triple, quadruple, quintuple, or sextuple mutation variant having substitutions at positions selected from the group consisting of 104, 162, 170, 192, and 220;
  g. when a substitution occurs at position 166, the substituting amino acid is Asn, Asp, Gln, Glu, Gly, His, Pro, Ser or Thr; but when position 166 is substituted the variant is not a double, triple, quadruple, quintuple, or sextuple mutation variant having substitutions at positions selected from the group consisting of 104, 162, 170, 192, and 220;
  h. when a substitution occurs at position 167, the substituting amino acid is Asp or Glu; but when position 167 is substituted the variant is not a double, triple, quadruple, quintuple, or sextuple mutation variant having substitutions at positions selected from the group consisting of 104, 162, 170, 192, and 220;
  i. when a substitution occurs at position 168, the substituting amino acid is Asp, Gln, Glu or Ser; but when position 168 is substituted the variant is not a double, triple, quadruple, quintuple, or sextuple mutation variant having substitutions at positions selected from the group consisting of 104, 162, 170, 192, and 220;
  j. when a substitution occurs at position 169, the substituting amino acid is Ala, Asn, Asp, Cys, Gln, Glu, Gly, His, Ile, Leu, Met, Pro, Ser, Thr or Val; but when position 169 is substituted the variant is not a double, triple, quadruple, quintuple, or sextuple mutation variant having substitutions at positions selected from the group consisting of 104, 162, 170, 192, and 220; and
  k. when a substitution occurs at position 170, the substituting amino acid is Asp or Glu; but when position 170 is substituted the variant is not a double, triple, quadruple, or quintuple mutation variant having substitutions at positions selected from the group consisting of 104, 162, 192, and 220;
E. when a substitution occurs in the fifth loop region, the substitution occurs at one or more of positions 190, 192, 193 or 194; wherein
  a. when a substitution occurs at position 190, the substituting amino acid is Asp or Glu;
  b. when a substitution occurs at position 192, the substituting amino acid is Asn, Cys, Gln, His, Ile, Met, Pro, Thr, Tyr or Val;
  c. when a substitution occurs at position 193, the substituting amino acid is Asp or Glu; and
  d. when a substitution occurs at position 194, the substituting amino acid is Asp, Gln, Glu or Ser; and
F. when a substitution occurs in the sixth loop region, the substitution occurs at one or more of positions 203, 204, 205, 206, 207, 208, 209, 210, 260, 212, 213, 214, 215, 216, 217, 218, 219, 220, 221, 222 or 223; wherein
  a. when a substitution occurs at position 203, the substituting amino acid is Asn, Asp, Gln, Glu, Pro or Ser;
  b. when a substitution occurs at position 204, the substituting amino acid is Asn, Asp, Gln, Glu, Gly or Ser;
  c. when a substitution occurs at position 205, the substituting amino acid is Asn, Asp, Gln, Glu, Pro or Ser;
  d. when a substitution occurs at position 206, the substituting amino acid is Asn, Asp, Gln, Glu, Gly, Pro or Ser;
  e. when a substitution occurs at position 207, the substituting amino acid is Asp or Glu;
  f. when a substitution occurs at position 208, the substituting amino acid is Ala, Asn, Asp, Cys, Gln, Glu, Gly, His, Leu, Met, Pro, Ser, Thr or Val;
  g. when a substitution occurs at position 209, the substituting amino acid is Ala, Asn, Asp, Cys, Gln, Glu, Gly, His, Ile, Met, Pro, Ser, Thr or Val;
  h. when a substitution occurs at position 210, the substituting amino acid is Asp or Glu;
  i. when a substitution occurs at position 211, the substituting amino acid is Asn, Asp, Gln, Glu, Gly, Pro or Ser;
  j. when a substitution occurs at position 212, the substituting amino acid is Ala, Asn, Asp, Cys, Gln, Glu, Gly, His, Ile, Leu, Met, Phe, Pro, Ser, Thr, Tyr or Val;
  k. when a substitution occurs at position 213, the substituting amino acid is Ala, Asn, Asp, Cys, Gln, Glu, Gly, His, Leu, Met, Pro, Ser, Thr or Val;

l. when a substitution occurs at position 214, the substituting amino acid is Asn, Asp, Gln, Glu, Pro or Ser;

m. when a substitution occurs at position 215, the substituting amino acid is Asn, Asp, Gln, Glu, Pro or Ser;

n. when a substitution occurs at position 216, the substituting amino acid is Asp or Glu; but when position 216 is substituted the variant is not a double, triple, quadruple, quintuple, sextuple, or septuple mutation variant having substitutions at positions selected from the group consisting of 104, 161, 162, 170, 192, and 220;

o. when a substitution occurs at position 217, the substituting amino acid is Asn, Asp, Gln, Glu, Gly, Pro or Ser; but when position 217 is substituted the variant is not a double, triple, quadruple, quintuple, sextuple, or septuple mutation variant having substitutions at positions selected from the group consisting of 104, 161, 162, 170, 192, and 220;

p. when a substitution occurs at position 218, the substituting amino acid is Asp or Glu; but when position 218 is substituted the variant is not a double, triple, quadruple, quintuple, sextuple, or septuple mutation variant having substitutions at positions selected from the group consisting of 104, 161, 162, 170, 192, and 220;

q. when a substitution occurs at position 219, the substituting amino acid is Asp or Glu;

r. when a substitution occurs at position 220, the substituting amino acid is Ala, Asn, Asp, Cys, Gln, Glu, Gly, His, Leu, Met, Pro, Ser, Thr or Val;

s. when a substitution occurs at position 221, the substituting amino acid is Asp or Glu;

t. when a substitution occurs at position 222, the substituting amino acid is Asn, Asp, Gln, Glu, Pro or Ser; and u. when a substitution occurs at position 223, the substituting amino acid is Asn, Asp, Gln, Glu, Gly, Pro or Ser;

whereby the Proteinase K variant has decreased adsorption to, and increased hydrolysis of, an insoluble substrate as compared to wild-type Proteinase K and wherein glutamate and asparate substitutions at positions 67 and 169 are combined with at least one further substitution at a proteinase K position selected from: 65, 66, 68, 70, 71, 105, 106, 137, 139, 140, 191, 193,203 to 206, 208 to 215, 219, 223.

44. The Proteinase K variant of claim 43, wherein two or more substitutions occur in the first loop region.

45. The Proteinase K variant of claim 43, wherein two or more substitutions occur in the second loop region.

46. The Proteinase K variant of claim 43, wherein two or more substitutions occur in the third loop region.

47. The Proteinase K variant of claim 43, wherein two or more substitutions occur in the fourth loop region.

48. The Proteinase K variant of claim 43, wherein two or more substitutions occur in the fifth loop region.

49. The Proteinase K variant of claim 43, wherein two or more substitutions occur in the sixth loop region.

50. A Proteinase K variant having a modified amino acid sequence of the Proteinase K wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 64, 65, 66, 67, 68, 70 or 71; wherein a. when a substitution occurs at position 64, the substituting amino acid is Asp or Glu;

b. when a substitution occurs at position 65, the substituting amino acid is Glu;

c. when a substitution occurs at position 66, the substituting amino acid is Asn, Asp, Gln, Glu, Pro or Ser;

d. when a substitution occurs at position 67, the substituting amino acid is Asp, Gln, Glu or Ser;

e. when a substitution occurs at position 68, the substituting amino acid is Asn, Asp, Gln, Glu, Pro or Ser;

f. when a substitution occurs at position 70, the substituting amino acid is Asn, Asp, Gln, Glu, Pro or Ser; and g. when a substitution occurs at position 71, the substituting amino acid is Asn, Asp, Gln, Glu, Gly, Pro or Ser;

B. when a substitution occurs in the second loop region, the substitution occurs at one or more of positions 95, 96, 97, 98, 99, 100, 101, 102, 103, 104, 105, 106 or 107; wherein a. when a substitution occurs at position 95, the substituting amino acid is Ala, Asn, Asp, Cys, Gln, Glu, Gly, His, Met, Pro, Ser or Thr;

b. when a substitution occurs at position 96, the substituting amino acid is Ala, Asn, Asp, Cys, Gln, Glu, Gly, His, Ile, Met, Pro, Ser, Thr or Val;

c. when a substitution occurs at position 97, the substituting amino acid is Glu; but when position 97 is substituted the variant is not a double, triple, quadruple, quintuple, sextuple, or septuple mutation variant having substitutions at positions selected from the group consisting of 104, 161, 162, 170, 192, and 220;

d. when a substitution occurs at position 98, the substituting amino acid is Glu; but when position 98 is substituted the variant is not a double, triple, quadruple, quintuple, or sextuple mutation variant having substitutions at positions selected from the group consisting of 104, 162, 170, 192, and 220;

e. when a substitution occurs at position 99, the substituting amino acid is Asp, Gln, Glu or Ser; but when position 99 is substituted the variant is not a double, triple, quadruple, quintuple, or sextuple mutation variant having substitutions at positions selected from the group consisting of 104, 162, 170, 192, and 220;

f. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 104, 162, 170, 192, and 220;

g. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 104, 162, 170, 192, and 220;

h. when a substitution occurs at position 102, the substituting amino acid is Asn, Asp, Gln, Glu, Pro or Ser; but when position 102 is substituted the variant is not a double, triple, quadruple, quintuple, or sextuple mutation variant having substitutions at positions selected from the group consisting of 104, 162, 170, 192, and 220;

i. when a substitution occurs at position 103, the substituting amino acid is Asn, Asp, Glu or Ser; but when position 103 is substituted the variant is not a double, triple, quadruple, quintuple, or sextuple mutation variant having substitutions at positions selected from the group consisting of 104, 162, 170, 192, and 220;

j. when a substitution occurs at position 104, the substituting amino acid is Ala, Asn, Asp, Cys, Gln, Glu, Gly, His, Ile, Leu, Met, Pro, Ser, Thr or Val;

k. when a substitution occurs at position 105, the substituting amino acid is Asp or Glu;

l. when a substitution occurs at position 106, the substituting amino acid is Asn, Asp, Gln, Glu, Gly, Pro or Ser; and m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, quintuple, sextuple, or septuple mutation variant having substitutions at positions selected from the group consisting of 104, 161, 162, 170, 192, and 220;

C. when a substitution occurs in the third loop region, the substitution occurs at one or more of positions 133, 134, 135, 136, 137, 138, 139 or 140; wherein a. when a substitution occurs at position 133, the substituting amino acid is Ala, Asn, Asp, Cys, Gln, Glu, Gly, His, Ile, Met, Pro, Ser, Thr or Val;

but when position 133 is substituted the variant is not a double, triple, quadruple, quintuple, sextuple, or septuple mutation variant having substitutions at positions selected from the group consisting of 104, 161, 162, 170, 192, and 220;

b. when a substitution occurs at position 134, the substituting amino acid is Asn, Asp, Gln, Glu, Pro or Ser; but when position 134 is substituted the variant is not a double, triple, quadruple, quintuple, sextuple, or septuple mutation variant having substitutions at positions selected from the group consisting of 104, 161, 162, 170, 192, and 220;

c. when a substitution occurs at position 135, the substituting amino acid is Asn, Asp, Gln, Glu, Pro or Ser; but when position 135 is substituted the variant is not a double, triple, quadruple, quintuple, sextuple, or septuple mutation variant having substitutions at positions selected from the group consisting of 104, 161, 162, 170, 192, and 220;

d. when a substitution occurs at position 136, the substituting amino acid is Asn, Asp, Gln, Glu, Pro or Ser; but when position 136 is substituted the variant is not a double, triple, quadruple, quintuple, sextuple, or septuple mutation variant having substitutions at positions selected from the group consisting of 104, 161, 162, 170, 192, and 220;

e. when a substitution occurs at position 137, the substituting amino acid is Ala, Asn, Asp, Cys, Gln, Glu, Gly, His, Ile, Leu, Met, Pro, Ser, Thr or Val;

f. when a substitution occurs at position 138, the substituting amino acid is Asp or Glu;

g. when a substitution occurs at position 139, the substituting amino acid is Asp or Glu; and h. when a substitution occurs at position 140, the substituting amino acid is Asp or Glu;

D. when a substitution occurs in the fourth loop region, the substitution occurs at one or more of positions 160, 161, 162, 163, 164, 165, 166, 167, 168, 169 or 170; wherein a. when a substitution occurs at position 160, the substituting amino acid is Asn, Asp, Gln, Glu, Pro or Ser; but when position 160 is substituted the variant is not a double, triple, quadruple, quintuple, or sextuple mutation variant having substitutions at positions selected from the group consisting of 104, 162, 170, 192, and 220;

b. when a substitution occurs at position 161, the substituting amino acid is Asp, Gln, Glu or Ser;

c. when a substitution occurs at position 162, the substituting amino acid is Asp, Gln, Glu or Ser;

d. when a substitution occurs at position 163, the substituting amino acid is Asp, Gln, Glu or Ser; but when position 163 is substituted the variant is not a double, triple, quadruple, quintuple, or sextuple mutation variant having substitutions at positions selected from the group consisting of 104, 162, 170, 192, and 220;

e. when a substitution occurs at position 164, the substituting amino acid is Asn, Asp, Gln, Glu, Gly, His, Pro, Ser or Thr; but when position 164 is substituted the variant is not a double, triple, quadruple, quintuple, or sextuple mutation variant having substitutions at positions selected from the group consisting of 104, 162, 170, 192, and 220;

f. when a substitution occurs at position 165, the substituting amino acid is Glu; but when position 165 is substituted the variant is not a double, triple, quadruple, quintuple, or sextuple mutation variant having substitutions at positions selected from the group consisting of 104, 162, 170, 192, and 220;

g. when a substitution occurs at position 166, the substituting amino acid is Asn, Asp, Gln, Glu, Gly, His, Pro, Ser or Thr; but when position 166 is substituted the variant is not a double, triple, quadruple, quintuple, or sextuple mutation variant having substitutions at positions selected from the group consisting of 104, 162, 170, 192, and 220;

h. when a substitution occurs at position 167, the substituting amino acid is Asp or Glu; but when position 167 is substituted the variant is not a double, triple, quadruple, quintuple, or sextuple mutation variant having substitutions at positions selected from the group consisting of 104, 162, 170, 192, and 220;

i. when a substitution occurs at position 168, the substituting amino acid is Asp, Gln, Glu or Ser; but when position 168 is substituted the variant is not a double, triple, quadruple, quintuple, or sextuple mutation variant having substitutions at positions selected from the group consisting of 104, 162, 170, 192, and 220;

j. when a substitution occurs at position 169, the substituting amino acid is Ala, Asn, Asp, Cys, Gln, Glu, Gly, His, Ile, Leu, Met, Pro, Ser, Thr or Val; but when position 169 is substituted the variant is not a double, triple, quadruple, quintuple, or sextuple mutation variant having substitutions at positions selected from the group consisting of 104, 162, 170, 192, and 220; and k. when a substitution occurs at position 170, the substituting amino acid is Asp or Glu; but when position 170 is substituted the variant is not a double, triple, quadruple, or quintuple mutation variant having substitutions at positions selected from the group consisting of 104, 162, 192, and 220;

E. when a substitution occurs in the fifth loop region, the substitution occurs at one or more of positions 190, 191, 192, 193 or 194; wherein
   a. when a substitution occurs at position 190, the substituting amino acid is Asp or Glu;
   b. when a substitution occurs at position 191, the substituting amino acid is Asp or Glu;
   c. when a substitution occurs at position 192, the substituting amino acid is Ala, Asn, Asp, Cys, Gln, Glu, Gly, His, Ile, Leu, Met, Pro, Ser, Thr, Tyr or Val;
   d. when a substitution occurs at position 193, the substituting amino acid is Asp or Glu; and
   e. when a substitution occurs at position 194, the substituting amino acid is Asp, Gln, Glu or Ser; and F. when a substitution occurs in the sixth loop region, the substitution occurs at one or more of positions 203, 204, 205, 206, 208, 209, 210, 260, 212, 213, 214, 215, 216, 217, 218, 219, 220, 221, 222 or 223; wherein
   a. when a substitution occurs at position 203, the substituting amino acid is Asn, Asp, Gln, Glu, Pro or Ser;
   b. when a substitution occurs at position 204, the substituting amino acid is Asn, Asp, Gln, Glu, Gly or Ser;
   c. when a substitution occurs at position 205, the substituting amino acid is Asn, Asp, Gln, Glu, Pro or Ser;
   d. when a substitution occurs at position 206, the substituting amino acid is Asn, Asp, Gln, Glu, Gly, Pro or Ser;
   e. when a substitution occurs at position 208, the substituting amino acid is Ala, Asn, Asp, Cys, Gln, Glu, Gly, His, Leu, Met, Pro, Ser, Thr or Val;
   f. when a substitution occurs at position 209, the substituting amino acid is Ala, Asn, Asp, Cys, Gln, Glu, Gly, His, Ile, Met, Pro, Ser, Thr or Val;
   g. when a substitution occurs at position 210, the substituting amino acid is Asp or Glu;
   h. when a substitution occurs at position 211, the substituting amino acid is Asn, Asp, Gln, Glu, Pro or Ser;
   i. when a substitution occurs at position 212, the substituting amino acid is Asp or Glu;
   j. when a substitution occurs at position 213, the substituting amino acid is Ala, Asn, Asp, Cys, Gln, Glu, Gly, His, Leu, Met, Pro, Ser, Thr or Val;
   k. when a substitution occurs at position 214, the substituting amino acid is Asn, Gln, Pro or Ser;
   l. when a substitution occurs at position 215, the substituting amino acid is Asn, Asp, Gln, Glu, Pro or Ser;
   m. when a substitution occurs at position 216, the substituting amino acid is Asp or Glu; but when position 216 is substituted the variant is not a double, triple, quadruple, quintuple, sextuple, or septuple mutation variant having substitutions at positions selected from the group consisting of 104, 161, 162, 170, 192, and 220;
   n. when a substitution occurs at position 217, the substituting amino acid is Asn, Asp, Gln, Glu, Gly, Pro or Ser; but when position 217 is substituted the variant is not a double, triple, quadruple, quintuple, sextuple, or septuple mutation variant having substitutions at positions selected from the group consisting of 104, 161, 162, 170, 192, and 220;
   o. when a substitution occurs at position 218, the substituting amino acid is Asp or Glu; but when position 218 is substituted the variant is not a double, triple, quadruple, quintuple, sextuple, or septuple mutation variant having substitutions at positions selected from the group consisting of 104, 161, 162, 170, 192, and 220;
   p. when a substitution occurs at position 219, the substituting amino acid is Asp or Glu;
   q. when a substitution occurs at position 220, the substituting amino acid is Ala, Asn, Asp, Cys, Gln, Glu, Gly, His, Leu, Met, Pro, Ser, Thr or Val;
   r. when a substitution occurs at position 221, the substituting amino acid is Asp or Glu;
   s. when a substitution occurs at position 222, the substituting amino acid is Asn, Asp, Gln, Glu, Pro or Ser; and
   t. when a substitution occurs at position 223, the substituting amino acid is Asn, Asp, Gln, Glu, Pro or Ser;

whereby the Proteinase K variant has decreased adsorption to, and increased hydrolysis of, an insoluble substrate as compared to wild-type Proteinase K and wherein glutamate and asparate substitutions at positions 67 and 169 are combined with at least one further substitution at a proteinase K position selected from: 65, 66, 68, 70, 71, 105, 106, 137, 139, 140, 191, 193, 203 to 206, 208 to 215, 219, 223.

51. The Proteinase K variant of claim 50, wherein two or more substitutions occur in the first loop region.

52. The Proteinase K variant of claim 50, wherein two or more substitutions occur in the second loop region.

53. The Proteinase K variant of claim 50, wherein two or more substitutions occur in the third loop region.

54. The Proteinase K variant of claim 50, wherein two or more substitutions occur in the fourth loop region.

55. The Proteinase K variant of claim 50, wherein two or more substitutions occur in the fifth loop region.

56. The Proteinase K variant of claim 50, wherein two or more substitutions occur in the sixth loop region.

57. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the Proteinase K variant of claim 8 and a cleaning composition carrier.

58. The cleaning composition of claim 57, wherein the cleaning composition is a hard surface cleaning composition.

59. The cleaning composition of claim 57, wherein the cleaning composition is a fabric cleaning composition.

60. The fabric cleaning composition of claim 59, wherein the composition is in the form of a liquid.

61. The fabric cleaning composition of claim 60, wherein the composition comprises at least about 5% surfactant and at least about 5% builder, by weight of the composition.

62. The fabric cleaning composition of claim 61, further comprising cleaning composition materials selected from the group consisting of solvents, buffers, enzymes, soil release agents, clay soil removal agents, dispersing agents, brighteners, suds suppressors, fabric softeners, suds boosters, enzyme stabilizers, bleaching agents, dyes, perfumes, and mixtures thereof.

63. The fabric cleaning composition of claim 61, further comprising at least one bleaching agent.

64. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the Proteinase K variant of claim 2 and a cleaning composition carrier.

65. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the Proteinase K variant of claim 3 and a cleaning composition carrier.

66. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the Proteinase K variant of claim 4 and a cleaning composition carrier.

67. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the Proteinase K variant of claim 5 and a cleaning composition carrier.

68. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the Proteinase K variant of claim 6 and a cleaning composition carrier.

69. A cleaning composition selected from the group consisting of a hard surface meaning composition, a dishwashing composition, an oral cleaning composition, a denture cleansing composition, a contact lens cleaning composition and a fabric cleaning composition, wherein the cleaning composition comprises the Proteinase K variant of claim 7 and a cleaning composition carrier.

70. A DNA sequence encoding the Proteinase K variant of claim 1.

* * * * *